(12) United States Patent
Hou et al.

(10) Patent No.: US 12,312,379 B2
(45) Date of Patent: May 27, 2025

(54) METHODS FOR PRODUCING CYCLIC COMPOUNDS COMPRISING N-SUBSTITUTED AMINO ACID RESIDUES

(71) Applicant: Chugai Seiyaku Kabushiki Kaisha, Tokyo (JP)

(72) Inventors: Zengye Hou, Tokyo (JP); Kentarou Seto, Tokyo (JP); Kota Tanaka, Tokyo (JP); Masahide Aoki, Gotemba (JP); Aya Sakon, Gotemba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/738,283

(22) Filed: May 6, 2022

(65) Prior Publication Data
US 2022/0411462 A1 Dec. 29, 2022

(30) Foreign Application Priority Data

May 7, 2021 (JP) .................................. 2021-079014
Nov. 19, 2021 (JP) .................................. 2021-188473

(51) Int. Cl.
C07K 1/10 (2006.01)
C07K 1/107 (2006.01)
C07K 7/64 (2006.01)

(52) U.S. Cl.
CPC .............. C07K 1/1075 (2013.01); C07K 7/64 (2013.01); *C07B 2200/13* (2013.01)

(58) Field of Classification Search
CPC ........ C07K 1/1075; C07K 7/64; C07K 1/113; C07K 7/56; C07K 1/107; C07B 2200/13
See application file for complete search history.

(56) References Cited

U.S. PATENT DOCUMENTS

| | | | |
|---|---|---|---|
| 9,409,952 B2 | 8/2016 | Kariyuki et al. | |
| 11,492,369 B2 | 11/2022 | Nomura et al. | |
| 11,542,299 B2 | 1/2023 | Nomura et al. | |
| 11,732,002 B2 | 8/2023 | Iwasaki et al. | |
| 11,787,836 B2 | 10/2023 | Nomura et al. | |
| 11,891,457 B2 | 2/2024 | Kariyuki et al. | |
| 12,071,396 B2 | 8/2024 | Wadamoto et al. | |
| 2013/0274205 A1 | 10/2013 | Guerlavais et al. | |
| 2014/0128572 A1* | 5/2014 | Monnaie ................ | C07K 1/145 530/344 |
| 2015/0080549 A1 | 3/2015 | Kariyuki et al. | |
| 2016/0264627 A1 | 9/2016 | Henning et al. | |
| 2016/0311858 A1 | 10/2016 | Kariyuki et al. | |
| 2020/0131669 A1 | 4/2020 | Muraoka et al. | |
| 2020/0277327 A1 | 9/2020 | Nomura et al. | |
| 2020/0339623 A1 | 10/2020 | Nomura et al. | |
| 2021/0024579 A1* | 1/2021 | Shipman ............ | G01N 33/6803 |
| 2021/0061860 A1 | 3/2021 | Kariyuki et al. | |
| 2022/0017456 A1 | 1/2022 | Ishizawa | |
| 2022/0024972 A1 | 1/2022 | Iwasaki et al. | |
| 2022/0144762 A1 | 5/2022 | Wadamoto | |
| 2023/0026641 A1 | 1/2023 | Nomura et al. | |
| 2023/0056969 A1 | 2/2023 | Kondo et al. | |
| 2023/0096766 A1 | 3/2023 | Muraoka et al. | |
| 2023/0138226 A1 | 5/2023 | Nomura et al. | |
| 2023/0151060 A1 | 5/2023 | Tanada et al. | |
| 2023/0295221 A1 | 9/2023 | Iwasaki et al. | |
| 2023/0303619 A1 | 9/2023 | Iwasaki et al. | |
| 2023/0391818 A1 | 12/2023 | Nomura et al. | |
| 2023/0406879 A1 | 12/2023 | Nomura et al. | |
| 2024/0067674 A1 | 2/2024 | Sekita et al. | |
| 2024/0124517 A1 | 4/2024 | Morita et al. | |
| 2024/0148821 A1 | 5/2024 | Tanada et al. | |
| 2024/0158446 A1 | 5/2024 | Kawada et al. | |
| 2024/0166689 A1 | 5/2024 | Kariyuki et al. | |
| 2024/0366711 A1 | 11/2024 | Ueto et al. | |
| 2024/0376044 A1 | 11/2024 | Wadamoto | |
| 2024/0400617 A1 | 12/2024 | Tanada et al. | |

FOREIGN PATENT DOCUMENTS

| | | |
|---|---|---|
| EP | 2813512 A1 | 12/2014 |
| EP | 3424941 A1 | 1/2019 |
| EP | 3636656 A1 | 4/2020 |
| EP | 3636807 A1 | 4/2020 |
| EP | 4043478 A1 | 8/2022 |
| EP | 4316503 A1 | 2/2024 |
| JP | 2015509940 A | 4/2015 |
| JP | 2020105162 A | 7/2020 |
| WO | WO0015656 A1 | 3/2000 |
| WO | WO2013100132 A1 | 7/2013 |
| WO | WO2015179434 A1 | 11/2015 |
| WO | WO2016100608 A1 | 6/2016 |
| WO | WO2017181061 A1 | 10/2017 |

(Continued)

OTHER PUBLICATIONS

Das et al.(UJPB, 2013, 01(02), 21-24) (Year: 2013).*
Isidro-Llobet et al.(Chem.Rev., 2009, 109, 2455-2504) (Year: 2009).*
Lambert et al.(J.Chem.Soc., Perkin Trans. 1, 2001, 471-484) (Year: 2001).*
Eggen et al (J. Peptides, 2005, 11, 633-641) (Year: 2005).*
Boehm, M., et al., "Discovery of Potent and Orally Bioavailable Macrocyclic Peptide-Peptoid Hybrid CXCR7 Modulators," J Med Chem., 60:9653-9663 (2017).
Chatterjee, J., et al., "N-Methylation of Peptides: A New Perspective in Medicinal Chemistry," Acc Chem Res., 40(10):1331-1342 (2008).
Chatterjee, J., et al., "N-Methylation of Peptides and Proteins: An Important Element for Modulating Biological Functions," Angew Chem Int Ed., 52:254-269 (2013).

(Continued)

*Primary Examiner* — Sudhakar Katakam
(74) *Attorney, Agent, or Firm* — Nixon & Vanderhye P.C.

(57) ABSTRACT

The present invention provides methods for producing peptide compounds. The inventors have found that a cyclic peptide compound can be produced efficiently by linking the N-terminal amino acid residue and the C-terminal amino acid residue of a peptide compound in a solvent containing one or more selected from the group consisting of water-immiscible solvents, water-soluble alkyl nitriles, and water-soluble ethers.

28 Claims, 13 Drawing Sheets

(56) References Cited

FOREIGN PATENT DOCUMENTS

| | | |
|---|---|---|
| WO | WO2018225851 A1 | 12/2018 |
| WO | WO2018225864 A1 | 12/2018 |
| WO | WO2019117274 A1 | 6/2019 |
| WO | WO2020095983 A1 | 5/2020 |
| WO | WO2020106647 A2 | 5/2020 |
| WO | WO2020111238 A1 | 6/2020 |
| WO | WO2020122182 A1 | 6/2020 |
| WO | WO2020189540 A1 | 9/2020 |
| WO | WO2021030855 A1 | 2/2021 |
| WO | WO2021090855 A1 | 5/2021 |
| WO | WO2021090856 A1 | 5/2021 |
| WO | WO2021132545 A1 | 7/2021 |
| WO | WO2021246471 A1 | 12/2021 |
| WO | WO2022097540 A1 | 5/2022 |
| WO | WO2022138891 A1 | 6/2022 |
| WO | WO2022145444 A1 | 7/2022 |
| WO | WO2022234850 A1 | 11/2022 |
| WO | WO2022234851 A1 | 11/2022 |
| WO | WO2022234852 A1 | 11/2022 |
| WO | WO2022234853 A1 | 11/2022 |
| WO | WO2023127752 A1 | 7/2023 |
| WO | WO2023127869 A1 | 7/2023 |
| WO | WO2023140329 A1 | 7/2023 |
| WO | WO2023190748 A1 | 10/2023 |
| WO | WO2023195516 A1 | 10/2023 |
| WO | WO2023214576 A1 | 11/2023 |
| WO | WO2023214577 A1 | 11/2023 |
| WO | WO2023219152 A1 | 11/2023 |
| WO | WO2023219156 A1 | 11/2023 |
| WO | WO2024080333 A1 | 4/2024 |

OTHER PUBLICATIONS

Gracia, S. R., et al., "Synthesis of chemically modified bioactive peptides: recent advances, challenges and developments for medicinal chemistry," Future Med Chem., 1(7):1289-1310 (2009).
Huang, Y., et al., "RNA Display Methods for the Discovery of Bioactive Macrocycles," Chem Rev., 119:10360-10391 (2019).
Hughes, A. B., editor, "Amino Acids, Peptides and Proteins in Organic Chemistry," Building Blocks, Catalysis and Coupling Chemistry, Chapters 6 and 7, 3:203-251, 253-272 (2011).
Lipinski, C. A., et al., "Experimental and computational approaches to estimate solubility and permeability in drug discovery and development settings," Adv Drug Del Rev., 23:3-25 (1997).
Shankaramma, S. C., et al., "A family of macrocyclic antibiotics with a mixed peptide-peptoid β-hairpin backbone conformation," Chem Commun., 15:1842-1843 (2003).
Teixido, M., et al., "Solid-phase synthesis and characterization of N-methyl-rich peptides," J Peptide Res., 65:153-166 (2005).
Wegner, K., et al., "Evaluation of greener solvents for solid-phase peptide synthesis," Green Chem Lett Rev., 14(1):153-164 (2021).
Yang, Y., "Side Reactions in Peptide Synthesis," Academic Press, Chapters 5, 10, 11 and 14, pp. 95-118, 235-256, 257-292 and 311-322 (2015).
Zhang, Z., et al., "GTP-State-Selective Cyclic Peptide Ligands of K-Ras(G12D) Block Its Interaction with Raf," ACS Cent Sci., 6:1753-1761 (2020).
Di Gioia, M. L., et al., "N-Methylation of Peptides on Selected Positions during the Elongation of the Peptide Chain in Solution Phase," J Org Chem., 70(10):3892-3897 (2005).
Räder, A. F. B., et al., "Improving oral bioavailability of cyclic peptides by N-methylation," Biorg Med Chem., 26(10):2766-2773 (2018).
U.S. Appl. No. 14/368,564, filed Jun. 25, 2014, Kariyuki et al., related application.
U.S. Appl. No. 15/166,550, filed May 27, 2016, Kariyuki et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Apr. 29, 2022, Muraoka et al., related application.
U.S. Appl. No. 17/437,535, filed Sep. 9, 2021, Wadamoto, related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/788,506, filed Jun. 23, 2022, Kondo et al., related application.
U.S. Appl. No. 17/976,942, filed Oct. 31, 2022, Nomura et al., related application.
U.S. Appl. No. 18/034,424, filed Apr. 28, 2023, Nomura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,392, filed Nov. 3, 2023, Ueto et al., related application.
U.S. Appl. No. 18/289,451, filed Nov. 3, 2023, Tanada et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
Brandt, W., et al., "Systematic Conformational Investigations of Peptoids and Peptoid-Peptide Chimeras," Biopolymers (Pept Sci), 96(5):651-668 (2011).
Brown, Z.Z., et al., "Exploiting an Inherent Neighboring Group Effect of α-Amino Acids to Synthesize Extremely Hindered Dipeptides," J Am Chem Soc., 130(44):14382-14383 (2008).
Carpino, L.A., et al., "Protected Amnio Acid Chlorides vs Protected Amino Acid Fluorides: Reactivity Comparisons," Tetrahedron Letters, 39:241-244 (1998).
Miller, S.C. and Scanlan, T.S., "Site-Selective N-Methylation of Peptides on Solid Support," J Am Chem Soc., 119:2301-2302 (1997).
Turner, R.A., et al., "Selective, On-Resin N-Methylation of Peptide N-Trifluoroacetamides," Org Lett., 15(19):5012-5015 (2013).
U.S. Appl. No. 17/928,759, filed Nov. 30, 2022, Iwasaki et al., related application.
U.S. Appl. No. 18/289,071, filed Mar. 27, 2024, Hayashi et al., related application.
U.S. Appl. No. 18/723,993, filed Jun. 25, 2024, Komiya et al., related application.
U.S. Appl. No. 18/724,369, filed Jun. 26, 2024, Shinoda et al., related application.
U.S. Appl. No. 18/728,922, filed Jul, 15, 2024, Sase et al.
U.S. Appl. No. 18/773,066, filed Jul. 15, 2024, Tanada et al.
U.S. Appl. No. 18/781,112, filed Jul. 23, 2024, Wadamoto.
U.S. Appl. No. 18/829,566, filed Sep. 10, 2024, Kawada et al.
U.S. Appl. No. 18/854,568, filed Oct. 7, 2024, Shinohara et al.
U.S. Appl. No. 18/860,859, filed Oct. 28, 2024, Kage et al.
U.S. Appl. No. 18/864,039, filed Nov. 8, 2024, Ishiyama et al.
U.S. Appl. No. 18/864,049, filed Nov. 8, 2024, Ejima et al.
Aurelio, L., et al., "Determination of the Complete Absolute Configuration of Petriellin A," Aust J Chem., 59:407-414 (2006).

(56) References Cited

OTHER PUBLICATIONS

Di Gioia, M. L., et al., "'One-Pot' Methylation of N-Nosyl-α-amino Acid Methyl Esters with Diazomethane and Their Coupling To Prepare N-Methyl Dipeptides," J Org Chem., 68:7416-7421 (2003).

Ikawa, T., et al., "Selective N-alkylation of amines using nitriles under hydrogenation conditions: facile synthesis of secondary and tertiary amines," Org Biomol Chem., 10:293-304 (2012).

Li, P., et al., "Total synthesis and biological evaluation of ustiloxin natural products and two analogs," Bioorg Med Chem Lett. 16:4804-4807 (2006).

Sajiki, H., et al., "Reductive and Catalytic Monoalkylation of Primary Amines Using Nitriles as an Alkylating Reagent," Org Lett., 6(26):4977-4980 (2004).

White, K. N. and Konopelski, J. P., "Facile Synthesis of Highly Functionalized N-Methyl Amino Acid Esters without Side-Chain Protection," Org Lett., 7(19):4111-4112 (2005).

Boltromeŭk, V. V., "General chemistry," Minsk, Vyŝejaŝaâŝkola, 65 (2012).

Nomura, K., et al., "Broadly Applicable and Comprehensive Synthetic Method for N-Alkyl-Rich Drug-like Cyclic Peptides," J Med Chem., 65:13401-13412 (2022).

Osumi, H., et al., "Cetuximab treatment for metastatic colorectal cancer with KRAS p.G13D mutations improves progression-free survival," Mol Clin Oncol., 3:1053-1057 (2015).

Purkey, H., "Discovery of GDC 6036, a clinical stage treatment for KRAS G12C-positive cancers," AACR Annual Meeting, 11-17 (2022).

Purkey, H., "Abstract ND11: Discovery of GDC-6036, a clinical stage treatment for KRAS G12C-positive cancers," Cancer Res., 82(12_Supplement):ND11 (2022).

Tabernero, J. et al., "Krystal-10: A randomized phase 3 study of adagrasib (MRTX849) in combination with cetuximab vs chemotherapy in patients with previously treated advanced colorectal cancer with KRASG12C mutation," Ann Oncol., Abstract P-71, 32(S3):S121 (2021).

Tejpar, S., et al., "Association of KRAS G13D Tumor Mutations With Outcome in Patients With Metastatic Colorectal Cancer Treated With First-Line Chemotherapy With or Without Cetuximab," J Clin Oncol., 30:3570-3577 (2012).

Xu, J., et al., "Atroposelective Negishi Coupling Optimization Guided by Multivariate Linear Regression Analysis: Asymmetric Synthesis of KRAS G12C Covalent Inhibitor GDC-6036," J Am Chem Soc., 144:20955-20963 (2022).

U.S. Appl. No. 18/728,922, filed Jul. 15, 2024, Sase et al., related application.

U.S. Appl. No. 18/773,066, filed Jul. 15, 2024, Tanada et al., related application.

U.S. Appl. No. 18/781,112, filed Jul. 23, 2024, Wadamoto, related application.

U.S. Appl. No. 18/829,566, filed Sep. 10, 2024, Kawada et al., related application.

U.S. Appl. No. 18/854,568, filed Oct. 7, 2024, Shinohara et al., related application.

U.S. Appl. No. 18/860,859, filed Oct. 28, 2024, Kage et al., related application.

U.S. Appl. No. 18/864,039, filed Nov. 8, 2024, Ishiyama et al., related application.

U.S. Appl. No. 18/864,049, filed Nov. 8, 2024, Ejima et al., related application.

\* cited by examiner

METHODS FOR PRODUCING CYCLIC COMPOUNDS COMPRISING N-SUBSTITUTED AMINO ACID RESIDUES

CROSS-REFERENCE TO RELATED APPLICATIONS

This application claims the priority of Japanese Patent Application No. 2021-079014, filed May 7, 2021, and Japanese Patent Application No. 2021-188473, filed Nov. 19, 2021, each of which is incorporated herein by reference in its entirety.

TECHNICAL FIELD

The present invention relates to methods for producing a cyclic compound comprising an N-substituted amino acid residue.

BACKGROUND ART

As known as Lipinski's rule, it has been considered desirable for compounds used conventionally as oral drugs to have a molecular weight of not more than 500 g/mol (NPL 1). In recent years, it has become known that compounds with a molecular weight greater than 500 g/mol may contribute, for example, to blockage of the interaction of target proteins on their surface, namely protein-protein interactions, which are difficult for conventional small molecule compounds to target and thus called tough targets. These molecules are called middle molecules (molecular weight 500 to 2,000 g/mol), which are neither small molecules with a molecular weight of not more than 500 g/mol that are used as oral drugs, nor high-molecular-weight molecules with a molecular weight of greater than 100,000 g/mol like antibody drugs, and they draw attention as a novel modality that may achieve drug development against tough targets (NPL 2).

As with insulin used to treat hyperglycemia, peptides consisting of naturally occurring amino acids are poor in metabolic stability, and their development as oral drugs is conventionally considered difficult. However, cyclization of peptides and the use of unnatural amino acids such as N-methyl amino acids in peptides have been found to improve their metabolic stability and membrane permeability (NPLs 3 and 4).

Among cyclic peptides containing unnatural amino acids, those containing N-substituted amino acids in particular have increasingly been known to potentially have metabolic stability and membrane permeability, or in other words, have druglikeness (PTL 1).

It has been suggested that cyclic peptide compounds containing unnatural amino acids are useful to develop protein-protein interaction inhibitors (NPL 5).

As peptides have increasingly been seen as important as drugs, their synthesis methods have been studied more and more actively (NPL 6). The synthesis of a peptide is achieved by subjecting amino acids sequentially to amide bond formation reaction such that a desired amino acid sequence is elongated. However, for the production of a peptide whose sequence contains unnatural amino acids, particularly N-methyl amino acids, reduced yield of a product of interest due to, for example, their low reactivity in condensation reaction by steric hindrance of the N-methyl group and racemization of amino acid residues at the α position, have been recognized as problems (NPL 7). Though halogenated hydrocarbon solvents (for example, dichloromethane) and amide solvents (for example, DMF) are widely used in peptide synthesis, such side reactions may be observed in the peptide synthesis with low reactive amino acids, such as N-substituted amino acids (NPL 8). In addition, use of halogenated hydrocarbon solvents (for example, dichloromethane) and amide solvents (for example, DMF) is restricted from the viewpoint of environmental burden (NPL 9)."

CITATION LIST

Patent Literature

[PTL 1] WO 2013/100132

Non-Patent Literature

[NPL 1] Adv. Drug Del. Rev. 1997, 23, 3-25.
[NPL 2] Future Med. Chem., 2009, 1, 1289-1310.
[NPL 3] Acc. Chem. Res., 2008, 41, 1331-1342.
[NPL 4] Angew. Chem. Int. Ed., 2013, 52, 254-269.
[NPL 5] Chem. Rev., 2019, 119, 10360-10391.
[NPL 6] Amino Acids, Peptides and Proteins in Organic Chemistry: Building Blocks, Catalysis and Coupling Chemistry, Volume 3, 2011.
[NPL 7] J. Peptide Res., 2005, 65, 153-166.
[NPL 8] Side Reactions in Peptide Synthesis, Academic Press, 2015.
[NPL 9] Green Chem. Lett. Rev., 2021, 14, 153-164.

SUMMARY OF INVENTION

Technical Problem

The present invention has been made under the circumstances as described above. In one aspect, an objective of the present invention is to provide a method for efficiently producing a peptide compound, particularly a linear or cyclic peptide compound containing a plurality of unnatural amino acids such as N-substituted amino acids, by using a technique applicable to large scale production in which intermediates are not isolated, e.g. prior to the next subsequent reaction where present. In one aspect, an objective of the present invention is to provide a method for isolating and purifying a cyclic peptide compound of interest, or a salt thereof, or a solvate thereof without using column chromatography. In one aspect, an objective of the present invention is to provide a method for removing stabilizing agents (for example, antioxidants such as BHT) contained in solvents without isolating products produced in each step by washing with a solvent which solubilize the stabilizing agents. In one aspect, an objective of the present invention is to provide a method to shorten the work time in each step and to perform the next step continuously without isolating a peptide compound, e.g. the intermediates of the individual reaction steps, particularly a linear or cyclic peptide compound containing a plurality of unnatural amino acids such as N-substituted amino acids. Accordingly, as explained herein, one aspect of the present invention is to provide methods for the production of chemical compounds, which may comprise one or more reaction steps, comprising the use of solvents capable of solubilizing stabilizing agents.

Peptide synthesis is generally carried out by repeating the step of linking the C-terminal carboxyl group of an amino acid or peptide with the N-terminal amino group of an amino acid or peptide, thereby elongating a peptide chain. During this step, various side reactions are known to possibly occur (Side Reactions in Peptide Synthesis, Academic Press, 2015). Thus, it is common practice in peptide synthesis, particularly in liquid-phase peptide synthesis, to isolate and purify a product between elongation steps, and before a cyclization step. However, in industrial-scale peptide synthesis, since isolation and purification of intermediates lead to prolonged synthesis time and increased cost, it is desired that subsequent elongation and cyclization reactions can be carried out consecutively without isolation or purification of intermediates before resulting in a peptide of interest.

Meanwhile, in the elongation reaction of a peptide chain, the carboxyl group of an amino acid or peptide to be elongated and the amino group of an amino acid or peptide that elongates it are often protected, and the ω-chain of an amino acid is also often protected (Nobuo IZUMIYA, Principle and Practice of Peptide Synthesis, Maruzen (1985)). Such protected amino acids and peptides precipitate easily from reaction solutions, and are often insoluble in organic solvents (WO 2017/038650, WO 2018/021233, WO 2018/155669, WO 2019/123994, and WO 2017/221889). Unprotected amino acids and peptides are also difficult to dissolve in organic solvents due to their hydrophilicity. Furthermore, in many cases, aggregation is enhanced as the peptide chain is elongated, resulting in reduced solubility of the peptide compound (Kagaku To Seibutsu (Chemistry and Biology), 2018, 56(8): 558; J. Biol. Chem., 1963, 238: 4074; and Sci Rep, 2016, 6(28): 1).

To dissolve these amino acids and peptides, solvents with high solubilizing ability, such as DMF and dimethyl sulfoxide, are used in peptide synthesis reactions. Dichloromethane, which has excellent solubilizing ability, is also frequently used. For example, it has been reported that DMF and dichloromethane are used in 47% and 36% of the total peptide synthesis reactions, respectively; thus, these solvents taken together account for 83% of the total (Green Chem., 2013, 15, 596-600).

However, because dichloromethane is toxic and DMF is subject to legal regulations depending on the amount of use, the use of these solvents should be avoided in industrial production. In addition, since DMF and dimethyl sulfoxide are degraded by heating and have high boiling points, they are difficult to remove once they contaminate the product. Moreover, dimethylamine generated by degradation of DMF may be involved in peptide elongation reaction, and therefore could lead to generation of undesirable by-products (Side Reactions in Peptide Synthesis, Academic Press, 2015.). The malodor of dimethyl sulfide, generated from dimethyl sulfoxide, is also problematic.

In particular, industrial scale production, which uses large amounts of solvents and requires extensive time and heating for their removal by distillation, is readily expected to cause an increase in degradation products. Therefore, it is important to discover a solvent that is thermally stable when removed by distillation and in which the elongation and cyclization reactions of a peptide chain proceed efficiently.

Since DMF and dimethyl sulfoxide have high water solubility and are miscible with water, products of interest sometimes distribute into aqueous phases together with these organic solvents, thereby leading to reduced yields. This also makes the operation of liquid separation from aqueous solution inefficient. For example, if water enters an organic phase, water remains after distillation of the organic solvent containing a product of interest and, in some cases, causes hydrolysis of peptide bonds (Side Reactions in Peptide Synthesis, Academic Press, 2015.).

Industrial production processes, which require longer time to distill off solvents, have problems of not only reduced yields but also higher chances of side reactions caused by contamination with water.

Thus, there are demands for discovering a technique for forming an organic phase that can be separated well from aqueous phases in liquid separation operation, and for a solvent that allows peptide synthesis and is less miscible with water because of its low water solubility.

Furthermore, some solvents may contain stabilizing agents (for example, antioxidants such as BHT). In small-scale or short-step synthesis, stabilizing agents do not remain in large amounts in total and are not significant as impurities. However, when the number of processes or production volume increases, stabilizing agents may remain in such large amounts that their influence on the subsequent processes cannot be ignored (for example, the stabilizing agents contained in an intermediate may affect chemical reaction in the next step, or the stabilizing agents contained in the final compound of interest, such as an active pharmaceutical ingredient, may cause an unexpected effect other than the pharmacological efficacy.). When intermediates are isolated and purified, stabilizing agents are removed through these processes. However, for industrial production processes, in which such operations are preferably omitted, the stabilizing agents may be accumulated in the intermediate and the final compound. In industrial production processes, there is a demand for discovering a general technique for removing stabilizing agents in an efficient manner.

To synthesize a final product by elongating a peptide chain consecutively without isolating or purifying intermediates, each step of condensation, deprotection, or such needs to be performed under such reaction conditions that side reactions are prevented and only workup such as liquid separation are required before proceeding to the next step. Particularly, in the case of peptide synthesis on an industrial scale, it is inefficient to purify products of interest by column chromatography. Thus, there is a need for a technique for obtaining a crude product that can be purified by crystallization rather than by column chromatography, or a technique for obtaining a product of interest only by workup such as liquid separation. There is also a need for finding new reaction or workup conditions for those techniques.

Solution to Problem

As a result of dedicated studies to solve the above-mentioned problems, the present inventors have discovered particular solvents useful for peptide synthesis that differ from the conventional, commonly-used solvents including DMF, dichloromethane, and dimethyl sulfoxide, for example, those that satisfy the following requirements: (i) being resistant to heat degradation; (ii) showing good separation from aqueous phases in liquid separation operations; and (iii) allowing peptide chain elongation and cyclization reactions to proceed well. Solvents useful for the methods described herein may be resistant to heat degradation. Such resistance is preferably determined by a stability study of solvents at a certain temperature with a measuring instrument (for example, GC, LC or NMR, preferably GC). Solvents of particular use may have resistances at high temperature (for example, stable at boiling point for 48 hours, or stable around room temperature for 2 months, preferably stable at boiling point for 48 hours), and may keep their purity more than 99%, preferably more than 99.9%, during a certain condition described above. The solvents of the invention may show good separation from aqueous phases in liquid separation operations. Such separation may be preferably determined by mixing equal amounts of a solvent and water in a separatory funnel, a reaction vessel, or a reactor at around room temperature (for example, 15° C. to 40° C., preferably 20° C. to 30° C.) within 30 minutes, preferably 15 minutes. The solvents of the invention may allow peptide chain elongation and cyclization reactions to proceed well. Such proceeding may be preferably determined by a chemical yield of a product of interest or a chemical conversion of a starting material to a product of interest with a measuring instrument (for example, GC, LC or NMR, preferably GC). Solvents of particular use may give 70% to 100% chemical yield or more than 70% to 100% chemical conversion, preferably 80% to 100% both chemical yield and chemical conversion. More preferably, the solvents of the invention may be stable at boiling point for 48 hours, show good separation at 20° C. to 30° C. within 15 minutes, and give both chemical yield and chemical conversion of a starting material more than 80% to 100%. When one or more solvents that satisfy these requirements are used in combination as appropriate in performing each reaction or aftertreatment of the reaction, it is possible to consecutively elongate peptide chains, cyclize peptide compounds, and remove stabilizing agents contained in the solvents only by simple operations such as separation and filtration without isolating intermediates. That is, for the subsequent reaction, the intermediate(s) need not be isolated as understood in the art, e.g. a sole product. Rather, pursuant to the invention, the solution used in a subsequent reaction comprises the intermediates (product of the previous reaction) and may further comprise one or more reactants or agents of the previous reaction, which one or more reactants or agents may be solubilized prior to the subsequent reaction. The present inventors have also discovered that in liquid separation operations, organic or aqueous phases can be efficiently washed by using particular aqueous solutions or organic solvents. The present inventors have further discovered that a cyclic peptide compound produced by the method of the present invention without isolating or purifying intermediates can be isolated and purified by crystallization rather than by column chromatography to obtain a crystal of the cyclic peptide compound or a salt thereof, or a solvate thereof. Furthermore, the present inventors have discovered reaction conditions that can prevent or reduce generation of byproducts in each of condensation and deprotection reactions.

In one non-limiting embodiment, the present invention encompasses the following:

[1] A method for producing a cyclic peptide compound or a salt thereof, or a solvate thereof, by a liquid phase method, comprising linking the N-terminal amino acid residue and the C-terminal amino acid residue of a peptide compound in a solvent (Solvent A), which comprises one or more solvents selected from the group consisting of one or more water-immiscible solvents, one or more water-soluble alkyl nitriles, and one or more water-soluble ethers.

[2] The method of [1], wherein Solvent A comprises one or more solvents selected from the group consisting of 2-MeTHF, THF, 4-methyltetrahydropyran, MTBE, CPME, dimethyl carbonate, ethyl acetate, isopropyl acetate, anisole, MeCN, heptane, and toluene.

[3] The method of [1] or [2], wherein the N-terminal amino acid residue and the C-terminal amino acid residue are linked by an amide bond, or a bond selected from —(CH$_2$)$_n$S(CH$_2$)$_m$—, —(CH$_2$)$_n$S(O)(CH$_2$)$_m$—, or —(CH$_2$)$_n$S(O)$_2$(CH$_2$)$_m$—, wherein n and m are each independently 1 or 2.

[4] The method of any one of [1] to [3], wherein the cyclic peptide compound comprises 8 to 20 amino acid residues, and wherein at least one of the amino acid residues is an unnatural amino acid residue.

[5] The method of any one of [1] to [4], wherein the cyclic peptide compound comprises 9 to 15 amino acid residues, and wherein at least one of the amino acid residues is an unnatural amino acid residue.

[6] The method of any one of [1] to [5], wherein the cyclic peptide compound comprises at least one N-substituted unnatural amino acid residue.

[7] The method of any one of [1] to [6], wherein the cyclic peptide compound comprises at least one N-unsubstituted unnatural amino acid residue.

[8] The method of any one of [1] to [7], wherein the cyclic peptide compound comprises at least one α,α di-substituted amino acid residue.

[9] The method of any one of [1] to [8], wherein either or both of the C-terminal amino acid residue and the N-terminal amino acid residue are amino acid residues that do not have an asymmetric carbon at the α-carbon of the carboxyl group.

[10] The method of any one of [1] to [9], wherein the C-terminal amino acid residue is an amino acid residue that does not have an asymmetric carbon at the α-carbon of the carboxyl group.

[11] The method of any one of [1] to [9], wherein the N-terminal amino acid residue is an N-unsubstituted amino acid residue.

[12] The method of any one of [1] to [11], wherein the cyclic peptide compound or salt thereof, or solvate thereof, is a solvate of the cyclic peptide compound.

[13] The method of any one of [1] to [12], wherein the solvate of the cyclic peptide compound is a hydrate of the cyclic peptide compound.

[14] The method of any one of [1] to [13], wherein the cyclic peptide compound is represented by the following formula:

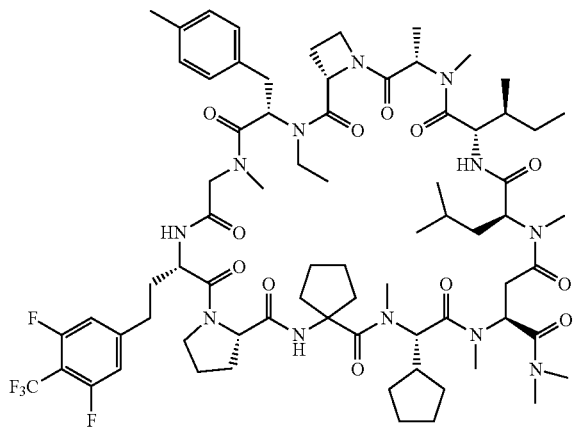 [SMILES: CC[C@H](C)[C@@H]1NC(=O)[C@H](CC(C)C)N(C)C(=O)C[C@@H](C(=O)N(C)C)N(C)C(=O)[C@H](C2CCCC2)N(C)C(=O)C2(CCCC2)NC(=O)[C@@H]2CCCN2C(=O)[C@H](CCc2cc(F)c(C(F)(F)F)c(F)c2)NC(=O)CN(C)C(=O)[C@H](Cc2ccc(C)cc2)N(CC)C(=O)[C@@H]2CCN2C(=O)[C@H](C)N(C)C1=O]

[15] The method of any one of [1] to [14], wherein no column chromatography is used for isolation and/or purification of the cyclic peptide compound.

[16] The method of any one of [1] to [15], further comprising isolating and/or purifying the cyclic peptide compound by crystallization to obtain a crystal of the cyclic peptide compound.

[17] The method of [16], wherein the crystal of the cyclic peptide compound is an unsolvate crystal or solvate crystal of the cyclic peptide compound represented by the following formula:

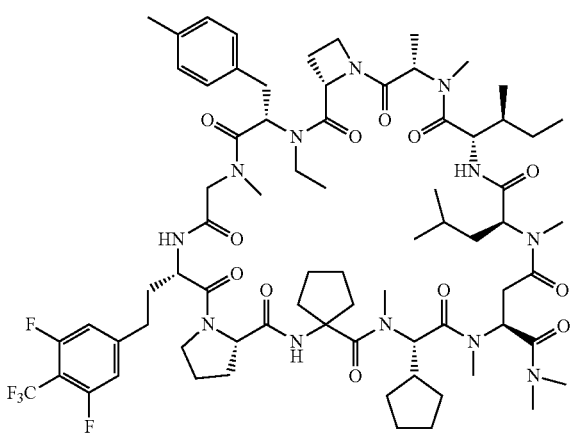 [SMILES: CC[C@H](C)[C@@H]1NC(=O)[C@H](CC(C)C)N(C)C(=O)C[C@@H](C(=O)N(C)C)N(C)C(=O)[C@H](C2CCCC2)N(C)C(=O)C2(CCCC2)NC(=O)[C@@H]2CCCN2C(=O)[C@H](CCc2cc(F)c(C(F)(F)F)c(F)c2)NC(=O)CN(C)C(=O)[C@H](Cc2ccc(C)cc2)N(CC)C(=O)[C@@H]2CCN2C(=O)[C@H](C)N(C)C1=O]

[18] The method of [17], wherein the solvate crystal of the cyclic peptide compound is a hydrate crystal.

[19] The method of [18], wherein the hydrate crystal is a Form C crystal characterized by powder X-ray diffraction peaks at diffraction angles (2θ values) comprising 7 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-1] The method of [18], wherein the hydrate crystal is a Form C crystal characterized by powder X-ray diffraction peaks at diffraction angles (2θ values) comprising 8 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-2] The method of [18], wherein the hydrate crystal is a Form C crystal characterized by powder X-ray diffraction peaks at diffraction angles (2θ values) comprising 9 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-3] The method of [18], wherein the hydrate crystal is a Form C crystal characterized by powder X-ray diffraction peaks at diffraction angles (2θ values) comprising 10 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-4] The method of [18], wherein the hydrate crystal is a Form C crystal characterized by powder X-ray diffraction peaks at diffraction angles (2θ values) comprising 11 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-5] The method of [18], wherein the hydrate crystal is a Form C crystal characterized by powder X-ray diffraction peaks at diffraction angles (2θ values) comprising 12 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[19-6] The method of [18], wherein the hydrate crystal is a Form C crystal characterized by powder X-ray diffraction peaks at diffraction angles (2θ values) of 4.964°, 7.921°, 8.296°, 8.855°, 9.956°, 10.435°, 11.729°, 12.704°, 13.552°, 13.901°, 15.895°, 16.643°, and 17.8130 (±0.2°).

[20] The method of [17], wherein the unsolvate crystal is a Form F crystal characterized by powder X-ray diffraction peaks at diffraction angles (2θ values) of 5.370°, 6.934°, 8.940°, 9.838°, 10.771°, 12.181°, 13.525°, 15.179°, 16.202°, and 17.5540 (±0.20).

[21] The method of [17], wherein the solvate crystal is a Form A DMSO-hydrate crystal characterized by powder X-ray diffraction peaks at diffraction angles (2θ values) of 8.006°, 9.002°, 9.943°, 11.501°, 13.067°, 14.854°, 16.320°, 17.275°, 19.261°, and 20.324° (±0.2°).

[22] The method of [17], wherein the solvate crystal is a Form B DMSO-hydrate crystal characterized by powder X-ray diffraction peaks at diffraction angles (2θ values) of 8.223°, 9.594°, 9.976°, 11.879°, 13.841°, 14.572°, 15.934°, 16.350°, 19.805°, and 20.480° (±0.2°).

[23] The method of [17], wherein the solvate crystal is a Form H acetone-hydrate crystal characterized by powder X-ray diffraction peaks at diffraction angles (2θ values) of 7.942°, 8.283°, 8.861°, 10.097°, 10.491°, 11.805°, 12.673°, 12.830°, 13.514°, 13.855°, 16.405°, 16.642°, and 17.7720 (±0.2°).

[24] The method of any one of [1] to [23], wherein Solvent A comprises or consist of 2-MeTHF.

[25] The method of any one of [1] to [23], wherein Solvent A comprises one or more water-immiscible solvents selected from the group consisting of 2-MeTHF, 4-methyltetrahydropyran, MTBE, CPME, dimethyl carbonate, ethyl acetate, isopropyl acetate, anisole, heptane, and toluene.

[26] The method of any one of [1] to [23], wherein Solvent A comprises one or more water-soluble alkyl nitriles selected from the group consisting of acetonitrile and propionitrile.

[27] The method of any one of [1] to [23], wherein Solvent A comprises one or more water-soluble ethers selected from the group consisting of THF; 1,4-dioxane; and dimethoxyethane.

[28] The method of any one of [1] to [27], wherein the peptide compound is a linear peptide compound.

[29] A method for producing a peptide compound by a liquid phase method, comprising:
  step 1: linking an N-protected amino acid or N-protected peptide to a C-protected amino acid or C-protected peptide;
  step 2: removing the N-protecting group after step 1; and optionally repeating steps 1 and 2 a plurality of times to produce the peptide compound;
  wherein the method does not comprise isolating the product of each of steps 1 and 2.

[30] The method of [29], wherein the peptide compound is a linear peptide compound.

[31] The method of [29] or [30], wherein the peptide compound comprises a cyclic structure as a partial structure.

[32] The method of any one of [29] to [31], wherein steps 1 and 2 are each performed once, or steps 1 and 2 are repeated 2 to 20 times.

[33] The method of any one of [29] to [32], wherein the method for producing a peptide compound further comprises step 3 of removing the C-protecting group.

[34] The method of any one of [29] to [33], wherein the final round of the repetition does not comprise step 2.

[35] The method of [33] or [34], wherein step 3 is carried out after step 1 in the final round of the repetition.

[36] The method of any one of [29] to [35], wherein each of the steps comprised in the method for producing a peptide compound is carried out in one or more solvents (Solvent B) selected independently from the group consisting of toluene, acetone, DMF, acetonitrile, THF, 2-MeTHF, dimethyl carbonate, anisole, isopropyl acetate, heptane, ethyl acetate, and 4-methyltetrahydropyran.

[37] The method of [36], wherein Solvent B comprises one or more solvents selected from the group consisting of 2-MeTHF, MTBE, isopropyl acetate, and ethyl acetate.

[38] The method of [36], wherein Solvent B is 2-MeTHF.

[39] The method of any one of [29] to [38], wherein workup in each of the steps comprised in the method for producing a peptide compound comprises one or more operations selected from the group consisting of a liquid separation operation, a filtration operation, and a concentration operation.

[40] The method of [39], wherein a water-immiscible solvent (Solvent C), a water-soluble alkyl nitrile, and/or a water-soluble ether is added prior to the liquid separation operation.

[41] The method of [40], wherein Solvent C comprises one or more solvents selected from the group consisting of 2-MeTHF, dimethyl carbonate, anisole, isopropyl acetate, ethyl acetate, MTBE, CPME, 4-methyltetrahydropyran, and heptane.

[42] The method of [40] or [41], wherein Solvent C is 2-MeTHF.

[43] The method of any one of [40] to [42], wherein Solvent C is added in an amount that allows separation of aqueous and organic phases.

[44] The method of [43], wherein the amount that allows separation is about 50% by weight to 100% by weight of the total organic phase.

[45] The method of any one of [43] to [44], wherein the organic phase comprises 2-MeTHF.

[46] The method of any one of [39] to [45], wherein the liquid separation operation comprises a washing operation of the organic phase.

[47] The method of [46], wherein the washing operation is performed using an aqueous solution comprising citrate and dipotassium hydrogenphosphate, or comprising acetonitrile and an aqueous potassium carbonate solution.

[48] The method of [46], wherein the washing operation is performed using an aqueous sodium carbonate solution, an aqueous sodium hydrogensulfate solution, and/or an aqueous sodium carbonate solution.

[48-1] The method of [46], wherein the washing operation is performed using an aqueous sodium carbonate solution, an aqueous sodium hydrogensulfate solution, and an aqueous sodium carbonate solution.

[49] The method of any one or [39] to [45], wherein the liquid separation operation comprises a washing operation of the aqueous phase performed using 2-MeTHF, heptane, MTBE, or isopropyl acetate.

[50] The method of any one of [39] to [49], wherein after the liquid separation operation the organic phase comprises 2% or less BHT relative to the product of interest, as determined by UV area % value relative to the product of interest in an HPLC analysis at 210 nm.

[51] The method of any one of claims [1] to [25],
(i) wherein said peptide compound is produced by the method of any one of [29] to [50]; and
(ii) wherein said Solvent A further comprises a solvent used in the method of any one of [39] to [50].

[52] The method of any one of [29] to [50], wherein step 1 comprises condensing the N-terminal amino group of a C-protected amino acid or C-protected peptide with the C-terminal carboxyl group of an N-protected amino acid or N-protected peptide.

[53] The method of [52], wherein the carboxyl group is activated.

[54] The method of [52], wherein step 1 is carried out in the presence of a condensing reagent.

[55] The method of [54], wherein the condensing reagent comprises a condensing agent selected from the group consisting of T3P, EDCI, HATU, COMU, BEP, PyBOP, DMT-MM, and PyOxim.

[56] The method of any one of [29] to [55], wherein step 2 is carried out by catalytic hydrogenation in the presence of a catalyst.

[57] The method of [56], wherein the catalyst is selected from Pd/C, Pd(OH)$_2$/C, or PtO$_2$.

[58] The method of any one of [29] to [55], wherein step 2 is carried out in the presence of a deprotecting reagent.

[59] The method of [58], wherein the deprotecting reagent is selected from TBAF, LiBH$_4$, piperidine, trifluoroacetic acid, or methanesulfonic acid.

[60] The method of any one of [29] to [59], wherein the N-protecting group is selected from Cbz, p-nitrobenzyloxycarbonyl, 2-naphthylmethyloxycarbonyl, diphenylmethyloxycarbonyl, 9-anthrylmethyloxycarbonyl, Teoc, Boc, trifluoroacetyl, Fmoc, or Alloc.

[61] The method of any one of [29] to [49], wherein step 3 is carried out in the presence of a deprotecting reagent.

[62] The method of [61], wherein the deprotection reaction is carried out under acidic conditions.

[63] The method of [62], wherein the acidic conditions are achieved by combining HMDS with a reagent selected from the group consisting of TMSOTf, TMSI, TMSBr, and TMSCl.

[64] The method of any one of [29] to [63], wherein the C-protecting group is selected from t-Bu, trityl, cumyl, methyl, or ethyl.

[65] The method of any one of [29] to [64], wherein either or both of the C-protected peptide and the N-protected peptide comprise 2 to 20 amino acid residues, and wherein either or both of the C-protected peptide and the N-protected peptide comprise at least one unnatural amino acid residue.

[66] The method of any one of [29] to [65], wherein either or both of the C-protected peptide and the N-protected peptide comprise at least one N-substituted amino acid residue.

[67] The method of any one of [29] to [66], wherein either or both of the C-protected peptide and the N-protected peptide comprise at least one N-unsubstituted unnatural amino acid residue.

[68] The method of any one of [29] to [67], wherein either or both of the C-protected peptide and the N-protected peptide used in step 1 in the final round of the repetition comprise four or more N-substituted amino acid residues, or comprise two or more N-substituted amino acid residues and one or more α,α di-substituted amino acid residues.

[69] The method of any one of [29] to [68], wherein either or both of the C-protected peptide and the N-protected peptide used in step 1 in the final round of the repetition consist of 5 or 6 amino acid residues and comprise 4 or 5 unnatural amino acid residues.

[70] The method of [69], wherein the C-protected peptide used in step 1 in the final round of the repetition is C-protected MeLeu-Ile-MeAla-Aze(2)-EtPhe(4-Me)-MeGly, and the N-protected peptide used in step 1 in the final round of the repetition is N-protected Hph(4-CF3-35F2)-Pro-cLeu-MeGly(cPent)-MeAsp-NMe2.

[71] The method of any one of [29] to [67], wherein the C-protected amino acid or a salt thereof or the C-protected peptide or a salt thereof is:

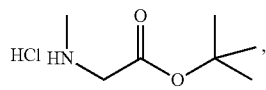

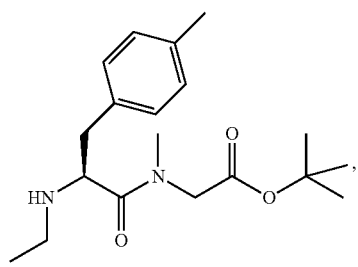

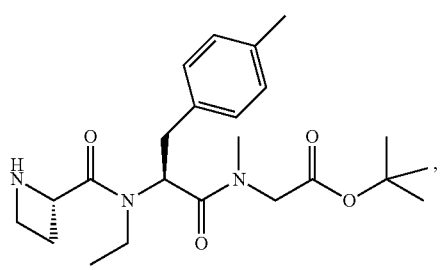

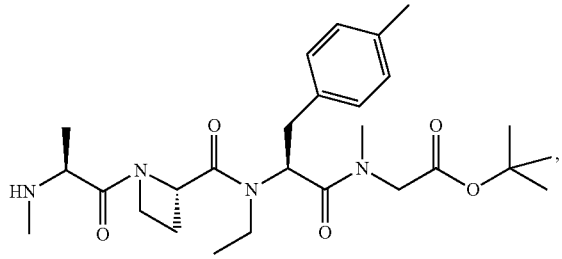

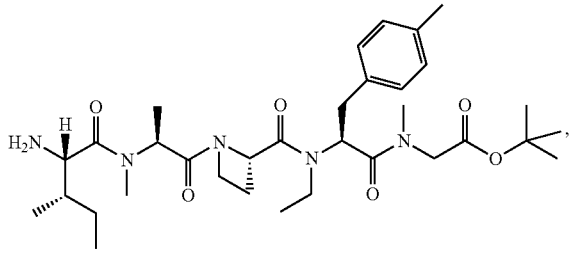

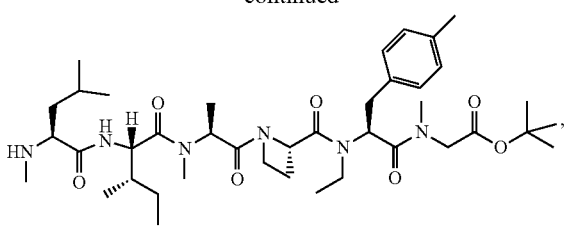

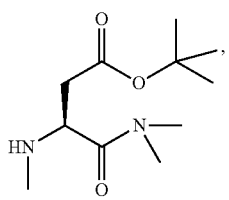

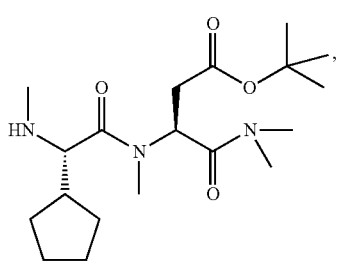

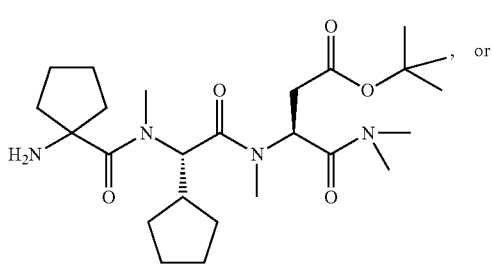

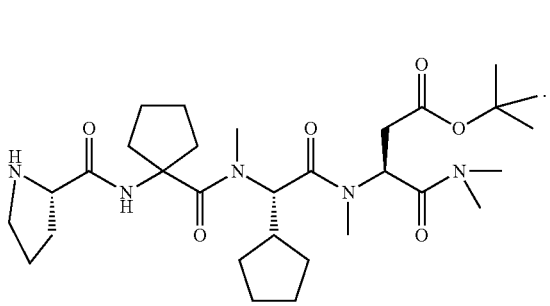

[72] The method of any one of [29] to [67], wherein the N-protected amino acid or a salt thereof or the N-protected peptide or a salt thereof is:

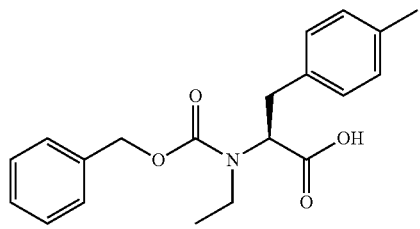
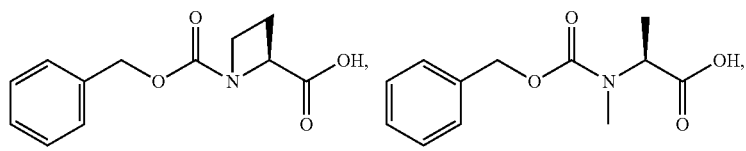
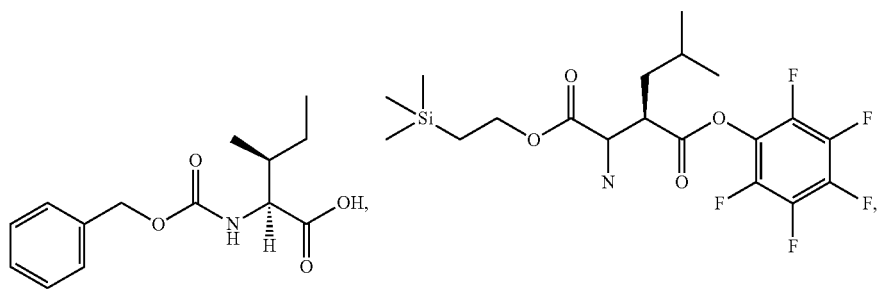
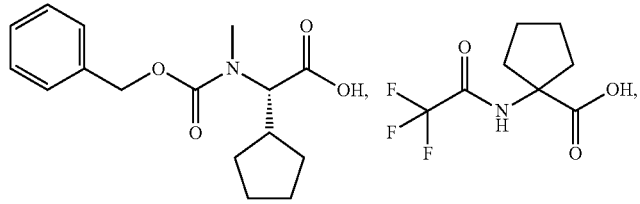
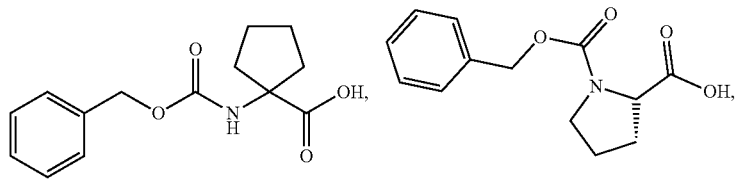
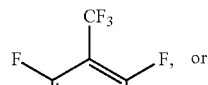
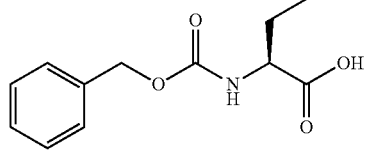
Cy₂NH
Cy₂NH -continued
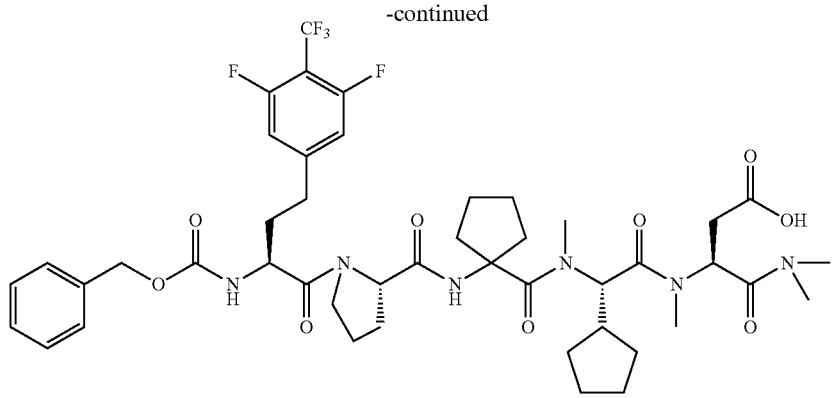
[73] The method of any one of [129] to [67], wherein the peptide compound is:
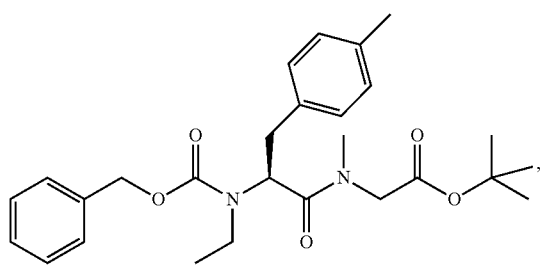
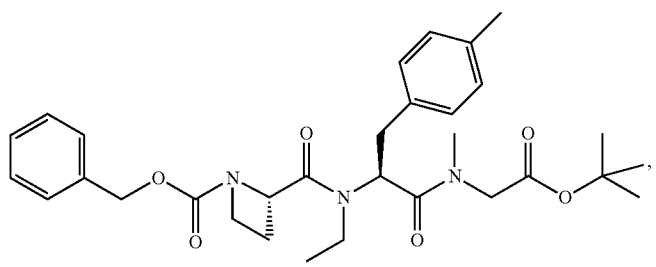
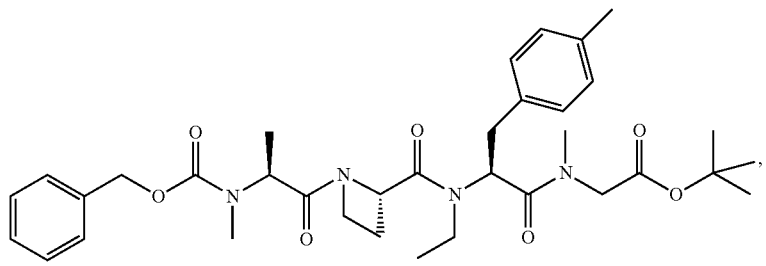
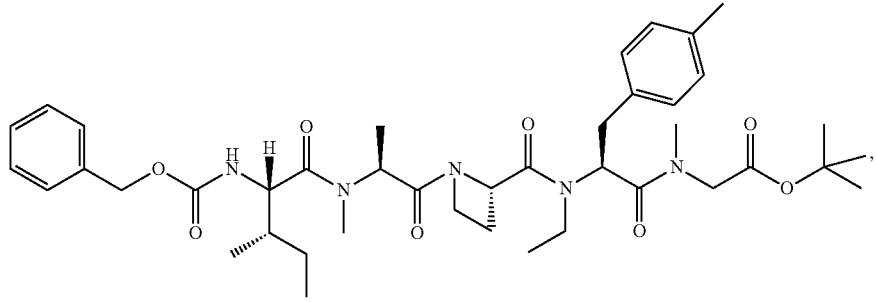

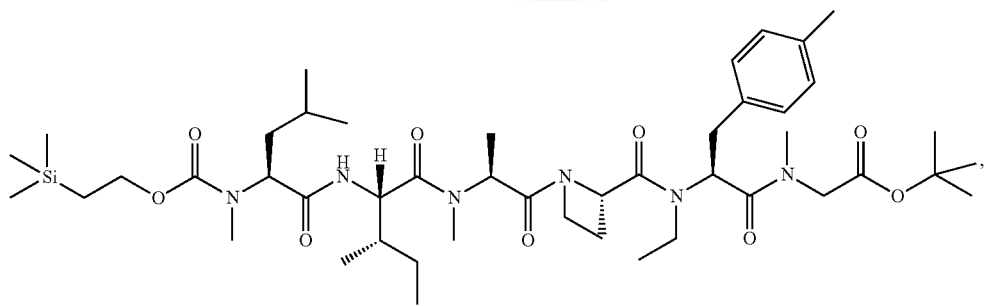
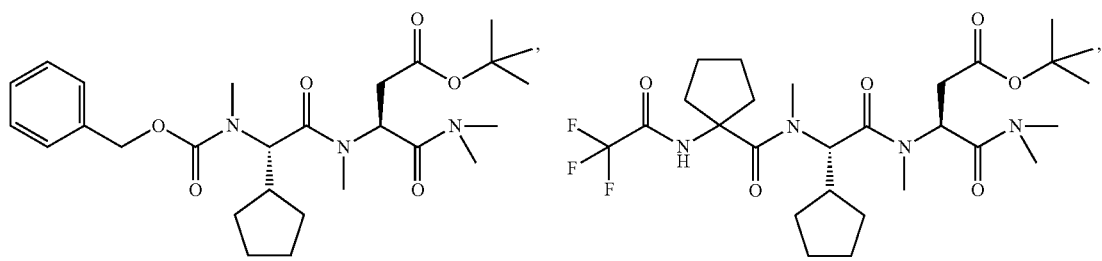
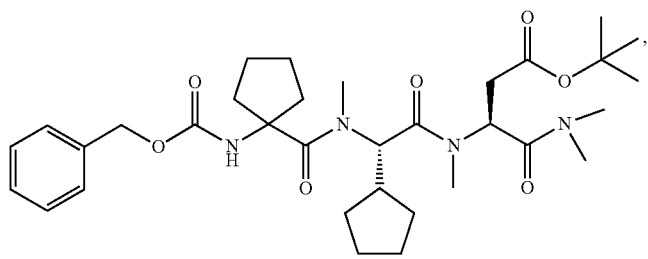
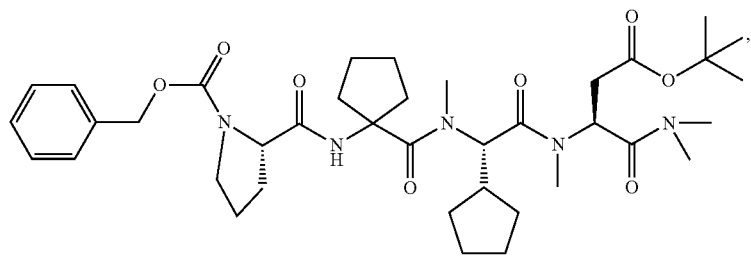
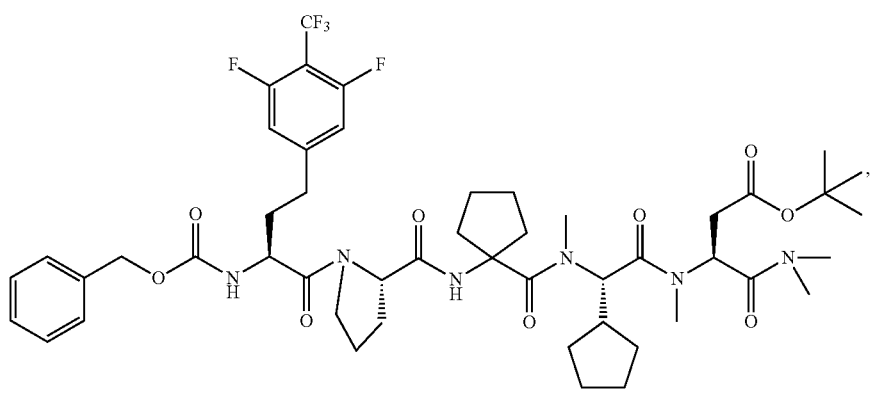

-continued

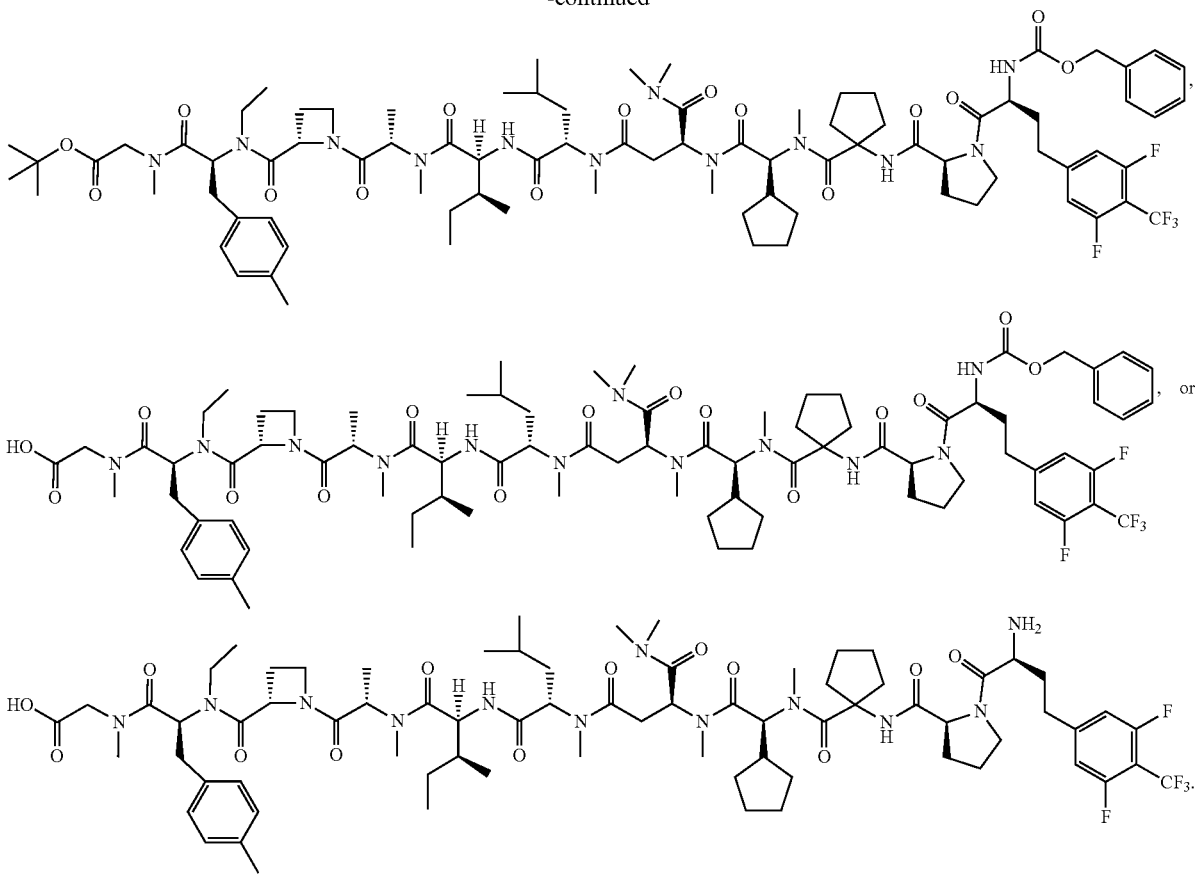

[74] The method of any one of [29] to [73], further comprising linking the N-terminal amino acid residue and the C-terminal amino acid residue of the peptide compound.

[75] A method for producing a cyclic peptide compound represented by the following formula:

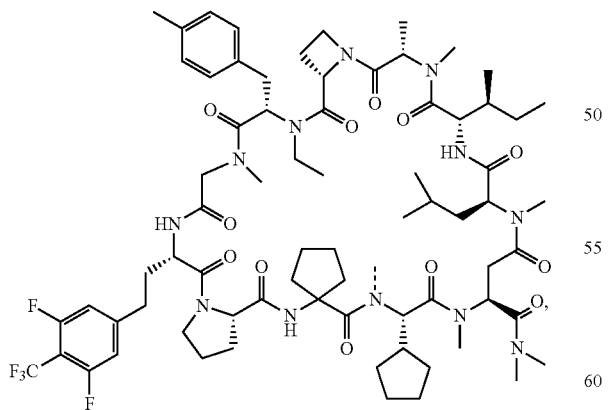

or a salt thereof, or a solvate thereof, wherein the method comprises the steps of:

(1) preparing a linear peptide compound represented by the following formula:

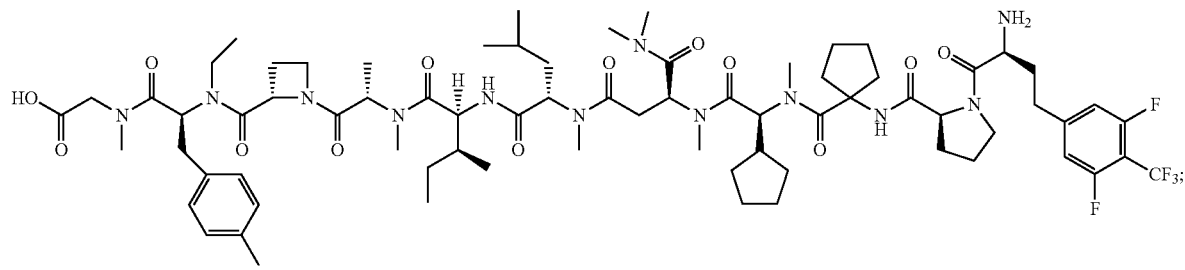 [SMILES: CC[C@H](C)[C@H](NC(=O)[C@H](CC(C)C)N(C)C(=O)C[C@@H](C(=O)N(C)C)N(C)C(=O)[C@H](C1CCCC1)N(C)C(=O)C1(NC(=O)[C@@H]2CCCN2C(=O)[C@@H](N)CCc2cc(F)c(C(F)(F)F)c(F)c2)CCCC1)C(=O)N(C)[C@@H](C)C(=O)N1CC[C@H]1C(=O)N(CC)[C@@H](Cc1ccc(C)cc1)C(=O)N(C)CC(=O)O]

and
(2) linking the N-terminal amino acid residue and the C-terminal amino acid residue.

[76] A salt, solvate, or solvate of the salt of a cyclic compound represented by the following formula:

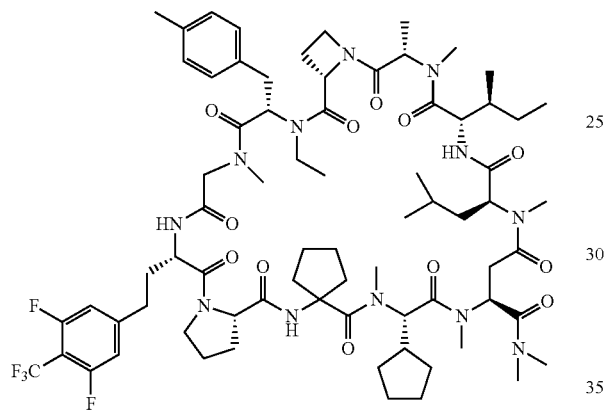

[76-1] A compound represented by formula (1), or a salt thereof, or a solvate thereof, having a purity of 90% or greater, such as 95% or greater, 98% or greater, 99% or greater, as determined by UVArea % value in HPLC analysis at 210 nm.

[76-2] A high purity compound represented by formula (1), or a salt thereof, or a solvate thereof, characterized as having less than 5% of total impurities, such as less than 2%, less than 1%, less than 0.5%, or an undetectable amount, of total impurities, as determined by UVArea % value in HPLC analysis at 210 nm.

[76-3]. The high purity compound of [76-2], characterized as having less than 1%, such as less than 0.5%, less than 0.1%, or an undetectable amount, of any single impurity, as determined by UVArea % value in HPLC analysis at 210 nm.

[76-4]. The high purity compound of [76-2] or [76-3], characterized as having less than 1%, such as less than 0.5%, or less than 0.1%, or an undetectable amount, of an impurity selected from epimers, elongated products, defective products, dimers and trimers, as determined by UVArea % value in HPLC analysis at 210 nm.

[76-5] The high purity compound of [76-2] or [76-3], characterized as having less than 1%, such as less than 0.5%, or less than 0.1%, or an undetectable amount, of an impurity selected from cyclic dimer represented by following formula and cyclic trimer represented by following formula, as determined by UVArea % value in HPLC analysis at 210 nm:

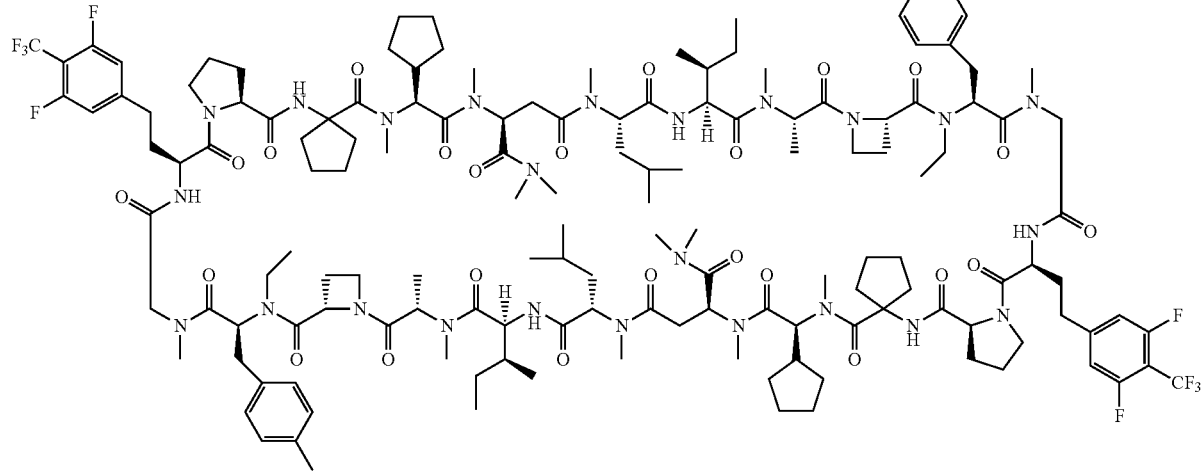

Cyclic dimer

-continued

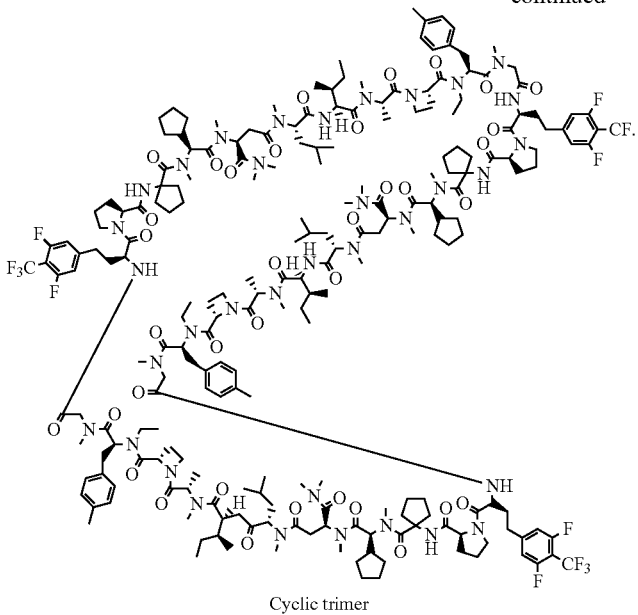

Cyclic trimer

[77] The solvate of the cyclic peptide compound of [76], which is a hydrate, DMSO-hydrate, acetone-hydrate, or DMSO solvate.

[78] A crystal of a cyclic peptide compound represented by the following formula:

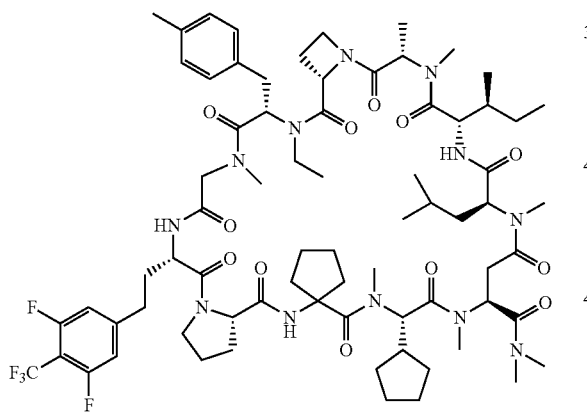

or a salt thereof, or a solvate thereof.

[79] The crystal of [78], wherein the crystal is selected from the group consisting of an unsolvate crystal, a solvate crystal, a crystal of a salt, and a solvate crystal of a salt.

[80] The crystal of [79], wherein the crystal is a solvate crystal.

[81] The crystal of [78], wherein the solvate crystal is a hydrate crystal.

[82] The crystal of [81], wherein the hydrate crystal is a Form C crystal characterized by powder X-ray diffraction peaks at diffraction angles (2θ values) comprising 7 peaks selected from the group consisting of 4.964°, 7.921°, 8.296°, 8.855°, 9.956°, 10.435°, 11.729°, 12.704°, 13.552°, 13.901°, 15.895°, 16.643°, and 17.813° (±0.2°).

[82-1] The crystal of [81], wherein the hydrate crystal is a Form C crystal characterized by powder X-ray diffraction peaks at diffraction angles (2θ values) comprising 8 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[82-2] The crystal of [81], wherein the hydrate crystal is a Form C crystal characterized by powder X-ray diffraction peaks at diffraction angles (2θ values) comprising 9 peaks selected from the group consisting of 4.964°, 7.921°, 8.296°, 8.855°, 9.956°, 10.435°, 11.729°, 12.704°, 13.552°, 13.901°, 15.895°, 16.643°, and 17.8130 (±0.2°).

[82-3] The crystal of [81], wherein the hydrate crystal is a Form C crystal characterized by powder X-ray diffraction peaks at diffraction angles (2θ values) comprising 10 peaks selected from the group consisting of 4.964°, 7.921°, 8.296°, 8.855°, 9.956°, 10.435°, 11.729°, 12.704°, 13.552°, 13.901°, 15.895°, 16.643°, and 17.813° (±0.2°).

[82-4] The crystal of [81], wherein the hydrate crystal is a Form C crystal characterized by powder X-ray diffraction peaks at diffraction angles (2θ values) comprising 11 peaks selected from the group consisting of 4.964°, 7.921°, 8.296°, 8.855°, 9.956°, 10.435°, 11.729°, 12.704°, 13.552°, 13.901°, 15.895°, 16.643°, and 17.813° (±0.2°).

[82-5] The crystal of [81], wherein the hydrate crystal is a Form C crystal characterized by powder X-ray diffraction peaks at diffraction angles (2θ values) comprising 12 peaks selected from the group consisting of 4.964°, 7.921°, 8.296°, 8.855°, 9.956°, 10.435°, 11.729°, 12.704°, 13.552°, 13.901°, 15.895°, 16.643°, and 17.813° (±0.2°).

[82-6] The crystal of [81], wherein the hydrate crystal is a Form C crystal characterized by powder X-ray diffraction peaks at diffraction angles (2θ values) of 4.964°, 7.921°, 8.296°, 8.855°, 9.956°, 10.435°, 11.729°, 12.704°, 13.552°, 13.901°, 15.895°, 16.643°, and 17.813° (±0.2°).

[83] The crystal of [79], wherein the unsolvate crystal is a Form F crystal characterized by powder X-ray diffraction peaks at diffraction angles (2θ values) of 5.370°, 6.934°, 8.940°, 9.838°, 10.771°, 12.181°, 13.525°, 15.179°, 16.202°, and 17.554° (±0.2°).

[84] The crystal of [79], wherein the solvate crystal is a Form A DMSO-hydrate crystal characterized by powder X-ray diffraction peaks at diffraction angles (2θ values) of 8.006°, 9.002°, 9.943°, 11.501°, 13.067°, 14.854°, 16.320°, 17.275°, 19.261°, and 20.324° (±0.2°).

[85] The crystal of [79], wherein the solvate crystal is a Form B DMSO-hydrate crystal characterized by powder X-ray diffraction peaks at diffraction angles (2θ values) of 8.223°, 9.594°, 9.976°, 11.879°, 13.841°, 14.572°, 15.934°, 16.350°, 19.805°, and 20.480° (±0.2°).

[86] The crystal of [79], wherein the solvate crystal is a Form H acetone-hydrate crystal characterized by powder X-ray diffraction peaks at diffraction angles (2θ values) of 7.942°, 8.283°, 8.861°, 10.097°, 10.491°, 11.805°, 12.673°, 12.830°, 13.514°, 13.855°, 15.853°, 16.405°, 16.642°, and 17.772° (±0.2°).

[87] A method for producing a hydrate crystal of a cyclic peptide compound represented by the following formula:

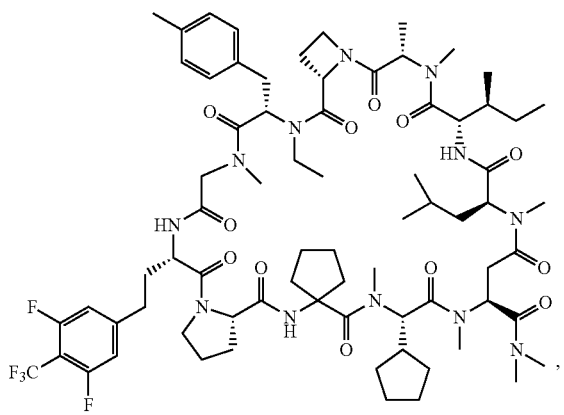 [SMILES: CC[C@H](C)[C@@H]1NC(=O)[C@H](CC(C)C)N(C)C(=O)C[C@@H](C(=O)N(C)C)N(C)C(=O)[C@H](C2CCCC2)N(C)C(=O)C2(CCCC2)NC(=O)[C@@H]2CCCN2C(=O)[C@H](CCc2cc(F)c(C(F)(F)F)c(F)c2)NC(=O)CN(C)C(=O)[C@H](Cc2ccc(C)cc2)N(CC)C(=O)[C@@H]2CCN2C(=O)[C@H](C)N(C)C1=O]

wherein the method comprises the steps of:
dissolving the cyclic peptide compound in a first polar organic solvent to obtain a solution, wherein the first polar organic solvent is provided in an amount sufficient for the cyclic peptide compound to be dissolved;
concentrating the solution to obtain a residue of the cyclic peptide compound; and adding a mixture of water and a second polar organic solvent to the residue to obtain a hydrate crystal of the cyclic peptide compound.

[88] A method for producing a hydrate crystal of a cyclic peptide compound represented by the following formula:

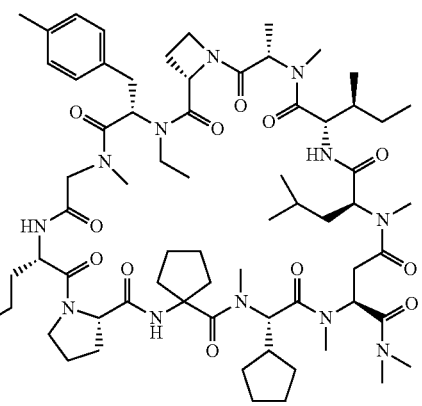

wherein the method comprises the steps of:
dissolving the cyclic peptide compound in an amorphous state in DMSO to obtain a solution;
lyophilizing the solution to obtain a lyophilisate of the cyclic peptide compound; and
adding a mixture of water and acetonitrile to the lyophilisate to obtain a hydrate crystal of the cyclic peptide compound.

Effects of the Invention

The present invention allows efficient production of a cyclic peptide compound or a salt thereof, or a solvate thereof by preventing racemization and intermolecular reaction of amino acid residues even if the peptide compound has a complex amino acid sequence containing a plurality of unnatural amino acid residues. In addition, the present invention allows efficient production of a peptide compound of interest because it enables consecutive elongation and subsequent cyclization of a peptide chain with simple workup such as liquid separation, filtration, and concentration, without isolation and purification of intermediates. Since the production method of the present invention can reduce the cost of peptide compound production and also alleviate environmental burdens, it is particularly useful for large-scale peptide synthesis.

BRIEF DESCRIPTION OF DRAWINGS

In FIG. 10, "Cycle 1 Sorp" (solid diamond) denotes the sorption in cycle 1; "Cycle 1 Desorp" (solid square) denotes the desorption in cycle 1; "Cycle 2 Sorp" (solid triangle) denotes the sorption in cycle 2; and "Cycle 2 Desorp" (solid square) denotes the desorption in cycle 2.

DESCRIPTION OF EMBODIMENTS

Figure 1:
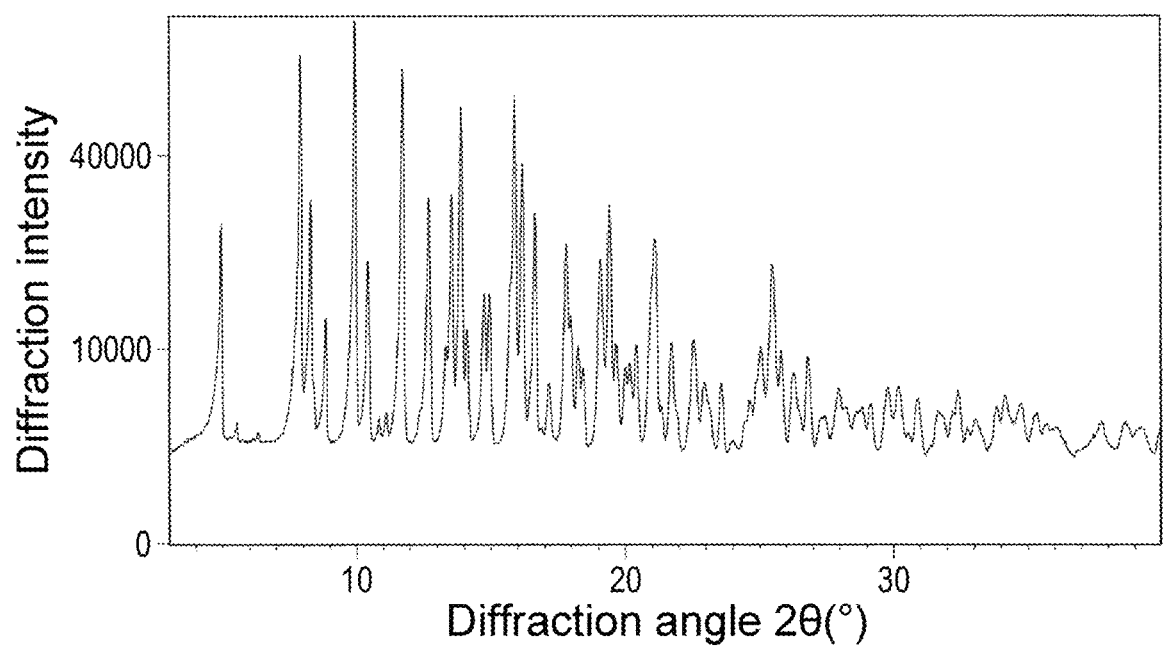
FIG. 1 shows the results of the powder X-ray diffraction measurement of the hydrate crystal (Form C) of Compound 1 obtained in Example 25. The vertical axis indicates the diffraction intensity, and the horizontal axis indicates the diffraction angle 2θ (°).

The following abbreviations are used herein:
2-MeTHF: 2-methyltetrahydrofuran
AcOEt: ethyl acetate
Alloc: allyloxycarbonyl
BEP: 2-bromo-1-ethylpyridinium tetrafluoroborate
BHT: 2,6-di-tert-butyl-4-methylphenol
Boc: t-butoxycarbonyl
Cbz: benzyloxycarbonyl
COMU: (1-cyano-2-ethoxy-2-oxoethylidenaminooxy)dimethylamino-morpholino-carbenium hexafluorophosphate
CPME: cyclopentyl methyl ether
CSA: 10-camphorsulfonic acid
DIPEA: N,N-diisopropylethylamine
DMA: N,N-dimethylacetamide
DMAP: 4-dimethylaminopyridine
DMF: N,N-dimethylformamide
DMT-MM: 4-(4,6-dimethoxy-1,3,5-triazin-2-yl)-4-methylmorpholinium chloride
EDCI: 1-ethyl-3-(3-dimethylaminopropyl)carbodiimide
HATU: O-(7-azabenzotriazol-1-yl)-N,N,N',N'-tetramethyluronium hexafluorophosphate
HMDS: 1,1,1,3,3,3-hexamethyldisilazane
HOAt: 1-hydroxy-7-azabenzotriazole
HOBt: 1-hydroxybenzotriazole
IPAc: isopropyl acetate
MeCN: acetonitrile
MTBE: methyl tert-butyl ether
MTHP: 4-methyltetrahydropyran
NMP: N-methylpyrrolidone
PyBOP: 1H-benzotriazol-1-yloxytripyrrolidinophosphonium hexafluorophosphate
PyOxim: (ethylcyano(hydroxyimino)acetato-O2)-tri-(1-pyrrolidinyl)-phosphonium hexafluorophosphate
T3P: propylphosphonic acid anhydride
TBAF: tetrabutylammonium fluoride
Teoc: 2-(trimethylsilyl)ethoxycarbonyl
THF: tetrahydrofuran
TMSOTf: trimethylsilyl trifluoromethanesulfonate Definitions of functional groups and the like (All terms and phrases herein are used in as commonly understood in the art. Non-limiting exemplary definitions are provided below.)

Examples of "halogen atoms" herein include F, Cl, Br, and I.

"Alkyl" herein means a monovalent group derived by removing any one hydrogen atom from an aliphatic hydrocarbon, and has a subset of hydrocarbyl or hydrocarbon group structures not containing either a heteroatom (which refers to an atom other than carbon and hydrogen atoms) or an unsaturated carbon-carbon bond but containing hydrogen and carbon atoms in its backbone. The alkyl includes linear and branched alkyls. Specifically, the alkyl has 1 to 20 carbon atoms ($C_1$-$C_{20}$, hereinafter "$C_p$-$C_q$" means that the number of carbon atoms is p to q), and is preferably $C_1$-$C_{10}$ alkyl, and more preferably $C_1$-$C_6$ alkyl. Specific examples of alkyl include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

"Alkenyl" herein means a monovalent group having at least one double bond (two adjacent $SP^2$ carbon atoms). Depending on the configuration of a double bond and a substituent (if present), the geometrical form of the double bond can be entgegen (E) or zusammen (Z) as well as cis or trans configuration. The alkenyl includes linear and branched alkenyls. The alkenyl is preferably $C_2$-$C_{10}$ alkenyl, and more preferably $C_2$-$C_6$ alkenyl, and specific examples include vinyl, allyl, 1-propenyl, 2-propenyl, 1-butenyl, 2-butenyl (including cis and trans forms), 3-butenyl, pentenyl, 3-methyl-2-butenyl, and hexenyl.

"Alkynyl" herein means a monovalent group having at least one triple bond (two adjacent SP carbon atoms). The alkynyl includes linear and branched alkynyls. The alkynyl is preferably $C_2$-$C_{10}$ alkynyl, and more preferably $C_2$-$C_6$ alkynyl, and specific examples include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

"Cycloalkyl" herein means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl, and specific examples include cyclopropyl, cyclobutyl, cyclopentyl, cyclohexyl, cycloheptyl, cyclooctyl, bicyclo[2.2.1]heptyl, and spiro[3.3]heptyl.

"Aryl" herein means a monovalent aromatic hydrocarbon ring, and is preferably $C_6$-$C_{10}$ aryl. Specific examples of the aryl include phenyl and naphthyl (e.g., 1-naphthyl and 2-naphthyl).

"Heterocyclyl" herein means a non-aromatic cyclic monovalent group containing 1 to 5 hetero atoms in addition to carbon atoms. The heterocyclyl may have a double and/or triple bond within the ring, a carbon atom within the ring may be oxidized to form carbonyl, and heterocyclyl may be a monocyclic ring or a condensed ring. The number of atoms constituting the ring is preferably 4 to 10 (4- to 10-membered heterocyclyl), and more preferably 4 to 7 (4- to 7-membered heterocyclyl). Specific examples of the heterocyclyl include azetidinyl, oxiranyl, oxetanyl, azetidinyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, sultam, and 2-oxaspiro[3.3]heptyl.

"Heteroaryl" herein means an aromatic cyclic monovalent group containing 1 to 5 heteroatoms in addition to carbon atoms. The ring may be a monocyclic ring, may be a condensed ring formed with another ring, or may be partially saturated. The number of atoms constituting the ring is preferably 5 to 10 (5- to 10-membered heteroaryl) and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

"Alkoxy" herein means an oxy group to which the above-defined "alkyl" is bonded, and is preferably $C_1$-$C_6$ alkoxy. Specific examples of the alkoxy include methoxy, ethoxy, 1-propoxy, 2-propoxy, n-butoxy, i-butoxy, s-butoxy, t-butoxy, pentyloxy, and 3-methylbutoxy.

"Alkenyloxy" herein means an oxy group to which the above-defined "alkenyl" is bonded, and is preferably $C_2$-$C_6$ alkenyloxy. Specific examples of the alkenyloxy include vinyloxy, allyloxy, 1-propenyloxy, 2-propenyloxy, 1-butenyloxy, 2-butenyloxy (including cis and trans forms), 3-butenyloxy, pentenyloxy, and hexenyloxy.

"Cycloalkoxy" herein means an oxy group to which the above-defined "cycloalkyl" is bonded, and is preferably $C_3$-$C_8$ cycloalkoxy. Specific examples of the cycloalkoxy include cyclopropoxy, cyclobutoxy, and cyclopentyloxy.

"Aryloxy" herein means an oxy group to which the above-defined "aryl" is bonded, and is preferably $C_6$-$C_{10}$ aryloxy. Specific examples of the aryloxy include phenoxy, 1-naphthyloxy, and 2-naphthyloxy.

"Amino" herein means —$NH_2$ in a narrow sense and —NRR' in a broad sense, wherein R and R' are independently selected from hydrogen, alkyl, alkenyl, alkynyl, cycloalkyl, heterocyclyl, aryl, or heteroaryl, or R and R', together with the nitrogen atom to which they are attached, form a ring. The amino is preferably —$NH_2$, mono-$C_1$-$C_6$ alkylamino, di-$C_1$-$C_6$ alkylamino, 4- to 8-membered cyclic amino, or the like.

"Monoalkylamino" herein means a group corresponding to the above-defined "amino" wherein R is hydrogen and R' is the above-defined "alkyl", and is preferably mono-$C_1$-$C_6$ alkylamino. Specific examples of the monoalkylamino include methylamino, ethylamino, n-propylamino, i-propylamino, n-butylamino, s-butylamino, and t-butylamino.

"Dialkylamino" herein means a group corresponding to the above-defined "amino" wherein R and R' are independently the above-defined "alkyl", and is preferably di-$C_1$-$C_6$ alkylamino. Specific examples of the dialkylamino include dimethylamino and diethylamino.

"Cyclic amino" herein means a group corresponding to the above-defined "amino" wherein R and R', together with the nitrogen atom to which they are attached, form a ring, and is preferably 4- to 8-membered cyclic amino. Specific examples of the cyclic amino include 1-azetidyl, 1-pyrrolidyl, 1-piperidyl, 1-piperazyl, 4-morpholinyl, 3-oxazolidyl, 1,1-dioxidethiomorpholinyl-4-yl, and 3-oxa-8-azabicyclo[3.2.1]octan-8-yl.

"Protected amino" herein means an amino group protected with any protecting group. Specific examples of the protected amino include amino protected with a protecting group such as Boc, Fmoc, Cbz, Troc, Alloc, Teoc, or trifluoroacetyl.

"Aminocarbonyl" herein means a carbonyl group to which the above-defined "amino" is bonded, and is preferably —$CONH_2$, mono-$C_1$-$C_6$ alkylaminocarbonyl, di-$C_1$-$C_6$ alkylaminocarbonyl, and 4- to 8-membered cyclic aminocarbonyl. Specific examples of the aminocarbonyl include —$CONH_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidethiomorpholinyl-4-ylcarbonyl, and 3-oxa-8-azabicyclo[3.2.1]octan-8-ylcarbonyl.

"Alkenyloxycarbonyl" herein means a carbonyl group to which the above-defined "alkenyloxy" is bonded, and is preferably $C_2$-$C_6$ alkenyloxycarbonyl. Specific examples of the alkenyloxycarbonyl include vinyloxycarbonyl, allyloxycarbonyl, 1-propenyloxycarbonyl, 2-propenyloxycarbonyl, 1-butenyloxycarbonyl, 2-butenyloxycarbonyl (including cis and trans forms), 3-butenyloxycarbonyl, pentenyloxycarbonyl, and hexenyloxycarbonyl.

"Alkylsulfonyl" herein means a sulfonyl group to which the above-defined "alkyl" is bonded, and is preferably $C_1$-$C_6$ alkylsulfonyl. Specific examples of the alkylsulfonyl include methylsulfonyl.

"Hydroxyalkyl" herein means a group in which one or more hydrogens of the above-defined "alkyl" are replaced with hydroxyl groups, and is preferably $C_1$-$C_6$ hydroxyalkyl. Specific examples of the hydroxyalkyl include hydroxymethyl, 1-hydroxyethyl, 2-hydroxyethyl, 2-hydroxy-2-methylpropyl, and 5-hydroxypentyl.

"Haloalkyl" herein means a group in which one or more hydrogens of the above-defined "alkyl" are replaced with halogen, and is preferably $C_1$-$C_6$ haloalkyl, and more preferably $C_1$-$C_6$ fluoroalkyl. Specific examples of the haloalkyl include difluoromethyl, trifluoromethyl, 2,2-difluoroethyl, 2,2,2-trifluoroethyl, 3,3-difluoropropyl, 4,4-difluorobutyl, and 5,5-difluoropentyl.

"Cyanoalkyl" herein means a group in which one or more hydrogens of the above-defined "alkyl" are replaced with cyano, and is preferably $C_1$-$C_6$ cyanoalkyl. Specific examples of the cyanoalkyl include cyanomethyl and 2-cyanoethyl.

"Aminoalkyl" herein means a group in which one or more hydrogens of the above-defined "alkyl" are replaced with the above-defined "amino", and is preferably $C_1$-$C_6$ aminoalkyl. Specific examples of the aminoalkyl include 1-pyridylmethyl, 2-(1-piperidyl)ethyl, 3-(1-piperidyl)propyl, and 4-aminobutyl.

"Carboxyalkyl" herein means a group in which one or more hydrogens of the above-defined "alkyl" are replaced with carboxy, and is preferably $C_2$-$C_6$ carboxyalkyl. Specific examples of the carboxyalkyl include carboxymethyl.

"Alkenyloxycarbonylalkyl" herein means a group in which one or more hydrogens of the above-defined "alkyl" are replaced with the above-defined "alkenyloxycarbonyl", and is preferably $C_2$-$C_6$ alkenyloxycarbonyl $C_1$-$C_6$ alkyl, and more preferably $C_2$-$C_6$ alkenyloxycarbonyl $C_1$-$C_2$ alkyl. Specific examples of the alkenyloxycarbonylalkyl include allyloxycarbonylmethyl and 2-(allyloxycarbonyl)ethyl.

"Alkoxyalkyl" herein means a group in which one of more hydrogens of the above-defined "alkyl" are replaced with the above-defined "alkoxy", and is preferably $C_1$-$C_6$ alkoxy $C_1$-$C_6$ alkyl, and more preferably $C_1$-$C_6$ alkoxy $C_1$-$C_2$ alkyl. Specific examples of the alkoxyalkyl include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, and 2-ethoxyethyl.

"Cycloalkylalkyl" herein means a group in which one or more hydrogens of the above-defined "alkyl" are replaced with the above-defined "cycloalkyl", and is preferably $C_3$-$C_8$ cycloalkyl $C_1$-$C_6$ alkyl, and more preferably $C_3$-$C_6$ cycloalkyl $C_1$-$C_2$ alkyl. Specific examples of the cycloalkylalkyl include cyclopropylmethyl, cyclobutylmethyl, cyclopentylmethyl, and cyclohexylmethyl.

"Cycloalkoxylalkyl" herein means a group in which one or more hydrogens of the above-defined "alkyl" are replaced with the above-defined "cycloalkoxy", and is preferably $C_3$-$C_8$ cycloalkoxy $C_1$-$C_6$ alkyl, and more preferably $C_3$-$C_6$ cycloalkoxy $C_1$-$C_2$ alkyl. Specific examples of the cycloalkoxyalkyl include cyclopropoxymethyl and cyclobutoxymethyl.

"Heterocyclylalkyl" herein means a group in which one or more hydrogens of the above-defined "alkyl" are replaced with the above-defined "heterocyclyl", and is preferably 4- to 7-membered heterocyclyl $C_1$-$C_6$ alkyl, and more preferably 4- to 7-membered heterocyclyl $C_1$-$C_2$ alkyl. Specific examples of the heterocyclylalkyl include 2-(tetrahydro-2H-pyran-4-yl)ethyl and 2-(azetidin-3-yl)ethyl.

"Alkylsulfonylalkyl" herein means a group in which one or more hydrogens of the above-defined "alkyl" are replaced with the above-defined "alkylsulfonyl", and is preferably $C_1$-$C_6$ alkylsulfonyl $C_1$-$C_6$ alkyl, and more preferably $C_1$-$C_6$ alkylsulfonyl $C_1$-$C_2$ alkyl. Specific examples of the alkylsulfonylalkyl include methylsulfonylmethyl and 2-(methylsulfonyl)ethyl.

"Aminocarbonylalkyl" herein means a group in which one or more hydrogens of the above-defined "alkyl" are replaced with the above-defined "aminocarbonyl", and is preferably aminocarbonyl $C_1$-$C_6$ alkyl, and more preferably aminocarbonyl $C_1$-$C_4$ alkyl. Specific examples of the aminocarbonylalkyl include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl, 2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl)propyl, and 4-(dimethylaminocarbonyl)butyl.

"Aryloxyalkyl" herein means a group in which one or more hydrogens of the above-defined "alkyl" are replaced with the above-defined "aryloxy", and is preferably $C_6$-$C_{10}$ aryloxy $C_1$-$C_6$ alkyl, and more preferably $C_6$-$C_{10}$ aryloxy $C_1$-$C_2$ alkyl. Specific examples of the aryloxyalkyl include phenoxymethyl and 2-phenoxyethyl.

"Aralkyl (arylalkyl)" herein means a group in which one or more hydrogen atoms of the above-defined "alkyl" are replaced with the above-defined "aryl", and is preferably $C_7$-$C_{14}$ aralkyl, and more preferably $C_7$-$C_{10}$ aralkyl. Specific examples of the aralkyl include benzyl, phenethyl, and 3-phenylpropyl.

"Aralkoxy" herein means an oxy group to which the above-defined "aralkyl" is bonded, and is preferably $C_7$-$C_{14}$ aralkoxy, and more preferably $C_7$-$C_{10}$ aralkoxy. Specific examples of the aralkoxy include benzyloxy, phenethyloxy, and 3-phenylpropoxy.

"Aralkoxyalkyl" herein means a group in which one or more hydrogens of the above-defined "alkyl" are replaced with the above-defined "aralkoxy", and is preferably $C_7$-$C_{14}$ aralkoxy $C_1$-$C_6$ alkyl, and more preferably $C_7$-$C_{14}$ aralkoxy $C_1$-$C_2$ alkyl. Specific examples of the aralkoxyalkyl include benzyloxymethyl and 1-(benzyloxy)ethyl.

"Heteroarylalkyl" herein means a group in which one or more hydrogen atoms of the above-defined "alkyl" are replaced with the above-defined "heteroaryl", and is preferably 5- to 10-membered heteroaryl $C_1$-$C_6$ alkyl, and more preferably 5- to 10-membered heteroaryl $C_1$-$C_2$ alkyl. Specific examples of the heteroarylalkyl include 3-thienylmethyl, 4-thiazolylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

"Heteroarylalkoxy" herein means an oxy group to which the above-defined "heteroarylalkyl" is bonded, and is preferably 5- to 10-membered heteroaryl $C_1$-$C_6$ alkoxy, and more preferably 5- to 10-membered heteroaryl $C_1$-$C_2$ alkoxy. Specific examples of the heteroarylalkoxy include 3-thienylmethoxy and 3-pyridylmethoxy.

"Heteroarylalkoxyalkyl" herein means a group in which one or more hydrogens of the above-defined "alkyl" are replaced with the above-defined "heteroarylalkoxy", and is preferably 5- to 10-membered heteroaryl $C_1$-$C_6$ alkoxy $C_1$-$C_6$ alkyl, and more preferably 5- to 10-membered heteroaryl $C_1$-$C_2$ alkoxy $C_1$-$C_2$ alkyl. Specific examples of the heteroarylalkoxyalkyl include 3-pyridylmethoxymethyl.

"Heterocycloalkylidenealkyl" herein means a group in which one or more hydrogens of the above-defined "alkyl" are replaced with the above-defined "heterocycloalkylidene", and is preferably 4- to 7-membered heterocycloalkylidene $C_1$-$C_6$ alkyl, and more preferably 4- to 7-membered heterocycloalkylidene $C_1$-$C_2$ alkyl. Specific examples of the heteroarylalkoxyalkyl include tetrahydro-4H-pyran-4-ylidenemethyl and azetidin-3-ylidenemethyl.

"Alkoxyalkenyl" herein means a group in which one or more hydrogens of the above-defined "alkenyl" are replaced with the above-defined "alkoxy", and is preferably $C_1$-$C_6$ alkoxy $C_2$-$C_6$ alkenyl. Specific examples of the alkoxyalkenyl include (E)-4-methoxybut-2-en-1-yl.

"Aminocarbonylalkenyl" herein means a group in which one or more hydrogens of the above-defined "alkenyl" are replaced with the above-defined "aminocarbonyl", and is preferably aminocarbonyl $C_2$-$C_6$ alkenyl. Specific examples of the aminocarbonylalkenyl include (E)-3-(dimethylaminocarbonyl)-prop-2-en-1-yl.

"Haloalkoxy" herein means a group in which one or more hydrogens of the above-defined "alkoxy" are replaced with halogen, and is preferably $C_1$-$C_6$ haloalkoxy. Specific examples of the haloalkoxy include difluoromethoxy, trifluoromethoxy, 2,2-difluoroethoxy, and 2,2,2-trifluoroethoxy.

"Alkylene" herein means a divalent group derived by further removing any one hydrogen atom from the above "alkyl", and is preferably $C_4$-$C_8$ alkylene. Specific examples of the alkylene include —$CH_2$—, —$(CH_2)_2$—, —$(CH_2)_3$—, —$CH(CH_3)CH_2$—, —$C(CH_3)_2$—, —$(CH_2)_4$—, —$CH(CH_3)CH_2CH_2$—, —$C(CH_3)_2CH_2$—, —$CH_2CH(CH_3)CH_2$—, —$CH_2C(CH_3)_2$—, —$CH_2CH_2CH(CH_3)$—, —$(CH_2)_5$—, —$(CH_2)_6$—, —$(CH_2)_7$—, and —$(CH_2)_8$—.

"Alicyclic ring" herein means a non-aromatic hydrocarbon ring. The alicyclic ring may have an unsaturated bond within the ring, and may be a polycyclic ring having two or more rings. A carbon atom constituting the ring may be oxidized to form carbonyl. The alicyclic ring is preferably a 3- to 8-membered alicyclic ring, and specific examples include a cyclopropane ring, a cyclobutane ring, a cyclopentane ring, a cyclohexane ring, a cycloheptane ring, a cyclooctane ring, and a bicyclo[2.2.1]heptane ring.

"Saturated heterocyclic ring" herein means a non-aromatic heterocyclic ring containing 1 to 5 hetero atoms in addition to carbon atoms and not containing a double bond and/or a triple bond within the ring. The saturated heterocyclic ring may be a monocyclic ring, or may form a condensed ring with another ring, e.g., an aromatic ring such as a benzene ring. The saturated heterocyclic ring is preferably a 4- to 7-membered saturated heterocyclic ring, and specific examples include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, and an indoline ring.

A "peptide" herein is not particularly limited as long as it is a peptide formed by amide or ester bonding of natural amino acids and/or unnatural amino acids, but is preferably a peptide of 5 to 30 residues, more preferably of 7 to 15 residues, and still more preferably of 9 to 13 residues. A peptide may be a linear peptide or a cyclic peptide.

"Peptide chain" herein refers to a peptide chain in which 1, 2, 3, 4, or more natural amino acids and/or non-natural amino acids are connected by an amide bond and/or an ester bond. The peptide chain is preferably a peptide chain comprising 1 to 4 amino acid residues, and more preferably a peptide chain consisting of 1 to 4 amino acid residues.

"Optionally substituted" herein means that a group may be substituted with any substituent.

"Optionally protected" herein means that a group may be protected with any protecting group.

"One or more" herein means one or two or more. When "one or more" is used in a context relating to the substituent of a group, the phrase means a number encompassing one to the maximum number of substituents permitted by that group. Specific examples of "one or more" include 1, 2, 3, 4, 5, 6, 7, 8, 9, 10, and/or a greater number.

The compound of the present invention can be a salt thereof, and preferably a chemically or pharmaceutically acceptable salt thereof. Also, the compound of the present invention or a salt thereof can be a solvate thereof, and preferably a chemically or pharmaceutically acceptable solvate thereof. Examples of salts of the compound of the present invention include hydrochloride; hydrobromide; hydroiodide; phosphate; phosphonate; sulfate; sulfonates such as methanesulfonate and p-toluenesulfonate; carboxylates such as acetate, citrate, malate, tartrate, succinate, and salicylate; alkali metal salts such as a sodium salt and a potassium salt; alkaline earth metal salts such as a magnesium salt and a calcium salt; and ammonium salts such as an ammonium salt, an alkylammonium salt, a dialkylammonium salt, a trialkylammonium salt, and a tetraalkylammonium salt. These salts are produced by, for example, bringing the compound into contact with an acid or a base usable in the production of pharmaceutical products. In the present invention, a solvate of a compound refers to a phenomenon in which solute molecules strongly attract solvent molecules in a solution and form one molecular group, and is called a hydrate when the solvent is water. The solvate of the compound of the present invention is preferably a hydrate, and specific examples of such hydrates include mono- to deca-hydrates, preferably mono- to penta-hydrates, and more preferably mono- to tri-hydrates. The solvate of the compound of the present invention includes not only a solvate formed of a single solvent such as water, alcohol (e.g., methanol, ethanol, 1-propanol, or 2-propanol), or dimethylformamide, but also a solvate formed of a plurality of solvents.

The term "amino acid" as used herein includes natural and unnatural amino acids. The term "natural amino acid" as used herein refers to Gly, Ala, Ser, Thr, Val, Leu, Ile, Phe, Tyr, Trp, His, Glu, Asp, Gln, Asn, Cys, Met, Lys, Arg, or Pro. Examples of the unnatural amino acid include, but are not particularly limited to, β-amino acids, γ-amino acids, D-amino acids, N-substituted amino acids, α, α-disubstituted amino acids, amino acids having side chains that are different from those of natural amino acids, and hydroxycarboxylic acids. Amino acids herein may have any conformation. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, and a cycloalkyl group. One or two non-adjacent methylene groups in such a group are optionally substituted with an oxygen atom, a carbonyl group (—CO—), or a sulfonyl group (—$SO_2$—). Each group may have a substituent, and there are no limitations on the substituent. For example, one or more substituents may be freely and independently selected from any substituents including a halogen atom, an O atom, an S atom, an N atom, a B atom, an Si atom, or a P atom. Examples include an optionally substituted alkyl group, alkenyl group, alkynyl group, aryl group, heteroaryl group, aralkyl group, and cycloalkyl group. In a non-limiting embodiment, amino acids herein may be compounds having a carboxy group and an amino group in the same molecule (even in this case, imino acids such as proline and hydroxyproline are also included in amino acids).

The main chain amino group of an amino acid may be unsubstituted (an $NH_2$ group) or substituted (i.e., an —NHR group, where R represents alkyl, alkenyl, alkynyl, aryl, heteroaryl, aralkyl, or cycloalkyl which may have a substituent, one or two non-adjacent methylene groups in such a group may be substituted with an oxygen atom, a carbonyl group (—CO—), or a sulfonyl group (—$SO_2$—), and the carbon chain bonded to the N atom and the carbon atom at the position a may form a ring, as in proline). The R substituent is selected as the substituent in the aforementioned amino acid side chain is selected. When the main chain amino group is substituted, the R is included in the "amino acid side chain" as used herein. Such amino acids in which the main chain amino group is substituted are herein called "N-substituted amino acids." Preferred examples of the "N-substituted amino acids" as used herein include, but are not limited to, N-alkylamino acids, N—$C_1$-$C_6$ alkylamino acids, N—$C_1$-$C_4$ alkylamino acids, and N-methylamino acids.

"Amino acids" as used herein which constitute a peptide compound include all isotopes corresponding to each amino acid. The isotope of the "amino acid" refers to one having at least one atom replaced with an atom of the same atomic number (number of protons) and different mass number (total number of protons and neutrons) that differs from natural abundance. Examples of isotopes contained in the "amino acid" constituting the peptide compounds of the present invention include a hydrogen atom, a carbon atom, a nitrogen atom, an oxygen atom, a phosphorus atom, a sulfur atom, a fluorine atom, and a chlorine atom, which respectively include $^2H$ and $^3H$; $^{13}C$ and $^{14}C$; $^{15}N$; $^{17}O$ and $^{18}O$; $^{31}P$ and $^{32}P$; $^{35}S$; $^{18}F$; and $^{36}Cl$.

Substituents containing a halogen atom as used herein include a halogen-substituted alkyl group, cycloalkyl group, alkenyl group, alkynyl group, aryl group, heteroaryl group, or aralkyl group. More specific examples include fluoroalkyl, difluoroalkyl, and trifluoroalkyl.

Substituents containing an O atom include groups such as hydroxy (—OH), oxy (—OR), carbonyl (—C=O—R), carboxy (—$CO_2H$), oxycarbonyl (—C=O—OR), carbonyloxy (—O—C=O—R), thiocarbonyl (—C=O—SR), carbonylthio (—S—C=O—R), aminocarbonyl (—C=O—NHR), carbonylamino (—NH—C=O—R), oxycarbonylamino (—NH—C=O—OR), sulfonylamino (—NH—$SO_2$—R), aminosulfonyl (—$SO_2$—NHR), sulfamoylamino (—NH—$SO_2$—NHR), thiocarboxyl (—C(=O)—SH), and carboxylcarbonyl (—C(=O)—$CO_2H$).

Examples of oxy (—OR) include alkoxy, cycloalkoxy, alkenyloxy, alkynyloxy, aryloxy, heteroaryloxy, and aralkyloxy. The alkoxy is preferably $C_1$-$C_4$ alkoxy and $C_1$-$C_2$ alkoxy, and particularly preferably methoxy or ethoxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl (examples of which include $C_1$-$C_6$ or $C_1$-$C_4$ alkylaminocarbonyl, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Additional examples include groups in which the H atom bonded to the N atom in —C=O—NHR is further replaced with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include groups in which the H atom bonded to the N atom in —NH—C=O—R is further replaced with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include groups in which the H atom bonded to the N atom in —NH—C=O—OR is further replaced with alkyl, cycloalkyl, alkenyl, alkynyl, aryl, heteroaryl, or aralkyl.

Examples of sulfonylamino (—NH—$SO_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include groups in which the H atom attached to the N atom in —NH—$SO_2$—R is further replaced with alkyl, cycloalkyl, alkenyl, alkynyl, aryl, heteroaryl, or aralkyl.

Examples of aminosulfonyl (—$SO_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include groups in which the H atom attached to the N atom in —$SO_2$—NHR is further replaced with alkyl, cycloalkyl, alkenyl, alkynyl, aryl, heteroaryl, or aralkyl.

Examples of sulfamoylamino (—NH—$SO_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—$SO_2$—NHR may be further replaced with substituents independently selected from the group consisting of alkyl, cycloalkyl, alkenyl, alkynyl, aryl, heteroaryl, and aralkyl, and these two substituents may form a ring.

Substituents containing an S atom include groups such as thiol (—SH), thio (—S—R), sulfinyl (—S=O—R), sulfonyl (—$SO_2$—R), and sulfo (—$SO_3H$).

Examples of thio (—S—R) include alkylthio, cycloalkylthio, alkenylthio, alkynylthio, arylthio, heteroarylthio, and aralkylthio.

Examples of sulfonyl (—$SO_2$—R) include alkylsulfonyl, cycloalkylsulfonyl, alkenylsulfonyl, alkynylsulfonyl, arylsulfonyl, heteroarylsulfonyl, and aralkylsulfonyl.

Substituents containing an N atom include groups such as azido (—$N_3$, also called "azido group"), cyano (—CN), primary amino (—$NH_2$), secondary amino (—NH—R; also called monosubstituted amino), tertiary amino (—NR(R'); also called disubstituted amino), amidino (—C(=NH)—$NH_2$), substituted amidino (—C(=NR)—NR'R"), guanidino (—NH—C(=NH)—$NH_2$), substituted guanidino (—NR—C(=NR')—NR'R"), aminocarbonylamino (—NR—CO—NR'R"), pyridyl, piperidino, morpholino, and azetidinyl.

Examples of secondary amino (—NH—R; monosubstituted amino) include alkylamino, cycloalkylamino, alkenylamino, alkynylamino, arylamino, heteroarylamino, and aralkylamino.

Examples of tertiary amino (—NR(R'); disubstituted amino) include amino groups having any two substituents each independently selected from alkyl, cycloalkyl, alkenyl, alkynyl, aryl, heteroaryl, and aralkyl, such as alkyl(aralkyl)amino, where any two such substituents may form a ring. Specific examples include dialkylamino, in particular, $C_1$-$C_6$ dialkylamino, $C_1$-$C_4$ dialkylamino, dimethylamino, and diethylamino. The term "$C_p$-$C_q$ dialkylamino group" as used herein refers to an amino group substituted with two $C_p$-$C_q$ alkyl groups, where the two $C_p$-$C_q$ alkyl groups may be the same or different.

Examples of substituted amidino (—C(=NR)—NR'R") include groups in which three substituents R, R', and R" on the N atom are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')—NR'R") include groups in which R, R', R", and R''' are each independently selected from alkyl, cycloalkyl, alkenyl, alkynyl, aryl, heteroaryl, and aralkyl, or groups in which these substituents form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, or groups in which these substituents form a ring.

Herein, an "amino acid residue" constituting the peptide compound may be simply referred to as an "amino acid".

As used herein, the term "and/or" includes any and all combinations in which "and" and "or" are suitably combined. Specifically, for example, "A, B, and/or C" includes the following seven variations: (i) A, (ii) B, (iii) C, (iv) A and B, (v) A and C, (vi) B and C, and (vii) A, B, and C.

The phrase "substantially consisting of/substantially consist(s) of" as used herein means that main components are those listed herein (examples of which include, but are not limited to, crystal forms of cyclic peptide compounds, cyclic peptide compounds and peptide compounds), and other components may be contained if they do not have a negative impact on the effects of an embodiment of the present invention or if they are contained in such an amount or embodiment that does not have such a negative impact. For example, components not listed herein (impurities, such other crystal forms of interests, reaction by-products and unreacted products) may be contained if they do not have a negative impact on the effects of an embodiment of the present invention or if they are contained in such an amount or embodiment that does not have such a negative impact.

The phrase "substantially not comprising/do(es) not substantially comprise" as used herein means that components listed herein (examples of which include, but are not limited to, crystal forms of cyclic peptide compounds, cyclic peptide compounds and peptide compounds) are not contained, or even if such components are contained, they do not have a negative impact on the effects of an embodiment of the present invention or they are contained in such an amount or embodiment that does not have such a negative impact. For example, such components listed herein may be contained if they do not have a negative impact on the effects of an embodiment of the present invention or if they are contained in such an amount or embodiment that does not have such a negative impact.

As used herein, the term "negative impact" used in the context of the effects of the invention refers to an impact that negates the effects of the invention. For example, when the effects of the invention are reduced to 30%, 20%, 10%, or 5% or less based on the effects that should be naturally demonstrated as 100%, it can be said that there is a "negative impact."

Method for Producing Cyclic Peptide Compounds

In an embodiment, the present invention relates to a method for producing a cyclic peptide compound or a salt thereof, or a solvate thereof by a liquid phase method, and the method comprises linking the N-terminal amino acid residue of a peptide compound with the C-terminal amino acid residue of the peptide compound in a solvent (Solvent A) comprising one or more solvents selected from the group consisting of one or more water-immiscible solvents (e.g., solvents with low water solubility, solvents with large water/octanol coefficient (log Kow) values, or solvents with large predicted water/octanol coefficient values), one or more water-soluble alkyl nitriles, and one or more water-soluble ethers.

In certain embodiments, the water immiscible solvent can be characterized as an ester having 3 or more and 10 or less carbon atoms, such as ethyl acetate, isopropyl acetate, n-propyl acetate, t-butyl acetate, methyl propionate or ethyl propionate.

In certain embodiments, the water immiscible solvent can be characterized as a cyclic ether having 4 or more and 10 or less carbon atoms, such as 2-MeTHF, THF, 4-methyltetrahydropyran or 1,4-dioxane.

In certain embodiments, the water immiscible solvent can be characterized as an acyclic ether having 4 or more and 10 or less carbon atoms, such as MTBE, diisopropyl ether or diethyl ether.

In certain embodiments, the water immiscible solvent can be characterized as an ether having both cyclic and acyclic alkyl group, such as CPME.

In certain embodiments, the water immiscible solvent can be characterized as a carbonate having 3 or more and 10 or less carbon atoms, such as dimethyl carbonate, diethyl carbonate or diisopropyl carbonate.

In certain embodiments, the water immiscible solvent can be characterized as a hydrocarbon having 5 or more and 10 or less carbon atoms, such as pentane, hexane or heptane.

In certain embodiments, the water immiscible solvent can be characterized as an aromatic having 6 or more and 10 or less carbon atoms, such as toluene, xylene or benzene.

In certain embodiments, the water immiscible solvent can be characterized to have a low boiling point at ambient-pressure (around 1 atm). The low boiling point at ambient-pressure (around 1 atm) is exemplified as more than 35° C. and less than 140° C.

The solvents having boiling point at ambient-pressure (around 1 atm) more than 140° C., such as DMF, DMA, NMP or DMSO can be excluded in this invention.

In certain embodiments, a solvent that may have possibility to react with the peptide compounds or the cyclic peptide compounds can be excluded from the water immiscible solvent in this invention. In certain embodiments, inappropriate solvents as the water immiscible solvent can be characterized as an amine (e.g. n-propylamine or diisopropylamine), or an alcohol (e.g. methanol, ethanol, n-propanol, phenol).

As used herein, a water-immiscible solvent includes, but is not limited to, a solvent with low water solubility (e.g. having a solubility of below 150 g/L). The water solubility may be determined by any method known in art or described herein. Exemplary methods to determine solubility include, but are not limited to, gas chromatography wherein the analysis determines the concentration of said solvent in water prepared by mixing said solvent with water in equal amounts at room temperature (e.g. 15° C. to 40° C., preferably 20° C. to 30° C.). As used herein, a solvent with a large water/octanol coefficient (log Kow) value preferably has a coefficient of greater than 0 (zero) and less than 5. The water/octanol coefficient (log Kow) may be determined by any method known in art or described herein. Solvents having a large water/octanol coefficient (log Kow) also include solvents having large predicted water/octanol coefficient value which may be determined by means known in the art apart explicit measurement, for example but not limited to a database search or a literature search.

In certain embodiments, the water immiscible solvent is THF, 2-MeTHF, MTHP, dimethyl carbonate, AcOEt, IPAc, anisole; preferably THF, or 2-MeTHF; and more preferably 2-MeTHF. The miscibility of solvents with water is described in the Merck Index 14$^{th}$ Edition. For instance, it states DMSO is soluble in water and acetonitrile is miscible with water. In contrast, it states heptane is insoluble in water. 2-MeTHF is not miscible with water (Org. Process Res. Dev. 2007, 11(1): 156-159). Determination of the miscibility of a solvent with is routinely practiced and can be performed by any method known in the art or described herein. For example, a water immiscible solvent may indicate that when the solvent is mixed with water in equal amounts at about room temperature (for example, 15° C. to 40° C., preferably 20° C. to 30° C.), the solvent and water separate into two phases. The miscibility study of a solvent can be done by mixing equal amounts of a solvent and water in a reservoir, such as a separatory funnel, a reaction vessel, or a reactor, at about room temperature (for example, 15° C. to 40° C., preferably 20° C. to 30° C.), and then determining, such as by visual inspection or by analyzing (e.g. by GC) both upper portion and lower portion of the mixture in a reservoir, whether the solvent and water separate into two phases; if the solvent and water separate into two phases, the solvent can be characterized as being water immiscible.

The miscibility of a solvent with water may depend on the solubility of the solvent in water. Water-immiscible solvents include solvents with low water solubility. Although the water solubility may vary depending on temperature, the solubility herein refers to solubility at around room temperature, for example, 20° C. to 30° C. The water solubility of solvents can be determined by actual measurement (non-limiting exemplary methods provided herein, e.g. herein above), but is described in commercial suppliers' catalogues or the Merck Index 14$^{th}$ Edition. The Merck Index 14$^{th}$ Edition states that 139 g of dimethyl carbonate, 43 g of isopropyl acetate, and 100 g of ethyl acetate dissolve in 1 L of water, and that heptane is insoluble in water. It also states that 140 g of 2-MeTHF (Org. Process Res. Dev. 2007, 11(1): 156-159) and 139 g of dimethyl carbonate (J. Mol. Catal. A Chem. 2010, 317: 1-18) dissolve in 1 L of water. Predicted solubility of a solvent in water can be found using a database search tool such as SciFinder®. It states that 3.2 g of anisole, 20 g of isopropyl acetate, 39 g of ethyl acetate, and 4.7 mg of heptane dissolve in 1 L of water. ChemIDplus Advanced (NIH) (https://chem.nlm.nih.gov/chemidplus/) can also be used to find water solubility. It states that acetonitrile, THF, and DMSO, which are miscible with water, have a water solubility of 1000 g/L. Thus, a water-immiscible solvent has a water solubility of 999 g/L or less, 500 g/L or less, 250 g/L or less, preferably 200 g/L or less, and more preferably 150 g/L or less. It is noted that the water solubility of 2-MeTHF at room temperature (e.g. 25° C.) is 150 g/L. Therefore, the more preferred characteristic of having a water solubility of 150 g/L or less may be alternately (and equivalently) expressed as having a water solubility at room temperature (e.g. 25° C.) equivalent to or no greater than 2-MeTHF. As described herein, the methods of the invention allow the use of water-immiscible solvents in peptide compound syntheses such that (1) the reaction solvent can be utilized as the extraction solvent in aqueous aftertreatment of the reaction mixture (as it is water-immiscible), and (2) the extraction solution containing the peptide compound can be used as the starting material for the next subsequent step/reaction (i.e. the solution containing the starting compound for the next step). In certain embodiments, this allows the entire reaction to be performed and completed without having to isolate from the starting reaction solvent.

Solvents with low water solubility include solvents with a water solubility of 999 g/L or less. Non-limiting examples include, 2-MeTHF, dimethyl carbonate, ethyl acetate, isopropyl acetate, heptane, anisole, MTBE, CPME, 4-methyltetrahydropyran, and toluene. With the view toward enhancing the rate of conversion into a product of interest and preventing generation of byproducts in a cyclization reaction, 2-MeTHF, dimethyl carbonate, or anisole, or a solvent containing one or more of them are preferably used.

The miscibility of a solvent with water may depend on the water/octanol coefficient (log Kow), which is intrinsic to the solvent, or the predicted water/octanol coefficient as described herein. The water/octanol coefficient indicates the lipid solubility of a compound, and it is known that compounds with higher lipid solubility have higher coefficient values. The log Kow can be determined by actual measurement as is known in the art or herein described. Alternately the log Kow value can be the predicted value, for example, as reported in the literature (obtained, e.g. by searching using a database search tool such as SciFinder©, or by searching ChemIDplus Advanced (NIH) (https://chem.nlm-.nih.gov/chemidplus/)). Examples of log Kow values or predicted log Kow values of water-immiscible solvents are 1.35 for 2-MeTHF, 0.23 for dimethyl carbonate, 2.11 for anisole, 1.02 for isopropyl acetate, 0.73 for ethyl acetate, and 4.66 for heptane, which are all positive values. By contrast, the log Kow or predicted log Kow values of water-miscible solvents are −0.34 for acetonitrile and −0.31 for DMSO, which are all negative values. Thus, water-immiscible solvents will have positive log Kow or predicted log Kow values, which are preferably greater than 0 and less than 5.

Solvents with a large water/octanol coefficient (log Kow) or a large predicted water/octanol coefficient according to the methods described herein include, but are not limited to, 2-MeTHF, dimethyl carbonate, ethyl acetate, isopropyl acetate, heptane, anisole, MTBE, CPME, and 4-methyltetrahydropyran.

Water-immiscible solvents include solvents with low water solubility, or solvents with a positive water/octanol coefficient (log Kow) value.

Water-soluble alkyl nitriles include acetonitrile and propionitrile.

Water-soluble ethers include THF, 1,4-dioxane, and dimethoxyethane.

In an embodiment, Solvent A may contain one or more solvents selected from the group consisting of water-immiscible solvents, water-soluble alkyl nitriles, and water-soluble ethers. For example, in one embodiment, Solvent A may contain one or more of 2-MeTHF, THF, MTHP, dimethyl carbonate, AcOEt, IPAc, anisole, MeCN, DCM, and toluene. Solvent A may consist only of one or more water-immiscible solvent(s), only of one or more water-soluble alkyl nitrile(s), or only of one or more water-soluble ether(s). Alternately, Solvent A may contain solvents selected from two or more of the groups water-immiscible solvent(s), water-soluble alkyl nitrile(s), and water-soluble ether(s). As disclosed herein, where Solvent A contains water-immiscible solvent(s) one or more such solvents may be contained in Solvent A. Similarly, where Solvent A contains water-soluble alkyl nitrile(s), one or more such solvents may be contained in Solvent A; and where Solvent A contains water-soluble ether(s), one or more such solvents may be contained in Solvent A.

In an embodiment, Solvent A may contain, in addition to water-immiscible solvents, water-soluble alkyl nitriles, and water-soluble ethers, a solvent(s) categorized as none of these solvents, such as DMF and acetone. In an embodiment, Solvent A may not contain solvents selected from protic solvents such as alcohols (MeOH, EtOH, n-PrOH, iPrOH, nBuOH, iBuOH, tBuOH), primary amines (nPrNH$_2$, iPrNH$_2$, nBuNH$_2$, tBuNH$_2$), secondary amines (Et$_2$NH, nPr$_2$NH, iPr$_2$NH, nBu$_2$NH, tBu$_2$NH) and carboxylic acid (AcOH, EtCO$_2$H, nPrCO$_2$H). When Solvent A contains a solvent(s) categorized as none of water-immiscible solvents, water-soluble alkyl nitriles, and water-soluble ethers, the water-immiscible solvent(s) preferably accounts for not more than 40% by weight of entire Solvent A, more preferably not more than 30% by weight, not more than 25% by weight, not more than 20% by weight, not more than 15% by weight, not more than 10% by weight, or not more than 5% by weight.

In an embodiment, a peptide compound of the present invention may be a linear peptide compound. In another embodiment, a peptide compound of the present invention may be a cyclic peptide compound. In an embodiment, the linear or cyclic peptide compound may contain a cyclic structure as a partial structure. Cyclic structures specifically include those in which a side chain of an amino acid residue is linked to a side chain of another amino acid residue, those in which an N-substituent of an amino acid residue is linked to a side chain of another amino acid residue, and those in which an N-substituent of an amino acid residue is linked to an N-substituent of another amino acid residue. Two amino acid residues involved in linkage for a cyclic structure may be contiguous or may be intervened by any number of amino acid residues, for example, 1, 2, 3, 4, 5, 6, 7, 8, 9, 10, 11, 12, 13, 14, 15, 16, 17, 18, or 19 amino acid residues. When the peptide compound has cyclic structures, there is no limitation on the number of cyclic structures, but the compound preferably has 1, 2, 3, 4, or 5 cyclic structures.

In the present invention, the N-terminal amino acid residue and the C-terminal amino acid residue of a peptide compound are linked by an amide bond, or a bond selected from —(CH2)nS(CH2)m-, —(CH2)nS(O)(CH$_2$)$_m$—, or —(CH$_2$)$_n$S(O)$_2$(CH$_2$)$_m$—, where n and m are each independently 1 or 2.

When the N-terminal amino acid residue and the C-terminal amino acid residue of a peptide compound are linked by an amide bond, a cyclic peptide compound or a salt thereof, or a solvate thereof may be produced by condensing the amino group of the N-terminal amino acid residue and the carboxyl group of the C-terminal amino acid residue. The amide bond may be formed between the amino group of the main chain of the N-terminal amino acid residue and the carboxyl group of the main chain of the C-terminal amino acid residue; may be formed between the amino group of the main chain of the N-terminal amino acid residue and the carboxyl group of a side chain of the C-terminal amino acid residue; may be formed between the amino group of a side chain of the N-terminal amino acid residue and the carboxyl group of the main chain of the C-terminal amino acid residue; or may be formed between the amino group of a side chain of the N-terminal amino acid residue and the carboxyl group of a side chain of the C-terminal amino acid residue. In condensation, the carboxyl group may be activated in the system using a condensing reagent, or may be converted into active ester in advance of use. As used herein, the term "condensation of the amino group and carboxyl group" refers to linking the amino group and carboxyl group by an amide bond.

In an embodiment, the condensation reaction may be carried out by stirring the reaction mixture for 10 minutes to 48 hours in Solvent A in the presence or absence of a condensing reagent at a temperature ranging from −20° C. to about the boiling point of the solvent, preferably −20° C. to 100° C., or preferably −5° C. to 60° C. When a condensing reagent is used in condensation reaction, the condensing reagent or a solution containing the condensing reagent may be added to a solvent containing raw materials and optionally a base, or a solution containing raw materials and optionally a base may be added to a solution containing the condensing reagent. Herein, the operation of adding a solution containing raw materials and optionally a base dropwise to a solution containing a condensing reagent may be referred to as "reverse dropwise addition". Generation of byproduct dimers and trimers can be prevented by reverse dropwise addition of a solution containing a condensing reagent over a long period of time, for example, over a few hours to a few days, preferably 1 to 24 hours, or more preferably 1 to 10 hours.

The condensing reagent and its amount used for the condensation of the amino group and carboxyl group are not particularly limited as long as they may form amide bonds, and are preferably a condensing agent and amount generally used for peptide synthesis (see, e.g., Peptide Coupling Reagents, More than a Letter Soup (Chem. Rev. 2011, 111, 6557-6602)).

Specific examples of such condensing agents include those having a carbodiimide group. For example, a condensing agent having a carbodiimide group can be used for condensation reaction in combination with a hydroxy compound that can form active ester. Condensing agents having a carbodiimide group include, for example, N,N'-dicyclohexylcarbodiimide (DCC), N,N'-diisopropylcarbodiimide (DIC), and 1-ethyl-3-(3-dimethylaminopropyl)carbodiimide hydrochloride (EDCI) (see, for example, the catalogue of WATANABE Chemical, Amino acids and chiral building blocks to new medicine). Hydroxy compounds that can form active ester include, for example, 1-hydroxy-1H-benzotriazole (HOBt), 1-hydroxy-7-azabenzotriazole (HOAt), ethyl 2-cyano-2-(hydroxyimino)acetate (oxyma), 3,4-dihydro-3-hydroxy-4-oxo-1,2,3-benzotriazine (HOOBt or HODhbt), N-hydroxy-5-norbornene-2,3-dicarboximide (HONB), 2,3,4,5,6-pentafluorophenol (HOPfp), N-hydroxysuccinimide (HOSu), and 6-chloro-1-hydroxy-1H-benzotriazole (Cl-HOBt) (see, for example, the catalogue of WATANABE Chemical, Amino acids and chiral building blocks to new medicine). Also, salts having these structures such as K-oxyma, a potassium salt of oxyma, may be used. Among these, HOBt, HOAt, oxyma, and HOOBt are particularly preferred. Inter alia, the use of DIC and HOAt in combination, or the use of DIC and oxyma in combination is preferred. In addition, as a phosphonium condensing agent or uronium condensing agent, any one of O-(1H-benzotriazol-1-yl)-N,N,N',N'-tetramethyluronium hexafluorophosphate (HBTU), O-(7-aza-1H-benzotriazol-1-yl)-N,N,N',N'-tetramethyluronium hexafluorophosphate (HATU), N-[1-(cyano-2-ethoxy-2-oxoethylidenaminooxy)dimethylamino(morpholino)]uronium hexafluorophosphate (COMU), O-[(ethoxycarbonyl)cyanomethyleneamino]-N,N,N',N'-tetramethyluronium hexafluorophosphate (HOTU), O-(1H-benzotriazol-1-yl)-N,N,N',N'-tetramethyluronium tetrafluoroborate (TBTU), O-(7-azabenzotriazol-1-yl)-N,N,N',N'-tetramethyluronium tetrafluoroborate (TATU), [ethylcyano(hydroxyimino)acetato-$O^2$]tri-1-pyrrolidinylphosphonium hexafluorophosphate (PyOxim), 2-bromo-1-ethylpyridinium tetrafluoroborate (BEP), 1H-benzotriazol-1-yloxytri(pyrrolidino)phosphonium hexafluorophosphate (PyBOP), 1H-benzotriazol-1-yloxy-tris(dimethylamino)phosphonium hexafluorophosphate (BOP), bromotri(pyrrolidino)phosphonium hexafluorophosphate (PyBroP), chlorotri(pyrrolidino)phosphonium hexafluorophosphate (PyCloP), (7-azabenzotriazol-1-yloxy)tripyrrolidinophosphonium hexafluorophosphate (PyAOP), bromotris(dimethylamino)phosphonium hexafluorophosphate (Brop), 3-(diethoxyphosphoryloxy)-1,2,3-benzotriazin-4(3H)-one (DEPBT), N,N,N',N'-tetramethyl-O—(N-succinimidyl)uronium tetrafluoroborate (TSTU), N,N,N',N'-tetramethyl-O—(N-succinimidyl)uronium hexafluorophosphate (HSTU), O-(3,4-dihydro-4-oxo-1,2,3-benzotriazin-3-yl)-N,N,N',N'-tetramethyluronium tetrafluoroborate (TDBTU), tetramethylthiuronium S-(1-oxido-2-pyridyl)-N,N,N',N'-tetrafluoroborate (TOTT), and O-(2-oxo-1(2H)-pyridyl)-N,N,N',N'-tetramethyluronium tetrafluoroborate (TPTU) can be used in condensation reaction in combination with any of the following bases: N,N-diisopropylethylamine (DIPEA), triethylamine (TEA), 2,4,6-trimethylpyridine (2,4,6-collidine), and 2,6-dimethylpyridine (2,6-lutidine). In particular, the use of HATU and DIPEA in combination, or the use of COMU and DIPEA in combination is preferred. Other condensing agents, including N,N'-carbonyldiimidazole (CDI), 1,1'-carbonyl-di-(1,2,4-triazole) (CDT), 4-(4,6-dimethoxy-1,3,5-triazin-2-yl)-4-methylmorpholinium chloride (DMT-MM), and propylphosphonic acid anhydride (T3P), can also be used. With the view toward enhancing the rate of conversion in cyclization reaction and preventing generation of byproducts, HATU, PyBOP, and PyOxim are preferred condensing agents in the present invention. Preferred solvent/condensing agent combinations are HATU and anisole, dimethyl carbonate, or 2-MeTHF; PyBOP and acetonitrile, anisole, dimethyl carbonate, 2-MeTHF, 4-methyltetrahydropyran, or ethyl acetate; or PyOxim and acetonitrile, anisole, dimethyl carbonate, 2-MeTHF, or ethyl acetate. More preferred solvent/condensing agent combinations are anisole and PyBOP, dimethyl carbonate and PyBOP, and 2-MeTHF and PyBOP.

When the N-terminal amino acid residue and the C-terminal amino acid residue of a peptide compound are linked by a bond selected from —$(CH_2)_nS(CH_2)_m$—, —$(CH_2)_nS(O)(CH_2)_m$—, or —$(CH_2)_nS(O)_2(CH_2)_m$—, a cyclic peptide compound or a salt thereof, or a solvate thereof may be produced by, for example, allowing the haloalkyl or vinyl group contained in the N-terminal amino acid residue to react with the thiol group contained in the C-terminal amino acid residue to form a C—S—C bond and, if necessary, converting the sulfur atom into sulfoxide or sulfone by oxidation.

In an embodiment, a cyclic peptide compound produced by the method of the present invention contains 8 to 20 amino acid residues, and preferably 9 to 15 amino acid residues. Of those amino acid residues, at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 amino acid residues may be unnatural amino acid residues. In an embodiment, the percentage of unnatural amino acids contained in a cyclic peptide compound produced by the method of the present invention is, for example, 30% or more, 40% or more, 50% or more, 60% or more, 70% or more, or 80% or more of the total amino acids contained in the peptide compound.

An unnatural amino acid residue contained in the cyclic peptide compound may be an N-substituted unnatural amino acid residue or N-unsubstituted unnatural amino acid residue. An amino acid residue in which the amino group of the main chain of the natural amino acid is substituted with any atom or functional group, and an amino acid residue which has a structure different from that of natural amino acids in the side chain and in which the amino group of the main chain is substituted with any atom or functional group are included in N-substituted amino acid residues. An amino acid residue in which the amino group of the main chain is not substituted but which has a structure different from that of natural amino acids in the side chain is included in N-unsubstituted unnatural amino acid residues.

In an embodiment, a cyclic peptide compound produced by the method of the present invention may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-substituted amino acid residues. In an embodiment, the percentage of N-substituted amino acid residues contained in a cyclic peptide compound produced by the method of the present invention is, for example 30% or more, 40% or more, 50% or more, 60% or more, 70% or more, or 80% or more of the total amino acids contained in the peptide compound. The N-substituted amino acid residues may be unnatural amino acid residues.

In an embodiment, a cyclic peptide compound produced by the method of the present invention may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-unsubstituted unnatural amino acid residues. In an embodiment, the percentage of unsubstituted unnatural amino acid residues contained in a cyclic peptide compound produced by the method of the present invention is, for example 30% or more, 40% or more, 50% or more, 60% or more, 70% or more, or 80% or more of the total amino acids contained in the peptide compound.

In an embodiment, a cyclic peptide compound produced by the method of the present invention may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 α,α di-substituted amino acid residues. In an embodiment, the percentage of α,α di-substituted amino acid residues contained in a cyclic peptide compound produced by the method of the present invention is, for example 30% or more, 40% or more, 50% or more, 60% or more, 70% or more, or 80% or more of the total amino acids contained in the peptide compound.

A cyclic peptide compound produced by the method of the present invention may consist of 9 to 11 amino acid residues, among which one or more, two or more, three or more, four or more, five or more, or six or more residues may be N-substituted amino acid residues, and among which one or more, or two or more residues may be N-unsubstituted unnatural amino acid residues. The method of the present invention is particularly useful for large-scale production of cyclic peptide compounds containing such a large number of unnatural amino acid residues.

In an embodiment, a cyclic peptide compound produced by the method of the present invention is preferably a solvate, more preferably a hydrate, DMSO-hydrate, acetone-hydrate, or DMSO solvate, and still more preferably a hydrate.

In an embodiment, either or both of the C-terminal and the N-terminal amino acid residues of a linear peptide compound may be amino acid residues that do not have an asymmetric carbon at the α-carbon of the carboxyl group. Subjecting such an amino acid residue with no asymmetric carbon to cyclization makes it possible to prevent racemization during the cyclization reaction. Amino acid residues that do not have an asymmetric carbon at the α-carbon of the carboxyl group include those having the same substituents on the α-carbon. For example, an amino acid residue in which the α-carbon is substituted with two hydrogen atoms, i.e., the α-carbon is —CH$_2$— (e.g., glycine and N-substituted glycine such as N-methylglycine) does not have an asymmetric carbon. An amino acid residue having the same substituents, e.g., a methyl group and methyl group, on the α-carbon does not have an asymmetric carbon. Also, an amino acid residue in which the α-carbon is substituted with a spirocyclyl group such as a spirocyclopropyl group, a spirocyclobutyl group, a spirocyclopentyl group, and a spirocyclohexyl group, in other words, an amino acid in which the substituents on the α-carbon form a ring together with the α-carbon (such as cLeu), does not have an asymmetric carbon at the α-carbon of the carboxyl group, either.

In an embodiment, a cyclic peptide compound produced by the method of the present invention is a cyclic peptide compound represented by formula (1):

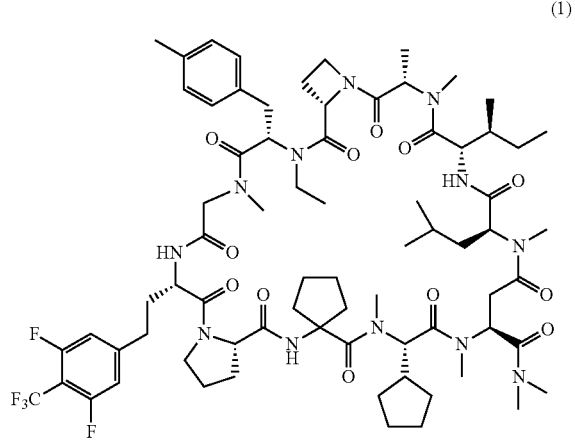 [SMILES: CC[C@H](C)[C@@H]1NC(=O)[C@H](CC(C)C)N(C)C(=O)C[C@@H](C(=O)N(C)C)N(C)C(=O)[C@H](C2CCCC2)N(C)C(=O)C2(CCCC2)NC(=O)[C@@H]2CCCN2C(=O)[C@H](CCc2cc(F)c(C(F)(F)F)c(F)c2)NC(=O)CN(C)C(=O)[C@H](Cc2ccc(C)cc2)N(CC)C(=O)[C@@H]2CCN2C(=O)[C@H](C)N(C)C1=O]

(1)

or a salt thereof or a solvate thereof. As described in WO2021/090855, the cyclic peptide compound of formula (1) is useful as a KRAS inhibitor and can be used for treating various diseases associated with KRAS, such as cancer.

The cyclic peptide compound represented by formula (1) may be produced by a method comprising linking the N-terminal amino acid residue and the C-terminal amino acid residue of a linear peptide compound having formula (2) below.

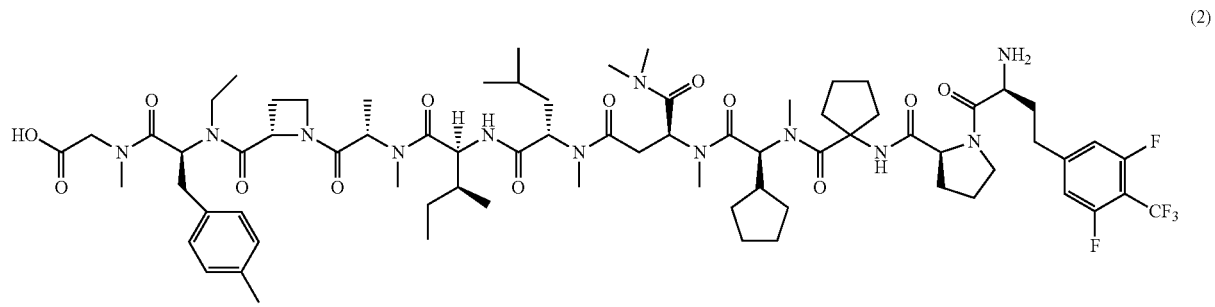 [SMILES: CC[C@H](C)[C@H](NC(=O)[C@H](CC(C)C)N(C)C(=O)C[C@@H](C(=O)N(C)C)N(C)C(=O)[C@H](C1CCCC1)N(C)C(=O)C1(NC(=O)[C@@H]2CCCN2C(=O)[C@@H](N)CCc2cc(F)c(C(F)(F)F)c(F)c2)CCCC1)C(=O)N(C)[C@@H](C)C(=O)N1CC[C@H]1C(=O)N(CC)[C@@H](Cc1ccc(C)cc1)C(=O)N(C)CC(=O)O]

(2)

In an embodiment, the linking step comprises condensing the N-terminal amino group and the C-terminal carboxyl group of the compound of formula (2) in a solvent containing one or more solvents selected from the group consisting of one or more water-immiscible solvents, one or more water-soluble alkyl nitriles, and one or more water-soluble ethers. In the production of this cyclic peptide compound, the use of a solvent containing water-soluble alkyl nitriles such as acetonitrile, or water-immiscible solvents such as anisole, dimethyl carbonate, and/or 2-MeTHF is preferred.

In an embodiment, it is preferable not to use column chromatography for the isolation and/or purification of a cyclic peptide compound produced by the method of the present invention, or a salt thereof, or a solvate thereof.

A cyclic peptide compound produced by the method of the present invention, or a salt thereof, or a solvate thereof may be isolated and/or purified, for example, by crystallization instead of by column chromatography.

Specifically, for example, a crystal of a cyclic peptide compound or a salt thereof, or a solvate thereof may be obtained by subjecting the reaction solution after condensation reaction to liquid separation; concentrating and/or filtering the organic phase if necessary; and adding a solvent suitable for crystallization and optionally a seed crystal to the residue obtained, followed by stirring if necessary. The solvent added for crystallization is not particularly limited as long as it allows crystal formation of cyclic peptide compounds, but is preferably a solvent that allows the operation of reducing the solubility of the cyclic peptide compound to be performed on the solution in which the cyclic peptide compound is dissolved. For example, when a cyclic peptide compound can be crystalized by reducing the solubility of the cyclic peptide compound by adding a poor solvent or cooling the solution, solvents that allow such operation are included as examples. When a crystal of a cyclic peptide compound can be obtained by keeping a crude crystal of the cyclic peptide compound in a suspension state for any given period of time under suspension conditions, solvents that allow such operation may be used for the crystallization. Specific examples of the solvent added for the crystallization include acetone, water, DMSO, acetonitrile, or ethanol, and mixed solvents thereof.

In an embodiment, a crystal of a cyclic peptide compound produced by the method of the present invention or a salt thereof, or a solvate thereof may be an unsolvate crystal, a solvate crystal, crystal of a salt, or a solvate crystal of a salt, of the compound of formula (1), as described below. In an embodiment, an unsolvate (or non-solvate) crystal means that the crystal is not a solvate or hydrate. The solvate crystal of the compound represented by formula (1) is preferably a DMSO-hydrate crystal (Form A crystal or Form B crystal), a hydrate crystal (Form C crystal), or an acetone-hydrate crystal (Form H crystal), and more preferably a hydrate crystal.

Method for Producing Peptide Compound

In an embodiment, the present invention relates to a method for producing a peptide compound by a liquid phase process. The method does not comprise isolating the product generated in each step, but comprises steps 1 and 2 below, and optionally comprises repeating steps 1 and 2 a plurality of times:

(step 1): linking/condensing an N-protected amino acid or N-protected peptide to a C-protected amino acid or C-protected peptide; and (step 2): removing/deprotecting the N-protecting group after step 1, thereby producing the peptide compound.

In an embodiment, the method of the present invention may comprise a single round of steps 1 and 2. In an embodiment, in the method of the present invention, steps 1 and 2 can be repeated a plurality of times. To elongate the peptide chain in a consecutive manner, it is preferred to repeat steps 1 and 2 a plurality of times, for example, 2 to 20 times.

As used herein, the term "C-protected amino acid" refers to a natural or unnatural amino acid whose carboxyl group is protected, and the term "C-protected peptide" refers to a peptide in which the carboxyl group of the C-terminal amino acid residue is protected. The peptide may consist solely of natural amino acid residues or unnatural amino acid residues, or may consist of any combination of natural and unnatural amino acid residues.

A C-protected peptide may contain 2 to 20 amino acid residues, among which at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 amino acid residues are preferably unnatural amino acid residues. The unnatural amino acid residues contained in the C-protected peptide may be N-substituted amino acid residues or N-unsubstituted unnatural amino acid residues. In an embodiment, the percentage of the unnatural amino acid residues contained in the C-protected peptide is, for example, 30% or more, 40% or more, 50% or more, 60% or more, 70% or more, or 80% or more of the total amino acids contained in the C-protected peptide.

When the C-protected peptide contains N-substituted amino acid residues, the C-protected peptide may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-substituted amino acid residues. In an embodiment, the percentage of the N-substituted amino acid residues contained in the C-protected peptide is, for example, 30% or more, 40% or more, 50% or more, 60% or more, 70% or more, or 80% or more of the total amino acids contained in the C-protected peptide. The N-substituted amino acid residues may be unnatural amino acid residues.

When the C-protected peptide contains N-unsubstituted unnatural amino acid residues, the C-protected peptide may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-unsubstituted unnatural amino acid residues. In an embodiment, the percentage of the N-unsubstituted unnatural amino acid residues contained in the C-protected peptide is, for example, 30% or more, 40% or more, 50% or more, 60% or more, 70% or more, or 80% or more of the total amino acids contained in the C-protected peptide.

Any protecting group known in the art may be used as the protecting group on the carboxyl group of a "C-protected amino acid" and "C-protected peptide" as long as it does not reduce the solubility of the peptide in a solvent. It is preferred that the peptide containing the C-protected amino acid has a solubility of at least 1% (w/v) or, more preferably, 5% (w/v) or more. Such carboxyl protecting groups specifically include methyl, ethyl, t-Bu, trityl, and cumyl groups. Of these, the t-Bu group is preferred.

As used herein, the term "N-protected amino acid" refers to a natural or unnatural amino acid whose amino group is protected, and the term "N-protected peptide" refers to a peptide in which the amino group of the N-terminal amino acid residue is protected. The peptide may consist solely of natural amino acid residues or unnatural amino acid residues, or may consist of any combination of natural and unnatural amino acid residues.

An N-protected peptide may contain 2 to 20 amino acid residues, among which at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 amino acid residues are preferably unnatural amino acid residues. The unnatural amino acid residues contained in the N-protected peptide may be N-substituted amino acid residues or N-unsubstituted unnatural amino acid residues. In an embodiment, the percentage of the unnatural amino acid residues contained in the N-protected peptide is, for example, 30% or more, 40% or more, 50% or more, 60% or more, 70% or more, or 80% or more of the total amino acids contained in the N-protected peptide.

When the N-protected peptide contains N-substituted amino acid residues, the N-protected peptide may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-substituted amino acid residues. In an embodiment, the percentage of the N-substituted amino acid residues contained in the N-protected peptide is, for example, 30% or more, 40% or more, 50% or more, 60% or more, 70% or more, or 80% or more of the total amino acids contained in the N-protected peptide. The N-substituted amino acid residues may be unnatural amino acid residues.

When the N-protected peptide contains N-unsubstituted unnatural amino acid residues, the N-protected peptide may contain at least one, at least two, at least three, at least four, at least five, at least six, at least seven, at least eight, at least nine, at least 10, at least 11, at least 12, at least 13, at least 14, at least 15, at least 16, at least 17, at least 18, or at least 19 N-unsubstituted unnatural amino acid residues. In an embodiment, the percentage of the N-unsubstituted unnatural amino acid residues contained in the N-protected peptide is, for example, 30% or more, 40% or more, 50% or more, 60% or more, 70% or more, or 80% or more of the total amino acids contained in the N-protected peptide.

Any protecting group known in the art may be used as the protecting group on the amino group of "N-protected amino acid" and "N-protected peptide" as long as it does not reduce the solubility of the peptide in a solvent. Such amino protecting groups specifically include Cbz, p-nitrobenzyloxycarbonyl, 2-naphthylmethyloxycarbonyl, diphenylmethyloxycarbonyl, 9-anthrylmethyloxycarbonyl, Teoc, Boc, trifluoroacetyl, and Alloc. Of these, Cbz, Teoc, or trifluoroacetyl is preferred.

As is known in the art for both N- and C-protected amino acids and/or peptides, the protective group usually is chosen depending on chemical reaction condition and can be determined by routine methods known in the art. For example, where a water-immiscible organic solvent (e.g. a lipophilic solvent) is used in the reaction, a hydrophilic protective group is not suitable because such a hydrophilic protective group would decrease solubility of a protected compound in the organic solvent. Accordingly, where a water-immiscible solvent is used (as described herein) a lipophilic protective group is the preferred protective group in view of it (maintaining) solubility (e.g. of the peptide) in a water-immiscible solvent. Selection of protective groups can be made by methods known in the art or described herein, e.g. as described in "Greene's Protective Groups in Organic Synthesis, Fifth Edition, 2014". A non-limiting example of an N-protective group that may be used in accordance with the methods of the invention is Cbz. Trifluoroacetyl is also preferred if an amino acid has a sterically hindered functional group such as spiro-cycloalkyl group in α-position in an amino acid residue."

Condensation

Step 1 is a step of linking an N-protected amino acid or an N-protected peptide to a C-protected amino acid or a C-protected peptide to obtain a linear peptide compound whose N- and C-termini are both protected.

In an embodiment, the linkage between a C-protected amino acid or C-protected peptide and an N-protected amino acid or N-protected peptide in step 1 is carried out by condensing the N-terminal amino group of the C-protected amino acid or peptide with the C-terminal carboxyl group of the N-protected amino acid or peptide in the presence or absence of a condensing reagent. When the reaction is carried out in the presence of a condensing reagent, the carboxyl group can be activated in the system. When the reaction is carried out in the absence of a condensing reagent, an N-protected amino acid or peptide whose carboxyl group has been activated in advance can be used.

In step 1, the method described in the section "Method for producing cyclic peptide compound" above except for the solvents, for example, the reaction conditions and reagents, may be employed. The condensing reagents used preferably in this step include a condensing agent selected from the group consisting of T3P, EDCI, HATU, COMU, BEP, PyBOP, DMT-MM, and PyOxim.

The reaction and the subsequent workup in Step 1 can be carried out in one or more solvents (Solvent B) selected independently from the group consisting of toluene, acetone, DMF, acetonitrile, THF, 2-MeTHF, dimethyl carbonate, anisole, isopropyl acetate, heptane, ethyl acetate, and 4-methyltetrahydropyran, and the subsequent process can be carried out without isolating or purifying the product, i.e., the condensation product of interest. Solvent B preferably contains 2-MeTHF, a mixed solvent of 2-MeTHF and acetonitrile (mixing ratio: relative to 1 part by weight of acetonitrile, 0.5 parts or more by weight of 2-MeTHF, preferably 0.5 to 20 parts by weight, more preferably 1 to 10 parts by weight, and still more preferably 1 to 5 parts by weight), 4-methyltetrahydropyran, dimethyl carbonate, ethyl acetate, and/or anisole in an amount of at least 1% or more by weight, at least 5% or more by weight, at least 10% or more by weight, at least 15% or more by weight, at least 20% or more by weight, at least 25% or more by weight, at least 30% or more by weight, at least 35% or more by weight, at least 40% or more by weight, at least 45% or more by weight, at least 50% or more by weight, at least 55% or more by weight, at least 60% or more by weight, at least 65% or more by weight, at least 70% or more by weight, at least 75% or more by weight, at least 80% or more by weight, at least 85% or more by weight, at least 90% or more by weight, or at least 95% or more by weight. This tendency is remarkable when HATU is used as a condensing agent. When step 1 is repeated a plurality of times, Solvent B preferably contains 2-MeTHF in an amount of at least 1% or more by weight, 5% or more by weight, 10% or more by weight, 15% or more by weight, 20% or more by weight, 25% or more by weight, 30% or more by weight, 35% or more by weight, 40% or more by weight, 45% or more by weight, 50% or more by weight, 55% or more by weight, 60% or more by weight, 65% or more by weight, 70% or more by weight, 75% or more by weight, 80% or more by weight, 85% or more by weight, 90% or more by weight, or 95% or more by weight in at least once, at least twice, at least three times, at least four times, at least five times, at least six times, at least seven times, at least eight times, at least nine times, or at least 10 times in the repetition, or alternatively, in at least 10%, at least 20%, at least 30%, at least 40%, at least 50%, at least 60%, at least 70%, at least 80%, or at least 90% of the total rounds of step 1.

Deprotection

Step 2 is a step of removing the N-terminal protecting group from the peptide obtained in step 1, whose N- and C-termini are protected.

In an embodiment, when the N-protecting group is, for example, Cbz, p-nitrobenzyloxycarbonyl, 2-naphthylmethyloxycarbonyl, diphenylmethyloxycarbonyl, or 9-anthrylmethyloxycarbonyl, step 2 can be carried out by catalytic hydrogenation. For the catalytic hydrogenation, any catalyst known in the art can be used. Specifically, the catalysts include, for example, Pd/C, Pd(OH)$_2$/C, and PtO$_2$, and Pd/C is preferred. Hydrogen used for the catalytic hydrogenation may be used under normal pressure or increased pressure. When used under increased pressure, the pressure may be not less than 1 atm (14.7 psi), preferably not less than 1 atm (14.7 psi) and not more than 3 atm (44.1 psi), preferably not less than 1 atm (14.7 psi) and not more than 2 atm (29.4 psi), and more preferably not less than 1 atm (14.7 psi) and not more than 1.8 atm (26.5 psi). When the hydrogen pressure decreases as the reaction proceeds, hydrogen can be added again. For example, when the hydrogen pressure in the reactor deceases to below 90% of the initial pressure, hydrogen can be added to increase hydrogen pressure to the initial value. In this respect, hydrogen can be added any number of times until the intended deprotection reaction reaches the intended conversion rate. It is also possible to start the reaction by purging the interior of the reaction vessel with hydrogen in the presence of starting materials, or by purging the interior of the reaction vessel with hydrogen in the absence of starting materials, followed by feeding of the starting materials into the reaction vessel.

In an embodiment, step 2 may be carried out in the presence of a deprotecting reagent. Any reagent known in the art, for example, the reagents described in "Greene's Protective Groups in Organic Synthesis, Fifth Edition, 2014" may be used depending on the type of the N-protecting group. For example, when the N-protecting group is Teoc, trifluoroacetyl, Fmoc, Boc, or the like, TBAF, LiBH$_4$, piperidine, trifluoroacetic acid, methanesulfonic acid, or the like is preferably used.

It is known that when a trifluoroacetyl group is used as a protecting group for the nitrogen atom of an unnatural amino acid and peptide, it can be removed using a metal hydride reducing agent, such as sodium boron hydride (Greene's Protective Groups in Organic Synthesis, Fifth Edition, 2014). However, in some cases, such reducing agents fail to remove the protecting group completely, or lead to generation of byproducts. The present inventors encountered the case where the treatment of a cLeu derivative protected with a trifluoroacetyl group (TFA-cLeu-MeGly(cPent)-MeAsp (OtBu)NMe2) with sodium boron hydride gave rise to MeGly(cPent)-MeAsp(OtBu)NMe2, a by-product resulting from amide bond cleavage, in addition to the desired deprotected compound. Then, the inventors found that the side reaction is prevented when lithium boron hydride is used. The inventors also found that over-reduced products are generated as by-products when an aqueous ammonium chloride solution is used as a reaction terminating agent immediately after the reaction. Thus, the inventors studied the reaction conditions and found that the generation of by-products can be prevented when, before an aqueous ammonium chloride solution is added as a reaction terminating agent, trifluoroethanol is added at −20 to −10° C. to the reaction solution, allowed to reach 0° C. over one hour, and stirred for one hour, and then an aqueous ammonium chloride solution is added and subjected to liquid separation. The inventors further found that since a boron atom is bound to nitrogen atoms of the deprotected compound after the liquid separation, the desired peptide, in which the boron-nitrogen bond is cleaved, can be obtained by adding trifluoroacetic acid at 10° C. to 30° C., stirring at 25° C., mixing with an aqueous sodium hydroxide solution, and then subjecting the mixture to liquid separation. The inventors have found that in this process, to prevent the rebinding of boron to nitrogen, it is essential that the solution treated with trifluoroacetic acid as described above is added dropwise to the aqueous sodium hydroxide solution over 50 to 90 minutes at 10° C. to 30° C. Accordingly, also provided are methods comprising the use of trifluoroacetyl groups as protecting groups, further comprising (1) the use of lithium borohydride as the reducing reagent and/or (2) the use of trifluoroethanol prior to the addition of aqueous ammonia as a terminating agent. It is preferred that where trifluoroacetyl groups are used as protecting groups, the method comprises both (1) the use of lithium borohydride as the reducing reagent; and (2) the use of trifluoroethanol prior to the addition of aqueous ammonia as a terminating agent.

In step 2, as in step 1, the reaction and subsequent workup can be carried out in one or more solvents (Solvent B) selected independently from the group consisting of toluene, acetone, DMF, acetonitrile, THF, 2-MeTHF, dimethyl carbonate, anisole, isopropyl acetate, heptane, ethyl acetate, and 4-methyltetrahydropyran, and the subsequent process can be carried out without isolating or purifying the product, i.e., the deprotected product of interest. Solvent B preferably contains 2-MeTHF.

In an embodiment, step 2 may be carried out by stirring the reaction mixture for 15 minutes to 48 hours at a temperature of −40° C. to near the boiling point of the solvent, preferably at a temperature of −30° C. to 100° C., and preferably at a temperature of −5° C. to 40° C.

Exemplary reaction parameters and conditions are provided below.

In one embodiment, the methods comprise the deprotection of the C-terminal amino acid of the peptide compound wherein the protective group of the C-protected peptide is tBu; the deprotection reagent is the combination of HMDS and TMSOTf; the solvent in the deprotection step comprises IPAc or 2-MeTHF; and the C-protected peptide consists of 2 to 13 amino acid residues.

In related or separate embodiments, the methods comprise the deprotection of the N-terminal amino acid of the peptide compound wherein the protective group of the N-protected peptide is Cbz; the deprotection condition is catalytic hydrogenation; the catalyst in hydrogenation is Pd/C; the H$_2$ pressure in hydrogenation is not less than 1 atm (14.7 psi) and not more than 3 atm (44.1 psi); the solvent in the deprotection step comprises 2-MeTHF or THF; and the N-protected peptide consists of 2 to 13 amino acid residues.

In related or separate embodiments, the methods comprise the deprotection of the N-terminal amino acid of the peptide compound wherein the protective group of the N-protected peptide is Teoc; the deprotection reagent is capable of generating a fluoride anion; the deprotection reagent is TBAF; the solvent in the deprotection step comprises 2-MeTHF, isopropyl acetate, dimethyl carbonate or anisole; and the N-protected peptide consists of 2 to 13 amino acid residues In related or separate embodiments, the methods comprise the deprotection of the N-terminal amino acid of the peptide compound wherein the protective group of the N-protected peptide is trifluoroacetyl (TFA); the deprotection reagent is reducing reagent; the deprotection reagent is lithium borohydride; the solvent in the deprotection step comprises 2-MeTHF or methanol; and the N-protected peptide consists of 2 to 13 amino acid residues.

It is known that in some cases the removal of the protecting group on the nitrogen atom of the N-terminal amino acid residue of a peptide does not yield the deprotected peptide of interest because of the formation of diketopiperazine (J. Chem. Soc., Chem. Commun., 1987, 1155-1156).

The present inventors have found that when a Cbz-Ile-MeAla-Aze derivative is subjected to hydrogenolysis reaction to remove the Cbz group, which is a protecting group for the N-terminal nitrogen atom of the derivative, diketopiperazine formation occurs during the reaction and inhibits subsequent peptide elongation.

Thus, the inventors studied the reaction conditions for Cbz removal reaction and peptide elongation, and found that peptide elongation can be performed efficiently by subjecting a Cbz compound to hydrogenolysis to remove Cbz in the presence of an amino acid active ester. J. CHEM. SOC., CHEM. COMMUN., 1987, 1155 reports examples of peptide elongation by subjecting Cbz compounds to hydrogenolysis in the presence of an amino acid active ester. However, this reference reports only Cbz-Ala-D-Pro-OMe, Cbz-Asu(OBut)-D-Pro-OMe-, and Cbz-D-Val-Pro-OMe as Cbz compounds, and provides no example for Aze derivatives. Neither does it disclose any example for reaction with N-alkyl amino acid active esters. N-alkyl amino acid active esters are, in view of the steric factors, easily expected to have decreased reactivity compared to normal amino acid active esters, in which nitrogen is not alkylated. Therefore, if Cbz removal occurs earlier than when an N-alkyl amino acid active ester reacts, diketopiperazine is formed. Thus, it is necessary to find out conditions under which Cbz removal is immediately followed by reaction with an N-alkyl amino acid active ester. As a result of studying the reaction conditions, the present inventors have found that when the compound Cbz-Ile-MeAla-Aze-EtPh(4-Me)-MeGly is subjected to hydrogenolysis reaction in the presence of the N-alkyl amino acid active ester Teoc MeLeu-pFp under a hydrogen pressure of 0.10 to 0.18 MPaG in isopropyl acetate to which N-methylmorpholine and Pd/C have been added, the compound TeocMeLeu-Ile-MeAla-Aze-EtPh(4-Me)-MeGly can be obtained while avoiding the formation of diketopiperazine. The present inventors have also found that in this process, unreacted deprotected peptides can be removed by performing this reaction in the presence of acetone and performing liquid separation after the reaction. Specifically, it has been revealed that when hydrogenolysis reaction is performed in the presence of 36 equivalents of acetone, the amine nitrogen of an unreacted deprotected peptide is isopropylidenated and thereby inhibited from being converted into diketopiperazine, and this isopropylidenated peptide, which is not amidated at the terminal nitrogen, can easily be removed by acid washing in the liquid separation process after the reaction.

The method of the present invention for producing a peptide compound may further include step 3: removing the C-protecting group Step 3 may be carried out under acidic conditions in the presence of a deprotecting reagent when the C-protecting group is, for example, t-Bu, trityl, cumyl, methyl, or ethyl. As the deprotecting reagent, any reagent known in the art, for example, the reagents described in "Greene's Protective Groups in Organic Synthesis, Fifth Edition, 2014", may be used. In the present invention, to achieve acidic conditions, for example, a combination of HMDS with a reagent selected from the group consisting of TMSOTf, TMSI, TMSBr, and TMSCl is preferably used.

In step 3, as in steps 1 and 2, the reaction and workup can be carried out in one or more solvents (Solvent B) selected independently from the group consisting of toluene, acetone, DMF, acetonitrile, THF, 2-MeTHF, dimethyl carbonate, anisole, isopropyl acetate, heptane, ethyl acetate, and 4-methyltetrahydropyran, and the subsequent process can be carried out without isolating or purifying the product, i.e., the deprotected product of interest. Solvent B preferably contains 2-MeTHF.

Step 3 may be carried out either after step 1 (i.e., between step 1 and step 2) or after step 2. More specifically, since steps 1 and 2 may be repeated a plurality of times in the method of the present invention as described below, step 3 may be performed after step 1 or step 2 in the first round, after step 1 or step 2 in a certain round of the repetition of steps 1 and 2, or after step 1 or step 2 in the final round of the repetition of steps 1 and 2. In an embodiment, step 3 is preferably carried out after step 1 or step 2 in the final round of the repetition of steps 1 and 2, and more preferably after step 1 in the final round of the repetition. When step 3 is carried out after step 1, a linear peptide compound protected only at the N-terminus can be obtained. When step 3 is carried out after step 2, a linear peptide compound deprotected both at the N- and C-termini can be obtained.

In an embodiment, step 3 may be carried out by stirring the reaction mixture for 15 minutes to 48 hours at a temperature of −20° C. to near the boiling point of the solvent, and preferably at a temperature of 0° C. to 180° C.

Repetition of steps 1 and 2

In an embodiment, the method of producing a peptide compound of the present invention comprises repeating steps 1 and 2 as described above, by which the peptide chain can be elongated. There is no limitation on the number of repetition, and is preferably 2 to 20 repetitions, and more preferably, 2 to 15 repetitions. When repeating steps 1 and 2, it is possible for the final round of repetition to not include step 2. In an embodiment, when the final round of repetition does not include step 2, the final step of the method of the present invention may be step 1. In this case, the linear peptide compound produced may be a linear peptide compound whose N- and C-termini are both protected. In an embodiment, when the final round of repetition does not include step 2, step 3 carried out after step 1 may be the final step of the method of the present invention. In this case, the linear peptide compound produced may be a linear peptide compound protected only at the N-terminus.

Workup

After each reaction of steps 1 to 3, workup can be carried out, which can allow subsequent reactions to be performed without the need to isolate the intermediate as a sole product. For example, the workup may include one or a plurality of operations selected from the group consisting of liquid separation operation including washing of organic and aqueous layers, filtration operation, and concentration operation. These operations may be combined appropriately so as to provide conditions suitable for the subsequent steps. For example, when each reaction of steps 1 to 3 is carried out using a condensing reagent or deprotecting reagent, at least one or more liquid separation operation is usually performed as workup. When the reaction of step 2 is performed by catalytic hydrogenation, filtration operation is usually performed as workup. In either case, part of the solvent can be distilled away by performing further concentration operation in order, for example, to adjust the volume of the solvent in preparation for the next step, or to displace the solvent.

In an embodiment, liquid separation may be carried out after completion of each reaction of steps 1 to 3 for liquid-liquid extraction of a product of interest. This operation may include washing of an organic layer or an aqueous layer. When liquid separation is carried out, water and/or an aqueous solution, and/or an organic solvent are added in the system in an amount appropriate for liquid separation, for example, within the range of volume ratio of the organic layer:aqueous layer of 20:80 to 80:20. Aqueous solutions added for liquid separation include aqueous sodium hydrogensulfate solution, aqueous potassium carbonate solution, aqueous sodium carbonate solution, aqueous dipotassium hydrogenphosphate solution, aqueous disodium hydrogenphosphate solution, aqueous sodium dihydrogen phosphate solution, aqueous sodium chloride solution, aqueous citrate solution, aqueous ammonia solution, and aqueous hydrochloric acid solution. Organic solvents added for liquid separation include water-immiscible solvents, water-soluble alkyl nitriles, and water-soluble ethers. Water-immiscible solvents added for liquid separation are herein sometimes referred to as "Solvent C". Specifically, organic solvents added for liquid separation include, for example, one or a plurality of solvents selected from the group consisting of 2-methyltetrahydrofuran (2-MeTHF), dimethyl carbonate, anisole, isopropyl acetate, ethyl acetate, MTBE, CPME, 4-methyltetrahydropyran, heptane, and acetonitrile. For liquid separation, it is preferred that the organic layer contains 2-MeTHF, which shows stability to basicity and good solubility for compounds.

In an embodiment, when solvent B is water-miscible and the aqueous and organic layers do not appropriately separate after each reaction of steps 1 to 3, for example, in cases where a large amount of acetonitrile or THF is contained, the aqueous and organic layers can be separated by adding a water-immiscible solvent (solvent C), in addition to water and/or an aqueous solution, prior to the liquid separation. Whether or not the aqueous and organic layers appropriately separate can be determined by standard methods, for example (but not limited to), where the layers fail to separate into 2 layers after leaving to stand for 1 to 30 minutes after each reaction step 1 to 3. Examples of solvent C include a solvent with low aqueous solubility, for example, a solvent with an aqueous solubility of 999 g/L or less, 500 g/L or less, 250 g/L or less, preferably 200 g/L or less, and more preferably 150 g/L or less. Also, solvents preferable as solvent C include solvents that have positive log Kow or predicted log Kow values, e.g. greater than 0 and less than 5. Specific examples include 2-MeTHF, dimethyl carbonate, ethyl acetate, isopropyl acetate, heptane, anisole, MTBE, CPME, and 4-methyltetrahydropyran. In view of the point that reaction products can be efficiently extracted with an organic solvent, 2-MeTHF, ethyl acetate, isopropyl acetate, or heptane, or a solvent containing them is preferably used.

Solvent C is preferably added in an amount that allows separation of aqueous and organic layers; for example, it may be added in the system in an amount of about 50% by weight to 100% by weight of total organic layer. Separation can be determined by standard methods, for example (but not limited to), subsequent to the addition of Solvent C allowing the mixture to stand for 1 to 30 minutes and monitoring for separation into 2 phases.

In an embodiment, liquid separation operation may include washing of the organic layer or the aqueous layer. The washing in liquid separation may be carried out to remove substances that may become impurities other than the product of interest from the solution that contains the product of interest by using a solution that does not contain the product of interest. The product of interest is usually present in the organic layer, in which cases, substances that may become impurities can be extracted into the aqueous layer and removed by washing the organic layer with an aqueous solution. Meanwhile, in cases where the product of interest is present in the aqueous layer due to, for example, the temporary transfer of the product of interest from the organic layer to the aqueous layer during the process of liquid separation, the aqueous layer is washed.

For the washing of an organic layer, a neutral, basic, or acidic aqueous solution may be used. Specifically, aqueous solutions that can be used for washing organic layers include, aqueous solutions such as an aqueous sodium hydrogensulfate solution, aqueous potassium hydrogensulfate solution, aqueous potassium carbonate solution, aqueous sodium carbonate solution, aqueous dipotassium hydrogenphosphate solution, aqueous disodium hydrogenphosphate solution, aqueous sodium dihydrogen phosphate solution, aqueous sodium chloride solution, aqueous citrate solution, aqueous ammonia solution, and aqueous hydrochloric acid solution. In an embodiment, to sufficiently remove the unreacted amino acids or peptides present in the system, it is preferred to wash the organic layer with an aqueous sodium carbonate solution, an aqueous sodium hydrogensulfate solution, and an aqueous sodium carbonate solution in this order. When the amino acids or peptides still cannot be sufficiently removed, they may be efficiently removed by washing the organic layer with an aqueous solution containing citrate and dipotassium hydrogenphosphate. Also, in an embodiment, to remove amino acids and peptides that are highly lipophilic, it is effective to wash the organic layer with a mixture of acetonitrile and an aqueous potassium carbonate solution.

For washing aqueous layers, water-immiscible organic solvents may be used, and organic solvents such as 2-MeTHF, heptane, MTBE, and isopropyl acetate are suitably used.

The present invention relates to a method for removing BHT (2,6-di-tert-butyl-4-methylphenol), a solvent-derived stabilizing agent. Specifically, the method comprises using a solvent comprising acetonitrile, propionitrile, 2-MeTHF, and heptane, as an organic layer in the liquid separation operation, for example, in the liquid separation operation after each of the steps of the present invention, thereby allowing for efficient removal of BHT. According to this method, the residual amount of BHT in the organic layer may be, in UVArea % value at 210 nm by HPLC analysis, 2.0% or less, 1.9% or less, 1.8% or less, 1.7% or less, 1.6% or less, 1.5% or less, 1.4% or less, 1.3% or less, 1.2% or less, 1.1% or less, 1.0% or less, 0.9% or less, 0.8% or less, 0.7% or less, 0.6% or less, 0.5% or less, 0.4% or less, 0.3% or less, 0.2% or less, 0.1% or less, or 0.05% or less relative to the product of interest. BHT can be removed by using a particular solvent as an organic layer after dissolving the product of interest in an aqueous layer comprising water and water-soluble alkyl nitrile. The water-soluble alkyl nitrile used here is preferably acetonitrile. The organic layer that may be used for removing BHT preferably comprises a water-immiscible solvent. A plurality of water-immiscible solvents may be used in combination, and the preferred combination is 2-MeTHF and heptane, or MTBE and heptane. With regard to the preferred ratio of a solvent to a water-soluble alkyl nitrile, it is preferable to use 100% or more by weight of a water-immiscible solvent, and more preferable to use in the range of 100% or more by weight and 400% or less by weight, and still more preferable to use in the range of 100% or more by weight and 300% or less by weight, thereby allowing for efficient removal of BHT. When 2-MeTHF and heptane, or MTBE and heptane are combined and used, efficient removal of BHT is possible by using 2-MeTHF or MTBE in the range of 10% or more by weight and 100% or less by weight, preferably 10% or more by weight and 80% or less by weight relative to heptane.

Commercially available THF and 2-MeTHF sometimes contain about 150 to 400 ppm of BHT as a stabilizing agent. When such THF or 2-MeTHF is used in a large quantity, the residual amount of BHT would reach, e.g., 4% if the number of the steps is 20 or more, and its adverse effect to the reaction cannot be ignored. By using the method of the present invention, the operation of preliminary removal of BHT from the solvent or isolation operation (e.g., column chromatography) for removing the BHT accumulated during the process becomes unnecessary. Therefore, by applying this method to a large-scale, liquid-phase synthesis of peptides, which comprises multiple processes, sequential elongation of peptide chains may be realized and a peptide compound of interest may be obtained efficiently.

For filtration and concentration in the present invention, any filtration and concentration operations known in the present technical field may be used.

In an embodiment, a solvent, for example, the solvent used for washing a reaction vessel, such as a reaction tank, can be added to the system, before or after one or a plurality of the operations selected from the group consisting of liquid separation operation, filtration operation, and concentration operation as aftertreatments of each step, or before starting the reaction of the next step. Specifically, one or a plurality of solvents independently selected, for example, from the group consisting of toluene, acetone, DMF, acetonitrile, THF, 2-MeTHF, dimethyl carbonate, anisole, isopropyl acetate, heptane, ethyl acetate, and 4-methyltetrahydropyran may be added into the system. Herein, the operation for adding a solvent is included in the workup.

The method of the present invention for producing a peptide compound does not include the process of isolating the generated compounds as the sole product. Thus, the solvent after the workup of step 2 of the first round, or the solvent after the workup of step 2 of a round that comprises repeats of steps 1 and 2, may be used as the reaction solvent (solvent B) for step 1 of the next round thereof. Likewise, the solvent after the workup of step 1 of the first round, or the solvent after the workup of step 1 of a round that comprises repeats of steps 1 and 2, may be used as the reaction solvent (solvent B) for step 2 of that round. That is, as steps 1 and 2 are repeated, the composition of solvent B may change, however, the solvent species composing solvent B may be the same as those used in the reaction of steps 1 and 2 and their workup.

In an embodiment, the solvents (solvent A) used in the method of the present invention for producing a cyclic peptide compound include a solvent after the production of a linear peptide compound produced by the method of the present invention for producing a compound (solvent X). In an embodiment, solvent X may be directly used as solvent A for the cyclization reaction. In another embodiment, solvent A can be provided by further adding, to solvent X, one or more solvents selected from the group consisting of one or more water-immiscible solvents, one or more water-soluble alkyl nitriles, and one or more water-soluble ethers. When preparing solvent A by further adding solvents to solvent X, the solvents to be added include, preferably, 2-MeTHF, dimethyl carbonate, ethyl acetate, isopropyl acetate, anisole, acetonitrile, THF, 4-MeTHP, chlorobenzene, 1,3-dimethoxybenzene, MTBE, and CPME, and acetonitrile, 2-MeTHF, anisole, and dimethyl carbonate are particularly preferred. For example, when solvent A is prepared by adding a solvent, for example, acetonitrile, 2-MeTHF, anisole, or dimethyl carbonate to solvent X, the solvent is preferably added in an amount of 20- to 80-times by weight of solvent X.

While as previously described, steps 1 and 2 may be repeated in the method of the present invention for producing a peptide compound, it is preferred that either one or both of the C-protected peptide and the N-protected peptide used in step 1 of the final round of the repetition comprise 4 or more N-substituted amino acid residues, or 2 or more N-substituted amino acid residues, and comprise one or more α,α di-substituted amino acid residues. The N-substituted amino acid residues are preferably N-alkyl amino acid residues, such as N-methyl or N-ethyl amino acid residues, or N-substituted cyclic amino acid residues, such as proline or Aze(2). The α,α di-substituted amino acid residues are preferably α,α dialkyl amino acid residues, such as α,α dimethyl amino acid residues, and α,α di-substituted cyclic amino acid residues, such as cLeu, in which two groups present at the α-position are linked to form an alicyclic ring.

Also, in an embodiment, it is preferred that either one or both of the C-protected peptide and the N-protected peptide used in step 1 of the final round of the repetition consist of 5 amino acid residues, among which 4 are unnatural amino acid residues.

In another embodiment, it is preferred that either one or both of the C-protected peptide and the N-protected peptide used in step 1 of the final round of the repetition consist of 6 amino acid residues, among which 5 are unnatural amino acid residues.

In an embodiment, the method of the present invention for producing a peptide compound may be utilized to obtain a linear peptide compound to be used as a starting material for the method of the present invention for producing a cyclic peptide compound. For example, when the cyclic peptide compound of formula 1 as shown above is produced according to the method of the present invention for producing a cyclic peptide compound, C-protected MeLeu-Ile-MeAla-Aze(2)-EtPhe(4-Me)-MeGly may be used as the C-protected peptide used in step 1 of the final round of the repetition, and N-protected Hph(4-CF3-35F2)-Pro-cLeu-MeGly(cPent)-MeAsp-NMe2 may be used as the N-protected peptide in step 1 of the final round of the repetition, in order to produce a linear peptide compound that will serve as a starting material for the production.

In an embodiment, the method of the present invention for producing a peptide compound may be used to produce the linear peptide compound of formula (2) as shown above, which may serve as a starting material for producing the cyclic peptide compound of formula (1) as shown above.

Specifically, for example, as the first batch,

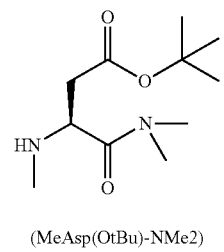

(MeAsp(OtBu)-NMe2)

may be used as the C-protected amino acid, and

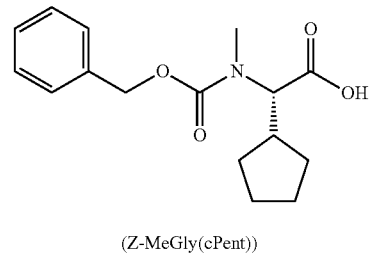 [SMILES: CN(C(=O)OCc1ccccc1)[C@H](C(=O)O)C1CCCC1]

(Z-MeGly(cPent))

may be used as the N-protected amino acid, and

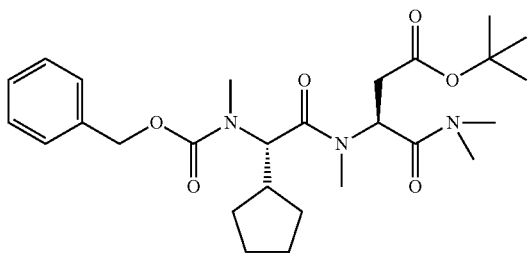

(Z-MeGly(cPent)-MeAsp(OtBu)-NMe2)

may be produced through step 1, and then

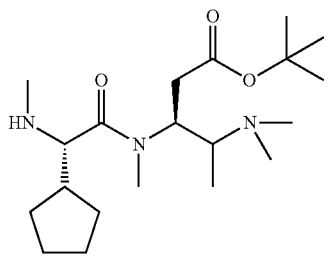

(MeGly(cPent)-MeAsp(OtBu)-NMe2)

may be produced through step 2.

Subsequently, this compound may be used as the C-protected amino acid, and

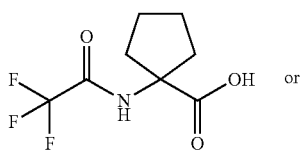

(TFA-cLeu)

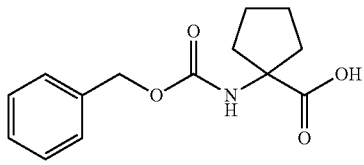

(Cbz-cLeu)

may be used as the N-protected amino acid, and

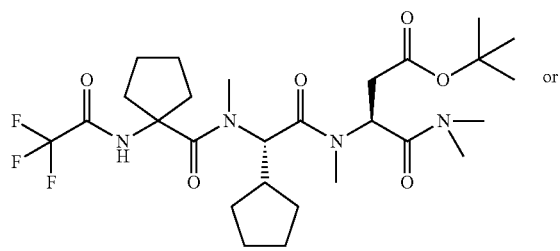

(TFA-cLeu-MEGly(cPent)-MeAsp(OtBu)-NMe2)

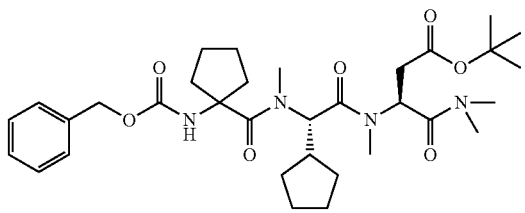

(Cbz-cLeu-MeGly(cPent)-MeAsp(OtBu)-NMe2)

may be produced through step 1, and then

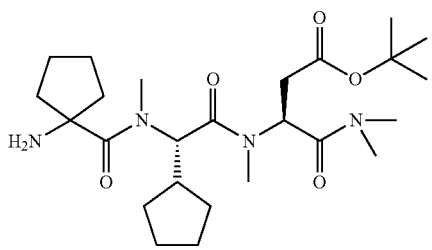

(cLeu-MeGly(cPent)-MeAsp(OtBu)-NMe2)

may be produced through step 2.

Subsequently, this compound may be used as the C-protected peptide, and

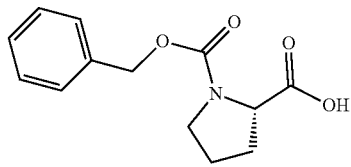

(Z-Pro)

may be used as the N-protected amino acid, and

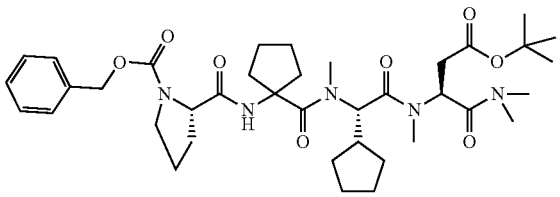

(Z-Pro-cLeu-MeGly(cPent)-MeAsp(OtBu)-NMe2)

may be produced through step 1, and then
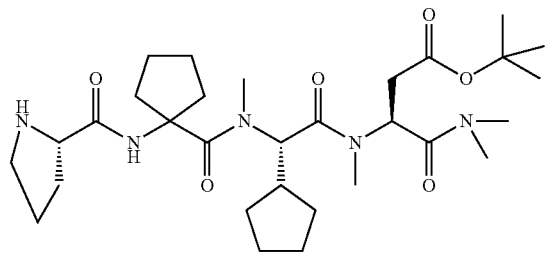
(Pro-cLeu-MeGly(cPent)-MeAsp(OtBu)-NMe2)
may be produced through step 2.
Subsequently, this compound may be used as the C-protected peptide, and
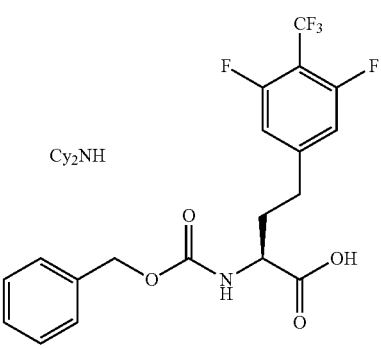
(Z-Hph(4-CF3-35F2) Cy₂NH)
may be used as the N-protected amino acid, and
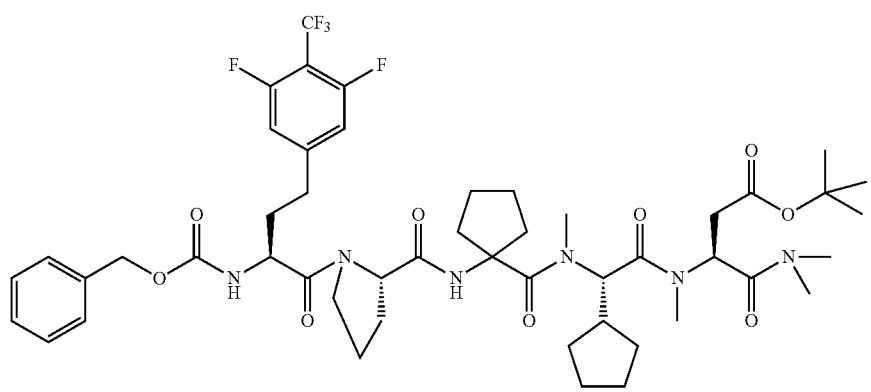
(Z-Hph(4-CF3-35F2)-Pro-cLeu-MeGly(cPent)-MeAsp(OtBu)-NMe2)
may be produced through step 1, and then
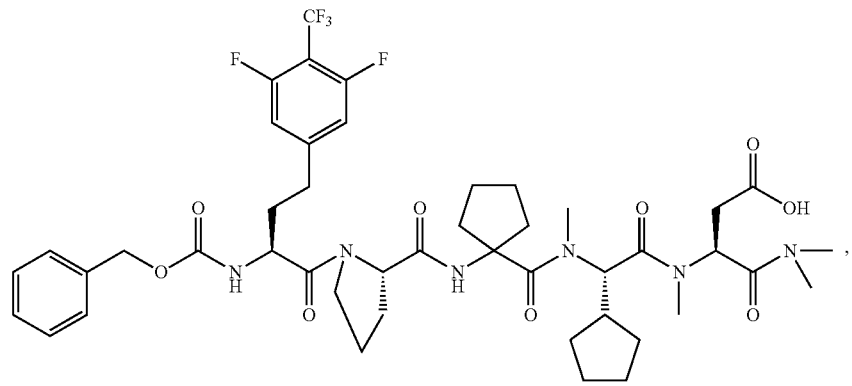
(Z-Hph(4-CF3-35F2)-Pro-cLeu-MeGly(cPent)-MeAsp-NMe2)

which is the product of interest in this batch, may be produced through step 3.

This batch represents the case where step 3 is included after step 1 and the final round of the repetition of steps 1 and 2 does not include step 2.

Next, as the second batch,

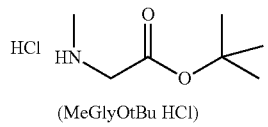

(MeGlyOtBu HCl)

may be used as the C-protected amino acid, and

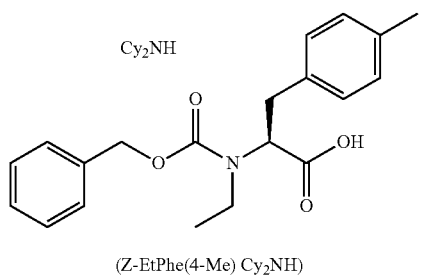 [SMILES: CCN(C(=O)OCc1ccccc1)[C@@H](Cc1ccc(C)cc1)C(=O)O ; "Cy2NH"]

(Z-EtPhe(4-Me) Cy₂NH)

may be used as the N-protected amino acid, and

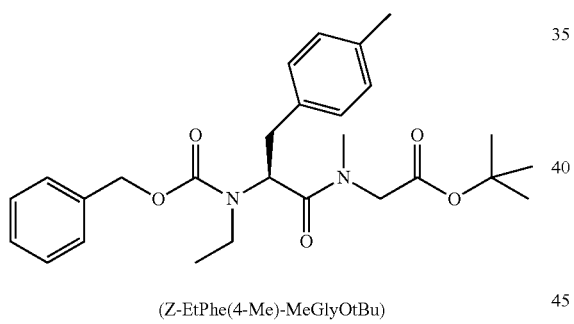

(Z-EtPhe(4-Me)-MeGlyOtBu)

may be produced through step 1, and then

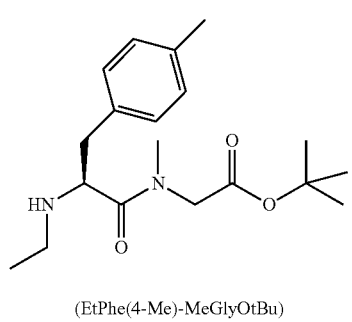 [SMILES: CCN[C@@H](Cc1ccc(C)cc1)C(=O)N(C)CC(=O)OC(C)(C)C]

(EtPhe(4-Me)-MeGlyOtBu)

may be produced through step 2.

Subsequently, this compound may be used as the C-protected peptide, and

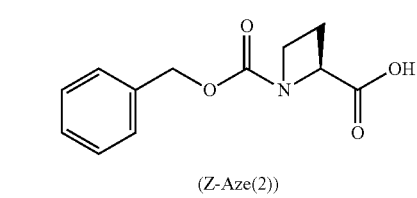 [SMILES: O=C(O)[C@@H]1CCN1C(=O)OCc1ccccc1]

(Z-Aze(2))

may be used as the N-protected amino acid, and

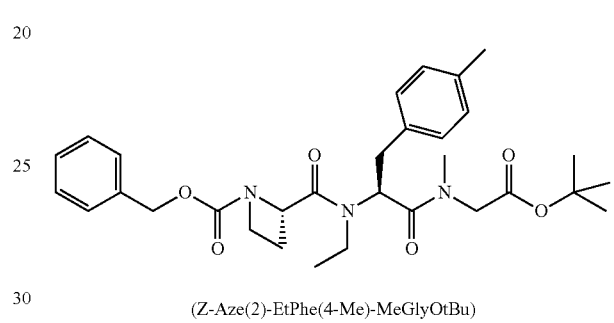

(Z-Aze(2)-EtPhe(4-Me)-MeGlyOtBu)

may be produced through step 1, and then

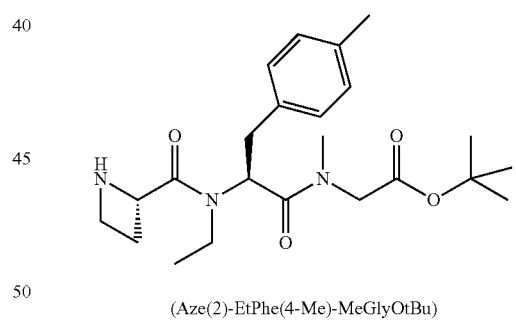

(Aze(2)-EtPhe(4-Me)-MeGlyOtBu)

may be produced through step 2.

Subsequently, this compound may be used as the C-protected peptide, and

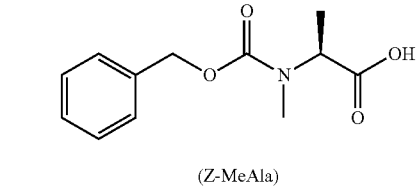 [SMILES: C[C@@H](C(=O)O)N(C)C(=O)OCc1ccccc1]

(Z-MeAla)

may be used as the N-protected amino acid, and

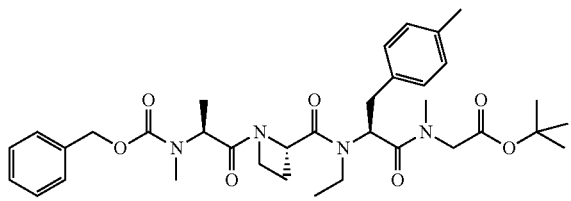

(Z-MeAla-Aze(2)-EtPhe(4-Me)-MeGlyOtBu)

may be produced through step 1, and then

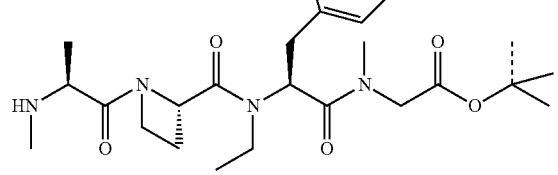

(MeAla-Aze(2)-EtPhe(4-Me)-MeGlyOtBu)

may be produced through step 2.
Subsequently, this compound may be used as the C-protected peptide, and

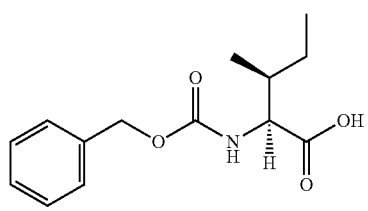

(Z-Ile)

may be used as the N-protected amino acid, and may be produced through step 1, and then

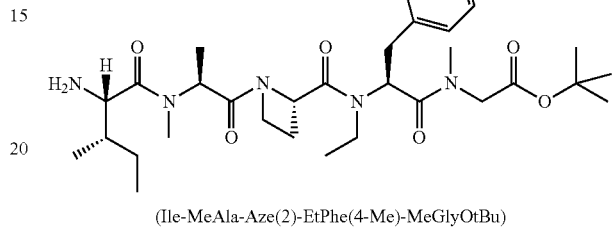

(Ile-MeAla-Aze(2)-EtPhe(4-Me)-MeGlyOtBu)

may be produced through step 2.
Subsequently, this compound may be used as the C-protected peptide, and

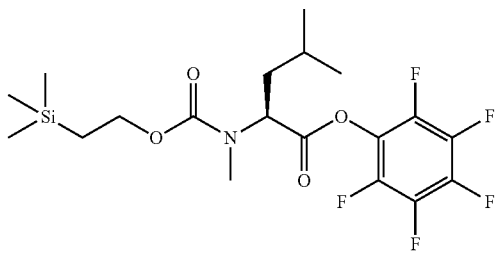

(Teoc-MeLeu-Opfp)

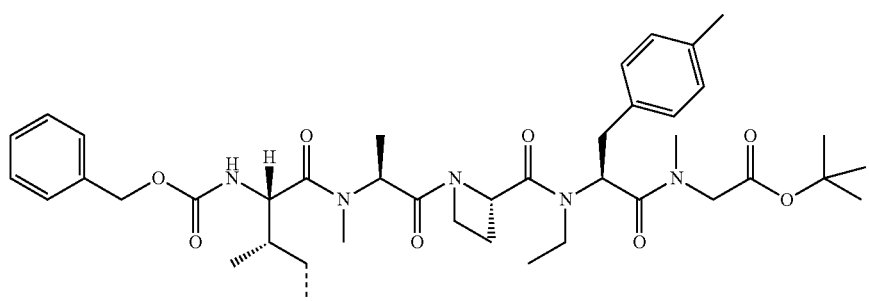

(Z-Ile-MeAla-Aze(2)-EtPhe(4-Me)-MeGlyOtBu)

may be used as the N-protected amino acid, and
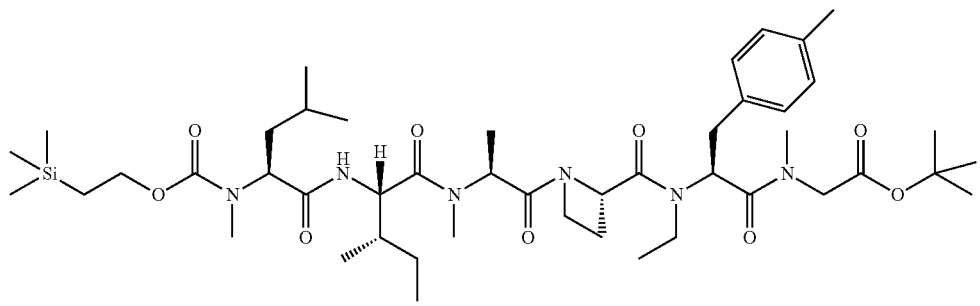
(Teoc-MeLeu-Ile-MeAla-Aze(2)-EtPhe(4-Me)-MeGlyOtBu)
may be produced through step 1, and then
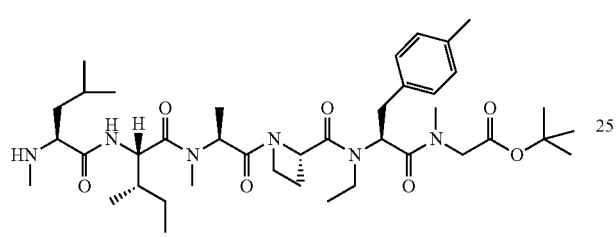
(MeLeu-Ile-MeAla-Aze(2)-EtPhe(4-Me)-MeGlyOtBu)
may be produced through step 2.
Subsequently, this compound may be used as the C-protected peptide, and
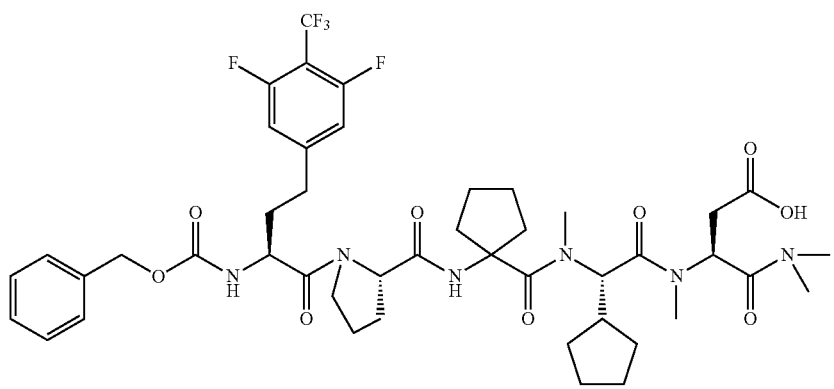 [SMILES: CN(C)C(=O)[C@H](CC(=O)O)N(C)C(=O)[C@H](C1CCCC1)N(C)C(=O)C1(NC(=O)[C@@H]2CCCN2C(=O)[C@H](CCc2cc(F)c(C(F)(F)F)c(F)c2)NC(=O)OCc2ccccc2)CCCC1]
which has been produced in the first batch, may be used as the N-protected amino acid, and

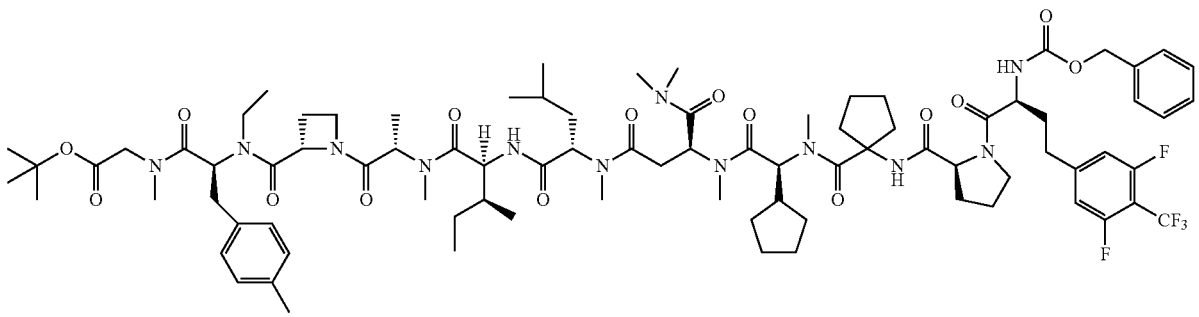

Z-Hph(4-CF3-35F2)-Pro-cLeu-MeGly(cPent)-MeAsp-NMe2-MeLeu-Ile-MeAla-Aze(2)-EtPhe(4-Me)-MeGlyOtBu)

may be produced through step 1, and

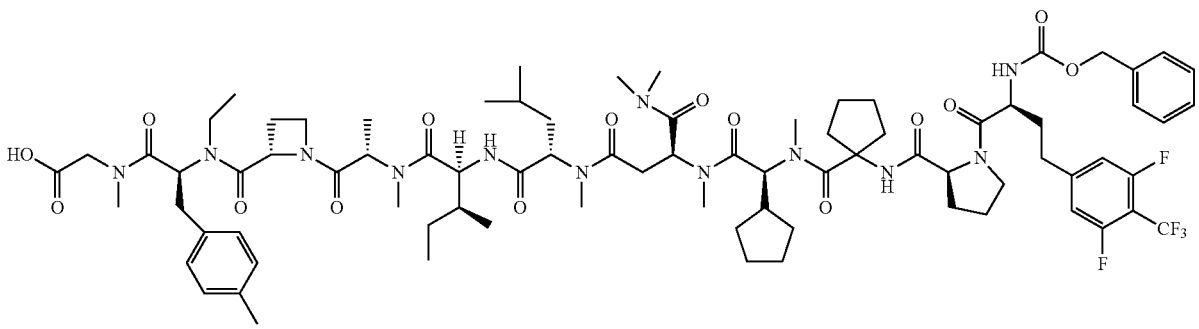

Z-Hph(4-CF3-35F2)-Pro-cLeu-MeGly(cPent)-MeAsp-NMe2-MeLeu-Ile-MeAla-Aze(2)-EtPhe(4-Me)-MeGly)

may be produced through step 3, and then the compound (2):

(2)

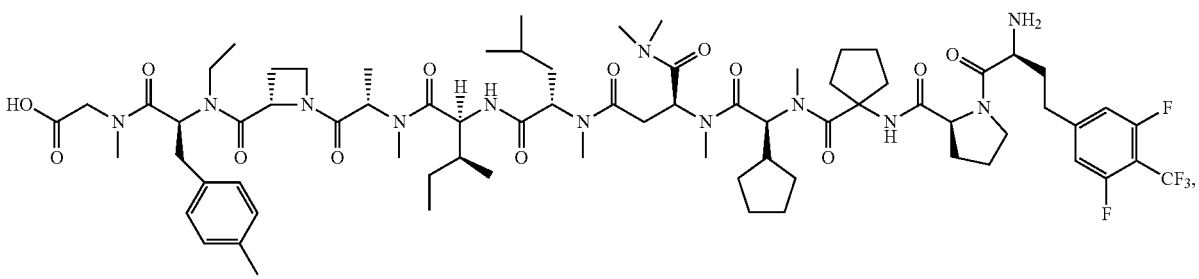

Hph(4-CF3-35F2)-Pro-cLeu-MeGly(cPent)-MeAsp-NMe2-MeLeu-Ile-MeAla-Aze(2)-EtPhe(4-Me)-MeGly)

which is the product of interest in this batch, may be produced through step 2.

This batch represents the case where step 3 is included after step 1 in the final round of the repetition of steps 1 and 2.

Compound 2 obtained in this batch may be utilized as a starting material for the method of the present invention for producing a cyclic peptide compound without performing isolation or purification.

Since a linear peptide compound of interest can be produced efficiently without requiring isolation or purification of intermediates, in any of the above-described batches, in which the method of the present invention is used, the method of the present invention is very useful for large-scale peptide synthesis.

In an embodiment, the method of the present invention for producing a peptide compound may further include the step of linking the N-terminal amino acid residue and the C-terminal amino acid residue of the peptide compound, through which step a cyclic peptide compound can be produced. In an embodiment, the linkage of the N-terminal amino acid residue and the C-terminal amino acid residue is achieved by linking the N-terminal amino acid residue and C-terminal amino acid residue of a linear peptide compound produced by repeating steps 1 and 2 multiple times. In an embodiment, the method described previously in the section "Method for producing cyclic peptide compounds", for example, the reaction conditions and reagents, may be applied in this step.

In an embodiment, the present invention relates to a salt, a solvate, or a solvate of the salt of the cyclic peptide compound represented by formula (1) as shown above. The solvate of the compound is preferably a hydrate or DMSO hydrate.

In an embodiment, the present invention relates to a crystal of a cyclic peptide compound of formula (1) as shown above, or a salt thereof or a solvate thereof. The crystals of the compound include, specifically, an unsolvate crystal or solvate crystal of the compound, or an unsolvate crystal or solvate crystal of a salt of the compound. The solvate crystal preferably includes a hydrate crystal, a DMSO-hydrate crystal, or an acetone-hydrate crystal.

The diffraction angle 2θ in powder X-ray diffraction is the diffraction peak measured using CuKα or CuKα1 radiation.

In an embodiment, when the crystal of the compound of formula (1) is a hydrate crystal, the crystal is a Form C crystal having a powder X-ray diffraction pattern characterized by, as the diffraction angle 2θ in powder X-ray diffraction, at least one peak (e.g., at least 2, at least 3, at least 4, at least 5, at least 6, at least 7, at least 8, at least 9, at least 10, at least 11, at least 12, or all of the peaks) among the following: 4.964°, 7.921°, 8.296°, 8.855°, 9.956°, 10.435°, 11.729°, 12.704°, 13.552°, 13.901°, 15.895°, 16.643°, and 17.813° (±0.2°).

In the notation of diffraction angle 2θ, when the listed diffraction angle 2θ values are followed by "(±0.2°)" in the end denotes that the range of ±0.2° for each of the values is acceptable in all of the listed diffraction angle 2θ.

In an embodiment, the Form C crystal has an X-ray diffraction pattern that is substantially the same as that shown in FIG. 1. In an embodiment, the Form C crystal has a DSC and TG thermogram substantially the same as that shown in FIG. 8.

In an embodiment, when the crystal of the compound of formula (1) is an unsolvate crystal, the crystal is a Form F crystal that has a powder X-ray diffraction pattern characterized by, as the diffraction angle 2θ in powder X-ray diffraction, at least one peak among the following: 5.370°, 6.934°, 8.940°, 9.838°, 10.771°, 12.181°, 13.525°, 15.179°, 16.202°, and 17.554° (±0.20).

Figure 2:
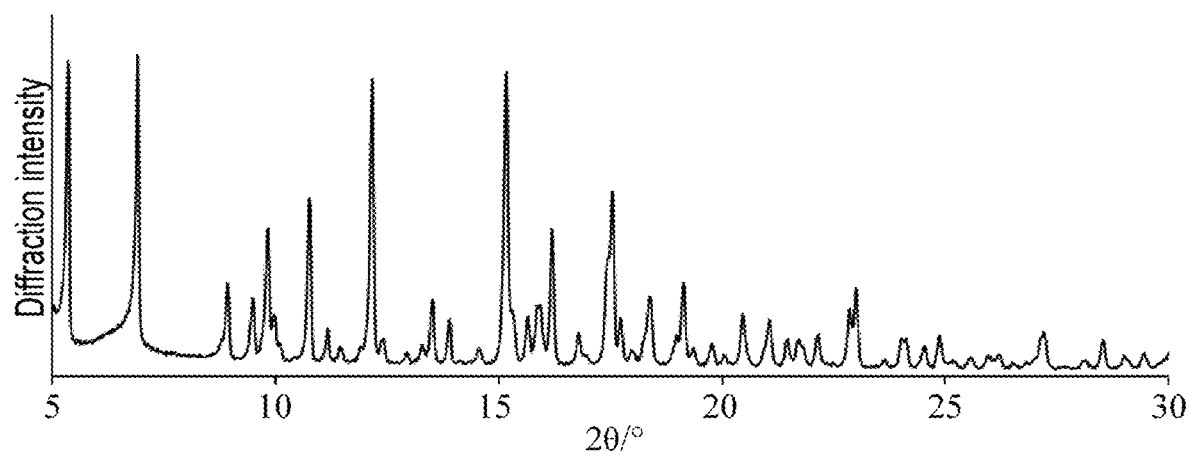
FIG. 2 shows the results of the powder X-ray diffraction measurement of the unsolvate crystal (Form F) of Compound 1 obtained in Example 25-2. The vertical axis indicates the diffraction intensity, and the horizontal axis indicates the diffraction angle 2θ (°).

In an embodiment, the Form F crystal has an X-ray diffraction pattern that is substantially the same as that shown in FIG. 2.

In an embodiment, when the crystal of the compound of formula (1) is a solvate crystal, the crystal is a Form A DMSO-hydrate crystal that has a powder X-ray diffraction pattern characterized by, as the diffraction angle 2θ in powder X-ray diffraction, at least one peak among the following: 8.006°, 9.002°, 9.943° 11.501°, 13.067°, 14.854°, 16.320°, 17.275°, 19.261°, and 20.324° (±0.2°).

Figure 3:
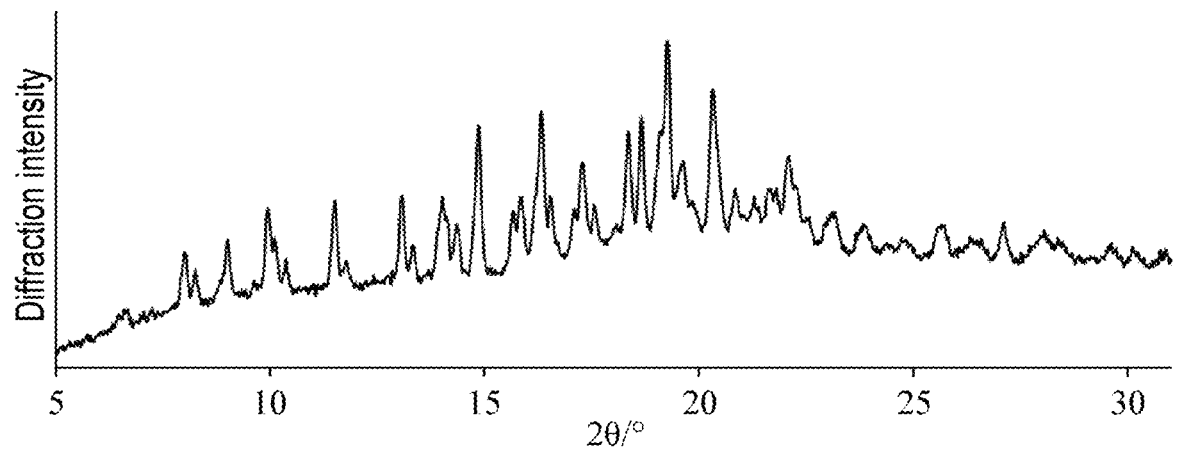
FIG. 3 shows the results of the powder X-ray diffraction measurement of the crystal (Form A) of Compound 1 obtained in Example 25-3. The vertical axis indicates the diffraction intensity, and the horizontal axis indicates the diffraction angle 2θ (°).

In an embodiment, the Form A crystal has an X-ray diffraction pattern that is substantially the same as that shown in FIG. 3.

In an embodiment, when the crystal of the compound of formula (1) is a solvate crystal, the crystal is a Form B DMSO-hydrate crystal that has a powder X-ray diffraction pattern characterized by, as the diffraction angle 2θ in powder X-ray diffraction, at least one peak among the following: 8.223°, 9.594° 9.976°, 11.879°, 13.841°, 14.572°, 15.934°, 16.350°, 19.805°, and 20.480° (±0.20).

Figure 4:
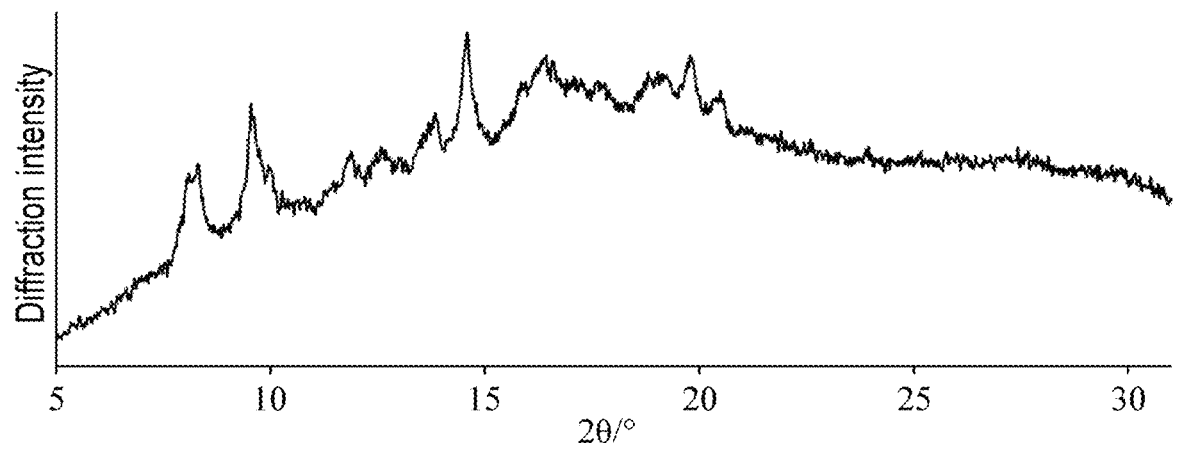
FIG. 4 shows the results of the powder X-ray diffraction measurement of the crystal (Form B) of Compound 1 obtained in Example 25-3. The vertical axis indicates the diffraction intensity, and the horizontal axis indicates the diffraction angle 2θ (°).

In an embodiment, the Form B crystal has an X-ray diffraction pattern that is substantially the same as that shown in FIG. 4. In an embodiment, the Form B crystal has a DTA thermogram that is substantially the same as that shown in FIG. 5.

In an embodiment, when the crystal of the compound of formula (1) is a solvate crystal, the crystal is a Form H acetone-hydrate crystal that has a powder X-ray diffraction pattern characterized by, as the diffraction angle 2θ in powder X-ray diffraction, at least one peak among the following: 7.942°, 8.283°, 8.861°, 10.097°, 10.491°, 11.805°, 12.673°, 12.830°, 13.514°, 13.855°, 15.853°, 16.405°, 16.642°, and 17.772° (±0.2°).

Figure 13:
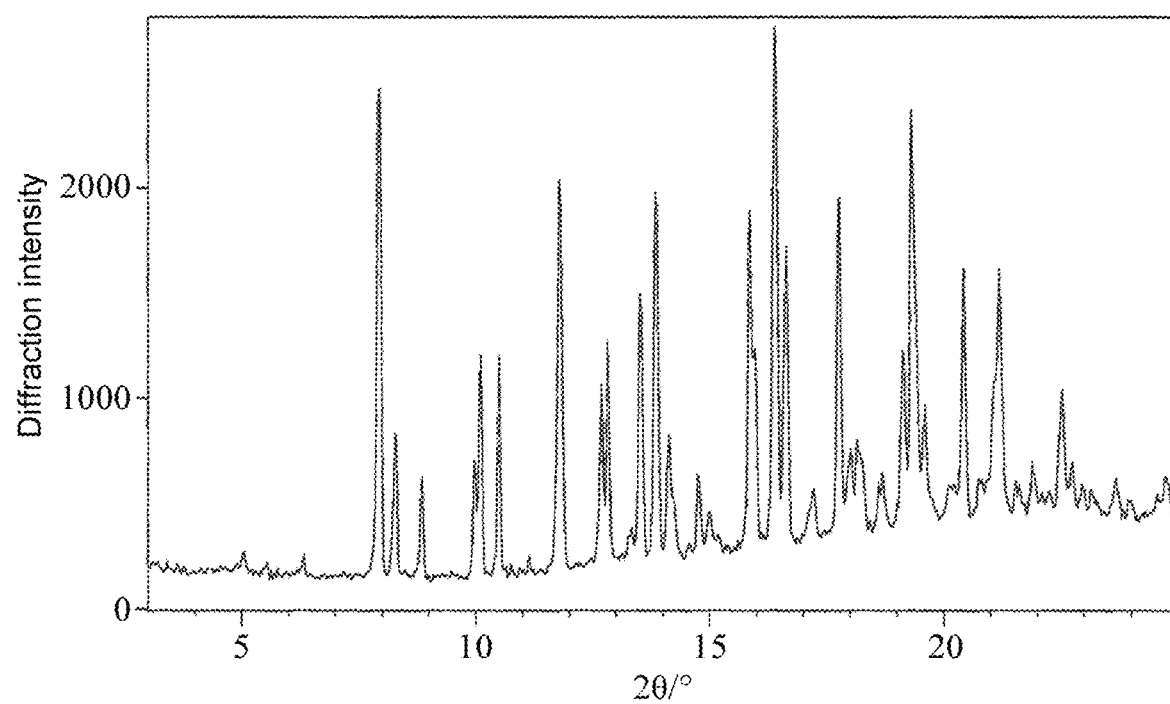
FIG. 13 shows the results of powder X-ray diffraction measurements of the acetone-hydrate crystal (Form H, for powder X-ray diffraction measurement) of Compound 1 obtained in Example 26-2. The vertical axis indicates the diffraction intensity, and the horizontal axis indicates the diffraction angle 2θ (°).

In an embodiment, the Form H crystal has an X-ray diffraction pattern that is substantially identical to that shown in FIG. 13.

In an embodiment, the crystals of the compound of formula (1) in any form do not substantially contain impurities. For example, the crystals of the compound of formula (1) may have a purity of at least about 90%. In an embodiment, the crystals of the compound of formula (1) has a purity of at least about 95%. In an embodiment, the crystals of the compound of formula (1) has a purity of at least about 98%. For example, the crystals of the compound of formula (1) may have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In an embodiment, the crystals of the compound represented by formula (1) do not substantially include other forms. In an embodiment, Form C is substantially free of other forms of the compound represented by formula (1). In an embodiment, Form F is substantially free of other forms of the compound represented by formula (1). In an embodiment, Form A is substantially free of other forms of the compound represented by formula (1). In an embodiment, Form B is substantially free of other forms of the compound represented by formula (1). In an embodiment, Form H is substantially free of other forms of the compound represented by formula (1).

In an embodiment, the present invention relates to a method for producing a hydrate crystal of the cyclic peptide compound represented by formula (1) as shown above. The method comprises the following steps:

Step A: dissolving the cyclic peptide compound in a polar organic solvent in an amount capable of dissolving the cyclic peptide compound to obtain a solution;

Step B: concentrating the solution to obtain a residue of the cyclic peptide compound; and Step C: adding a mixture of water and a polar organic solvent to the residue to obtain a hydrate crystal of the cyclic peptide compound.

In an embodiment, as the polar organic solvent used in step A, it is possible to use a solvent which is capable of dissolving the cyclic peptide compound of formula (1), for example, the cyclic peptide compound in a partially purified state. Specifically, DMSO, DMF, DMA, NMP, acetone, methanol, ethanol, and acetonitrile are preferably exemplified, and acetone, DMSO, and ethanol are more preferably exemplified. The amounts capable of dissolving include a range of from 3 to 10 w/v, and preferably a range of from 3 to 7 w/v, relative to the cyclic peptide compound of formula (1).

In an embodiment, the concentration in step B includes lyophilization. In an embodiment, the residue obtained in step B may be an amorphous, an oily material, or a solid. In an embodiment, the residue obtained in step B may be a lyophilizate.

In an embodiment, the polar organic solvent used in step C may be the same solvent as the polar organic solvent used in step A. The mixing ratio of water and polar organic solvent in the mixture used in step C may be 0.5 to 10 parts by weight of water, preferably 1 to 7 parts by weight of water, and further preferably 1 to 5 parts by weight of water to 1 part by weight of the polar organic solvent. The polar organic solvent used in step C is preferably acetonitrile, ethanol, or acetone.

The present invention relates to a method for producing a crystal of the cyclic peptide compound represented by formula (1) as shown above. The production method comprises the steps of:
- dissolving the cyclic peptide compound in an amorphous state into DMSO to obtain a solution;
- lyophilizing the solution to obtain a lyophilizate of the cyclic peptide compound; and
- adding a water-acetonitrile mixture to the lyophilizate to obtain a hydrate crystal of the cyclic peptide compound.

All prior art literature cited in the present specification are incorporated herein by reference.

EXAMPLES

The content of the present invention is explained further by the following Examples, but the invention is not limited thereto. Other than those described specifically, starting substances, starting materials, solvents, and reagents were obtained from commercial suppliers or synthesized by commonly known methods. Compound 2 and Compound 30 were produced by the method described in WO2020/189540.

HPLC Analysis Conditions were as Follows:
HPLC Analysis Conditions—Method 1
  Apparatus: Waters ACQUITY UPLC H-Class
  Column: Ascentis Express 90A $C_{18}$ (Sigma-Aldrich), 2.1 mm ID×50 mm, 2.7 μm
  Mobile phase: 0.05% TFA/water (A), 0.05% TFA/MeCN (B)
  Elution method: B) 5% (0 min)→100% (5 min)→5% (5.1 min)→5% (7 min)
  Flow rate: 0.5 mL/min
  Column temperature: 35° C.
  Detection wavelength: 210 nm (PDA)
HPLC Analysis Conditions—Method 2
  Apparatus: Waters ACQUITY UPLC H-Class
  Column: Ascentis Express 90A $C_{18}$ (Sigma-Aldrich), 2.1 mm ID×50 mm, 2.7 μm
  Mobile phase: 0.05% TFA/water (A), 0.05% TFA/MeCN (B)
  Elution method: B) 5% (0 min)→100% (6 min)→5% (6.1 min)→5% (8 min)
  Flow rate: 0.5 mL/min
  Column temperature: 35° C.
  Detection wavelength: 210 nm (PDA)
HPLC Analysis Conditions—Method 3
  Apparatus: Waters ACQUITY UPLC H-Class
  Column: CAPCELL CORE ADME (OSAKA SODA), 2.1 mm ID×50 mm, 2.7 μm
  Mobile phase: 0.05% TFA/water (A), 0.05% TFA/MeCN (B)
  Elution method: B) 5% (0 min)→100% (5 min)→5% (5.1 min)→5% (7 min)
  Flow rate: 0.5 mL/min
  Column temperature: 35° C.
  Detection wavelength: 210 nm (PDA)
HPLC Analysis Conditions—Method 4
  Apparatus: Waters ACQUITY UPLC H-Class
  Column: ACQUITY UPLC CSH C18 (Waters), 2.1 mm ID×100 mm, 1.7 μm
  Mobile phase: 0.05% TFA/water (A), 0.05% TFA/MeCN (B)
  Elution method: B) 20% (0 min)→100% (10 min)→100% (13.5 min)→20% (13.6 min)→20% (18.0 min)
  Flow rate: 0.3 mL/min
  Column temperature: 50° C.
  Detection wavelength: 210 nm (PDA)
HPLC Analysis Conditions—Method 5
  Apparatus: Waters ACQUITY UPLC H-Class
  Column: ACQUITY UPLC CSH C18 (Waters), 2.1 mm ID×150 mm, 1.7 μm
  Mobile phase: 0.05% TFA/water (A), 0.05% TFA/MeCN (B)
  Elution method: B) 20% (0 min)→100% (24 min)→100% (29 min)→20% (29.1 min)→20% (34 min)
  Flow rate: 0.3 mL/min
  Column temperature: 50° C.
  Detection wavelength: 220 nm (PDA)
HPLC Analysis Conditions—Method 6
  Apparatus: Waters ACQUITY UPLC H-Class
  Column: CAPCELL CORE ADME (OSAKA SODA), 2.1 mm ID×50 mm, 2.7 μm
  Mobile phase: 0.05% TFA/water (A), 0.05% TFA/MeCN (B)
  Elution method: B) 5%(0 min)→100% (10 min)→5% (10.1 min)→5% (12 min)
  Flow rate: 0.5 mL/min
  Column temperature: 35° C.
  Detection wavelength: 210 nm (PDA)

TABLE 1

| Example No. (Compound No.) | HPLC analysis condition | Retention time (min) |
| --- | --- | --- |
| Example 1 (Compound 4) | method 1 | 4.500 |
| Example 2 (Compound 5) | method 1 | 2.389 |
| Example 3 (Compound 7) | method 1 | 4.065 |
| Example 4 (Compound 8) | method 1 | 2.538 |
| Example 5 (Compound 10) | method 1 | 4.004 |
| Example 6 (Compound 11) | method 1 | 2.510 |
| Example 7 (Compound 13) | method 1 | 4.235 |
| Example 8 (Compound 15) | method 2 | 6.175 |
| Example 9 (Compound 16) | method 2 | 5.964 |
| Example 10 (Compound 17) | method 1 | 3.057 |
| Example 11 (Compound 19) | method 3 | 3.510 |
| Example 12 (Compound 20) | method 3 | 1.560 |
| Example 13 (Compound 22) | method 3 | 4.356 |
| Example 14 (Compound 23) | method 3 | 2.297 |
| Example 15 (Compound 25) | method 3 | 6.166 |
| Example 15-1 (Compound 25a) | method 6 | 6.712 |
| Example 16 (Compound 26) | method 3 | 2.725 |
| Example 17 (Compound 28) | method 3 | 4.189 |
| Example 18 (Compound 29) | method 3 | 2.846 |
| Example 19 (Compound 31) | method 3 | 4.978 |
| Example 20 (Compound 32) | method 3 | 4.220 |
| Example 21 (Compound 33) | method 4 | 10.272 |
| Example 22 (Compound 34) | method 4 | 9.215 |
| Example 23 (Compound 35) | method 4 | 6.480 |
| Example 24 (Compound 1) | method 5 | 18.008 |

LCMS analysis conditions were as follows:
LCMS Analysis Conditions—Method 1
  Apparatus: Waters ACQUITY UPLC H-Class+ACQUITY QDA
  Column: Ascentis Express 90A C18 (Sigma-Aldrich), 2.1 mm ID×50 mm, 2.7 μm
  Mobile phase: 0.05% TFA/water (A), 0.05% TFA/MeCN (B)
  Elution method: B) 5% (0 min)→100% (5 min)→5% (5.1 min)→5% (7 min)
  Flow rate: 0.5 mL/min
  Column temperature: 35° C.
  Detection wavelength: 210 nm (PDA)

LCMS Analysis Conditions—Method 2
  Apparatus: Waters ACQUITY UPLC H-Class+ACQUITY QDA
  Column: Ascentis Express 90A C18 (Sigma-Aldrich), 2.1 mm ID×50 mm, 2.7 μm
  Mobile phase: 0.05% TFA/water (A), 0.05% TFA/MeCN (B)
  Elution method: B) 5% (0 min)→100% (6 min)→5% (6.1 min)→5% (8 min)
  Flow rate: 0.5 mL/min
  Column temperature: 35° C.
  Detection wavelength: 210 nm (PDA)
LCMS Analysis Conditions—Method 3
  Apparatus: Waters ACQUITY UPLC H-Class+ACQUITY QDA
  Column: CAPCELL CORE ADME (OSAKA SODA), 2.1 mm ID×50 mm, 2.7 μm
  Mobile phase: 0.05% TFA/water (A), 0.05% TFA/MeCN (B)
  Elution method: B) 5% (0 min)→100% (5 min)→5% (5.1 min)→5% (7 min)
  Flow rate: 0.5 mL/min
  Column temperature: 35° C.
  Detection wavelength: 210 nm (PDA)
LCMS Analysis Conditions—Method 4
  Apparatus: Waters SQD2
  Column: ACQUITY UPLC CSH C18 (Waters), 2.1 mm ID×100 mm, 1.7 μm
  Mobile phase: 0.05% TFA/water (A), 0.05% TFA/MeCN (B)
  Elution method: B) 20% (0 min)→100% (10 min)→100% (13.5 min)→20% (13.6 min)→20% (18.0 min)
  Flow rate: 0.3 mL/min
  Column temperature: 50° C.
  Detection wavelength: 210 nm (PDA)
LCMS Analysis Conditions—Method 5
  Apparatus: Waters SQD2
  Column: ACQUITY UPLC CSH C18 (Waters), 2.1 mm ID×150 mm, 1.7 μm
  Mobile phase: 0.05% TFA/water (A), 0.05% TFA/MeCN (B)
  Elution method: B) 20% (0 min)→100% (24 min)→100% (29 min)→20% (29.1 min)→ 20% (34 min)
  Flow rate: 0.3 mL/min
  Column temperature: 50° C.
  Detection wavelength: 220 nm (PDA)
LCMS Analysis Conditions—Method 6
  Apparatus: Waters ACQUITY UPLC H-Class+ACQUITY QDA
  Column: CAPCELL CORE ADME (OSAKA SODA), 2.1 mm ID×5 mm, 2.7 m
  Mobile phase: 0.05% TFA/water (A), 0.05% TFA/MeCN (B)
  Elution method: B) 5% (0 min)→100% (10 min)→5% (10.1 min)→5% (12 min)
  Flow rate: 0.5 mL/min
  Column temperature: 35° C.
  Detection wavelength: 210 nm (PDA)

TABLE 2

| Example No. (Compound No.) | LCMS analysis condition | Retention time (min) | MS Found (m/z) | MS polarity |
| --- | --- | --- | --- | --- |
| Example 1 (Compound 4) | method 1 | 4.507 | 469 | [M+H]+ |
| Example 2 (Compound 5) | method 1 | 2.411 | 335 | [M+H]+ |
| Example 3 (Compound 7) | method 1 | 4.083 | 574 | [M+Na]+ |
| Example 4 (Compound 8) | method 1 | 2.578 | 418 | [M+H]+ |
| Example 5 (Compound 10) | method 1 | 4.011 | 659 | [M+Na]+ |
| Example 6 (Compound 11) | method 1 | 2.536 | 503 | [M+H]+ |
| Example 7 (Compound 13) | method 1 | 4.260 | 772 | [M+Na]+ |
| Example 8 (Compound 15) | method 2 | 5.791 | 428 | [M-CH2=CH2+H]+ |
| Example 9 (Compound 16) | method 2 | 5.950 | 910 | [M+Na]+ |
| Example 10 (Compound 17) | method 1 | 2.978 | 743 | [M+H]+ |
| Example 11 (Compound 19) | method 3 | 3.496 | 387 | [M+Na]+ |
| Example 12 (Compound 20) | method 3 | 1.532 | 231 | [M+H]+ |
| Example 13 (Compound 22) | method 3 | 4.329 | 526 | [M+Na]+ |
| Example 14 (Compound 23) | method 3 | 2.229 | 370 | [M+H]+ |
| Example 15 (Compound 25) | method 3 | 6.181 | 599 | [M+Na] |
| Example 15-1 (Compound 25a) | method 6 | 6.696 | 637 | [M+Na] |
| Example 16 (Compound 26) | method 3 | 2.749 | 503 | [M+Na] |
| Example 17 (Compound 28) | method 3 | 4.206 | 735 | [M+Na] |
| Example 18 (Compound 29) | method 3 | 2.839 | 578 | [M+H]+ |
| Example 19 (Compound 31) | method 3 | 4.827 | 1000 | [M+Na]+ |
| Example 20 (Compound 32) | method 3 | 4.133 | 943 | [M+Na]+ |
| Example 21 (Compound 33) | method 4 | 10.53 | 1669 | [M+Na]+ |
| Example 22 (Compound 34) | method 4 | 9.47 | 1613 | [M+Na]+ |
| Example 23 (Compound 35) | method 4 | 6.71 | 1457 | [M+H]+ |
| Example 24 (Compound 1) | method 5 | 18.36 | 1439 | [M+H]+ |

$^1$H-NMR spectra were obtained by taking measurements using a nuclear magnetic resonance apparatus ECX500II (manufactured by JEOL Ltd.), the chemical shift of Me$_4$Si used as the internal standard was set at 0 ppm, and the deuterium lock signal from the sample solvent was referenced. Sample solutions were prepared by using a commercially available deuterated solvent suitable for the purpose of the measurement as the sample solvent, and mixing the solvent with the compound to be measured. The integral values of the signals were calculated based on the ratio of signal area intensities of the respective signals.

Measurements by qNMR was performed by dissolving a residue containing the compound of interest and an internal standard into DMSO-d$_6$, and using the following analysis conditions. The yield was calculated by the following equation using the value for content of the product of interest in the residue as determined by qNMR, and the value for purity of the product of interest in the residue as determined by HPLC analysis.

$$\text{Yield (\%)} = \frac{\text{Weight of residue (mg)} \times \text{Content (\%)} \times \text{Purity (\%)}}{\text{Theoretical yield (mg)}} \times 100$$

Measurement Apparatus: JNM-ECZ500R
Internal standard substance: 3,5-bis(trifluoromethyl)benzoic acid
Measurement conditions ($^1$H-NMR): DMSO-$d_6$, 24.3° C., pulse angle: 90°, digital resolution: 0.25 Hz, relaxation time: 60 seconds, no spin, cumulative number: 8 times
Measurement conditions ($^{19}$F-NMR): DMSO-$d_6$, 24.3° C., pulse angle: 90°, digital resolution: 0.22 Hz, relaxation time: 60 seconds, no spin, cumulative number: 8 times X-ray powder diffraction (XRPD) measurements were taken under the following conditions, and the scanning range 2θ values were calculated. X-ray diffraction patterns were plotted with the diffraction angle (2θ value) on the horizontal axis and the diffraction intensity on the vertical axis.

Measurement Method 1
  Measurement apparatus: SmartLab System (manufactured by Rigaku Corporation)
  Radiation source: CuKα1
  Tube voltage: 45 kV
  Tube current: 200 mA
  Scanning range: 3-350
  Sampling width: 0.02°
Measurement Method 2
  Measurement apparatus: SmartLab System, D/Tex Ultra detector (manufactured by Rigaku Corporation)
  Radiation source: CuKα1
  Tube voltage: 45 kV
  Tube current: 200 mA
  Scanning range: 5-30°
  Scanning speed: 5°/min
  Sampling width: 0.02°
Measurement Method 3
  Measurement apparatus: D8 Discover, 2D VANTEC-500 solid state detector (manufactured by Bruker)
  Radiation source: CuKα
  Tube voltage, Tube current: 40 kV, 40 mA; or 50 kV, 1000 µA (when using IµS microfocus X-ray source)
  Measurement range: 5-31°
  Exposure time: 100 seconds or 600 seconds (when using IµS microfocus X-ray source)
Measurement Method 4
  Measurement apparatus: X'pert-pro MPD (manufactured by PANalytical)
  Radiation source: CuKα
  Tube voltage: 45 kV
  Tube current: 40 mA
  Scanning range: 3-40°
  Scanning speed: 4.2°/min
  Sampling width: 0.017°
Measurement Method 4
  Measurement apparatus: X'pert-pro MPD (manufactured by PANalytical)
  Radiation source: Cu
  Tube voltage: 45 kV
  Tube current: 40 mA
  Scanning range: 3-25°
  Scanning speed: 0.33°/sec
  Sampling width: 0.026°
  Measurement: Capillary for X-ray crystal analysis was loaded with the sampled suspension, and measurements were taken.

Thermal analysis measurements were taken under the following conditions.
(Measurement Method 1)
  Measurement apparatus: EXSTAR TG/DTA6200R apparatus (manufactured by Seiko Instruments (current company name: Hitachi High-Tech Science))
  Measurement range: 30-350° C.
  Heating rate: 10° C./min
  Atmosphere: Nitrogen
Measurement Method 2
  Measurement apparatus: SmartLab System, DSC attachment (manufactured by Rigaku Corporation)
  Measurement Range: 35-270° C.
  Atmosphere: Nitrogen
  DSC conditions are shown in Table 3

TABLE 3

| Temperature (° C.) | Heating rate (°C/min) | Retention time (min) |
|---|---|---|
| 35.0 | 5.0 | 0 |
| 270.0 | 5.0 | 5 |
| 35.0 | 20.0 | 5 |

Measurement Method 3
  Measurement apparatus: STA7200RV+AS-3T (manufactured by Hitachi High-Tech Science)
  Measurement range: 30-350° C.
  Heating rate: 10° C./min
  Atmosphere: Nitrogen
Measurement Method 4
  Measurement apparatus: TGA/DSC 3+(manufactured by Mettler Toledo)
  Measurement range: 25-350° C.
  Heating rate: 10° C./min
  Atmosphere: Dry Nitrogen A mixed solution containing the compound of interest was subjected to any of the following methods for sample preparation, and the HPLC measurement method was performed under the above-mentioned analysis conditions.
  Sample preparation method 1: a mixed solution containing the compound of interest was diluted with acetonitrile.
  Sample preparation method 2: a mixed solution containing the compound of interest was diluted with a mixed solution formed by mixing acetonitrile and propylamine at a ratio of 9:1.
  Sample preparation method 3: a mixed solution containing the compound of interest was diluted with methanol.
  Sample preparation method 4: a mixed solution containing the compound of interest was diluted with a mixed solution formed by mixing methanol and water at a ratio of 4:1.

The reaction conversion rate was calculated by any of the following equations by using the area value of the starting material and area value of the product of interest; or the area value of the starting material, the area value of the propylamide derivative of the starting material, and the area value of the product of interest; or the area value of the starting material before the reaction and the area value of the starting material after the reaction, that had been calculated from HPLC analyses.

Reaction conversion rate (%)=area value of the product of interest/(area value of the starting material+area value of the product of interest)× 100   Equation 1

Reaction conversion rate (%)=area value of the product of interest/(area value of the starting material+area value of the propylamide derivative of the starting material+area value of the product of interest)×100   Equation 2

Reaction conversion rate (%)=100−(area value of the starting material after the reaction/area value of the starting material before the reaction×100)   Equation 3

Example 1

Compound 4: Synthesis of (tert-butyl 2-[[(2S)-2-[benzyloxycarbonyl(ethyl)amino]-3-(p-tolyl)propanoyl]-methyl-amino]acetate)

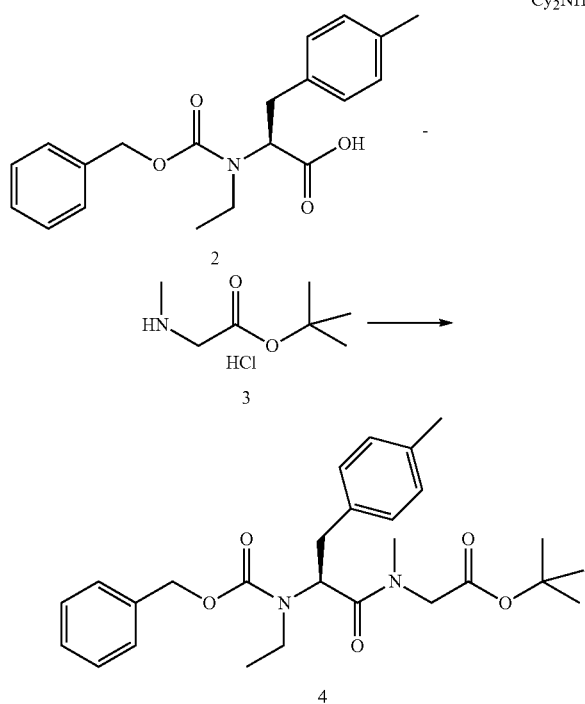

To a reaction tank purged with nitrogen, Compound 2 (4.60 kg) and Compound 3 (1.92 kg) were added at room temperature, then 2-MeTHF (22.8 kg) was added, and this mixture was stirred. The external temperature of the reaction tank was set at 10° C., and addition of DIPEA (6.15 kg) was followed by dropwise addition of T3P (50 w/w % 2-MeTHF solution, 13.45 kg). The external temperature of the reaction tank was set at 25° C., and the mixture was stirred for 5 hours. The reaction mixture was sampled, sample preparation was carried out (Sample preparation method 2), and the reaction conversion rate was confirmed to be 99.6% by HPLC analysis (Equation 2 for reaction conversion rate calculation). The external temperature of the reaction tank was set at 10° C., and while stirring, 5% aqueous sodium carbonate solution (26.6 kg) was added dropwise, and then water (6.9 kg) was added. The external temperature of the reaction tank was set at 25° C., and after stirring the mixture for 20 minutes, the aqueous layer was removed from the reaction tank. Similarly at an external temperature of 25° C., the resulting organic layer was washed with 5% aqueous sodium hydrogen sulfate monohydrate solution (34.5 kg×3) and 5% aqueous sodium carbonate solution (34.5 kg). The resulting organic layer was recovered in a storage container, and this was combined with a wash solution obtained by washing the reaction tank with 2-MeTHF (25.6 kg) to produce a storage solution, and this was recovered in the storage container. The storage solution was added to a reaction tank purged with nitrogen while washing the inside of the storage container with 2-MeTHF (1.7 kg). The external temperature of the reaction tank was set at 50° C., and the mixture was concentrated under reduced pressure until the liquid volume reached approximately 12 L. The obtained residue was recovered in a storage container, and this was combined with a wash solution obtained by washing the reaction tank with 2-MeTHF (8.5 kg) to afford a 2-MeTHF solution (17.8 kg) containing Compound 4. Retention time by HPLC analysis: 4.500 minutes (HPLC analysis conditions: method 1)

Example 2

Compound 5: Synthesis of (tert-butyl 2-[[(2S)-2-(ethylamino)-3-(p-tolyl)propanoyl]-methyl-amino]acetate)

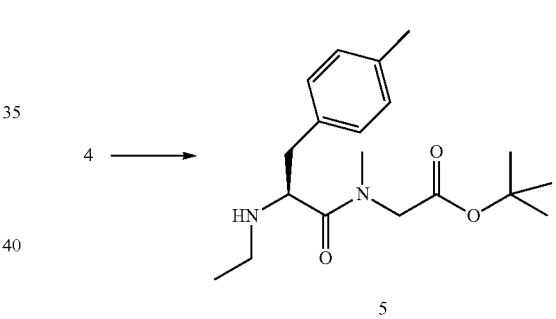

To a reaction tank purged with nitrogen, the 2-MeTHF solution (16.9 kg) containing Compound 4 obtained in Example 1 and 2-MeTHF (8.6 kg) were added, and then 5% Pd/C (1.78 kg, 50% wetted with water) was added. The external temperature of the reaction tank was set at 25° C., and the reaction tank was pressurized with hydrogen until the internal pressure reached 0.18 MPaG. One hour later, after confirming absence of internal pressure change, purging with nitrogen was followed by further pressurization with hydrogen to 0.18 MPaG, and the mixture was stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). After purging the interior of the reactor with nitrogen, the reaction mixture was subjected to pressure filtration. The reaction tank and the filtration apparatus were washed with 2-MeTHF (10.8 kg), and then the filtrate and the wash solution were recovered in a storage container as a storage solution. The obtained filtrate and the wash solution were concentrated under reduced pressure at an external temperature of 40° C. until the liquid volume reached approximately 5 L. This was combined with a wash solution

Example 3

Compound 7: Synthesis of (benzyl (2S)-2-[[(1S)-2-[(2-tert-butoxy-2-oxo-ethyl)-methyl-amino]-2-oxo-1-(p-tolylmethyl)ethyl]-ethyl-carbamoyl]azetidine-1-carboxylate)

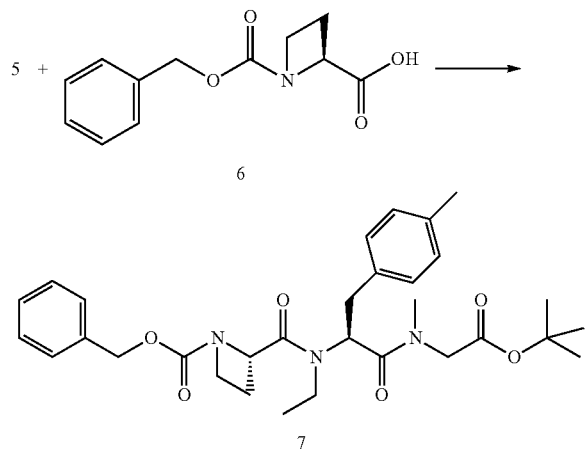

To a reaction tank purged with nitrogen, the 2-MeTHF solution (12.3 kg) containing Compound 5 obtained in Example 2 and a solution of Compound 6 (2.92 kg) dissolved in 2-MeTHF (3.87 kg) were added while stirring and washed them with 2-MeTHF (8.0 kg). The external temperature of the reaction tank was set at 10° C., DIPEA (5.35 kg) was added while stirring, and then T3P (1.6 M 2-MeTHF solution, 15.53 kg) was added dropwise. The external temperature of the reaction tank was set at 25° C., and the reaction mixture was stirred for 2 hours. The reaction mixture was sampled, sample preparation was carried out (Sample preparation method 1), and the reaction conversion rate was confirmed to be 99.6% by HPLC analysis (Equation 1 for reaction conversion rate calculation). The external temperature of the reaction tank was set at 10° C., and 5% aqueous sodium carbonate solution (25.2 kg) was added to the reaction mixture while stirring. The external temperature of the reaction tank was set at 25° C., and after stirring the mixture for 10 minutes, stirring was stopped, and the aqueous layer was removed from the reaction tank. The organic layer was washed twice with 5% aqueous sodium hydrogen sulfate monohydrate solution (33.2 kg), and then washed with 5% aqueous sodium carbonate solution (33.2 kg). The organic layer was recovered in a storage container, this was combined with a wash solution obtained by washing the reaction tank with 2-MeTHF (25.6 kg) and recovered in the storage container as a storage solution. The storage solution was added to a reaction tank purged with nitrogen while washing the inside of the storage container with 2-MeTHF (1.7 kg). The external temperature of the reaction tank was set at 50° C., and while stirring, the mixture was concentrated under reduced pressure until the liquid volume reached approximately 12 L. The resulting residue was obtained by washing the reaction tank with 2-MeTHF (8.5 kg) to afford a 2-MeTHF solution (12.4 kg) containing Compound 5.

Retention time by HPLC analysis: 2.389 minutes (HPLC analysis conditions: method 1)

Example 4

Compound 8: Synthesis of (tert-butyl 2-[[(2S)-2-[[(2S)-azetidine-2-carbonyl]-ethyl-amino]-3-(p-tolyl)propanoyl]-methyl-amino]acetate)

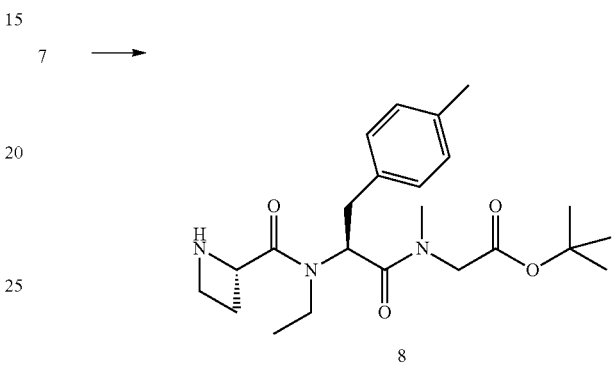

To a reaction tank purged with nitrogen, the 2-MeTHF solution (18.7 kg) containing Compound 7 obtained in Example 3 was added while washing the storage container with 2-MeTHF (6.9 kg). 5% Pd/C (1.74 kg, 50% wetted with water) was added to the reaction tank. The external temperature of the reaction tank was set to 25° C., and the reaction tank was pressurized with hydrogen until the internal pressure reached 0.18 MPaG. After stirring the mixture for 50 minutes, absence of internal pressure change was confirmed, and then purging with nitrogen was followed by further pressurization with hydrogen to 0.18 MPaG, and the mixture was stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). After purging the interior of the reactor with nitrogen, the reaction mixture was subjected to pressure filtration. The reaction tank and the filtration apparatus were washed with 2-MeTHF (10.6 kg), and then the filtrate and the wash solution were recovered in a storage container as a storage solution. The obtained filtrate and the wash solution were concentrated under reduced pressure at an external temperature of 40° C. until the liquid volume reached approximately 6 L. The residue was combined with a wash solution obtained by washing the reaction tank with 2-MeTHF (8.5 kg) to afford a 2-MeTHF solution (14.0 kg) containing Compound 8.

Retention time by HPLC analysis: 2.538 minutes (HPLC analysis conditions: method 1)

Example 5

Compound 10: Synthesis of (tert-butyl 2-[[(2S)-2-[[(2S)-1-[(2S)-2-[benzyloxycarbonyl(methyl)amino]propanoyl]azetidine-2-carbonyl]-ethyl-amino]-3-(p-tolyl)propanoyl]-methyl-amino]acetate)

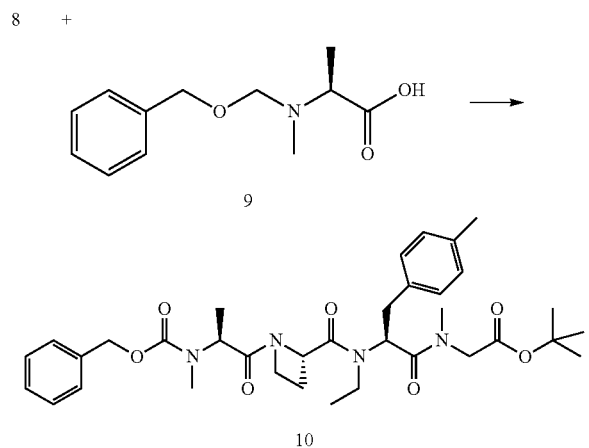

To a reaction tank purged with nitrogen, the 2-MeTHF solution (13.9 kg) containing Compound 8 obtained in Example 4, Compound 9 (2.31 kg), and 2-MeTHF (10.4 kg) were added sequentially. The external temperature of the reaction tank was set at 10° C., DIPEA (4.61 kg) was added while stirring, and then T3P (1.6 M 2-MeTHF solution, 12.15 kg) was added dropwise. The external temperature of the reaction tank was set at 25° C., and the reaction mixture was stirred for 1 hour. The reaction mixture was sampled, sample preparation was carried out (Sample preparation method 1), and the reaction conversion rate was confirmed to be 96.8% by HPLC analysis (Equation 1 for reaction conversion rate calculation). The external temperature of the reaction tank was set at 10° C., and 5% aqueous sodium carbonate solution (24.3 kg) was added to the reaction mixture while stirring. The external temperature of the reaction tank was set at 25° C., and after stirring for 10 minutes, stirring was stopped, and the aqueous layer was removed from the reaction tank. The organic layer was washed twice with 5% aqueous sodium hydrogen sulfate monohydrate solution (32.4 kg), and then washed with 5% aqueous sodium carbonate solution (32.4 kg). 2-MeTHF (25.6 kg) was added to the obtained organic layer. The external temperature of the reaction tank was set at 50° C., and while stirring, the mixture was concentrated under reduced pressure until the liquid volume reached approximately 12 L, and then the residue was recovered in a storage container. Combining this with a wash solution obtained by washing the reaction tank with 2-MeTHF (8.5 kg) afforded a solution (19.0 kg) containing Compound 10.

Retention time by HPLC analysis: 4.004 minutes (analysis conditions: method 1)

Example 6

Compound 11: Synthesis of (tert-butyl 2-[[(2S)-2-[ethyl-[(2S)-1-[(2S)-2-(methylamino)propanoyl]azetidine-2-carbonyl]amino]-3-(p-tolyl)propanoyl]-methyl-amino]acetate)

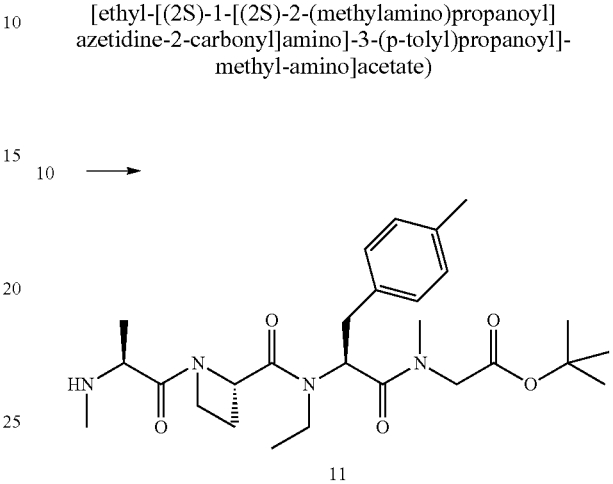

To a reaction tank purged with nitrogen, the solution (18.8 kg) containing Compound 10 obtained in Example 5 and 2-MeTHF (7.0 kg) were added sequentially. 5% Pd/C (1.70 kg, 50% wetted with water) was added to the reaction tank. The external temperature of the reaction tank was set at 25° C., and the reaction tank was pressurized with hydrogen until the internal pressure reached 0.18 MPaG. One hour 40 minutes later, absence of internal pressure change was confirmed, and after purging with nitrogen, pressurization with hydrogen to 0.18 MPaG was conducted, and the mixture was stirred for 2 hours. The reaction mixture was sampled, sample preparation was carried out (Sample preparation method 1), and the reaction conversion rate was confirmed to be 99.9% or more by HPLC analysis (Equation 1 for reaction conversion rate calculation). After purging the interior of the reaction tank with nitrogen, the reaction mixture was subjected to pressure filtration. The reaction tank and the filtration apparatus were washed with 2-MeTHF (10.3 kg), and then the filtrate and the wash solution were recovered as a storage solution. The obtained filtrate and the wash solution were concentrated under reduced pressure at an external temperature of 40° C. until the liquid volume reached approximately 7 L. The residue was combined with a wash solution obtained by washing the reaction tank with toluene (10.4 kg) to afford a solution containing Compound 11 (16.7 kg).

Retention time by HPLC analysis: 2.510 minutes (HPLC analysis conditions: method 1)

Example 7

Compound 13: Synthesis of (tert-butyl 2-[[(2S)-2-[[(2S)-1-[(2S)-2-[[(2S,3S)-2-(benzyloxycarbonylamino)-3-methyl-pentanoyl]-methyl-amino]propanoyl]azetidine-2-carbonyl]-ethyl-amino]-3-(p-tolyl)propanoyl]-methyl-amino]acetate)

11 +

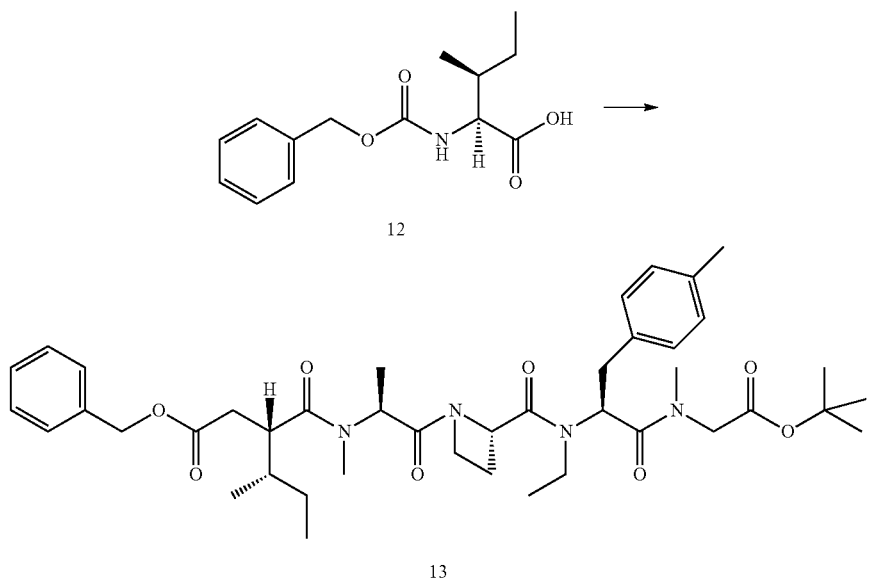

To a reaction tank purged with nitrogen, the solution (16.5 kg) containing Compound 11 obtained in Example 6 and 2-MeTHF (2.12 kg) were added sequentially at room temperature. This was followed by sequential addition of a solution of Compound 12 (2.52 kg) dissolved in 2-MeTHF (8.1 kg), 2-MeTHF (8.1 kg), and acetonitrile (3.1 kg) to the reaction tank at room temperature. DIPEA (4.51 kg) was added at room temperature while stirring, and then the external temperature of the reaction tank was set at 25° C., and after sequentially adding HATU (4.52 kg) and 2-MeTHF (0.3 L), this mixture was stirred at 25° C. for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). N-methylimidazole (0.65 kg) was added to the reaction tank, and further addition of 5% aqueous sodium carbonate solution (23.9 kg) while stirring was followed by stirring for 1 hour. Next, 2.5% aqueous ammonia solution (23.9 kg) was added, and after stirring for 30 minutes, the aqueous layer was removed from the reaction tank. The resulting organic layer was washed with 2.5% aqueous ammonia solution (31.9 kg), 10% aqueous sodium hydrogen sulfate monohydrate solution (31.9 kg×2), and 3% aqueous dipotassium hydrogen phosphate solution (31.9 kg). 2-MeTHF (25.6 kg) was added to the resulting organic layer. The external temperature of the reaction tank was set at 50° C., and while stirring, the mixture was concentrated under reduced pressure until the liquid volume reached approximately 12 L. The residue was combined with a wash solution obtained by washing the reaction tank with acetone (7.9 kg) to afford a solution (18.2 kg) containing Compound 13.

Retention time by HPLC analysis: 4.235 minutes (HPLC analysis conditions: method 1)

Condensation Reaction Between Compound 11 and Compound 12 (Examination of Reaction Conditions for Example 7)

Solvents were examined for the condensation reaction between Compound 11 and Compound 12. The condensation reaction was monitored by HPLC analysis. The yield was calculated based on area percent (Area %) determined by HPLC analysis.

11 +

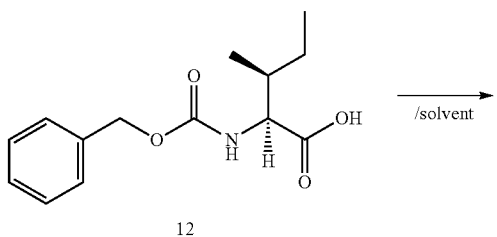

-continued

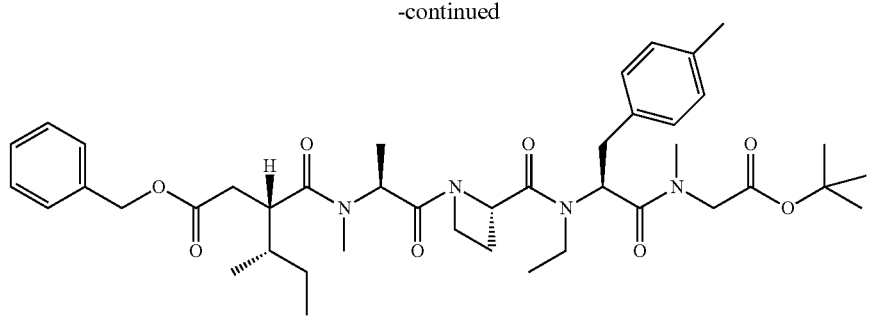

13

Example 7-1

Compound 13: Synthesis of (tert-butyl 2-[[(2S)-2-[[(2S)-1-[(2S)-2-[[(2S,3S)-2-(benzyloxycarbonylamino)-3-methyl-pentanoyl]-methyl-amino]propanoyl]azetidine-2-carbonyl]-ethyl-amino]-3-(p-tolyl)propanoyl]-methyl-amino]acetate) (Examination of solvents)

The solution (72.62 mg) containing Compound 11 (50.69 mg (0.100 mmol)) obtained in Example 6 was added to a reaction vessel, and this was concentrated to dryness under reduced pressure at an external temperature of 60° C. Next, Compound 12 (32.50 mg (0.122 mmol) was added to the reaction vessel, and a solvent (2-MeTHF (0.35 mL)) was added at room temperature. DIPEA (58.3 mg (0.451 mmol)) was added while stirring at room temperature, then the external temperature of the reaction container was set at 25° C., HATU (58.37 mg (0.154 mmol)) was added, and then the mixture was stirred at 25° C. for 4 hours. N-methylimidazole (8.17 mg (0.099 mmol)) was added to the reaction vessel, and after further addition of 5% aqueous sodium carbonate solution (300 µL) while stirring, the mixture was stirred for 2 hours 30 minutes. Next, insoluble matters were removed by filtration through a cotton plug, and then the aqueous layer was removed. 2.5% aqueous ammonia solution (300 µL) was added to the resulting organic layer, and after stirring this for 5 minutes, the aqueous layer was removed. The resulting organic layer was washed with 2.5% aqueous ammonia solution (320 L), 10% aqueous sodium hydrogen sulfate monohydrate solution (320 µL×2), and 3% aqueous dipotassium hydrogen phosphate solution (320 µL). The obtained organic layer was concentrated to dryness under reduced pressure at an external temperature of 60° C. The resulting residue was analyzed by HPLC. As a result of HPLC analysis using an authentic sample, the afforded Compound 13 was 56.77 mg (75.1% yield).

LCMS (ESI) of Compound 13: Retention time: 4.012 minutes, m/z=750 [M+H]$^+$ (LCMS analysis conditions: method 1)

Retention time by HPLC analysis: 4.261 minutes (HPLC analysis conditions: method 1)

The following table shows the results obtained when using 4-methyl tetrahydropyran, dimethyl carbonate, ethyl acetate, or anisole as a solvent in place of 2-MeTHF used in the above-mentioned method for synthesizing Compound 13 (Examination of solvents).

TABLE 4

Production of Compound 13

| Example No. | Solvent | Yield (%) |
|---|---|---|
| Example 7-1 | 2-MeTHF | 75 |
| Example 7-2 | 4-Methyltetrahydropyran | 63 |
| Example 7-3 | Dimethyl carbonate | 66 |
| Example 7-4 | Ethyl acetate | 62 |
| Example 7-5 | Anisole | 60 |

These results showed that in addition to 2-MeTHF, 4-methyltetrahydropyran, dimethyl carbonate, ethyl acetate, or anisole is a suitable solvent for the condensation reaction using HATU. The results also show that in addition to 2-MeTHF, 4-methyltetrahydropyran, dimethyl carbonate, ethyl acetate, or anisole is a suitable solvent for producing Compound 13 by condensation of Compounds 11 and 12. In particular, 2-MeTHF was shown to be a suitable solvent in terms of yield of the product of interest.

Example 8

Compound 15: Synthesis of ((2,3,4,5,6-pentafluorophenyl)(2S)-4-methyl-2-[methyl(2-trimethylsilylethoxycarbonyl)amino]pentanoate)

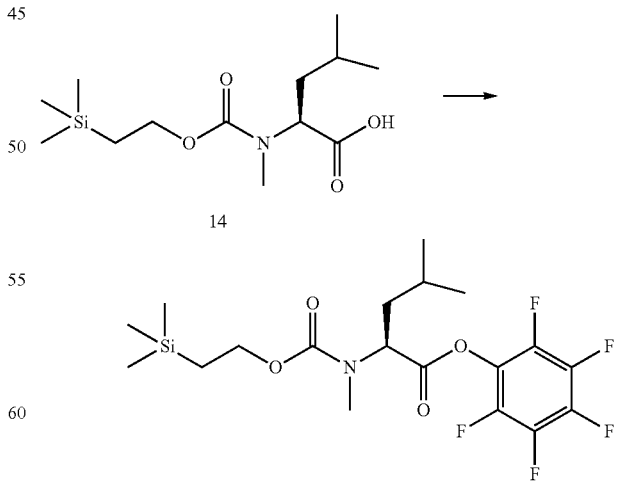

To a reaction tank purged with nitrogen, Compound 14 (3.0 kg), isopropyl acetate (13.7 kg), and DMF (18.3 kg)

were added sequentially at room temperature. A solution of pentafluorophenol (2.38 kg) dissolved in isopropyl acetate (2.8 kg) and isopropyl acetate (0.6 kg) were added sequentially while stirring the mixture at room temperature. The external temperature of the reaction tank was set at 0° C., and 1-(3-dimethylaminopropyl)-3-ethylcarbodiimide hydrochloride salt (2.48 kg) was added to the reaction tank. After the external temperature of the reaction tank was raised to 25° C. in 1 hour, the mixture was stirred at an external temperature of 25° C. for 2 hours. The reaction mixture was sampled, sample preparation was carried out (Sample preparation method 1), and HPLC analysis confirmed that Compound 14 used as the starting material was not detected (Equation 3 for reaction conversion rate calculation). The external temperature of the reaction tank was set at 0° C., and 0.5 M aqueous hydrochloric acid solution (19.4 kg) was added. After setting the external temperature of the reaction tank to 25° C., the mixture was stirred for 10 minutes, stirring was stopped, and then the aqueous layer was removed from the reaction tank. The resulting organic layer was washed with 0.5 M aqueous hydrochloric acid solution (27.5 kg). To the resulting organic layer, 5% aqueous potassium carbonate solution (27.5 kg×2) and then DMF (2.8 kg) were added. The reaction mixture was stirred for 10 minutes, stirring was stopped, and then the aqueous layer was removed from the reaction tank. The resulting organic layer was washed with 5% aqueous potassium carbonate solution (27.5 kg), and then with 10% aqueous sodium chloride solution (27.5 kg). Isopropyl acetate (27.6 kg) was added to this, and then the mixture was concentrated under reduced pressure at an external temperature of 40° C. until the liquid volume reached approximately 8 L. The residue was combined with a wash solution obtained by washing the reaction tank with acetone (8.7 kg) to afford a solution (16.2 kg) containing Compound 15.

Retention time by HPLC analysis: 6.175 minutes (HPLC analysis conditions: method 2)

Example 9

Compound 16: Synthesis of (tert-butyl 2-[[(2S)-2-[ethyl-[(2S)-1-[(2S)-2-[methyl-[(2S,3S)-3-methyl-2-[[(2S)-4-methyl-2-[methyl(2-trimethylsilylethoxy-carbonyl)-amino]pentanoyl]amino]pentanoyl]amino] propanoyl]azetidine-2-carbonyl]amino]-3-(p-tolyl) propanoyl]-methyl-amino]acetate)

solution (9.0 kg) containing Compound 13 obtained in Example 7, isopropyl acetate (4.0 kg), and N-methylmorpholine (2.38 kg) were added sequentially at room temperature. 5% Pd/C (0.83 kg, 50% wetted with water) was added to the reaction tank, and then the external temperature of the tank was set at 25° C., and the reaction tank was pressurized with hydrogen until the internal pressure reached 0.18 MPaG. One hour later, absence of internal pressure change was confirmed, and then this was pressurized with hydrogen to 0.18 MPaG and further stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (10.0 kg×2), and then the filtrate and the wash solution were combined to afford a storage solution (first batch).

To a reaction tank purged with nitrogen, the solution (7.4 kg) containing Compound 15 obtained in Example 8, the solution (9.0 kg) containing Compound 13 obtained in Example 7, isopropyl acetate (4.0 kg), and N-methylmorpholine (2.38 kg) were added sequentially at room temperature. 5% Pd/C (0.83 kg, 50% wetted with water) was added to the reaction tank, and then the external temperature of the tank was set at 25° C., and the reaction tank was pressurized with hydrogen until the internal pressure reached 0.18 MPaG. One hour later, absence of internal pressure change was confirmed, and then this was pressurized with hydrogen to 0.18 MPaG and further stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (10.0 kg×2), and then the filtrate and the wash solution were combined to afford a storage solution (second batch).

To a reaction tank purged with nitrogen, each of the above-mentioned storage solutions and 2-MeTHF (1.8 kg) were added, and this was concentrated under reduced pres-

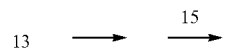

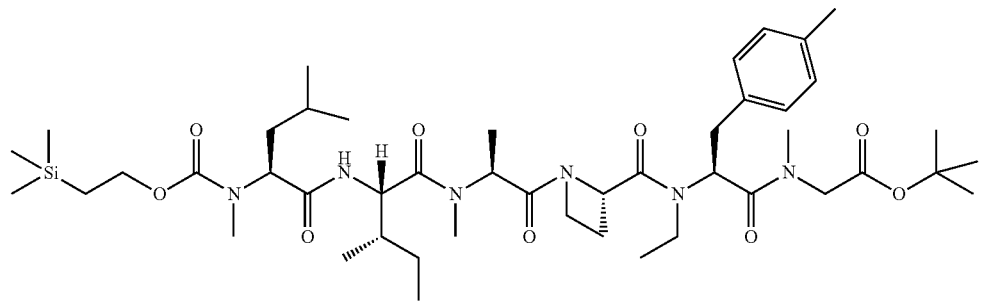

To a reaction tank purged with nitrogen, the solution (7.4 kg) containing Compound 15 obtained in Example 8, the sure at an external temperature of 40° C. until the liquid volume reached approximately 20 L. The concentrated residue was subjected to pressure filtration. The inside of the reaction tank and the filtration apparatus were washed with 2-MeTHF (8.5 kg×2), and then the filtrate and the wash solution were combined and recovered as a storage solution in a storage container. The storage solution and 2-MeTHF (3.1 kg) were added to a reaction tank purged with nitrogen. The external temperature of the reaction tank was set at 25° C., and 5% aqueous potassium carbonate solution (25.9 kg) and 4-dimethylaminopyridine (0.96 kg) were sequentially added while stirring. Thirty minutes later, stirring was stopped and the aqueous layer was removed from the reaction tank. The organic layer was washed twice with 5% aqueous potassium hydrogen sulfate solution (34.1 kg×2) and 5% aqueous potassium carbonate solution (34.1 kg). 2-MeTHF (26.5 kg) was added, and the mixture was concentrated under reduced pressure at an external temperature of 50° C. until the liquid volume reached approximately 12 L. The resulting residue was combined with a wash solution obtained by washing the inside of the reaction tank with 2-MeTHF (8.5 kg) to afford a solution (19.0 kg) containing Compound 16.

Retention time by HPLC analysis: 5.964 minutes (HPLC analysis conditions: method 2)

Example 9-1 (when Using 2-MeTHF Instead of Isopropyl Acetate which was Used in the Above-Mentioned Method for Synthesizing Compound 16)

Synthesis of Compound 16 (tert-butyl 2-[[(2S)-2-[ethyl-[(2S)-1-[(2S)-2-[methyl-[(2S,3S)-3-methyl-2-[[(2S)-4-methyl-2-[methyl(2-trimethylsilylethoxy-carbonyl)amino]-pentanoyl]amino]pentanoyl]amino] propanoyl]azetidine-2-carbonyl]amino]-3-(p-tolyl) propanoyl]-methyl-amino]acetate)

or more (Equation 1 for reaction conversion rate calculation). The reaction mixture was filtered, and the residue was washed with 2-MeTHF (400 µL×2). The external temperature of the reaction vessel containing the filtrate was set at 25° C., and 5% aqueous potassium carbonate solution (440 µL) and 4-dimethylaminopyridine (16.6 mg) were added sequentially while stirring. Thirty minutes later, stirring was stopped and the aqueous layer was removed. The organic layer was washed with 5% aqueous potassium hydrogen sulfate solution (440 µL×2) and 5% aqueous potassium carbonate solution (440 µL×2). Concentrating the resulting organic layer under reduced pressure gave a residue (113.3 mg) containing Compound 16. The obtained residue was diluted in acetonitrile, and this was subjected to LCMS analysis (method 2: retention time of Compound 16: 5.573 minutes, m/z=910 [M+Na]$^+$). The resulting residue and 3,5-bis(trifluoromethyl)benzoic acid were dissolved in DMSO-d6, and this was subjected to qNMR analysis (yield: 58%).

Example 9-2 (when Using Dimethyl Carbonate Instead of Isopropyl Acetate which was Used in the Above-Mentioned Method for Synthesizing Compound 16)

Synthesis of Compound 16 (tert-butyl 2-[[(2S)-2-[ethyl-[(2S)-1-[(2S)-2-[methyl-[(2S,3S)-3-methyl-2-[[(2S)-4-methyl-2-[methyl(2-trimethylsilylethoxy-carbonyl)amino]-pentanoyl]amino]pentanoyl]amino] propanoyl]azetidine-2-carbonyl]amino]-3-(p-tolyl) propanoyl]-methyl-amino]acetate)

The storage solution (477.4 mg) containing Compound 13 obtained in Example 7 was added to a reaction vessel, and concentrating this under reduced pressure gave a residue

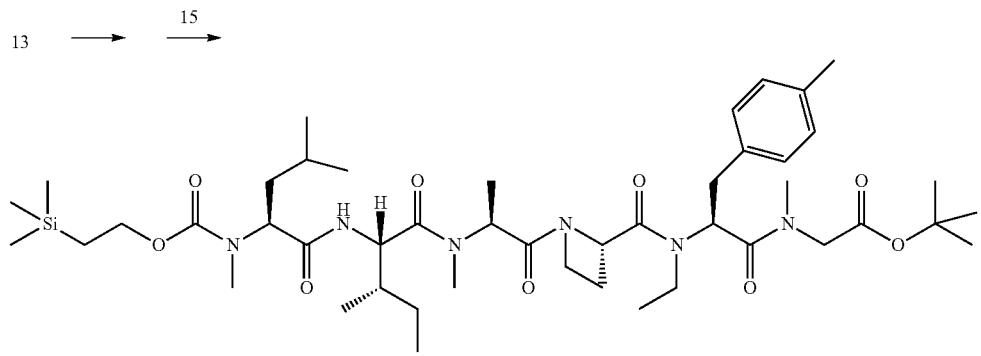

To a reaction vessel, the storage solution (482.7 mg) containing Compound 13 obtained in Example 7 was added and concentrating this under reduced pressure gave a residue containing Compound 13. To the reaction vessel, a Compound 15-containing residue (91.2 mg, 81.2 wt %) and 2-MeTHF (1000 µL) were added sequentially at room temperature. After adding 5% Pd/C (29.8 mg, 50% wetted with water) to the reaction vessel, the external temperature was set at 25° C., and this was degassed and purged with hydrogen gas and stirred for 1 hour. The reaction mixture was sampled, sample preparation was carried out (Sample preparation method 1), and by subjecting it to HPLC analysis, the reaction conversion rate was confirmed to be 99.9% containing Compound 13. To the reaction vessel, a Compound 15-containing residue (92.0 mg, 81.2 wt %) and dimethyl carbonate (1000 µL) were added sequentially at room temperature. After adding 5% Pd/C (29.7 mg, 50% wetted with water) to the reaction vessel, the external temperature was set at 25° C., and this was degassed and purged with hydrogen gas and stirred for 1 hour. The reaction mixture was sampled, sample preparation was carried out (Sample preparation method 1), and by subjecting it to HPLC analysis, the reaction conversion rate was confirmed to be 99.9% or more (Equation 1 for reaction conversion rate calculation). The reaction mixture was filtered, and the residue was washed with dimethyl carbonate (400 µL×2). The external temperature of the reaction vessel containing the filtrate was set at 25° C., and 5% aqueous potassium carbonate solution (880 µL) and 4-dimethylaminopyridine (17.1 mg) were added sequentially while stirring. Thirty minutes later, stirring was stopped and the aqueous layer was removed. The organic layer was washed with 5% aqueous potassium hydrogen sulfate solution (880 µL×2) and 5% aqueous potassium carbonate solution (880 µL×2). Concentrating the resulting organic layer under reduced pressure gave a residue (107.3 mg) containing Compound 16. The obtained residue was diluted in acetonitrile, and this was subjected to LCMS analysis (method 2: retention time of Compound 16: 5.579 minutes, m/z=910 [M+Na]$^+$). The resulting residue and 3,5-bis(trifluoromethyl)benzoic acid were dissolved in DMSO-d6, and this was subjected to qNMR analysis (yield: 62%).

Example 9-3 (when Using Anisole Instead of Isopropyl Acetate which was Used in the Above-Mentioned Method for Synthesizing Compound 16)

The following table shows the results when using dimethyl carbonate or anisole as the solvent instead of 2-MeTHF which was used in the above-mentioned method for synthesizing Compound 16.

TABLE 10

| Production of compound 16 | | |
|---|---|---|
| Example No. | Solvent | Yield (%) |
| Example 9-1 | 2-MeTHF | 58 |
| Example 9-2 | Dimethyl carbonate | 62 |
| Example 9-3 | Anisole | 78 |

Example 10

Compound 17: Synthesis of (tert-butyl 2-[[(2S)-2-[ethyl-[(2S)-1-[(2S)-2-[methyl-[(2S,3S)-3-methyl-2-[[(2S)-4-methyl-2-(methylamino)pentanoyl]amino]pentanoyl]amino]propanoyl]azetidine-2-carbonyl]amino]-3-(p-tolyl)propanoyl]-methyl-amino]acetate)

16 →

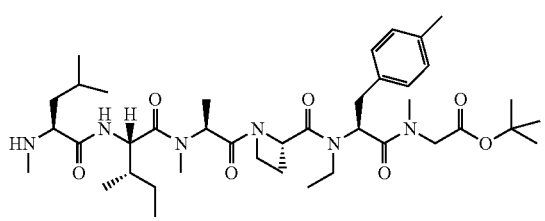

17

To a reaction tank purged with nitrogen, the solution (18.8 kg) containing Compound 16 obtained in Example 9 and 2-MeTHF (5.8 kg) were sequentially added at room temperature. The external temperature of the reaction tank was set at 47° C., and tetrabutylammonium fluoride (1 M THF solution, 17.6 kg) was added in 1 hour. The reaction mixture was sampled, sample preparation was carried out (Sample preparation method 1), and HPLC analysis confirmed that Compound 16 used as the starting material was not detected (Equation 1 for reaction conversion rate calculation). Stirring was stopped, and then the reaction mixture was divided in half. To the divided reaction mixture, isopropyl acetate (9.1 kg) was added, the external temperature of the reaction tank was set at 25° C., and the organic layer was washed with 5% aqueous potassium carbonate solution (10.3 kg×3) while stirring. The resulting organic layer was stored in a storage solution. A similar operation was performed on the other half of the reaction mixture. The resulting organic layers were combined, and this was concentrated under reduced pressure until the liquid volume reached approximately 12 L. The resulting residue was combined with a wash solution obtained by washing the inside of the reaction tank with 2-MeTHF (8.5 kg) to afford a solution (12.6 kg) containing Compound 17.

Retention time by HPLC analysis: 3.057 minutes (HPLC analysis conditions: method 1)

Example 11

Compound 19: Synthesis of (tert-butyl (3S)-3-[benzyloxycarbonyl(methyl)amino]-4-(dimethylamino)-4-oxo-butanoate)

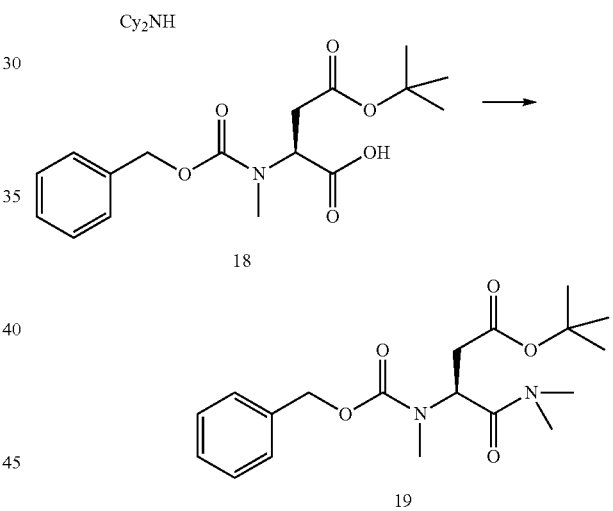

To a reaction tank purged with nitrogen, Compound 18 (4.78 kg) and 2-MeTHF (23.8 kg) were sequentially added at room temperature. The external temperature of the reaction tank was set at 10° C., and while stirring the reaction mixture, DIPEA (3.22 kg) and dimethylamine-THF solution (2 M, THF solution, 5.49 kg) were sequentially added, and this was stirred for 30 minutes. T3P (50% w/w 2-MeTHF solution, 8.64 kg) was added, then the external temperature of the reaction tank was set at 25° C., and this mixture was stirred for 6 hours. The reaction mixture was sampled, sample preparation was carried out (Sample preparation method 3), and the reaction conversion rate was confirmed to be 96.2% by HPLC analysis (Equation 1 for reaction conversion rate calculation). The external temperature of the reaction tank was set at 10° C., and 10% aqueous citric acid monohydrate solution (28.7 kg) was added to the reaction mixture. The external temperature of the reaction tank was set at 25° C., and after stirring the mixture for 10 minutes, stirring was stopped, and the aqueous layer was removed from the reaction tank. The resulting organic layer was washed with 10% aqueous citric acid monohydrate solution (28.7 kg×2) and 5% aqueous sodium carbonate solution (28.7 kg×3). 2-MeTHF (26.0 kg) was added to the resulting organic layer, and this was concentrated under reduced pressure at an external temperature of 60° C. until the liquid volume reached approximately 7 L. The residue was combined with a wash solution obtained by washing the reaction tank with 2-MeTHF (6.8 kg×2) to afford a solution (19.8 kg) containing Compound 19.

Retention time by HPLC analysis: 3.510 minutes (HPLC analysis conditions: method 3)

Example 12

Compound 20: Synthesis of (tert-butyl (3S)-4-(dimethylamino)-3-(methylamino)-4-oxo-butanoate

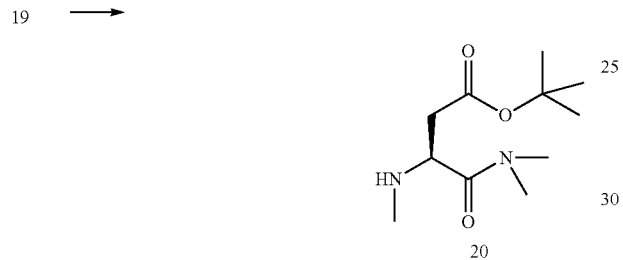

To a reaction tank purged with nitrogen, 5% Pd/C (1.31 kg, 50% wetted with water), the solution (19.8 kg) containing Compound 19 obtained in Example 11, and 2-MeTHF (6.0 kg) were sequentially added at room temperature. The external temperature of the reaction tank was set at 25° C., and the reaction tank was pressurized with hydrogen until the internal pressure reached 0.18 MPaG. After stirring the mixture for 2 hours, absence of internal pressure change was confirmed, and then the reaction tank was pressurized with hydrogen to 0.18 MPaG, and the mixture was stirred for another 1.5 hours. The reaction mixture was sampled, sample preparation was carried out (Sample preparation method 1), and the reaction conversion rate was confirmed to be 100% (starting material was not detected) by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (11.3 kg×3), and then the filtrate and the wash solution were recovered as a storage solution in a storage container. The storage solution and 2-MeTHF (0.4 kg) were added to a reaction tank purged with nitrogen, and this was concentrated under reduced pressure while stirring at an external temperature of 40° C. until the liquid volume reached approximately 4 L. The residue was combined with a wash solution obtained by washing the reaction tank with 2-MeTHF (6.8 kg) to afford a solution (10.4 kg) containing Compound 20.

Retention time by HPLC analysis: 1.560 minutes (HPLC analysis conditions: method 3)

Example 13

Compound 22: Synthesis of (tert-butyl (3S)-3-[[(2S)-2-[benzyloxycarbonyl-(methyl)amino]-2-cyclopentyl-acetyl]-methyl-amino]-4-(dimethylamino)-4-oxo-butanoate)

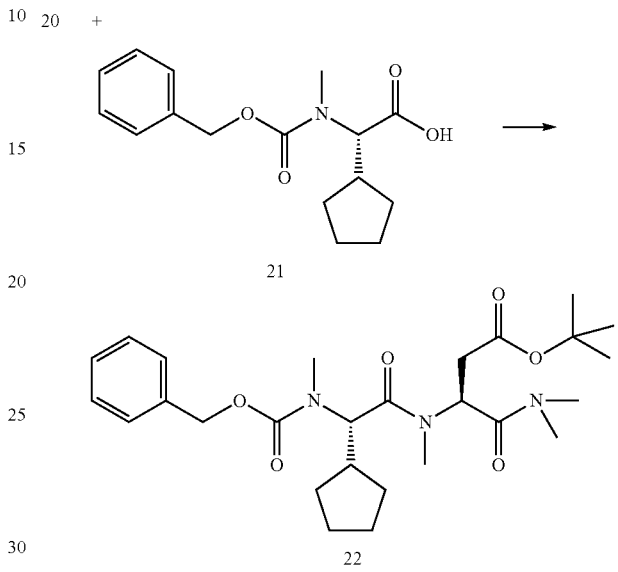

The solution (10.3 kg) containing Compound 20 obtained in Example 12 was added, and this was concentrated under reduced pressure while stirring at an external temperature of 40° C. until the liquid volume reached approximately 10 L. Compound 21 (61 w/w % MeTHF solution, 4.97 kg), 2-MeTHF (1.0 L), and acetonitrile (2.8 kg) were added to this at room temperature. The external temperature was cooled to 10° C., DIPEA (4.93 kg) and HATU (4.95 kg) were sequentially added, and then the external temperature was raised to 25° C. After stirring the reaction mixture at 25° C. for 4 hours, the reaction mixture was sampled, sample preparation was carried out (Sample preparation method 1), and the reaction conversion rate was confirmed to be 99.3% by HPLC analysis (Equation 1 for reaction conversion rate calculation). To the reaction tank, CPME (4.0 kg), 5% aqueous potassium carbonate solution (3.5 kg), and N-methylimidazole (712 g) were sequentially added, and the mixture was stirred for 30 minutes. This was followed by addition of 2.5% aqueous ammonia solution (14.1 kg) and 2-MeTHF (3.9 kg), and after stirring this for 10 minutes, the aqueous layer was removed. The resulting organic layer was washed with 2.5% aqueous ammonia solution (17.6 kg), 10% aqueous sodium hydrogen sulfate monohydrate solution (17.6 kg×3), and 5% aqueous potassium carbonate solution (17.6 kg). The resulting organic layer was concentrated under reduced pressure while stirring at an external temperature of 40° C. until the liquid volume reached approximately 9 L. A wash solution obtained by washing with 2-MeTHF (13.6 kg) was combined and added to afford a solution (21.6 kg) containing Compound 22.

Retention time by HPLC analysis: 4.356 minutes (HPLC analysis conditions: method 3)

Condensation Reaction Between Compound 20 and Compound 21 (Examination of Reaction Conditions for Example 13)

Solvents were examined for the condensation reaction between Compound 20 and Compound 21. The condensation reaction was monitored by HPLC analysis. The yield was calculated based on area percent (Area %) determined by HPLC analysis and from values determined by qNMR.

Example 13-1 (when Using Anisole Instead of 2-MeTHF and Acetonitrile which were Used in the Above-Mentioned Method for Synthesizing Compound 22)

Compound 22: Synthesis of (tert-butyl (3S)-3-[[(2S)-2-[benzyloxycarbonyl(methyl)amino]-2-cyclopentyl-acetyl]-methyl-amino]-4-(dimethylamino)-4-oxo-butanoate)

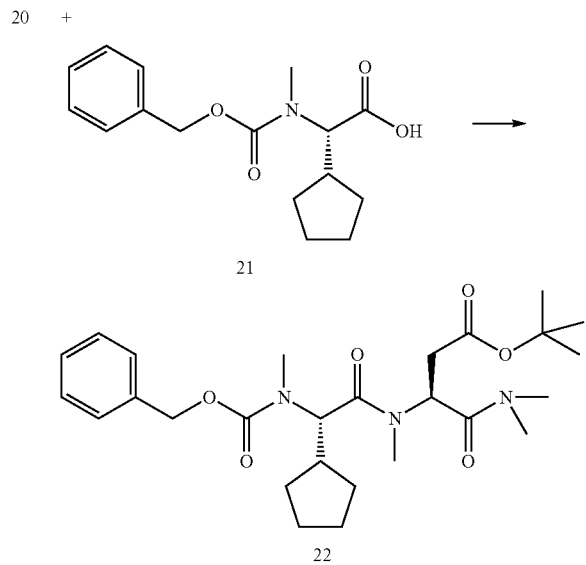

The solution (590.9 mg) containing Compound 20 obtained in Example 12 and Compound 21 (61 w/w % 2-MeTHF solution, 252.7 mg) were sequentially added to a reaction vessel, and this was concentrated under reduced pressure to afford a residue containing Compounds 20 and 21. Anisole (800 μL) was added to the reaction vessel at room temperature to dissolve the residue. The external temperature was cooled to 10° C., DIPEA (334 μL) and HATU (248.2 mg) were sequentially added to the reaction mixture, and then the external temperature was raised to 25° C. After stirring the reaction mixture at 25° C. for 5 hours, the reaction mixture was sampled, sample preparation was carried out (Sample preparation method 1), and the reaction conversion rate was confirmed to be 97.0% by HPLC analysis (Equation 1 for reaction conversion rate calculation). The external temperature was set at 10° C., N-methylimidazole (34.6 μL) and 5% aqueous potassium carbonate solution (200 μL) were sequentially added to the reaction vessel, then the external temperature was set at 25° C., and this was stirred for 30 minutes. Subsequently, 2.5% aqueous ammonia solution (800 μL) and anisole (260 μL) were added, and after stirring this for 10 minutes, the aqueous layer was removed. The resulting organic layer was washed with 2.5% aqueous ammonia solution (1000 μL) and 10% aqueous sodium hydrogen sulfate monohydrate solution (1000 μL×3). A solvent (anisole (260 μL)) was added to the resulting organic layer, and this was washed with 10% aqueous sodium hydrogen sulfate monohydrate solution (1000 μL×1) and 5% aqueous potassium carbonate solution (1000 μL×2). The resulting organic layer was concentrated under reduced pressure to afford a residue containing Compound 22 (175.7 mg, 82% yield).

LCMS (ESI): Retention time: 4.269 minutes, m/z=526 [M+Na]+ (LCMS analysis conditions: method 3)

Yield: 82% (The obtained residue and 3,5-bis(trifluoromethyl)benzoic acid were dissolved in DMSO-$d_6$, and this was subjected to qNMR analysis)

The following table shows the results obtained when using dimethyl carbonate, ethyl acetate, or 2-MeTHF as the solvent in place of anisole used in the above-mentioned method for synthesizing Compound 22 (Examination of solvents).

TABLE 5

| | Production of Compound 22 | |
| --- | --- | --- |
| Example No. | Solvent | Yield (%) |
| Example 13-1 | Anisole | 82 |
| Example 13-2 | Dimethyl carbonate | 67 |
| Example 13-3 | Ethyl acetate | 81 |
| Example 13-4 | 2-MeTHF | 64 |

These results showed that in place of acetonitrile, anisole, dimethyl carbonate, ethyl acetate, and 2-MeTHF are solvents suitable for the production of Compound 22. In particular, anisole or ethyl acetate was shown to be suitable for use as the solvent in terms of yield of the product of interest.

Example 14

Compound 23: Synthesis of (tert-butyl (3S)-3-[[(2S)-2-cyclopentyl-2-(methylamino)acetyl]-methyl-amino]-4-(dimethylamino)-4-oxo-butanoate)

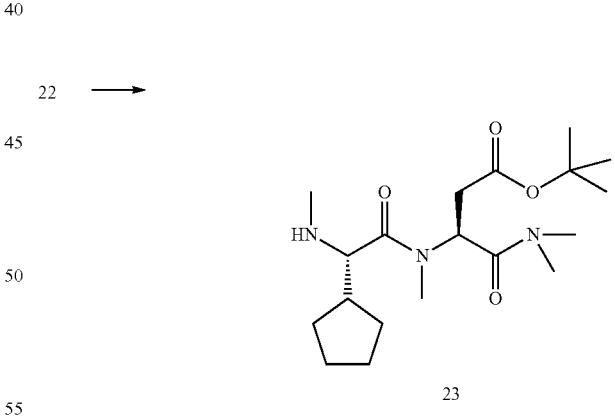

To a reaction tank purged with nitrogen, 5% Pd/C (1.26 kg, 50% wetted with water), the solution (21.0 kg) containing Compound 22 obtained in Example 13, and 2-MeTHF (5.1 kg) were sequentially added at room temperature. The external temperature of the reaction tank was set at 25° C., and the reactor was pressurized with hydrogen until the internal pressure of the reactor reached 0.18 MPaG. After stirring for 40 minutes, absence of internal pressure change was confirmed, and then the reaction tank was pressurized with hydrogen to 0.18 MPaG, and the mixture was stirred for another hour. The reaction mixture was sampled, sample preparation was carried out (Sample preparation method 1), and the reaction conversion rate was confirmed to be 100% (starting material was not detected) by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (10.9 kg×4, 5.4 kg), and then the filtrate and the wash solution were recovered as a storage solution. The obtained filtrate and wash solution were concentrated under reduced pressure while stirring at an external temperature of 60° C. until the liquid volume of the reaction mixture reached approximately 6 L. The residue was combined with a wash solution obtained by washing the reaction tank using 2-MeTHF (6.8 kg) to afford a solution (11.8 kg) containing Compound 23.

Retention time by HPLC analysis: 2.297 minutes (HPLC analysis conditions: method 3)

Example 15

Compound 25: Synthesis of (tert-butyl (3S)-3-[[(2S)-2-cyclopentyl-2-[methyl-[1-[(2,2,2-trifluoro-acetyl)amino]cyclopentanecarbonyl]amino]acetyl]-methyl-amino]-4-(dimethylamino)-4-oxo-butanoate)

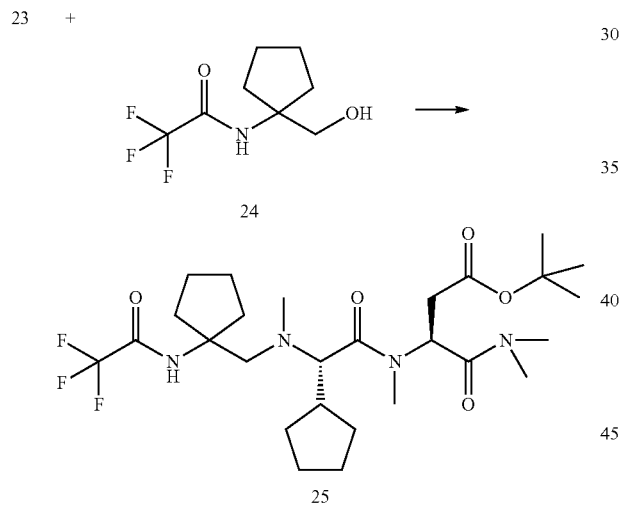

To a reaction tank purged with nitrogen, Compound 24 (3.76 kg) and 2-MeTHF (13.0 kg) were added at room temperature. The external temperature of the reaction tank was set at 10° C., and DIPEA (5.39 kg), the solution (11.7 kg) containing Compound 23 obtained in Example 14, T3P (50% 2-MeTHF solution, 14.1 kg), and DMAP (2.04 kg) were sequentially added. The external temperature of the reaction tank was set at 50° C., and the mixture was stirred for 4 hours. The reaction mixture was sampled, sample preparation was carried out (Sample preparation method 1), and the reaction conversion rate was confirmed to be 99.0% by HPLC analysis (Equation 1 for reaction conversion rate calculation). The external temperature of the reaction tank was set at 10° C., and 5% aqueous sodium carbonate solution (25.3 kg) was added. The external temperature of the reaction tank was set at 25° C., and after stirring the mixture for 30 minutes, stirring was stopped, and the aqueous layer was removed from the reaction tank. Subsequently, the external temperature of the reaction tank was set at 15° C., and 5% aqueous sodium hydrogen sulfate monohydrate solution (25.3 kg) was added. The external temperature of the reaction tank was set at 25° C., and after stirring the mixture for 10 minutes, stirring was stopped, and the aqueous layer was removed from the reaction tank. The resulting organic layer was washed with 5% aqueous sodium hydrogen sulfate monohydrate solution (25.3 kg) and 5% aqueous sodium carbonate solution (25.3 kg). 2-MeTHF (26.0 kg) was added, and this was concentrated under reduced pressure at an external temperature of 60° C. until the liquid volume reached approximately 10 L. The residue was combined with a wash solution obtained by washing the reaction tank with a mixed solvent made of 2-MeTHF (4.5 kg) and MeOH (2.1 kg), and a wash solution obtained by washing the reaction tank with 2-MeTHF (6.8 kg), to afford a solution (22.6 kg) containing Compound 25.

Retention time by HPLC analysis: 6.166 minutes (HPLC analysis conditions: method 3)

Example 16

Compound 26: Synthesis of (tert-butyl (3S)-3-[[(2S)-2-[(1-aminocyclopentanecarbonyl)-methyl-amino]-2-cyclopentyl-acetyl]-methyl-amino]-4-(dimethylamino)-4-oxo-butanoate)

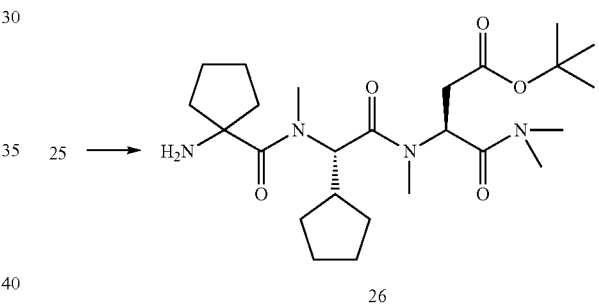

To a reaction tank purged with nitrogen, the solution (22.4 kg) containing Compound 25 obtained in Example 15 and 2-MeTHF (0.76 kg) were sequentially added at room temperature. The external temperature of the reaction tank was set at −20° C., and while stirring, LiBH₄ (10 w/w % THF solution, 3.67 kg) was added, and then this was stirred for 2 hours. The reaction mixture was sampled, sample preparation was carried out (Sample preparation method 1), and the reaction conversion rate was confirmed to be 100% (starting material was not detected) by HPLC analysis (Equation 1 for reaction conversion rate calculation). 2,2,2-trifluoroethanol (16.5 kg) was added dropwise over 3 hours to the reaction tank at an external temperature of −20° C. to −30° C. Subsequently, the external temperature of the reaction tank was raised to 0° C. in 1 hour, and then this was stirred for another hour at an external temperature of 0° C. To the reaction tank, 20% aqueous ammonium chloride solution (14.3 kg) was added, and after stirring for 13 minutes, stirring was stopped and the aqueous layer was removed from the reaction tank. The external temperature of the reaction tank was set at 10° C., and trifluoroacetic acid (1.88 kg) was added. The external temperature of the reaction tank was set at 25° C., and the mixture was stirred for 1 hour. The resulting reaction mixture was combined with a wash solution obtained by washing the reaction tank with 2-MeTHF (6.7 kg), and this was recovered in a storage container. To another reaction tank purged with nitrogen, 2 M aqueous sodium hydroxide solution (61.9 kg) was added at room temperature, and the external temperature of the reaction tank was set at 10° C. To this solution, the reaction mixture recovered in the above-mentioned storage container was added dropwise over 70 minutes, then 2-MeTHF (0.6 kg) was added, and the external temperature of the reaction tank was set at 25° C. After stirring this mixture for 10 minutes, the stirring was stopped, and the aqueous layer was removed from the reaction tank. The resulting organic layer was washed with 2 M aqueous sodium hydroxide solution (47.6 kg×2) and 10% aqueous dipotassium hydrogen phosphate solution (23.8 kg). The resulting organic layer was concentrated under reduced pressure at an external temperature of 40° C. until the liquid volume reached approximately 40 L. 2-MeTHF (30.5 kg) was added to the resulting concentrated solution, and then the organic layer was washed with 2.5% aqueous sodium hydrogen sulfate monohydrate solution (34 kg) and water (34 kg) to extract the product of interest into the aqueous layer. The combined aqueous layers were washed twice with a mixed solution made of 2-MeTHF (48.9 kg) and heptane (3.9 kg), then 2-MeTHF (53.8 kg) was added, and 15% aqueous sodium carbonate solution (15.2 kg) was added while stirring. After removing the aqueous layer, the organic layer was washed with 5% aqueous dipotassium hydrogen phosphate solution (31.5 kg). To the resulting organic layer, 2-MeTHF (25.9 kg) was added, and then this was concentrated under reduced pressure at an external temperature of 40° C. until the liquid volume of the reaction mixture reached approximately 8 L. 2-MeTHF (9.8 kg) was added to the resulting residue, and this was concentrated under reduced pressure at an external temperature of 40° C. until the liquid volume of the reaction mixture reached approximately 8 L. The residue was combined with a wash solution obtained by washing the reaction tank with acetonitrile (6.2 kg×2) to afford a solution (19.3 kg) containing Compound 26.

Retention time by HPLC analysis: 2.725 minutes (HPLC analysis conditions: method 3)

Example 15-1

Compound 25a: Synthesis of tert-butyl $N^2$-{(2S)-2-[(1-{[benzyloxy)carbonyl]-amino}cyclopentane-1-carbonyl)(methyl)amino]-2-cyclopentylacetyl}-N,N,$N^2$-trimethyl-L-α-asparaginate

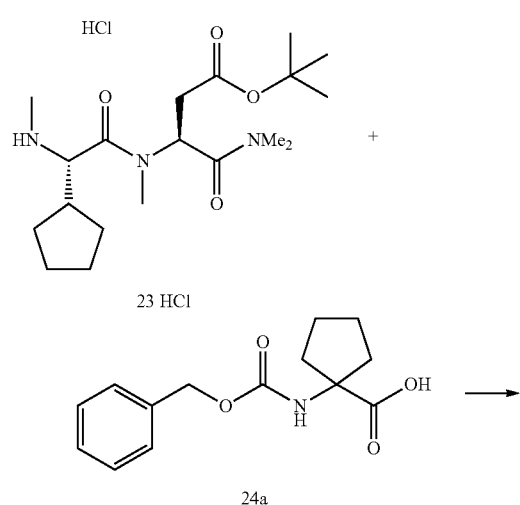

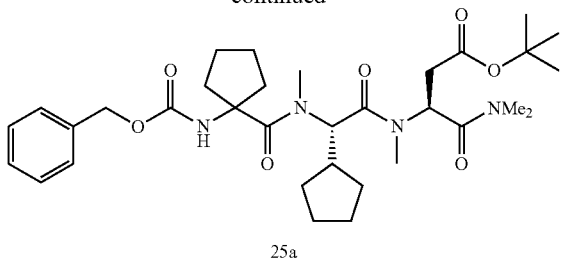

25a

The HCl salt of Compound 23 (1.00 g) and acetonitrile (10.01 mL) were added sequentially at room temperature to a reaction vessel. Next, DIPEA (2.72 mL) was added while stirring at room temperature, then Compound 24a (1.74 g) and HATU (2.75 g) were added, and this was stirred at 50° C. for 6 hours. The reaction mixture was sampled, sample preparation was carried out (Sample preparation method 1), and by subjecting it to HPLC analysis, the reaction conversion rate was confirmed to be 99.7% (Equation 1 for reaction conversion rate calculation). N-methylimidazole (0.78 mL) and water (3.99 mL) were added to the reaction vessel, and then this was stirred for 1 hour. Next, after cooling to 25° C., this was stirred for 14 hours. The reaction mixture was filtered, and the residue was washed with an acetonitrile/water mixture (8:3 (v/v), 5.33 mL). The solid that was filtered off was dried under reduced pressure to afford Compound 25a (1.27 g).

The obtained solids were diluted in acetonitrile and subjected to HPLC analysis (method 6, retention time of Compound 25a: 6.712 min).

LCMS (ESI): Retention time: 6.696 minutes, m/z=637.29 [M+Na]$^+$ (LCMS analysis conditions: method 6)

Yield: 84%

Example 16-1

Compound 26: Synthesis of tert-butyl $N^2$-{(2S)-2-[(1-aminocyclopentane-1-carbonyl)(methyl)amino]-2-cyclopentylacetyl}-N,N,$N^2$-trimethyl-L-α-asparaginate

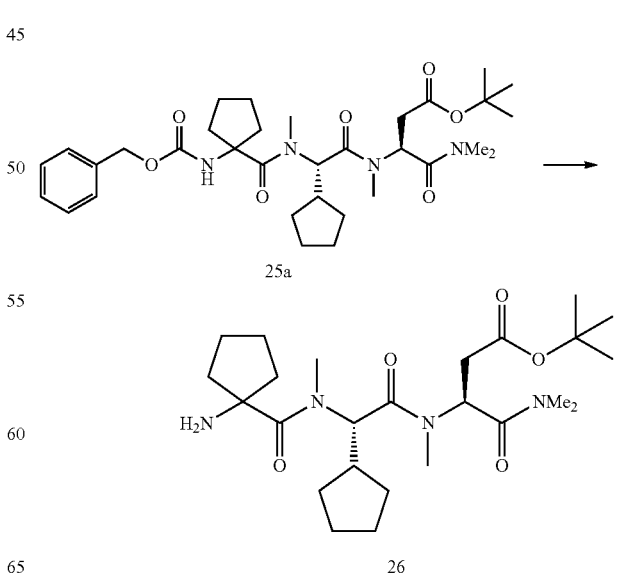

5% Pd/C (0.85 g, 50% wetted with water) and THF (14.04 mL) were added at room temperature to a reaction vessel, and then the external temperature was set at 25° C. Next, Compound 25a (3.51 g) dissolved in THF (42.12 mL) was added at room temperature to the reaction vessel, then the external temperature was set at 25° C., and this was degassed and purged with hydrogen gas and stirred for 2 hours. The reaction mixture was sampled, sample preparation was carried out (Sample preparation method 1), and by subjecting it to HPLC analysis, the reaction conversion rate was confirmed to be 99.9% or more (Equation 1 for reaction conversion rate calculation). The reaction mixture was filtered, and the residue was washed with THF (14.04 mL×2). Concentrating the resulting solution under reduced pressure gave a residue (7.37 g) containing Compound 26. The obtained residue and 1,3,5-trimethoxybenzene were dissolved in DMSO-d6, and this was subjected to qNMR analysis (yield: 93%).

LCMS (ESI): Retention time: 2.421 minutes, m/z=503.19 [M+Na]⁺ (LCMS analysis conditions: method 3)

Example 17

Compound 28: Synthesis of (benzyl (2S)-2-[[1-[[(1S)-2-[[(1S)-3-tert-butoxy-1-(dimethylcarbamoyl)-3-oxo-propyl]-methyl-amino]-1-cyclopentyl-2-oxo-ethyl]-methyl-carbamoyl]cyclopentyl]carbamoyl]pyrrolidine-1-carboxylate)

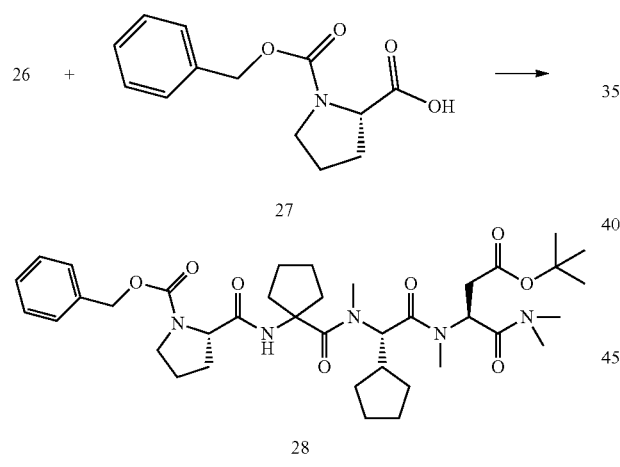

To a reaction tank purged with nitrogen, Compound 27 (2.65 kg) and acetonitrile (2.9 kg) were sequentially added at room temperature. The external temperature of the reaction tank was set at 10° C., and the solution (19.1 kg) containing Compound 26 obtained in Example 16, DIPEA (3.17 kg), and 2-bromo-1-ethylpyridinium tetrafluoroborate (3.36 kg) were sequentially added. The external temperature of the reaction tank was set at 25° C., and the mixture was stirred for 2 hours. The reaction mixture was sampled, sample preparation was carried out (Sample preparation method 1), and the reaction conversion rate was confirmed to be 99.3% by HPLC analysis (Equation 1 for reaction conversion rate calculation). The external temperature of the reaction tank was set at 10° C., and CPME (34.1 kg), 5% aqueous sodium carbonate solution (23.6 kg), and N-methylimidazole (0.67 kg) were sequentially added. The external temperature of the reaction tank was set at 25° C., and after stirring the mixture for 40 minutes, the aqueous layer was removed from the reaction tank. The external temperature of the reaction tank was set at 10° C., and 5% aqueous sodium hydrogen sulfate monohydrate solution (23.6 kg) was added. The external temperature of the reaction tank was set at 25° C., and after stirring the mixture for 10 minutes, the aqueous layer was removed from the reaction tank. The resulting organic layer was washed with 5% aqueous sodium hydrogen sulfate monohydrate solution (23.6 kg×2) and 5% aqueous sodium carbonate solution (23.6 kg×2), and then 2-MeTHF (26.0 kg) was added. The resulting organic layer was concentrated under reduced pressure while stirring at an external temperature of 40° C. until the liquid volume reached approximately 12 L. THF (19.7 kg) was added to the resulting residue, and then this was concentrated under reduced pressure while stirring at an external temperature of 40° C. until the liquid volume reached approximately 12 L. The external temperature of the reaction tank was set at 20° C., and then CPME (9.0 kg) was added to the reaction tank. This mixture was concentrated under reduced pressure while stirring at an external temperature of 40° C. until the liquid volume reached approximately 12 L. CPME (10.0 kg) was added to the reaction tank, and this mixture was concentrated under reduced pressure while stirring at an external temperature of 40° C. until the liquid volume reached approximately 12 L. Stirring was stopped, and then THF (14.1 kg) was added to the reaction tank. The resulting residue was combined with a wash solution obtained by washing the reaction tank with THF (5.2 kg) to afford a solution (28.8 kg) containing Compound 28.

Retention time by HPLC analysis: 4.189 minutes (HPLC analysis conditions: method 3)

Example 17-1 (when Using 2-MeTHF Instead of Acetonitrile which was Used in the Above-Mentioned Method for Synthesizing Compound 28)

Compound 28: Synthesis of (benzyl (2S)-2-[[1-[[(1S)-2-[[(1S)-3-tert-butoxy-1-(dimethylcarbamoyl)-3-oxo-propyl]-methyl-amino]-1-cyclopentyl-2-oxo-ethyl]-methyl-carbamoyl]cyclopentyl]carbamoyl]pyrrolidine-1-carboxylate)

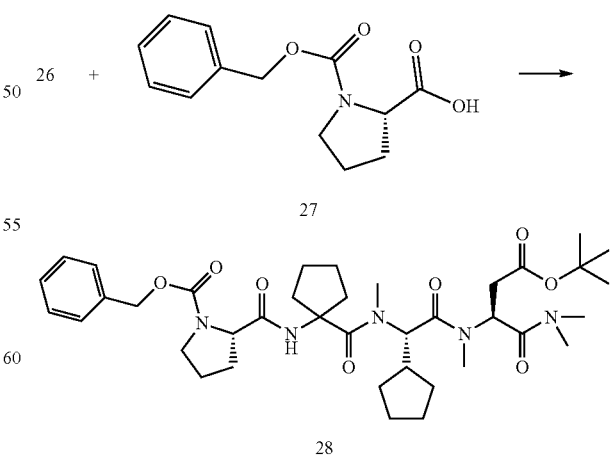

A stored solution (1.29 g) containing Compound 26 was added to a reaction vessel, and at an external temperature of 40° C., this was concentrated to dryness under reduced pressure. Subsequently, 2-MeTHF (0.91 mL) and Compound 27 (126.90 mg) were added to the reaction vessel. DIPEA (0.37 mL) was added while stirring at room temperature, then HATU (338.30 mg) was added, and this was stirred at room temperature for 3 hours. To the reaction vessel, 2-MeTHF (1.84 mL) and 5% aqueous sodium carbonate solution (1.09 mL), and additionally N-methylimidazole (30.30 L) were added and then this was stirred for 30 minutes. After removing the aqueous layer, the resulting organic layer was washed with 2.5% aqueous ammonia solution (1.09 mL), 5% aqueous sodium hydrogen sulfate monohydrate solution (1.09 mL×2), 5% aqueous sodium carbonate solution (1.09 mL×2), 2.5% aqueous ammonia solution (1.09 mL×3), 5% aqueous sodium hydrogen sulfate monohydrate solution (1.09 mL×2), and 5% aqueous sodium carbonate solution (1.09 mL×2). The resulting organic layer was concentrated to dryness under reduced pressure at an external temperature of 40° C. to afford a Compound 28-containing residue (0.19 g, 50.9% yield).

LCMS(ESI): Retention time: 4.178 minutes, m/z=735 [M+Na]$^+$ (LCMS analysis conditions: method 3)

Yield: 50.9% (The obtained residue and 3,5-bis(trifluoromethyl)benzoic acid were dissolved in DMSO-d6, and this was subjected to qNMR analysis.)

Example 18

Compound 29: Synthesis of (tert-butyl (3S)-3-[[(2S)-2-cyclopentyl-2-[methyl-[1-[[(2S)-pyrrolidine-2-carbonyl]amino]cyclopentanecarbonyl]amino]acetyl]-methyl-amino]-4-(dimethylamino)-4-oxo-butanoate)

28 ⟶

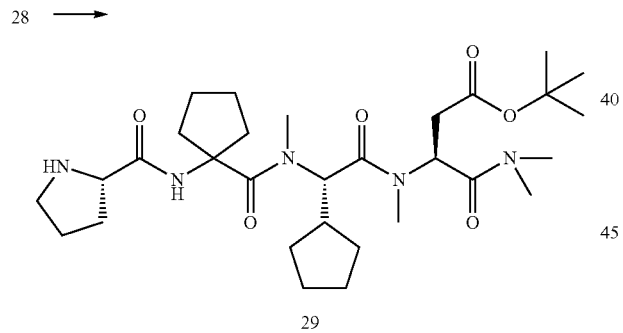

29

To a reaction tank purged with nitrogen, 5% Pd/C (1.16 kg, 50% wetted with water), the solution (27.4 kg) containing Compound 28 obtained in Example 17, and THF (0.4 kg) were sequentially added at room temperature. The external temperature of the reaction tank was set at 25° C., and the reaction tank was pressurized with hydrogen until the internal pressure of the reaction tank reached 0.18 MPaG. 2 hours and 30 minutes later, absence of internal pressure change was confirmed, and then after purging with nitrogen, this was pressurized with hydrogen to 0.18 MPaG, and the mixture was stirred for another hour. The reaction mixture was sampled, sample preparation was carried out (Sample preparation method 1), and the reaction conversion rate was confirmed to be 99.6% by HPLC analysis (Equation 1 for reaction conversion rate calculation). The interior of the reaction tank was purged with nitrogen, and then the reaction mixture was subjected to pressure filtration. The reaction tank and the filtration apparatus were washed with 2-MeTHF (10.0 kg×3). The obtained filtrate and wash solution were concentrated under reduced pressure while stirring at an external temperature of 40° C. until the liquid volume reached approximately 9 L. 2-MeTHF (6.9 kg) was added to the resulting residue, and again, this was concentrated under reduced pressure at an external temperature of 40° C. until the liquid volume of the reaction mixture reached approximately 9 L. Again, 2-MeTHF (4.3 kg) was added to the resulting residue, and this was concentrated under reduced pressure at an external temperature of 40° C. until the liquid volume of the reaction mixture reached approximately 9 L to afford a concentrated solution of the reaction mixture containing Compound 29.

Retention time by HPLC analysis: 2.846 minutes (HPLC analysis conditions: method 3)

Example 18-1 (When using 2-MeTHF instead of THF/2-MeTHF which was used in the above-mentioned method for synthesizing Compound 29)

Compound 29: Synthesis of (tert-butyl (3S)-3-[[(2S)-2-cyclopentyl-2-[methyl-[1-[[(2S)-pyrrolidine-2-carbonyl]amino]cyclopentanecarbonyl]amino]acetyl]-methyl-amino]-4-(dimethylamino)-4-oxo-butanoate)

28 ⟶

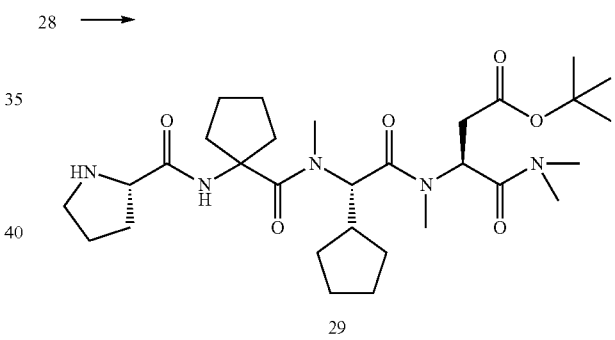

29

The solution (1014.92 mg) containing Compound 28 (121.49 mg) obtained in Example 17 was added to a reaction vessel, and this was concentrated to dryness under reduced pressure at an external temperature of 60° C. Next, to a reaction vessel purged with nitrogen, 2-MeTHF (2081 mg) and 5% Pd/C (25.89 mg, 50% wetted with water) were added sequentially at room temperature. The external temperature of the reaction vessel was set at 25° C., and the reaction vessel was pressurized with hydrogen until the internal pressure of the reaction vessel reached 0.18 MPaG. Seven hours later, the reaction mixture was sampled, sample preparation was carried out (Sample preparation method 1), and the reaction conversion rate was confirmed to be 99.9% by HPLC analysis (Equation 1 for reaction conversion rate calculation). After purging the interior of the reaction vessel with nitrogen, the reaction mixture was subjected to filtration under reduced pressure. The reaction vessel, Kiriyama funnel, and filter were washed with 2-MeTHF (1041 mg×3). The obtained solution was analyzed by HPLC. As a result of HPLC analysis using a standard, 91.00 mg (92.3% yield) of Compound 29 was found to be obtained.

LCMS (ESI) of Compound 29: Retention time: 2.826 minutes, m/z=578 [M+H]$^+$ (LCMS analysis conditions: method 3)

Example 19

Compound 31: Synthesis of (tert-butyl (3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoate)

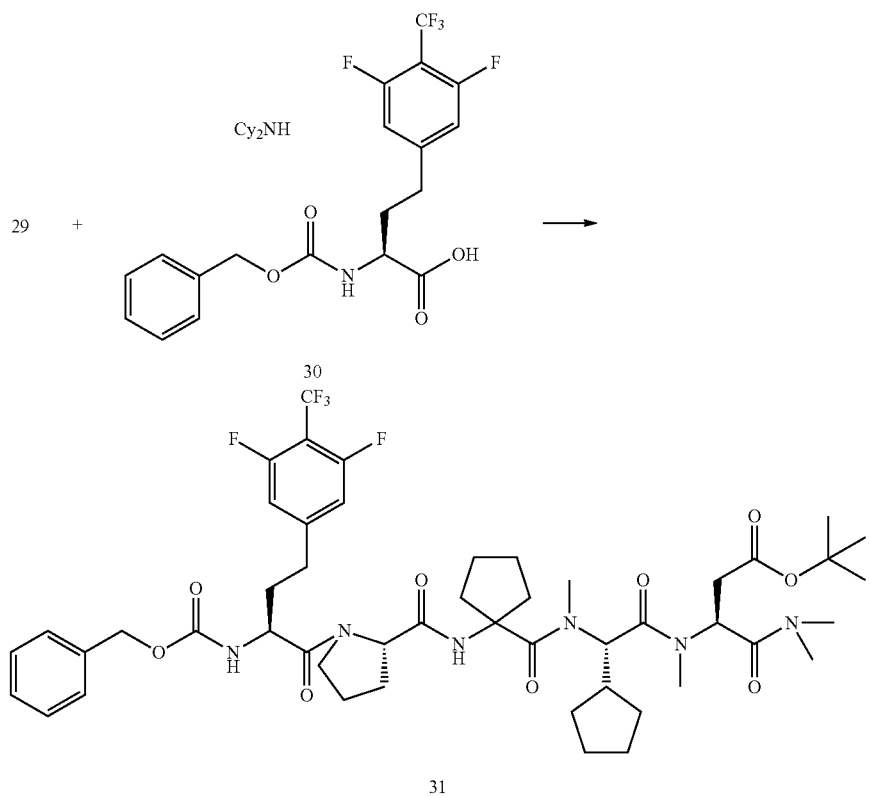 [SMILES: O=C(N[C@@H](CCc1cc(F)c(C(F)(F)F)c(F)c1)C(=O)O)OCc1ccccc1 ; "Cy2NH" ; CN(C)C(=O)[C@H](CC(=O)OC(C)(C)C)N(C)C(=O)[C@H](C1CCCC1)N(C)C(=O)C1(NC(=O)[C@@H]2CCCN2C(=O)[C@H](CCc2cc(F)c(C(F)(F)F)c(F)c2)NC(=O)OCc2ccccc2)CCCC1]

To a reaction tank containing the concentrated solution of the reaction mixture containing Compound 29 obtained in Example 18, which was purged with nitrogen, 2-MeTHF (5.0 kg) and Compound 30 (3.08 kg) were sequentially added at room temperature. The external temperature of the reaction tank was set at 10° C., and DIPEA (2.44 kg), T3P (50 wt % 2-MeTHF solution (6.56 kg)), and 2-MeTHF (0.4 kg) were sequentially added while stirring. The external temperature of the reaction tank was set at 25° C., and the mixture was stirred for 1 hour. The reaction mixture was sampled, sample preparation was carried out (Sample preparation method 1), and the reaction conversion rate was confirmed to be 99.3% by HPLC analysis (Equation 1 for reaction conversion rate calculation). The external temperature of the reaction tank was set at 15° C., and while stirring, 5% aqueous potassium carbonate solution (15.9 kg), and N-methylimidazole (352.4 g) were added. The external temperature of the reaction tank was set at 25° C., and after stirring the mixture for 3 hours and 30 minutes, the aqueous layer was removed from the reaction tank. The external temperature of the reaction tank was set at 20° C., and 10% aqueous sodium hydrogen sulfate monohydrate solution (14.9 kg) was added. The external temperature of the reaction tank was set at 25° C., and after stirring the mixture for 15 minutes, the aqueous layer was removed from the reaction tank. The resulting organic layer was washed with 10% aqueous sodium hydrogen sulfate monohydrate solution (14.9 kg), and then to the resulting organic layer, acetonitrile (4.5 kg), MTBE (4.4 kg), heptane (6.2 kg), and 2.5% aqueous potassium carbonate solution (14.1 kg) were sequentially added at an external temperature of 25° C. After stirring the mixture for 10 minutes, stirring was stopped, and then the aqueous layer was removed from the reaction tank. To the resulting organic layer, 2.5% aqueous potassium carbonate solution (21.3 kg), acetonitrile (6.6 kg), and 2-MeTHF (2.1 kg) were added, this was stirred for 10 minutes, stirring was stopped, and then the aqueous layer was removed from the reaction tank. To the resulting organic layer, 2.5% aqueous potassium carbonate solution (21.3 kg) and acetonitrile (6.6 kg) were added, this was stirred for 10 minutes, stirring was stopped, and then the aqueous layer was removed from the reaction tank. To the resulting organic layer, 2-MeTHF (26.0 kg) was added, and this was concentrated under reduced pressure while stirring at an external temperature of 40° C. until the liquid volume of the reaction mixture reached approximately 9 L. The operation of adding isopropyl acetate (15.1 kg) to the resulting residue, and concentrating this under reduced pressure until the liquid volume of the reaction mixture reaches approximately 9 L, was repeated twice. The residue was combined with a wash solution obtained by washing the reaction tank with isopropyl acetate (7.0 kg) to afford a solution (16.5 kg) containing Compound 31.

Retention time by HPLC analysis: 4.978 minutes (HPLC analysis conditions: method 3)

Example 20

Compound 32: Synthesis of ((3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoic acid)

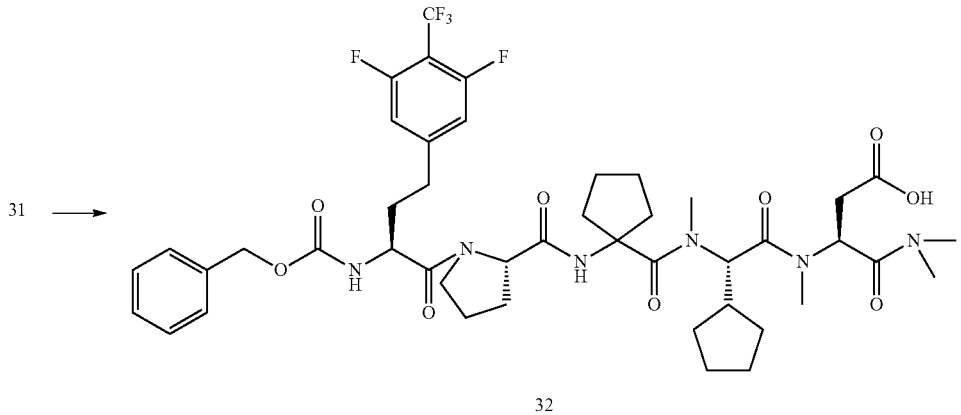 [SMILES: CN(C)C(=O)[C@H](CC(=O)O)N(C)C(=O)[C@H](C1CCCC1)N(C)C(=O)C1(NC(=O)[C@@H]2CCCN2C(=O)[C@H](CCc2cc(F)c(C(F)(F)F)c(F)c2)NC(=O)OCc2ccccc2)CCCC1]

To a reaction tank purged with nitrogen, the solution (16.3 kg) containing Compound 31 obtained in Example 19, isopropyl acetate (5.7 kg), and hexamethyldisilazane (1.69 kg) were sequentially added at room temperature. The external temperature of the reaction tank was set at 10° C., and trimethylsilyl trifluoromethanesulfonate (1.87 kg) was added while stirring. While keeping the external temperature at 20° C. to 30° C., the reaction mixture was stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). The external temperature of the reaction tank was set at 0° C., and 2-MeTHF (17.6 kg) and 5% aqueous dipotassium hydrogen phosphate solution (41.1 kg) were sequentially added to the reaction tank. The external temperature of the reaction tank was set at 25° C., and after stirring the reaction mixture for 10 minutes, stirring was stopped, and the aqueous layer was removed from the reaction tank. Subsequently, the organic layer was washed with 5% aqueous sodium dihydrogen phosphate solution (41.1 kg). To the resulting organic layer, DIPEA (2.39 kg) and 2-MeTHF (26.0 kg) were added while stirring, and then this was concentrated under reduced pressure at an external temperature of 30° C. to 33° C. until the liquid volume reached approximately 8 L. The residue was combined with a wash solution obtained by washing the reaction tank with 2-MeTHF (6.8 kg×2) to afford a solution (14.7 kg) containing Compound 32.

Retention time by HPLC analysis: 4.220 minutes (HPLC analysis conditions: method 3)

Example 20-1 (when Using 2-MeTHF Instead of Isopropyl Acetate which was Used in the Above-Mentioned Method for Synthesizing Compound 32)

Compound 32: Synthesis of ((3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoic acid)

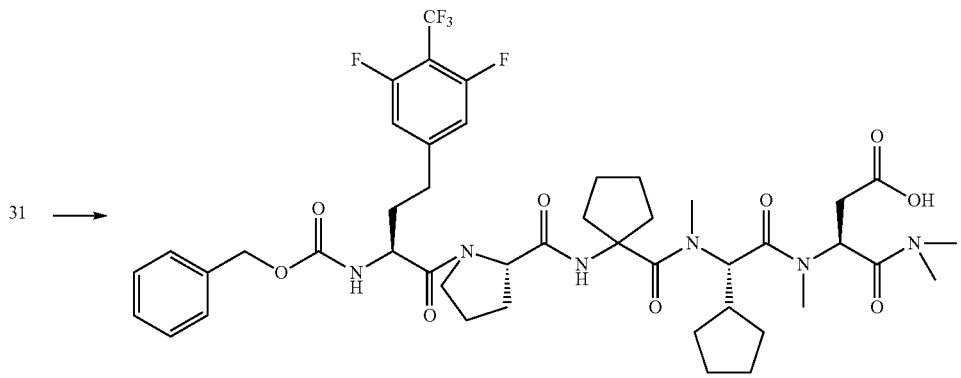

The solution (401.94 mg) containing Compound 31 (93.45 mg) obtained in Example 19 was added to a reaction vessel, and this was concentrated to dryness under reduced pressure at an external temperature of 60° C. 2-MeTHF (402 mg) and hexamethyldisilazane (38.6 mg) were sequentially added at room temperature. The external temperature of the reaction vessel was set at 0° C., and trimethylsilyl trifluoromethanesulfonate (43.4 mg) was added while stirring. The external temperature of the reaction vessel was set at 25° C., and the reaction mixture was stirred for 1 hour. The reaction mixture was sampled, sample preparation was carried out (Sample preparation method 1), and the reaction conversion rate was confirmed to be 99.9% or more by HPLC analysis (Equation 1 for reaction conversion rate calculation). The external temperature of the reaction vessel was set at 0° C., and 2-MeTHF (402 mg) and 5% aqueous dipotassium hydrogen phosphate solution (0.93 mL) were added sequentially to the reaction vessel. The external temperature of the reaction vessel was set at room temperature, and after stirring the reaction mixture for 10 minutes, stirring was stopped, and the aqueous layer was removed from the reaction vessel. Subsequently, the organic layer was washed with 5% aqueous sodium dihydrogen phosphate solution (0.93 mL). To the resulting organic layer, DIPEA (54.4 mg) was added while stirring. The obtained solution was analyzed by HPLC. As a result of HPLC analysis using a standard, 81.01 mg (92.0% yield) of Compound 32 was found to be obtained.

LCMS (ESI) of Compound 32: Retention time: 4.132 minutes, m/z=921 [M+H]$^+$ (LCMS analysis conditions: method 3)

Example 21

Compound 33: Synthesis of (tert-butyl 2-[[(2S)-2-[[(2S)-1-[(2S)-2-[[(2S,3S)-2-[[(2S)-2-[[(3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetate)

To a reaction tank purged with nitrogen, the solution (11.9 kg) containing Compound 17 obtained in Example 10, the solution (12.84 kg) containing Compound 32 obtained in Example 20, and 2-MeTHF (3.1 kg) were sequentially added at room temperature. The external temperature of the reaction tank was set at 10° C., and DMF (6.4 kg), DIPEA (1.6 kg) and HATU (2.78 kg) were added to the reaction mixture. While keeping the external temperature at 20° C., this was stirred for 3 hours. The reaction mixture was sampled, sample preparation was carried out (Sample preparation method 1), and the reaction conversion rate was confirmed to be 99.6% by HPLC analysis (Equation 1 for reaction conversion rate calculation). At an external temperature of 10° C., 2.5% aqueous ammonia solution (19.9 kg) was added, and then the external temperature of the reaction tank was set at 25° C., and this was stirred for 10 minutes. Stirring was stopped, the aqueous layer was removed from the reaction tank, then 10% aqueous sodium hydrogen sulfate monohydrate solution (19.9 kg) was added to the resulting organic layer at an external temperature of 20° C., then the external temperature of the reaction tank was set at 25° C., and this was stirred for 10 minutes. Stirring was stopped, the aqueous layer was removed from the reaction tank, and then the resulting organic layer was washed with 5% aqueous sodium carbonate solution (19.9 kg). The resulting organic layer was concentrated under reduced pressure while stirring at an external temperature of 40° C. until the liquid volume reached approximately 10 L. The operation of adding 2-MeTHF (17.0 kg) to the reaction mixture, and concentrating this under reduced pressure while stirring at an external temperature of 40° C. until the liquid volume reaches approximately 10 L, was repeated twice. The residue was combined with a wash solution obtained by washing the reaction tank with 2-MeTHF (6.8 kg), and this was recovered as a solution (23.9 kg) containing Compound 33 in a storage container. Retention time by HPLC analysis: 10.272 minutes (HPLC analysis conditions: method 4)

Condensation Reaction Between Compound 17 and Compound 32 (Examination of Reaction Conditions for Example 21)

Solvents were examined for the condensation reaction between Compound 17 and Compound 32. The condensation reaction was monitored by HPLC analysis. The yield was calculated based on area percent (Area %) determined by HPLC analysis and values measured by qNMR.

17 + 32 ⟶

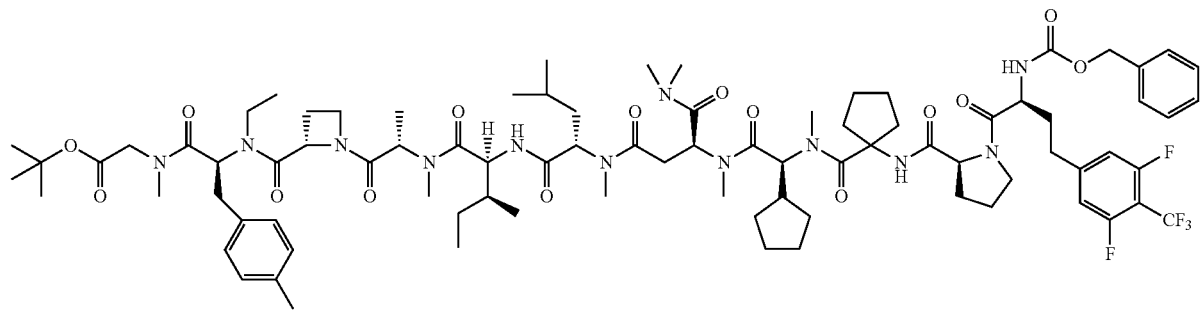

Example 21-1 (when Using 2-MeTHF and Acetonitrile Instead of 2-MeTHF and DMF which were Used in the Above-Mentioned Method for Synthesizing Compound 33)

Compound 33: Synthesis of (tert-butyl 2-[[(2S)-2-[[(2S)-1-[(2S)-2-[[(2S,3S)-2-[[(2S)-2-[[(3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino] acetate)

Example 21-2 (when Using 2-MeTHF Instead of 2-MeTHF and DMF which were Used in the Above-Mentioned Method for Synthesizing Compound 33)

Compound 33: Synthesis of (tert-butyl 2-[[(2S)-2-[[(2S)-1-[(2S)-2-[[(2S,3S)-2-[[(2S)-2-[[(3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino] acetate)

To a flask, the solution (4062.5 mg) containing Compound 17 obtained in Example 10, the solution (4534.0 mg)

17 + 32 →

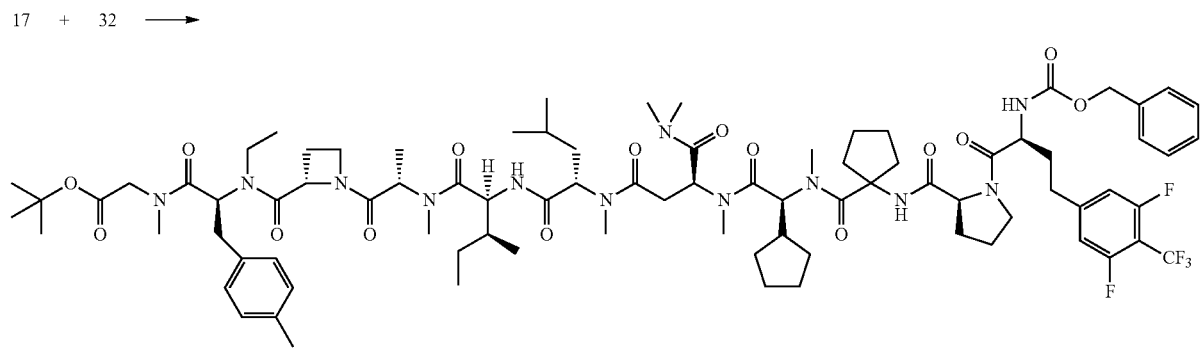

33

To a flask, the solution (1017.1 mg) containing Compound 17 obtained in Example 10, the solution (1133.0 mg) containing Compound 32 obtained in Example 20, and 2-MeTHF (313.7 μL) were sequentially added at room temperature. The external temperature was cooled to 10° C., and a solvent (acetonitrile (575 μL)), DIPEA (266 μL), and HATU (238.0 mg) were added to the reaction mixture, and then the external temperature was raised to 25° C. The reaction mixture was stirred at 25° C. for 3 hours, and then the reaction mixture was sampled, sample preparation was carried out (Sample preparation method 1), and the reaction conversion rate was confirmed to be 99.8% by HPLC analysis (Equation 1 for reaction conversion rate calculation). The external temperature was set at 10° C., 2.5% aqueous ammonia solution (1700 μL) was added, then the external temperature was set at 25° C. and the mixture was stirred for 10 minutes, and then the aqueous layer was removed. The resulting organic layer was washed with 10% aqueous sodium hydrogen sulfate monohydrate solution (1700 μL) and 5% aqueous sodium carbonate solution (1700 μL). The resulting organic layer was concentrated under reduced pressure to afford a residue (622.6 mg) containing Compound 33.

LCMS (ESI): Retention time: 10.35 minutes, m/z=1669 [M+Na]$^+$ (LCMS analysis conditions: method 4)

Yield: 83% (The obtained residue and 3,5-bis(trifluoromethyl)benzoic acid were dissolved in DMSO-d6, and this was subjected to qNMR analysis.)

containing Compound 32 obtained in Example 20, and 2-MeTHF (1254 μL) were sequentially added at room temperature to afford a solution containing Compound 17 and Compound 32. The solution (969.5 mg) containing Compound 17 and Compound 32 was added to a reaction vessel, and by concentrating this under reduced pressure at an external temperature of 40° C., a residue containing Compounds 17 and 32 was obtained. 2-MeTHF (1140 μL) was added at room temperature to the reaction vessel to dissolve the residue. The external temperature was cooled to 10° C., and DIPEA (106 μL) and HATU (94.9 mg) were added to the reaction mixture, and then the external temperature was raised to 25° C. The reaction mixture was stirred at 25° C. for 3 hours, and then the reaction mixture was sampled, sample preparation was carried out (Sample preparation method 1), and the reaction conversion rate was confirmed to be 99.8% by HPLC analysis (Equation 1 for reaction conversion rate calculation). The external temperature was set at 10° C., 2.5% aqueous ammonia solution (680 μL) was added, then the external temperature was set at 25° C. and the mixture was stirred for 10 minutes, and then the aqueous layer was removed. The resulting organic layer was washed with 10% aqueous sodium hydrogen sulfate monohydrate solution (680 μL) and 5% aqueous sodium carbonate solution (680 μL). The resulting organic layer was concentrated under reduced pressure to afford a residue (262.3 mg) containing Compound 33.

LCMS (ESI): Retention time: 10.49 minutes, m/z=1669 [M+Na]+ (LCMS analysis conditions: method 4)

Yield: 85% (The obtained residue and 3,5-bis(trifluoromethyl)benzoic acid were dissolved in DMSO-d6, and this was subjected to qNMR analysis.)

Example 21-3 (when Using Anisole Instead of 2-MeTHF and DMF which were Used in the Above-Mentioned Method for Synthesizing Compound 33)

Compound 33: Synthesis of (tert-butyl 2-[[(2S)-2-[[(2S)-1-[(2S)-2-[[(2S,3S)-2-[[(2S)-2-[[(3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetate)

To a flask, the solution (4062.5 mg) containing Compound 17 obtained in Example 10, the solution (4534.0 mg) containing Compound 32 obtained in Example 20, and 2-MeTHF (1254 µL) were sequentially added at room temperature to afford a solution containing Compound 17 and Compound 32. The solution (969.8 mg) containing Compound 17 and Compound 32 was added to a reaction vessel, and by concentrating this under reduced pressure at an external temperature of 40° C., a residue containing Compounds 17 and 32 was obtained. Anisole (1140 µL) was added at room temperature to the reaction vessel to dissolve the residue. The external temperature was cooled to 10° C., and DIPEA (106 µL) and HATU (97.7 mg) were added to the reaction mixture, and then the external temperature was raised to 25° C. The reaction mixture was stirred at 25° C. for 3 hours, and then the reaction mixture was sampled, sample preparation was carried out (Sample preparation method 1), and the reaction conversion rate was confirmed to be 99.9% by HPLC analysis (Equation 1 for reaction conversion rate calculation). The external temperature was set at 10° C., 2.5% aqueous ammonia solution (680 µL) was added, then the external temperature was set at 25° C., and this mixture was stirred for 10 minutes. Anisole (570 µL) and 2.5% aqueous ammonia solution (340 µL) were added to the reaction vessel, the mixture was stirred for 10 minutes, and then the aqueous layer was removed. The resulting organic layer was washed with 10% aqueous sodium hydrogen sulfate monohydrate solution (920 µL) and 5% aqueous sodium carbonate solution (920 µL). The resulting organic layer was concentrated under reduced pressure to afford a residue (207.3 mg) containing Compound 33.

LCMS (ESI): Retention time: 10.38 minutes, m/z=1669 [M+Na]+ (LCMS analysis conditions: method 4)

Yield: 68% (The obtained residue and 3,5-bis(trifluoromethyl)benzoic acid were dissolved in DMSO-d6, and this was subjected to qNMR analysis.)

Example 21-4 (when Using Dimethyl Carbonate Instead of 2-MeTHF and DMF which were Used in the Above-Mentioned Method for Synthesizing Compound 33)

Compound 33: Synthesis of (tert-butyl 2-[[(2S)-2-[[(2S)-1-[(2S)-2-[[(2S,3S)-2-[[(2S)-2-[[(3S)-3-[[(2S)-2-[[1-[[(2S)-1-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetate)

To a flask, the solution containing Compound 17 obtained in Example 10 (4062.5 mg), the solution containing Compound 32 obtained in Example 20 (4534.0 mg), and 2-MeTHF (1254 µL) were sequentially added at room temperature to afford a solution containing Compound 17 and Compound 32. The solution (968.4 mg) containing Compound 17 and Compound 32 was added to a reaction vessel, and by concentrating this under reduced pressure at an external temperature of 40° C., a residue containing Compounds 17 and 32 was obtained. Dimethyl carbonate (1140 µL) was added at room temperature to the reaction vessel to dissolve the residue. The external temperature was cooled to 10° C., and DIPEA (106 µL) and HATU (95.2 mg) were added to the reaction mixture, and then the external temperature was raised to 25° C. The reaction mixture was stirred at 25° C. for 3 hours, and then the reaction mixture was sampled, sample preparation was carried out (Sample preparation method 1), and the reaction conversion rate was confirmed to be 99.9% by HPLC analysis (Equation 1 for reaction conversion rate calculation). The external temperature was set at 10° C., 2.5% aqueous ammonia solution (680 µL) was added, then the external temperature was set at 25° C., and this was stirred for 10 minutes. Dimethyl carbonate (1140 µL) and 2.5% aqueous ammonia solution (680 µL) were added to the reaction vessel, this was stirred for 10 minutes, and then the aqueous layer was removed. The resulting organic layer was washed with 10% aqueous sodium hydrogen sulfate monohydrate solution (1360 µL) and 5% aqueous sodium carbonate solution (1360 µL). The resulting organic layer was concentrated under reduced pressure to afford a residue (264.6 mg) containing Compound 33.

LCMS (ESI): Retention time: 10.35 minutes, m/z=1669 [M+Na]+ (LCMS analysis conditions: method 4)

Yield: 84% (The obtained residue and 3,5-bis(trifluoromethyl)benzoic acid were dissolved in DMSO-d6, and this was subjected to qNMR analysis.)

Example 21-5 and Example 21-6

Other than using ethyl acetate (Example 21-5) or isopropyl acetate (Example 21-6) as a substitute for 2-MeTHF/acetonitrile, Compound 33 was synthesized by conditions similar to those of Example 21-1. The yield of Compound 33 was 76% in Example 21-5 and 75% in Example 21-6.

The results of Examples 21-1 to 21-6 are shown in the following table.

TABLE 6

Production of Compound 33

| Example No. | Solvent | Yield (%) |
|---|---|---|
| Example 21-1 | 2-MeTHF/acetonitrile | 83 |
| Example 21-2 | 2-MeTHF | 85 |
| Example 21-3 | Anisole | 68 |
| Example 21-4 | Dimethyl carbonate | 84 |
| Example 21-5 | Ethyl acetate | 76 |
| Example 21-6 | Isopropyl acetate | 75 |

According to these results, as a substitute for a mixed solvent made of 2-MeTHF and DMF used in Example 21, use of a mixed solvent made of 2-MeTHF and acetonitrile, 2-MeTHF, anisole, dimethyl carbonate, ethyl acetate, or isopropyl acetate was found to enable high-yield production of Compound 33.

Example 22

Compound 34: Synthesis of (2-[[(2S)-2-[[(2S)-1-[(2S)-2-[[(2S,3S)-2-[[(2S)-2-[[(3S)-3-[[(2S)-2-[[1-[[(2S-1)-[(2S)-2-(benzyloxycarbonylamino)-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetic acid)

33 ⟶

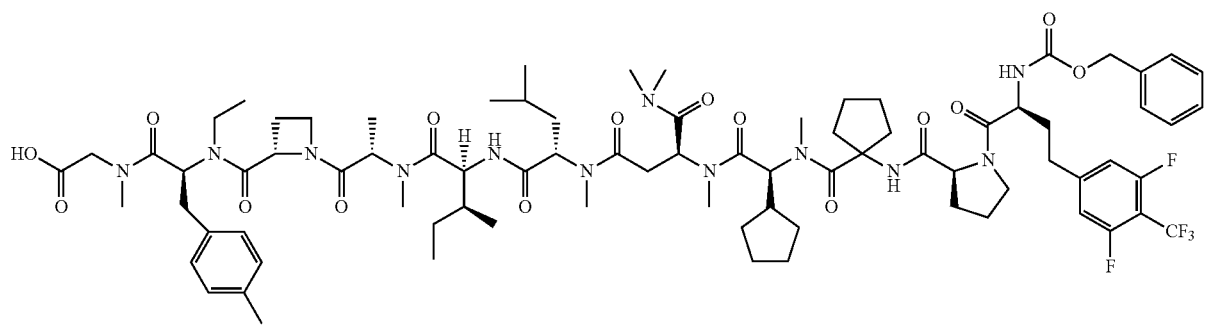

34

To a reaction tank purged with nitrogen, the solution (23.7 kg) containing Compound 33 obtained in Example 21, 2-MeTHF (32.0 kg), and hexamethyldisilazane (3.46 kg) were sequentially added at room temperature. The external temperature of the reaction tank was set at 0° C., and trimethylsilyl trifluoromethanesulfonate (3.99 kg) was added while stirring. While keeping the external temperature at 20° C. to 30° C., this mixture was stirred for 3 hours. The reaction mixture was sampled, sample preparation was carried out (Sample preparation method 1), and the reaction conversion rate was confirmed to be 99.6% or more by HPLC analysis (Equation 1 for reaction conversion rate calculation). The external temperature of the reaction tank was set at 0° C., and 5% aqueous dipotassium hydrogen phosphate solution (23.8 kg) was added to the reaction mixture. The external temperature of the reaction tank was set at 25° C., and after stirring this mixture for 10 minutes, the aqueous layer was removed from the reaction tank. The resulting organic layer was washed with an aqueous solution (23.3 kg×4) containing citric acid monohydrate (0.57 kg) and dipotassium hydrogen phosphate (0.88 kg), and then further washed with 5% aqueous sodium carbonate solution (23.8 kg). To the resulting organic layer, 2-MeTHF (26.0 kg) was added, and then this was concentrated under reduced pressure while stirring at an external temperature of 40° C. until the liquid volume reached approximately 10 L. THF (13.6 kg) was added to the resulting residue, and this was concentrated under reduced pressure while stirring at an external temperature of 40° C. until the liquid volume reached approximately 10 L. This was followed by addition of 2-MeTHF (8.5 kg), and this mixture was concentrated under reduced pressure while stirring at an external temperature of 40° C. until the liquid volume reached approximately 10 L. A solution produced by adding THF (6.8 kg) to the resulting residue was combined with a wash solution obtained by washing the reaction tank with THF (6.6 kg) and 2-MeTHF (7.1 kg) to afford a solution (29.0 kg) containing Compound 34. Retention time by HPLC analysis: 9.215 minutes (HPLC analysis conditions: method 4)

Example 23

Compound 35: Synthesis of (2-[[(2S)-2-[[(2S)-1-[(2S)-2-[[(2S,3S)-2-[[(2S)-2-[[(3S)-3-[[(2S)-2-[[1-[[(2S)-1-[(2S)-2-amino-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino] acetic acid)

34 ⟶

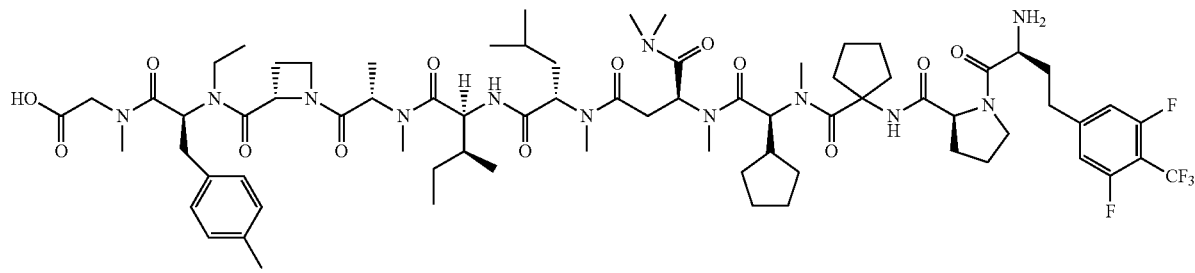

35

Example 23 used the solution (14.5 kg) containing Compound 34 obtained in Example 22, and was carried out by performing the following two-part operation.

To a reaction tank purged with nitrogen, 5% Pd/C (756.6 g, 50% wetted with water) was added, and then THF (7.5 kg) was added. The external temperature of the reaction tank was set at 25° C. The solution (14.5 kg) containing Compound 34 obtained in Example 22 and THF (0.7 kg) were added sequentially. The external temperature of the reaction tank was set at 25° C., and while stirring this mixture, the reaction tank was pressurized with hydrogen until the internal pressure of the reaction tank reached 0.18 MPaG. After 2.5 hours, absence of internal pressure change was confirmed, and then the reaction tank was pressurized with hydrogen to 0.18 MPaG, and the mixture was stirred for another hour. The reaction mixture was sampled, sample preparation was carried out (Sample preparation method 1), and the reaction conversion rate was confirmed to be 99.6% by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (4.9 kg×2), and then the filtrate and the wash solution were combined to afford a storage solution containing Compound 34 (first batch).

To a reaction tank purged with nitrogen, 5% Pd/C (756.6 g, 50% wetted with water) was added, and then THF (7.5 kg) was added. The external temperature of the reaction tank was set at 25° C. The solution (14.5 kg) containing Compound 34 obtained in Example 22 and THF (0.7 kg) were added sequentially. The external temperature of the reaction tank was set at 25° C., and while stirring, the reaction tank was pressurized with hydrogen until the internal pressure of the reaction tank reached 0.18 MPaG. 1 hour later, absence of internal pressure change was confirmed, and then the reaction tank was pressurized with hydrogen to 0.18 MPaG, and the mixture was stirred for another hour. The reaction mixture was sampled, sample preparation was carried out (Sample preparation method 1), and the reaction conversion rate was confirmed to be 99.6% by HPLC analysis (Equation 1 for reaction conversion rate calculation). After purging the interior of the reaction tank with nitrogen, the reaction mixture was subjected to pressure filtration. The interior of the reaction tank and the filtration apparatus were washed with 2-MeTHF (4.9 kg×3), and then the filtrate, the wash solution, and the storage solution of the first batch obtained above were combined to afford a storage solution (60.5 kg) containing Compound 34.

To a reaction tank purged with nitrogen, the above-mentioned storage solution (60.5 kg) containing Compound 34 and 2-MeTHF (0.4 kg) were sequentially added at room temperature. This mixture was concentrated under reduced pressure while stirring at an external temperature of 40° C. until the liquid volume reached 7.3 L, and then the external temperature was set at 25° C. To the resulting residue, acetonitrile (20.3 kg), 2-MeTHF (6.3 kg), and heptane (35.4 kg) were added, and this was stirred for 30 minutes. Stirring was stopped, and then the lower layer was recovered in a storage container. To the obtained lower organic layer, acetonitrile (52.7 kg) and DIPEA (1.6 kg) were added, to afford a solution (83.6 kg) containing Compound 35.

Retention time by HPLC analysis: 6.480 minutes (HPLC analysis conditions: method 4)

Example 23-1 (when Using 2-MeTHF Instead of THF which was Used in the Above-Mentioned Method for Synthesizing Compound 35)

Compound 35: Synthesis of (2-[[(2S)-2-[[(2S)-1-[(2S)-2-[[(2S,3S)-2-[[(2S)-2-[[(3S)-3-[[(2S)-2-[[1-[[(2S)-1-[(2S)-2-amino-4-[3,5-difluoro-4-(trifluoromethyl)phenyl]butanoyl]pyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetic acid)

34 →

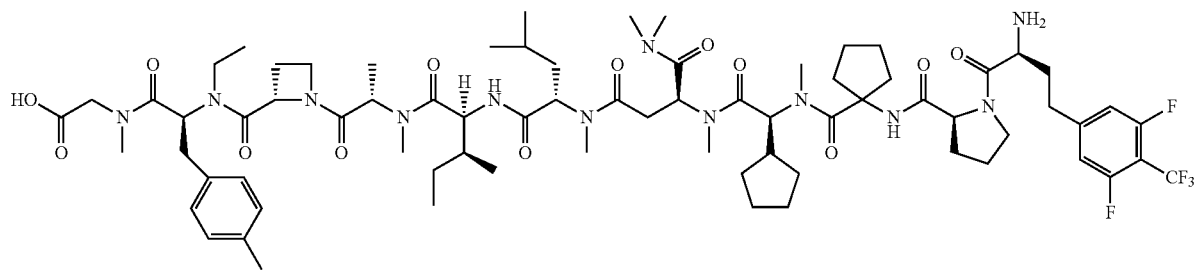

35

The solution (2447.7 mg) containing Compound 34 obtained in Example 22 was added to a reaction vessel, and concentrating this under reduced pressure gave a residue containing Compound 34. 2-MeTHF (2040 µL) and 5% Pd/C (96.8 mg, 50% wetted with water) were added to the reaction vessel, and then this was degassed and purged with hydrogen gas and stirred for 4 hours. 2-MeTHF (460 µL) and 5% Pd/C (47.3 mg, 50% wetted with water) were added to the reaction vessel, and then this was degassed and purged with hydrogen gas and stirred for 4 hours. The reaction mixture was sampled, sample preparation was carried out (Sample preparation method 1), and by subjecting it to HPLC analysis, the reaction conversion rate was confirmed to be 99.7% (Equation 1 for reaction conversion rate calculation). The reaction mixture was filtered, and the residue was washed with 2-MeTHF (690 µL×2). The obtained organic layer was concentrated under reduced pressure to afford a residue (670.1 mg) containing Compound 35. The obtained residue was diluted in acetonitrile, and subjected to LCMS analysis (LCMS analysis conditions: method 4: retention time for Compound 35; retention time: 6.94 minutes, m/z=1457 [M+H]$^+$). The obtained residue and 3,5-bis(trifluoromethyl)benzoic acid were dissolved in DMSO-d6, and this was subjected to qNMR analysis (yield: 95%).

Example 24

Compound 1: Synthesis of (((5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontin-21,1'-cyclopentane]-15-carboxamide)

35 →

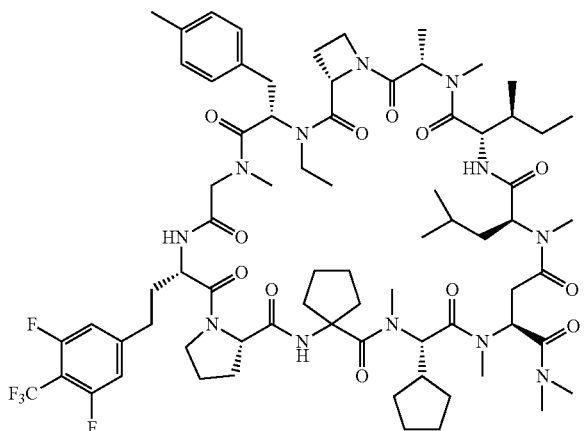

1

To a reaction tank purged with nitrogen, acetonitrile (21.4 kg) and HATU (3.86 kg) were added, and acetonitrile (55.0 kg) was further added. The external temperature of the reaction tank was set at 25° C., and the solution (82.8 kg) containing Compound 35 obtained in Example 23 was added dropwise to the reaction mixture at a rate of 0.3 kg/min to 0.4 kg/min. This solution was washed in with acetonitrile (6.1 kg), a rinse solution was added, and this mixture was stirred for 30 minutes. The reaction mixture was sampled, sample preparation was carried out (Sample preparation method 1), and the reaction conversion rate was confirmed to be 99.9% by HPLC analysis (Equation 1 for reaction conversion rate calculation). The external temperature of the reaction tank was set at 30° C., and while stirring, this was concentrated under reduced pressure until the liquid volume reached approximately 27 L. The external temperature of the reaction tank was set at 25° C., and ethyl acetate (104.7 kg) was added to the resulting residue. While stirring at an external temperature of 25° C., 2.5% aqueous ammonia solution (77.8 kg) was added, and this mixture was stirred for 85 minutes. The aqueous layer was removed from the reaction tank, and then 5% aqueous potassium hydrogen sulfate monohydrate solution (89.8 kg) was added to the resulting organic layer while stirring at an external temperature of 20° C. At an external temperature of 25° C., this mixture was stirred for 12 minutes. After removing the aqueous layer from the reaction tank, the resulting organic layer was washed at an external temperature of 25° C. with 5% aqueous disodium hydrogen phosphate solution (89.8 kg), 5% aqueous sodium chloride solution (89.8 kg), and 0.5% aqueous sodium chloride solution (89.8 kg×2). The resulting organic layer was concentrated under reduced pressure while stirring until the liquid volume reached approximately 19 L, by setting the external temperature of the reaction tank at 40° C. The resulting residue was subjected to pressure filtration, and after washing the reaction tank and the filtration apparatus with ethyl acetate (17.4 kg), the filtrate and the wash solution were washed in with ethyl acetate (17.4 kg) to afford a solution (63.1 kg) containing Compound 1. A storage solution (63.1 kg) containing the above-mentioned Compound 1 was subjected to the operation of adding acetone (15.3 kg) and concentrating this under reduced pressure until the liquid volume reaches approximately 8 L to 12 L, and this operation was repeated seven times. The resulting residue was subjected to pressure filtration, and the resulting solution was recovered as a storage solution. The reaction tank and the filtration apparatus were washed with acetone (15.3 kg×2), then this acetone wash solution was subjected to pressure filtration, this wash solution was combined with the storage solution, and this mixture was recovered it into a storage container as a solution (51.4 kg) containing Compound 1. Retention time by HPLC analysis: 18.008 minutes (HPLC analysis conditions: method 5)

Cyclization reaction of Compound 35 (Examination of reaction conditions for Example 24)

Condensing agents and solvents were examined for the cyclization reaction that uses Compound 35 as a starting material to form Compound 1. The cyclization reaction was monitored by HPLC analysis. The yield was calculated based on Area % ratio determined by HPLC analysis by using methyl benzoate as an internal standard substance.

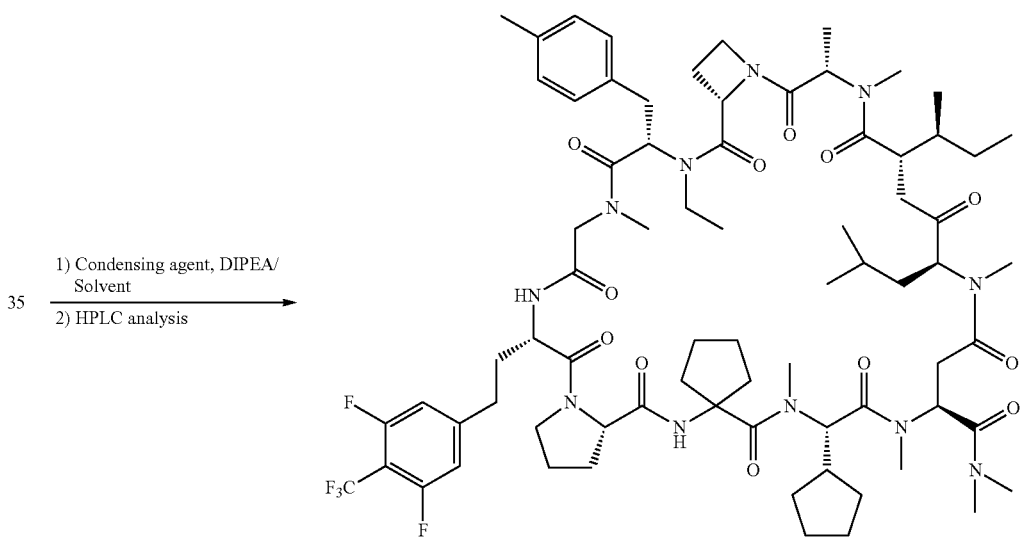

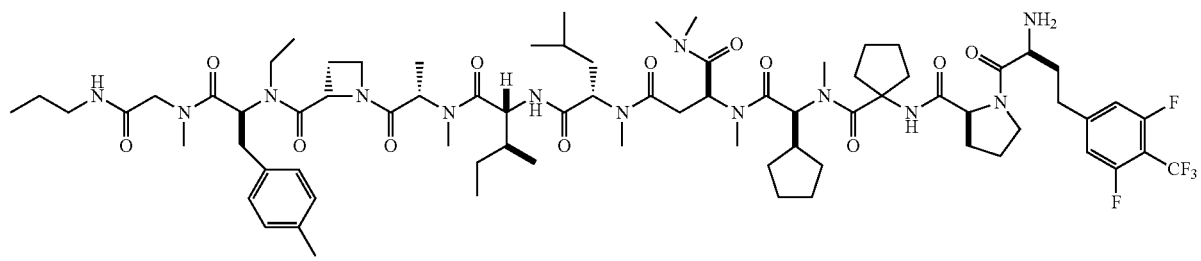
Propylamide of Compound 35
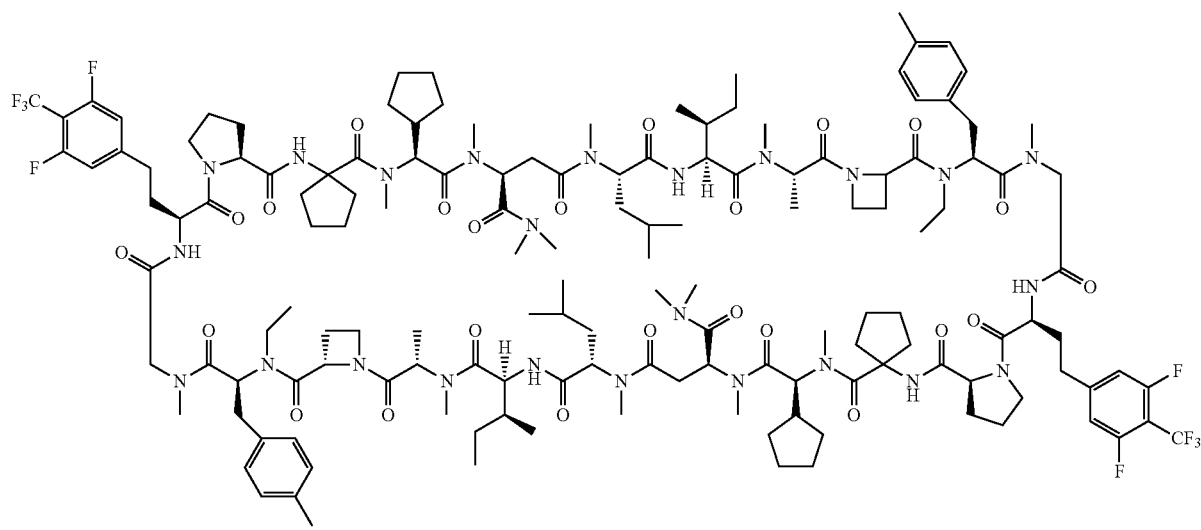
Cyclic dimer
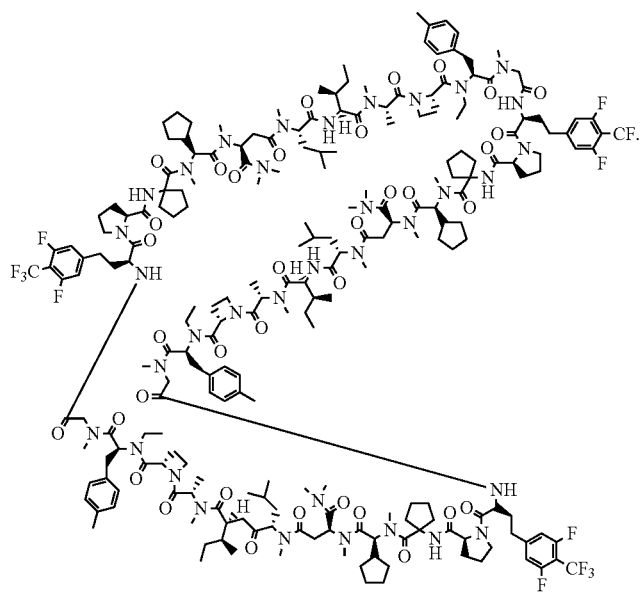
Cyclic trimer

Example 24-1

Compound 1: Synthesis of ((5S,8S,11S,15S,18S, 23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23, 28,31,34,37-undecaoxotetratriacontahydro-2H,4H-spiro[azeto[2,1-u]pyrrolo[2,1-i][1,4,7,10,13,16,19, 22,25,28,31]undecaazacyclotetratriacontin-21,1'-cyclopentane]-15-carboxamide) (using HATU as the condensing agent and using acetonitrile as the solvent)

To a reaction vessel, Compound 35 (10.44 mg (7.17 μmol)) and an internal standard substance (methyl benzoate, 3.60 mg (26.44 μmol)) were weighed in, and they were dissolved in a solvent (acetonitrile, 2 mL (200 v/w)). While stirring this at room temperature, DIPEA (5.74 μL (32.9 μmol)) was added. The external temperature of the reaction vessel was set at 25° C., a condensing agent (HATU, 10.39 mg (27.3 μmol)) was added, and this was stirred for 30 minutes. The reaction solution (50 μL) was diluted in a mixed solution of MeCN/propylamine (9:1) (100 μL) to prepare a solution for HPLC analysis. As a result of HPLC analysis using methyl benzoate as the internal standard substance, the yield was determined to be 76% (HPLC analysis conditions: method 5).

LCMS (ESI) of Compound 1: Retention time: 18.08 minutes, m/z=1439 [M+H]$^+$ (LCMS analysis conditions: method 5)

LCMS (ESI) of the propylamide of Compound 35: Retention time: 13.39 minutes, m/z=1498 [M+H]$^+$ (LCMS analysis conditions: method 5)

LCMS (ESI) of the cyclic dimer (c-Dimer): Retention time: 23.18 minutes, m/z=2898 [M+Na]$^+$ (LCMS analysis conditions: method 5)

LCMS (ESI) of the cyclic trimer (c-Trimer): Retention time: 25.74 minutes, m/z=2157 [M+2H]$^{2+}$ (LCMS analysis conditions: method 5)

The results of synthesizing Compound 1 using various condensing agents and solvents are shown in Table 7. The experimental procedure followed that when using HATU as the condensing agent and acetonitrile as the solvent (Example 24-1). In the table, SM represents the sum of the residual amounts of Compound 35 and the propylamide of Compound 35 (Area % ratio by HPLC). Furthermore, in the table, TM represents the target molecule (Compound 1), and c-Dimer and c-Trimer refer to the by-products which are the cyclic dimer and cyclic trimer, respectively. The amounts of by-products produced are indicated as Area % ratios from HPLC measurements (HPLC analysis conditions: method 5). The yields were calculated by HPLC analyses using methyl benzoate as the internal standard substance.

TABLE 7

| Condensing agent | Example No. | Solvent | SM | TM | c-Dimer | c-Trimer | Yield (%) |
|---|---|---|---|---|---|---|---|
| HATU | Example 24-1 | CH$_3$CN | 0.0 | 83.0 | 13.9 | 3.0 | 76 |
| | Example 24-2 | CH$_2$Cl$_2$ | 0.0 | 90.3 | 7.9 | 1.7 | 90 |
| | Example 24-3 | Toluene | 89.2 | 10.4 | 0.4 | 0.0 | 12 |
| | Example 24-4 | Anisole | 0.0 | 87.0 | 11.9 | 1.1 | 74 |
| | Example 24-5 | Dimethyl carbonate | 0.0 | 86.8 | 11.3 | 1.9 | 71 |
| | Example 24-6 | 2-MeTHF | 21.8 | 64.8 | 11.9 | 1.5 | 54 |
| | Example 24-7 | MTHP | 72.0 | 25.0 | 3.0 | 0.0 | 23 |
| | Example 24-8 | AcOEt | 0.1 | 82.1 | 14.1 | 3.6 | 59 |
| | Example 24-9 | DMF | 0.1 | 77.7 | 17.8 | 4.4 | 52 |
| | Example 24-10 | NMP | 0.0 | 75.8 | 19.4 | 4.8 | 69 |
| PyBOP | Example 24-11 | CH$_3$CN | 0.2 | 88.0 | 10.1 | 1.8 | 79 |
| | Example 24-12 | CH$_2$Cl$_2$ | 0.3 | 92.9 | 5.6 | 1.2 | 89 |
| | Example 24-13 | Toluene | 0.0 | 86.7 | 11.7 | 1.5 | 57 |
| | Example 24-14 | Anisole | 0.0 | 91.5 | 7.6 | 0.8 | 86 |
| | Example 24-15 | Dimethyl carbonate | 0.1 | 92.3 | 6.8 | 0.8 | 87 |
| | Example 24-16 | 2-MeTHF | 0.1 | 89.6 | 9.1 | 1.2 | 82 |
| | Example 24-17 | MTHP | 0.4 | 88.3 | 9.8 | 1.5 | 81 |
| | Example 24-18 | AcOEt | 0.4 | 90.5 | 7.6 | 1.5 | 78 |
| | Example 24-19 | DMF | 0.4 | 86.1 | 11.3 | 2.2 | 73 |
| | Example 24-20 | NMP | 0.1 | 86.4 | 11.8 | 1.7 | 78 |
| DMT-MM | Example 24-21 | CH$_3$CN | 0.1 | 83.7 | 13.7 | 2.6 | 78 |
| | Example 24-22 | Toluene | 40.8 | 47.7 | 9.2 | 2.3 | 32 |
| | Example 24-23 | Anisole | 0.0 | 87.2 | 11.2 | 1.6 | 71 |
| | Example 24-24 | Dimethyl carbonate | 0.1 | 89.1 | 9.4 | 1.5 | 78 |
| | Example 24-25 | 2-MeTHF | 3.0 | 80.6 | 13.9 | 2.6 | 82 |
| | Example 24-26 | MTHP | 23.4 | 62.4 | 11.4 | 2.9 | 53 |
| | Example 24-27 | AcOEt | 0.0 | 87.1 | 11.0 | 1.9 | 72 |
| | Example 24-28 | DMF | 0.0 | 80.8 | 15.8 | 3.4 | 68 |
| | Example 24-29 | NMP | 0.0 | 80.0 | 16.4 | 3.6 | 70 |
| PyOxim | Example 24-30 | CH$_3$CN | 0.4 | 80.0 | 15.3 | 4.3 | 74 |
| | Example 24-31 | Toluene | 66.7 | 32.3 | 1.0 | ND | 16 |
| | Example 24-32 | Anisole | 0.1 | 92.7 | 6.6 | 0.6 | 70 |
| | Example 24-33 | Dimethyl Carbonate | 0.3 | 90.8 | 7.6 | 1.4 | 82 |
| | Example 24-34 | 2-MeTHF | 3.6 | 87.0 | 8.5 | 1.0 | 77 |
| | Example 24-35 | MTHP | 14.8 | 76.8 | 7.4 | 1.0 | 68 |
| | Example 24-36 | EtOAc | 0.2 | 90.8 | 7.8 | 1.2 | 81 |
| | Example 24-37 | DMF | 0.8 | 76.4 | 17.7 | 5.0 | 68 |
| | Example 24-38 | NMP | 0.0 | 80.4 | 15.7 | 3.9 | 71 |

Based on these results, by taking into consideration high rate of conversion to the target molecule and low rate of by-product formation, as well as environmental burden, anisole, dimethyl carbonate, and 2-MeTHF were found to be favorable solvents. Favorable condensing agents were suggested to be HATU, PyBOP, and PyOxim. Favorable solvent/condensing agent combinations were found to be anisole and PyBOP, dimethyl carbonate and PyBOP, and 2-methyltetrahydrofuran and PyBOP.

The reactions of Example 24-15 and Example 24-16 were scaled up, and operations similar to the experiments for the synthesis of Compound 1 (using PyBOP as the condensing agent, and using 2-MeTHF or dimethyl carbonate as the solvent) were performed.

Example 24-39

Compound 1: Synthesis of ((3S,9S,12S,17S,20S, 23S,27S,30S,36S)-30-cyclopentyl-3-[2-[3,5-difluoro-4-(trifluoromethyl)phenyl]ethyl]-10-ethyl-23-isobutyl-N,N,7,17,18,24,28,31-octamethyl-20-[(1S)-1-methylpropyl]-2,5,8,11,16,19,22,25,29,32,35-undecaoxo-9-(p-tolylmethyl)spiro[1,4,7,10,15,18,21, 24,28,31,34-undecazatricyclo[34.3.0.0$^{12.15}$] nonatriacontane-33,1'-cyclopentane]-27-carboxamide)

1) Condensing agent, DIPEA/Solvent
2) HPLC analysis

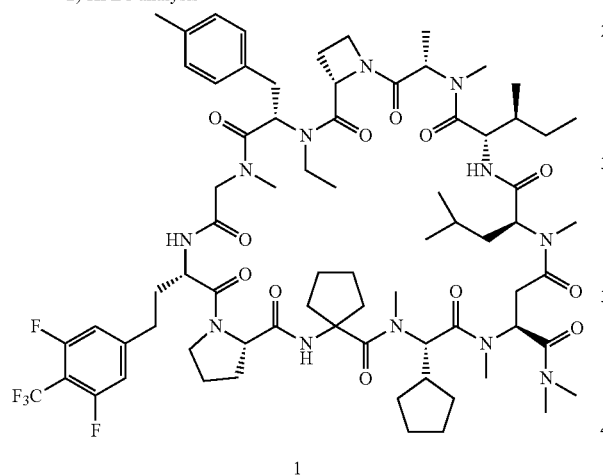

1

The solution (2152.63 mg) containing Compound 35 (100.16 mg (0.069 mmol)) obtained in Example 23 was added, and this was concentrated to dryness under reduced pressure at an external temperature of 40° C. 2-MeTHF (2150 mg) and DIPEA (42.2 mg) were added to the concentrated residue to afford a solution containing Compound 35. To a reaction vessel purged with nitrogen, PyBOP (141.10 mg) and 2-MeTHF (2150 mg) were added. The external temperature of the reaction vessel was set at 25° C., and the solution containing Compound 35 was added dropwise over 4 hours to the reaction mixture. 2-MeTHF (172 mg) was used for rinsing, the rinse solution was added, and this was stirred for 2 hours. While stirring at an external temperature of 25° C., 2.5% aqueous ammonia solution (2 mL) was added, and this was stirred for 90 minutes. The reaction mixture was filtered under reduced pressure. The reaction vessel and the Kiriyama funnel were washed with 2-MeTHF (172 mg). After removing the aqueous layer, 5% aqueous potassium hydrogen sulfate monohydrate solution (2 mL) was added to the obtained organic layer while stirring at an external temperature of 25° C. This was stirred at an external temperature of 25° C. for 4 minutes. After removing the aqueous layer, the obtained organic layer was washed with 5% aqueous disodium hydrogen phosphate solution (2 mL), 5% aqueous sodium chloride solution (2 mL), and 0.5% aqueous sodium chloride solution (2 mL×2) at an external temperature of 25° C. The resulting organic layer was analyzed by HPLC. As a result of HPLC analysis using an authentic sample, 78.38 mg (79.2% yield) of Compound 1 was found to be obtained.

Retention time by HPLC analysis: 17.992 minutes (HPLC analysis conditions: method 5)

The following table shows the results obtained when using dimethyl carbonate as the solvent instead of 2-MeTHF used in the above-mentioned method for synthesizing Compound 1 which used PyBOP as the condensing agent.

TABLE 11

| Condensing agent | Example No. | Solvent | Ratio of SM, TM, c-Dimer and c-Trimer | | | | Yield (%) |
|---|---|---|---|---|---|---|---|
| | | | SM | TM | c-Dimer | c-Trimer | |
| PyBOP | Example 24-39 | 2-MeTHF | 0.4 | 98.3 | 1.6 | <0.1 | 79 |
| | Example 24-40 | Dimethyl carbonate | 4.4 | 94.1 | 1.5 | <0.1 | 79 |

Example 25

Crystallization of Compound 1: Synthesis of Hydrate Crystals (Form C) of ((5S,8S,11S,15S,18S, 23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23, 28,31,34,37-undecaoxotetratriacontahydro-2H,4H-spiro[azeto[2,1-u]pyrrolo[2,1-i][1,4,7,10,13,16,19, 22,25,28,31]undecaazacyclotetratriacontin-21,1'-cyclopentane]-15-carboxamide)

A reaction tank holding a solution containing Compound 1 was purged with nitrogen, the external temperature of the reaction tank was set at 40° C., and purified water (10.9 kg) that had been filtered was added to it. To a mixed solution of acetone (59.2 g)/water (61.2 g), ground crystals of Compound 1 (10.2 g) obtained by operations similar to those of Example 25-1 were added, and the resulting suspension was added to the reaction tank. The container that had held the suspension was washed in with a mixed solution of acetone (59.2 g)/water (61.2 g), the wash was added to the reaction tank, and then this mixture was stirred for 2 hours and 1 minute. Purified water (2.7 kg) that had been filtered was added, and this mixture was stirred for 7 hours and 10 minutes. Furthermore, to a mixed solution of acetone (59.2 g)/water (61.2 g), ground crystals of Compound 1(10.2 g) obtained by operations similar to those of Example 25-1 were added, and the resulting suspension was added to the reaction tank. The container that had held the suspension was washed in with a mixed solution of acetone (59.2 g)/water (61.2 g), the wash was added to the reaction tank, and then this mixture was stirred for 12 hours and 40 minutes. Purified water (2.7 kg) that had been filtered was added, and this mixture was stirred for 2 hours. The external temperature of the reaction tank was lowered from 40° C. to 25° C. in 1 hour, and then the reaction mixture was stirred for 18 hours and 44 minutes. Crystals were obtained by pressure filtration of this mixture, and by washing the inside of the reaction tank and the filtration apparatus with a mixed solution of acetone (7.5 kg) and purified water (7.5 kg) that had been filtered; and the crystals were washed. The resulting crystals were washed with purified water (17.0 kg×2) that had been filtered. The external temperature of the filtration apparatus was set at 70° C., and the crystals were dried under reduced pressure for 17 hours. Furthermore, at an external temperature of the filtration apparatus ranging from room temperature to 30° C., the crystals were dried under reduced pressure for 27 hours. The dried powder was recovered from the filtration apparatus to obtain a white powder (2.6 kg). Retention time by HPLC analysis: 18.199 minutes (HPLC analysis conditions: method 5) As a result of powder X ray analysis (Measurement method 4) using an XRPD instrument, 2θ values of 4.964°, 7.921°, 8.296°, 8.855°, 9.956°, 10.435°, 11.729°, 12.704°, 13.552°, 13.901°, 15.895°, 16.643°, and 17.8130 (±0.2°) were observed as major peaks. The analysis results are shown in FIG. 1.

Example 25-1: Example of Production of Seed Crystals Used in Example 25

The amorphous state of Compound 1 (122.3 mg) was dissolved in DMSO (0.612 mL), and this solution (0.015 mL) was freeze-dried at −20° C. for 2 days. A mixed water-acetonitrile solution (3:1, 0.015 mL) was added to the resulting freeze-dried substance, and agitation and stirring of this mixture at room temperature for 7 days afforded hydrate crystals of Compound 1 (Form C).
Examination of Crystallization of Compound 1

Example 25-2

Synthesis of unsolvate crystals (Form F) of Compound 1 ((5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontin-21,1'-cyclopentane]-15-carboxamide)

Hydrate crystals (Form C) of Compound 1 obtained by a method similar to that of Example 24 were densely packed into a 7 mm×7 mm×0.25 mm aluminum sample container, and by performing an XRD-DSC simultaneous measurement under the following conditions (X-ray powder diffraction (XRPD) measurement: Measurement method 2; and thermal analysis: Measurement method 2), unsolvate crystals (Form F) of Compound 1 were obtained as a post-measurement sample.
As a result of powder X ray analysis (Measurement method 2) using an XRPD instrument, 2θ values of 5.370°, 6.934°, 8.940°, 9.838°, 10.771°, 12.181°, 13.525°, 15.179°, 16.202°, and 17.554° (±0.2°) were observed as major peaks. The analysis results are shown in FIG. 2.

Example 25-3

Synthesis of the DMSO-hydrate crystals (Form A and Form B) of Compound 1 ((5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontin-21,1'-cyclopentane]-15-carboxamide)

DMSO (0.52 mL) was added to the hydrate crystals of Compound 1 (Form C, 104.3 mg), and by agitation and stirring of this mixture at room temperature for 17 hours at 100 rpm, the DMSO-hydrate crystals of the title compound (33.8 mg) were obtained as powdered crystals. Powdered crystals immediately after filtration were defined as Form A DMSO-hydrate crystals, and powdered crystals that had been dried under reduced pressure at room temperature for 8 hours after filtration were defined as Form B DMSO-hydrate crystals.

The DMSO-hydrate crystals of Compound 1 (Form A DMSO-hydrate crystals and Form B DMSO-hydrate crystals) were individually subjected to powder X-ray diffraction measurements (Measurement method 3). The results are shown below.

As 2θ values of Form A DMSO-hydrate crystals, 8.006°, 9.002°, 9.943°, 11.501°, 13.067°, 14.854°, 16.320°, 17.275°, 19.261°, and 20.324° (±0.2°) were observed as major peaks. The analysis results are shown in FIG. 3.

Figure 5:
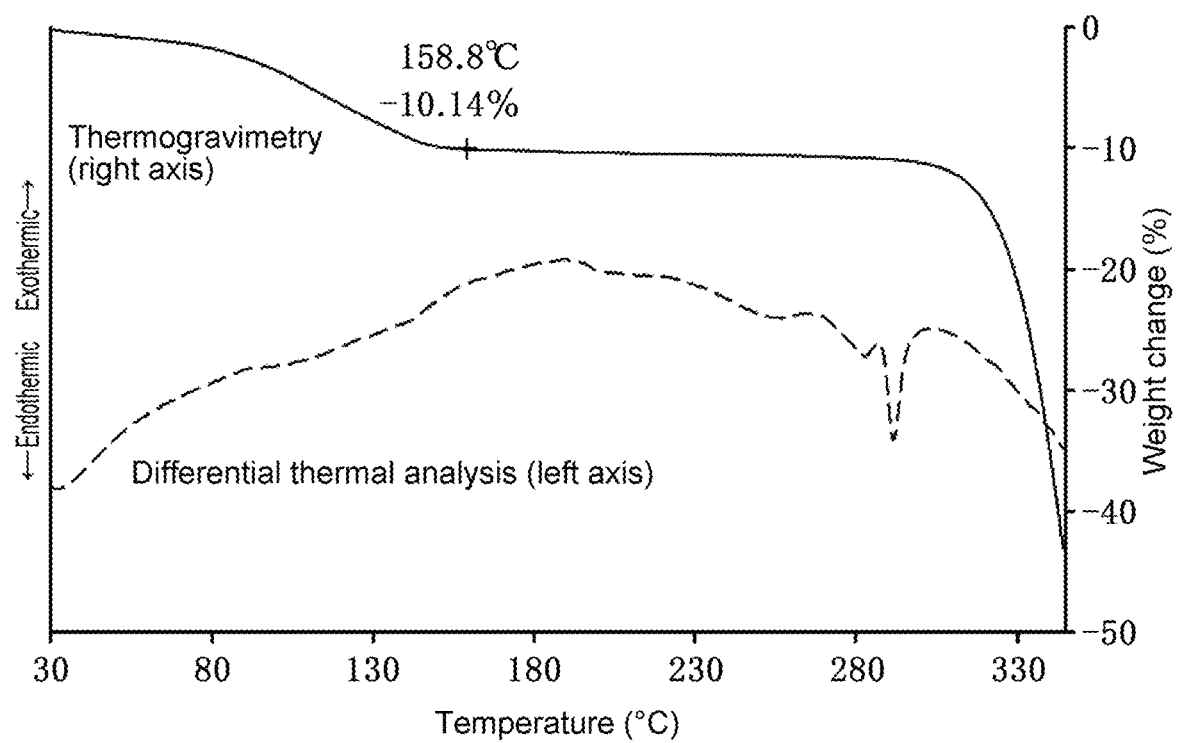
FIG. 5 shows the results of the thermogravimetry-differential thermal analysis of the crystal (Form B) of Compound 1 obtained in Example 25-3. The horizontal axis indicates the temperature (° C.), and the right vertical axis indicates the weight changes (%) of the sample in the thermogravimetric analysis. The left vertical axis indicates the heat flow observed in the differential thermal analysis.
Figure 6:
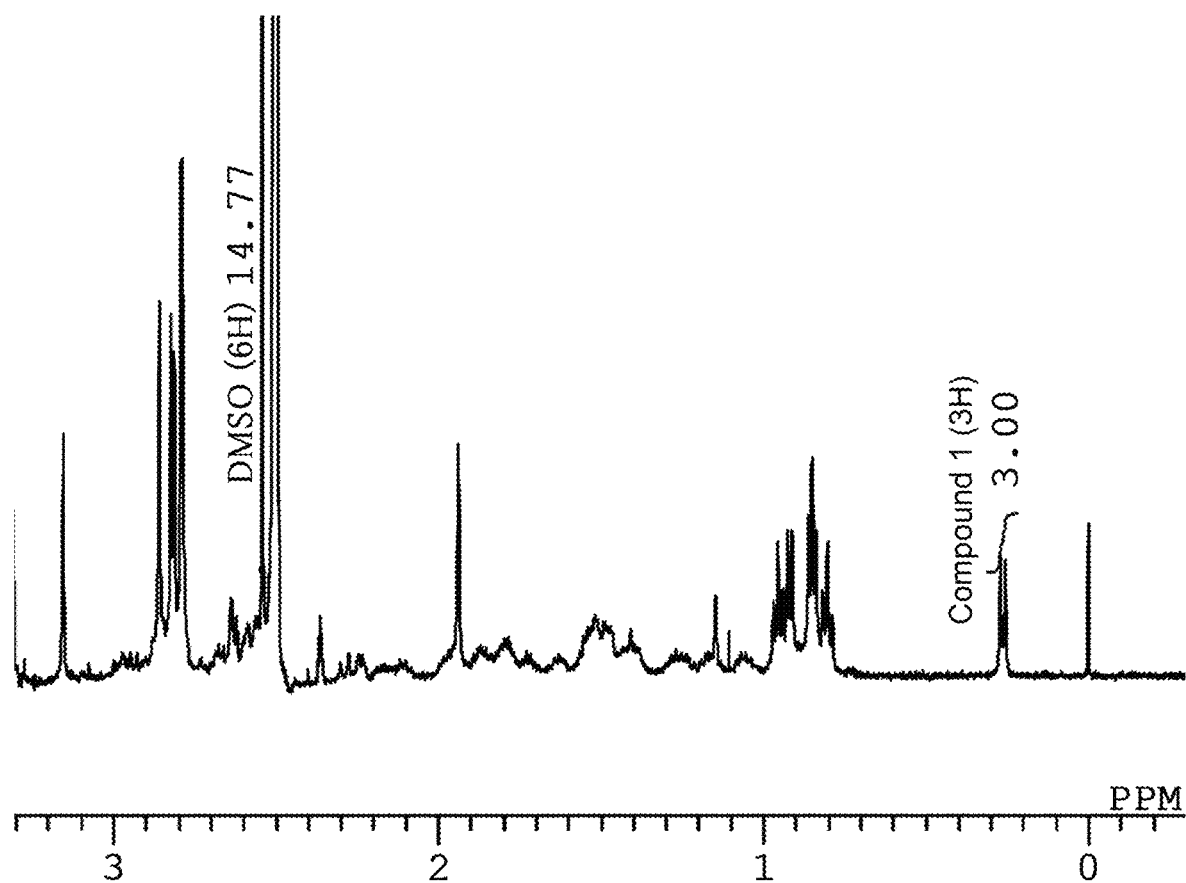
FIG. 6 shows the results of the $^1$H-NMR assay of the crystal (Form B) of Compound 1 obtained in Example 25-3.

As 2θ values of Form B DMSO-hydrate crystals, 8.223°, 9.594°, 9.976°, 11.879°, 13.841°, 14.572°, 15.934°, 16.350°, 19.805°, and 20.480° (±0.2°) were observed as major peaks. The analysis results are shown in FIG. 4.
Thermogravimetry/Differential Thermal Analysis The DMSO-hydrate crystals of Compound 1 obtained in Example 25-3 (Form B DMSO-hydrate crystals) were subjected to thermal analysis (Measurement method 3). The results are shown in FIG. 5.
$^1$H-NMR Measurement The DMSO-hydrate crystals of Compound 1 obtained in Example 25-3 (Form B DMSO-hydrate crystals) were subjected to $^1$H-NMR measurement. The results are shown in FIG. 6.

Based on the change in weight determined by thermogravimetry/differential thermal analysis and the integral peak area ratio between Compound 1 and DMSO determined from the $^1$H-NMR measurement, Form B DMSO-hydrate crystals were confirmed to be DMSO-hydrate crystals containing 2.5 equivalents of DMSO with respect to Compound 1.

Example 25-4

Synthesis of Hydrate Crystals (Form C) of Compound 1 ((5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontin-21,1'-cyclopentane]-15-carboxamide)

The amorphous state of Compound 1 (293.2 mg) was dissolved in ethanol (0.586 mL) at room temperature. To this solution, water (0.147 mL) and seed crystals of the hydrate crystals (Form C) of Compound 1 obtained by a method similar to that of Example 25-1 were added, and this was stirred at room temperature for 30 minutes. Further addition of water (0.147 mL) was followed by stirring at room temperature for 2 hours. Another addition of water (0.147 mL) and stirring at room temperature for 30 minutes was followed by addition of water (0.147 mL) and stirring at room temperature for 30 minutes, and after filtration and collection of the precipitates, these precipitates were washed with water and dried under reduced pressure to afford hydrate crystals of Compound 1 (Form C, 256.0 mg) as powdered crystals.

Example 26

Measurement of Physicochemical Properties of the Hydrate Crystals (Form C) of Compound 1
Using the Hydrate Crystals (Form C) of Compound 1 Obtained by a Method Similar to that of Example 25, powder X-ray diffraction measurement, thermogravimetry/differential thermal analysis, water content measurement, and single crystal X-ray structure analysis were performed.
(1) Powder X-ray diffraction measurement
Powder X-ray diffraction of the hydrate crystals (Form C) of Compound 1 prepared in Example 26 was measured at different humidities by the following method. Measurement apparatus: SmartLab System, D/Tex Ultra detector, humidity generator HUM-SL (manufactured by Rigaku Corporation)
Anticathode: Cu
Tube voltage: 45 kV
Tube current: 200 mA
Scanning range: 5-30°
Scanning speed: 0.7°/min
Sampling width: 0.02°
Varying humidity conditions:

TABLE 8

| Temperature (° C.) | Relative humidity (%) | Retention time (min) |
| --- | --- | --- |
| 35.0 | 75 | 120 |
| 35.0 | 70 | 120 |
| 35.0 | 60 | 120 |
| 35.0 | 50 | 120 |
| 35.0 | 40 | 120 |
| 35.0 | 30 | 120 |
| 35.0 | 20 | 120 |
| 35.0 | 10 | 120 |
| 35.0 | 0 | 120 |

Figure 7:
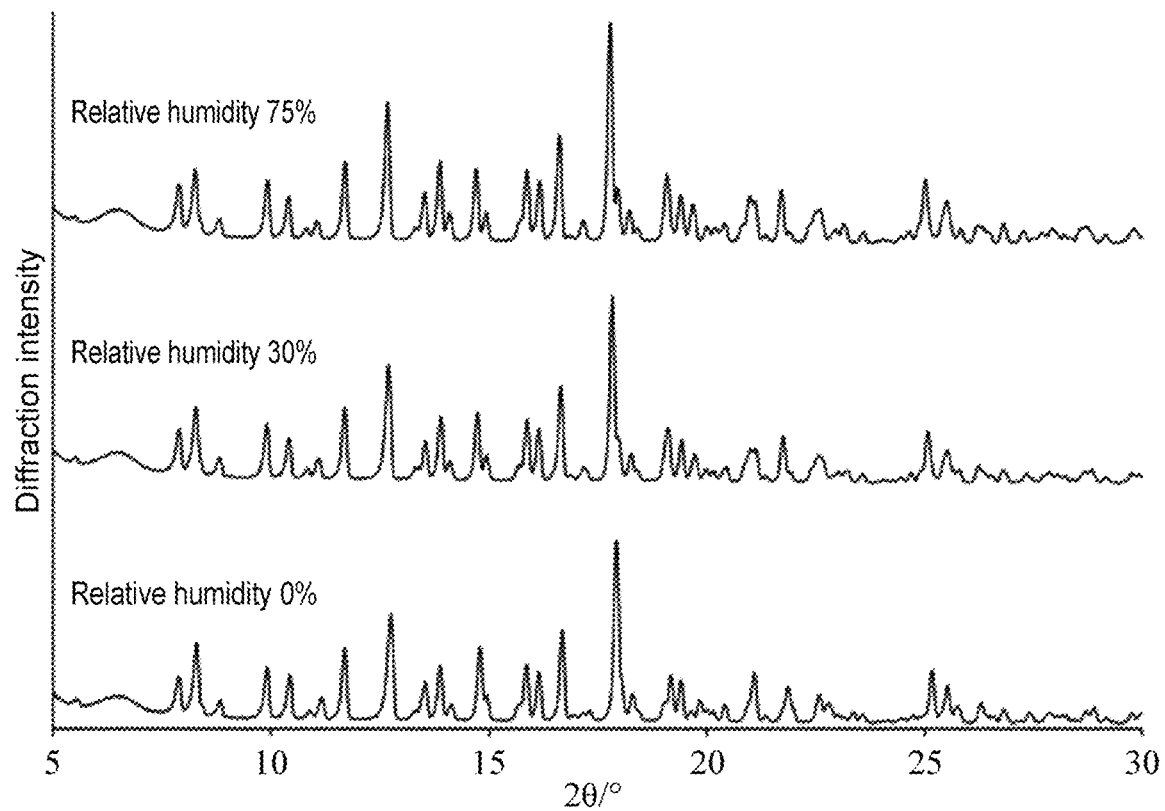
FIG. 7 shows the results of the powder X-ray diffraction measurement of the hydrate crystal (Form C) of Compound 1 obtained in Example 25-4 at relative humidities of 75%, 30%, and 0%. The vertical axis indicates the diffraction intensity, and the horizontal axis indicates the diffraction angle 2θ (°).
Figure 8:
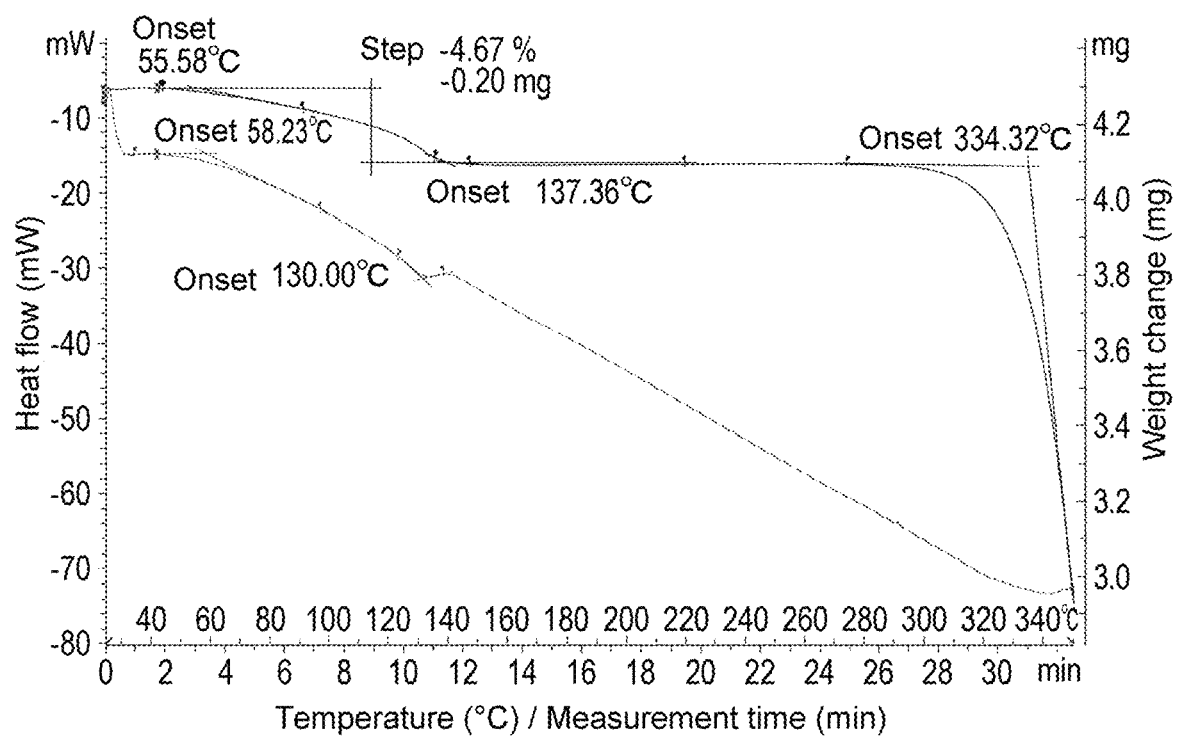
FIG. 8 shows the results of the thermogravimetry-differential thermal analysis of the hydrate crystal (Form C) of Compound 1 obtained in Example 26. The horizontal axis indicates the temperature (° C.) and measurement time (min), and the right vertical axis indicates the weight changes (mg) of the sample in the thermogravimetric analysis. The left vertical axis indicates the heat flow (mW) observed in the differential thermal analysis.
Figure 9:
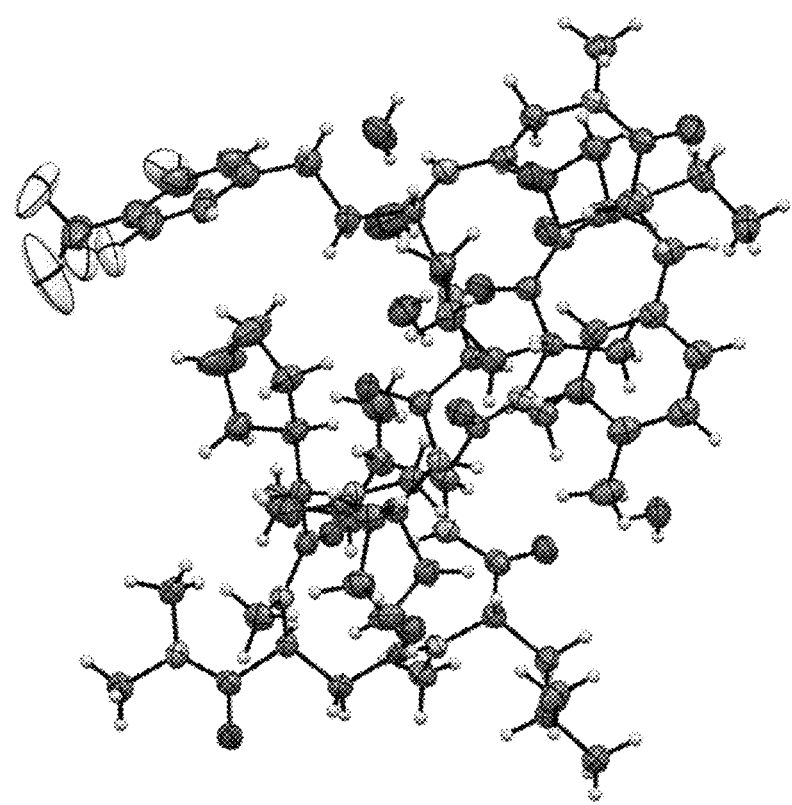
FIG. 9 shows the crystal structure of the hydrate crystal (Form C) of Compound 1 obtained in Example 26 as shown by X-ray single-crystal structure analysis.
Figure 10:
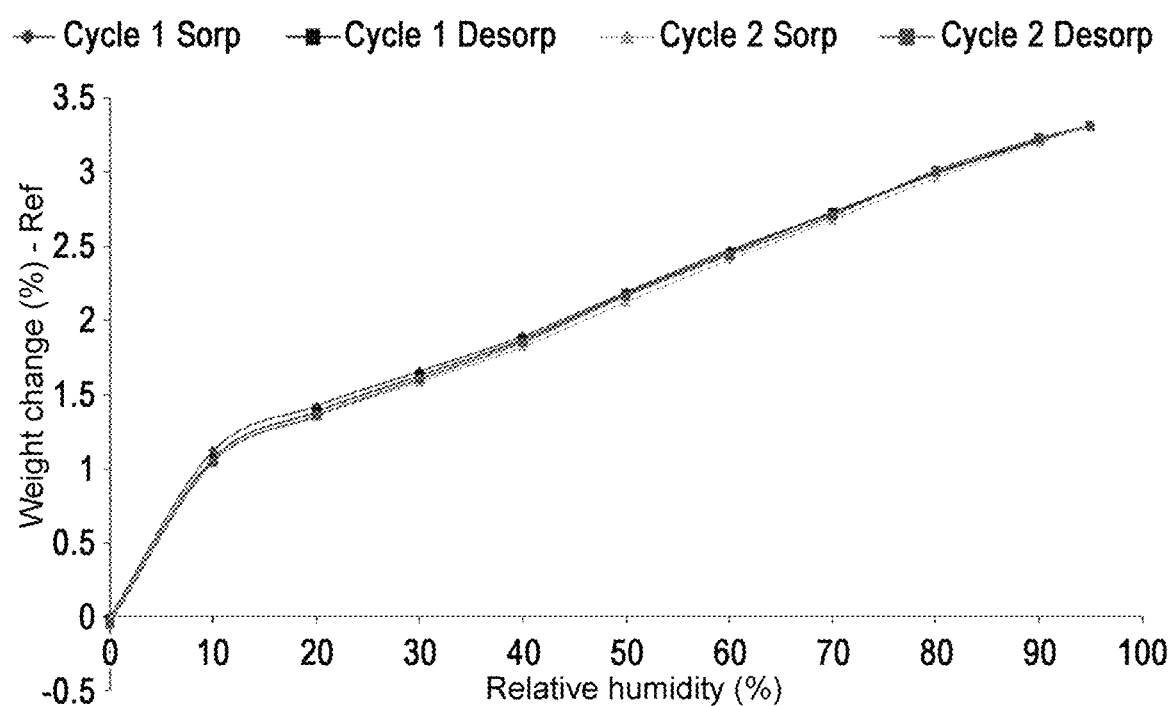
FIG. 10 shows the results of the dynamic vapor sorption measurement of the hydrate crystal (Form C) of Compound 1 obtained in Example 26. The vertical axis indicates the weight changes (%), and the horizontal axis indicates the relative humidity (%).

Under environment of relative humidity of 75% to 0%, the shift in 2θ values was confirmed to be within the range of 2θ values ±0.2° of the hydrate crystals (Form C) obtained in Example 25. The results are shown in FIG. 7.
2θ values of the hydrate crystals (Form C) at 75% humidity: diffraction peaks were present at 7.904°, 8.277°, 8.833°, 9.937°, 10.416°, 11.711°, 12.683°, 13.533°, 13.885°, 15.887°, 16.627°, and 17.799° (±0.20).
2θ values of the hydrate crystals (Form C) at 30% humidity: diffraction peaks were present at 7.892°, 8.286°, 8.839°, 9.921°, 10.424°, 11.703°, 12.710°, 13.556°, 13.903°, 15.891°, 16.664°, and 17.846° (±0.20).
2θ values of the hydrate crystals (Form C) at 0% humidity: diffraction peaks were present at 7.883°, 8.306°, 8.845°, 9.923°, 10.446°, 11.702°, 12.767°, 13.546°, 13.896°, 15.875°, 16.694°, and 17.935° (±0.2°).
(2) Thermogravimetry/Differential Thermal Analysis
Thermogravimetry/differential thermal analysis of the hydrate crystals (Form C) of Compound 1 prepared in Example 26 was performed by Measurement method 4 of thermal analysis. The results are shown in FIG. 8.
(3) Measurement of Water Content
The water content of the hydrate crystals (Form C) of Compound 1 prepared in Example 26 was measured by Karl Fischer titration method. After acclimatization of the sample to laboratory environment, the measurement was carried out using CA-310 (manufactured by Nittoseiko Analytech). As a result of the measurement, the water content of the hydrate crystals (Form C) of Compound 1 was found to be 6.50 wt %.
(4) Single Crystal X-Ray Structure Analysis
Single crystal X-ray structure analysis was performed on the hydrate crystals (Form C) of Compound 1 prepared in Example 26 by the following method.
Measurement apparatus: Rigaku R-AXIS RAPID-II with a VariMax Cu diffractometer (manufactured by Rigaku Corporation)
Anticathode: Cu
Tube voltage: 40 kV
Tube current: 30 mA
Temperature: −180° C.
Measurement: The measurement was carried out by strategies and exposure time that are considered to yield diffraction spots sufficient for structure analysis.
Structure analysis: Initial structure determination was performed by direct methods (SIR2004, CrystalStructure, Rigaku), and the structure was refined by full-matrix least-squares method (SHELXL-2017/1, APEX3, Bruker). All non-hydrogen atoms were refined anisotropically. Hydrogen atoms of the water molecules were placed at appropriate positions using restraints, and were refined with isotropic thermal parameters 1.5-times that of the bonded oxygen atom. Other hydrogen atoms were placed geometrically using a riding model, with isotropic thermal parameters 1.2-times that of the bonded non-hydrogen atom.
The results are shown in FIG. 9.
The results from powder X-ray diffraction measurement, thermogravimetry/differential thermal analysis, water content measurement, and single crystal X-ray structure analysis confirmed that the hydrate crystals (Form C) of Compound 1 prepared in Example 26 are truly hydrate crystals that carry water molecules within the crystal structure.
The dynamic water vapor adsorption properties of the hydrate crystals (Form C) of Compound 1 prepared in Example 26 were measured by the following method. The results are shown in FIG. 10.
Measurement apparatus: DVS Intrinsic (manufactured by Surface Measurement Systems)
Temperature: 25° C.
Relative humidity (%) measurement points:
Cycle 1: 0, 10, 20, 30, 40, 50, 60, 70, 80, 90, 95, 90, 80, 70, 60, 50, 40, 30, 20, 10, 0(%);
Cycle 2: 10, 20, 30, 40, 50, 60, 70, 80, 90, 95, 90, 80, 70, 60, 50, 40, 30, 20, 10, 0(%)
Threshold: 0.001 dm/dt (%/min)
Minimum adsorption time: 10 min
Maximum adsorption time: 1440 min
The results from the measurement confirmed that in the relative humidity range of 0% to 95%, as the hydration number changes, the hydration number of the hydrate crystals (Form C) of Compound 1 may change within the range of 3.3% weight relative to the weight when the relative humidity is 0%.

Example 26-1

Single Crystal X-Ray Measurement on the DMSO-Hydrate Crystal (Form A) of Compound 1

Synthesis of DMSO-Hydrate Crystals (Form A) of Compound 1 ((5S,8S,11S,15S,18S,23aS,29S,35S, 37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2, 1-u]pyrrolo[2,1-i][1,4,7,10,13,16,19,22,25,28,31] undecaazacyclotetratriacontin-21,1'-cyclopentane]-15-carboxamide)

The hydrate crystals (Form C) of Compound 1 (54.9 mg) were dissolved in DMSO (0.784 mL) at room temperature. When this solution was shaken at room temperature for 110 minutes, the DMSO-hydrate crystals (Form A) of Compound 1 were obtained in DMSO.

Single Crystal X-Ray Structure Analysis

Single crystal X-ray structure analysis was performed on the DMSO-hydrate crystal (Form A) of Compound 1 prepared in Example 26-1 by the following method.

Figure 11:
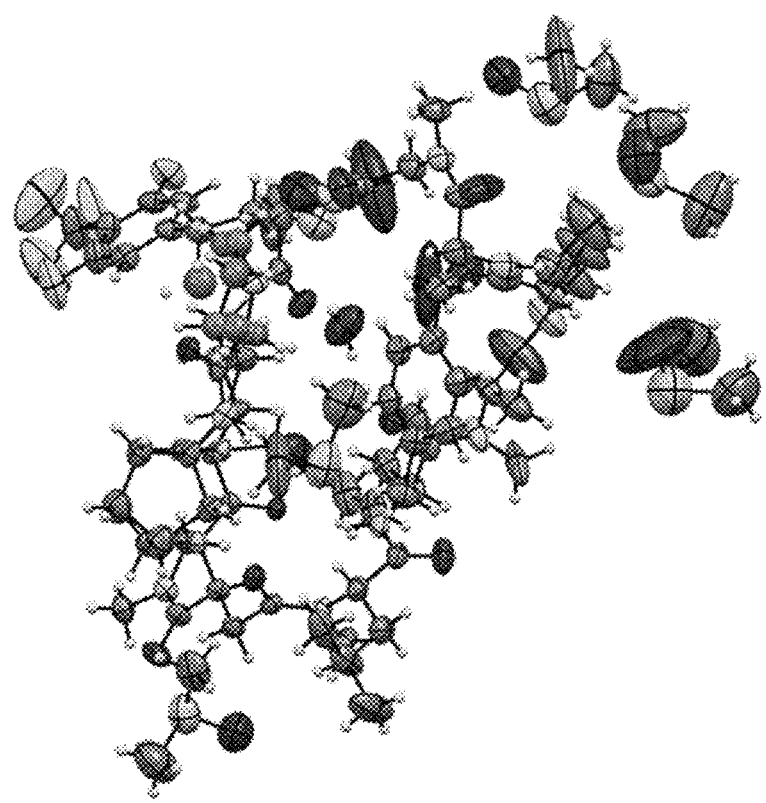
FIG. 11 shows the crystal structure of the DMSO-hydrate crystal (Form A) of Compound 1 obtained in Example 26-1 as shown by X-ray single-crystal structure analysis. This crystal structure is modeled with a Compound 1:DMSO:water ratio of 1:6:3.

Measurement apparatus: Rigaku XtaLAB Synergy Custom with a VariMax Cu diffractometer (manufactured by Rigaku Corporation)
Anticathode: Cu
Tube voltage: 40 kV
Tube current: 30 mA
Temperature: −180° C.
Measurement: The measurement was carried out by strategies and exposure time that are considered to yield diffraction spots sufficient for structure analysis.
Structure analysis: Initial structure determination was performed by direct methods (SHELXT-2018/2, CrysAlisPro, Rigaku), and the structure was refined by full-matrix least-squares method (SHELXL-2017/1, APEX3, Bruker). The non-hydrogen atoms were basically refined anisotropically, while disordered non-hydrogen atoms were refined isotropically. Hydrogen atoms of the water molecules were placed at appropriate positions using restraints, and were refined with isotropic thermal parameters 1.5-times that of the bonded oxygen atom. Other hydrogen atoms were placed geometrically using a riding model, with isotropic thermal parameters 1.2-times or 1.5-times that of the bonded non-hydrogen atom. The results are shown in FIG. 11.

Example 26-2

Measurement of Physicochemical Properties of the Acetone-Hydrate Crystals (Form H) of Compound 1
(1) Single Crystal X-Ray Structure Analysis Synthesis of Acetone-Hydrate Crystals (Form H, for Single Crystal X Ray Structure Analysis) of Compound 1 ((5S,8S,11S,15S,18S,23aS,29S,35S, 37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratria-contahydro-2H,4H-spiro[azeto[2, 1-u]pyrrolo[2,1-i][1,4,7,10,13,16,19,22, 25,28,31] undecaazacyclotetratriacontin-21,1'-cyclopentane]-15-carboxamide)

To a 9-mL vial, acetone (0.8 mL) and water (0.2 mL) were added, this was mixed, and then a 0.3-mL vial containing the amorphous solid of Compound 1 (approximately 1 mg) was placed into it, the 9-mL vial was capped, and by solvent vapor diffusion, crystals were obtained 3 hours later.

Single crystal X-ray structure analysis was performed on the acetone-hydrate crystal (Form H, for single crystal X-ray structure analysis) of Compound 1 obtained above, by the following method.

Figure 12:
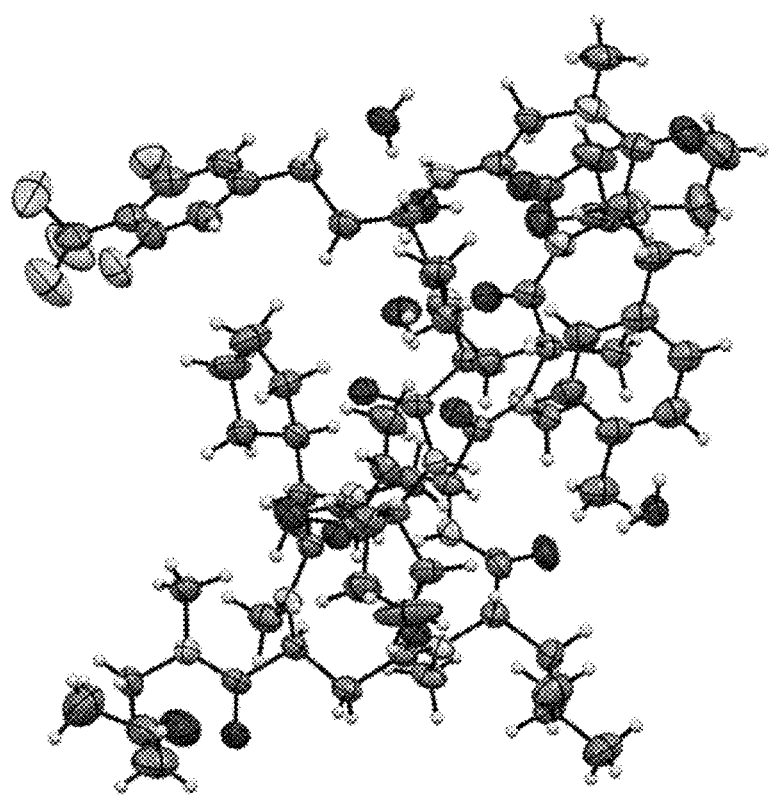
FIG. 12 shows the crystal structure of the acetone-hydrate crystal (Form H, for X-ray single-crystal structure analysis) of Compound 1 obtained in Example 26-2 as shown by X-ray single-crystal structure analysis. This crystal structure is modeled with a Compound 1:acetone:water ratio of 1:1:4.

Measurement apparatus: Rigaku XtaLAB Synergy Custom with a VariMax Cu diffractometer (manufactured by Rigaku Corporation)
Anticathode: Cu
Tube voltage: 40 kV
Tube current: 30 mA
Temperature: −180° C.
Measurement: The measurement was carried out by strategies and exposure time that are considered to yield diffraction spots sufficient for structure analysis.
Structure analysis: Initial structure determination was performed by direct methods (SHELXT-2018/2, CrysAlisPro, Rigaku), and the structure was refined by full-matrix least-squares method (SHELXL-2018/3, Olex2, OlexSys). Non-hydrogen atoms were refined anisotropically. Hydrogen atoms of the water molecules were placed at appropriate positions, and were refined with isotropic thermal parameters 1.5-times that of the bonded oxygen atom. Other hydrogen atoms were placed geometrically using a riding model with isotropic thermal parameters 1.2-times or 1.5-times that of the bonded non-hydrogen atom. The results are shown in FIG. 12.

(2) Powder X-Ray Diffraction Measurement

Synthesis of Acetone-Hydrate Crystals (Form H, for Measurement of Powder X-Ray Diffraction and Solvent Content) of Compound 1 ((5S,8S,11S,15S, 18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23, 28,31,34,37-undecaoxotetratriacontahydro-2H,4H-spiro[azeto[2,1-u]pyrrolo[2,1-i][1,4,7,10,13,16,19, 22,25,28,31]undecaazacyclotetratriacontin-21,1'-cyclopentane]-15-carboxamide)

Hydrate crystals (Form C) of Compound 1 (2.1 g) and acetone (16 mL) were added to a reaction vessel. The external temperature was set at 40° C., and water (6.4 mL) was added while stirring. Hydrate crystals of Compound 1 (6 mg) ground with a mortar were added to a glass vial, this was suspended in an acetone-water mixture (80 μL, 5/4 v/v), and then the suspension was added to the reaction vessel. Furthermore, an acetone-water mixture (80 μL, 5/4 v/v) was added to the glass vial and the suspension was added to the reaction vessel. The crystallizing solution was stirred for 2 hours. Water (1.6 mL) was added over 10 minutes, and then the suspension was stirred for 3 hours. Water (1.6 mL) was added over 10 minutes, and then the suspension was stirred for 2 hours. The suspension was cooled to external temperature of 25° C. in one hour. The suspension was stored overnight. The following day, this suspension was stirred at an external temperature of 25° C., then a portion of the suspension was sampled, and without further treatment, the suspension was subjected to powder X-ray diffraction measurement (Measurement method 4). The suspension was filtered using a Kiriyama funnel, and then the crystals were washed with an acetone-water mixture (5.6 mL, 4.4 mL). Next, the crystals were washed twice with water (10 mL). The resulting wet crystals were used to measure the solvent content.

The acetone-hydrate crystals of Compound 1 (Form H, for powder X-ray diffraction measurement) obtained above were subjected to powder X-ray diffraction measurement (Measurement method 4) by the following method. The results are shown below.

As 2θ values of the acetone-hydrate crystals (Form H), 7.942°, 8.283°, 8.861°, 10.097°, 10.491°, 11.805°, 12.673°, 12.830°, 13.514°, 13.855°, 15.853°, 16.405°, 16.642°, and 17.772° (±0.2°) were observed as major peaks. The analysis results are shown in FIG. 13.

(3) Measurement of Solvent Content

The conditions for analyzing the amount of acetone by GC are shown below.

Instrument: GC-2010 (manufactured by SHIMADZU CORPORATION)
Column: DB-624 (Agilent), 0.530 mm ID×30 m, 3.00 μm
Column temperature: 50° C. (5 min)→10° C./min→90° C. (0 min)→50° C./min→240° C. (5 min)
Injector temperature: 230° C.
Detector temperature: 250° C.
Split ratio: 20/1
Flow rate: 30 cm/sec The conditions for analyzing the water content by Karl Fischer titration method are shown below.

Instrument: CA-200 (manufactured by Nittoseiko Analytech Co., Ltd.)
Anolyte: Aquamicron AKX
Catholyte: Aquamicron CXU In these measurements, the acetone content in the wet crystals was 3.7% and the water content was 17.5%.

Preparation Example 1: Production of the Amorphous State of Compound 1

Compound 1 ("(5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontin-21,1'-cyclopentane]-15-carboxamide") having the following structure was synthesized according to Scheme 1 shown below.

Compound 1

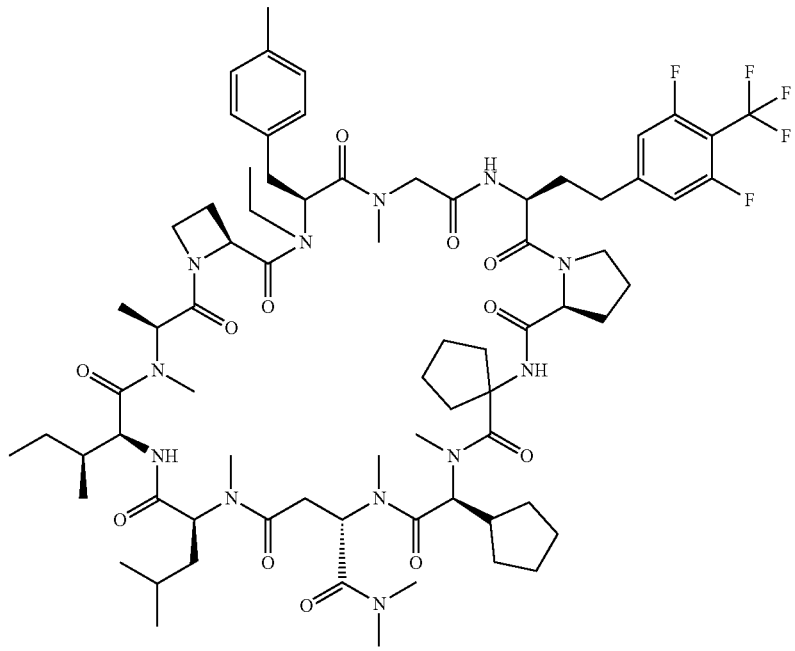

Scheme 1

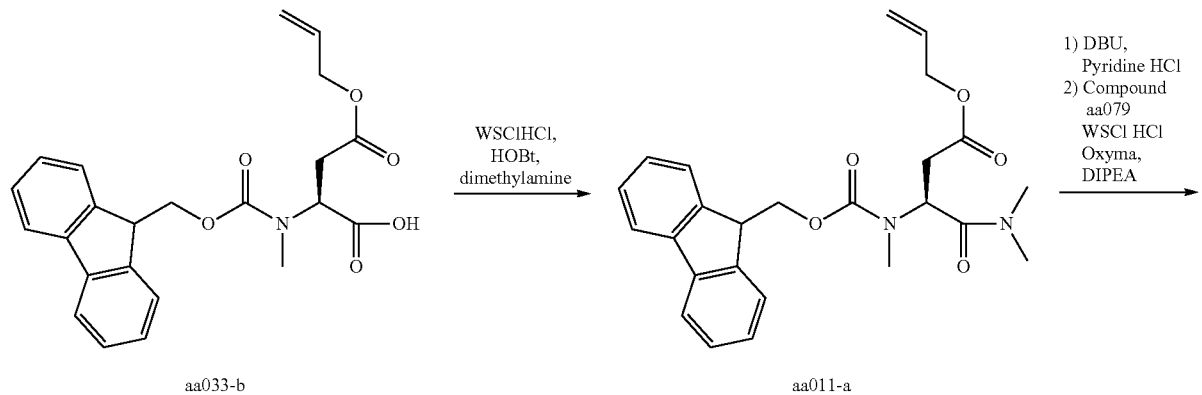

-continued
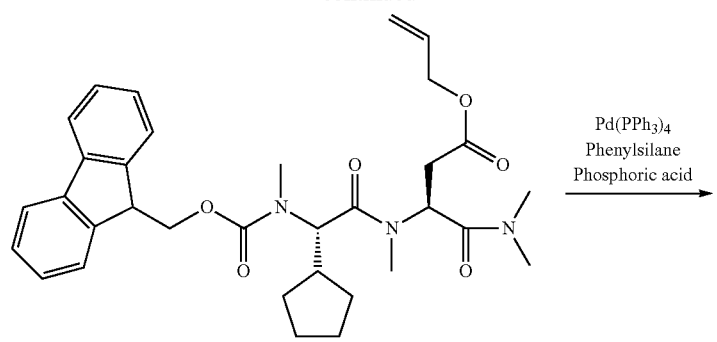
Compound 1217-a
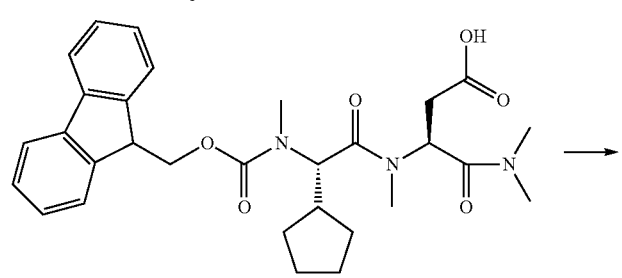
Compound 1217-b
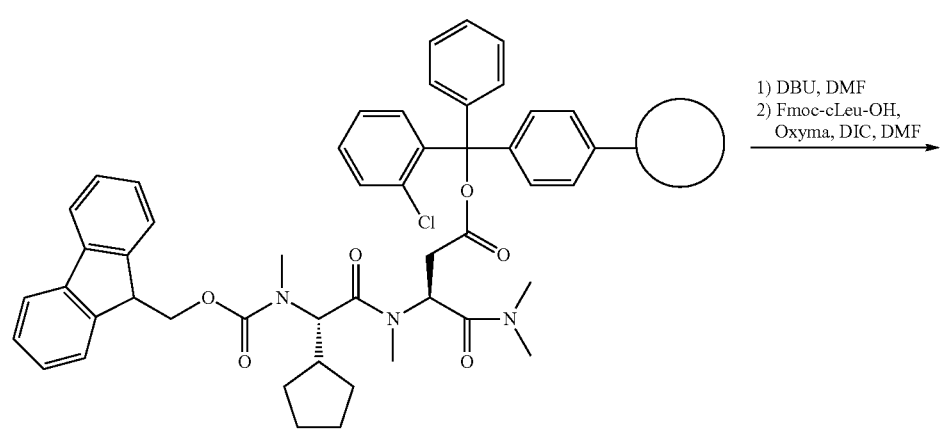
Compound 1217-b-resin
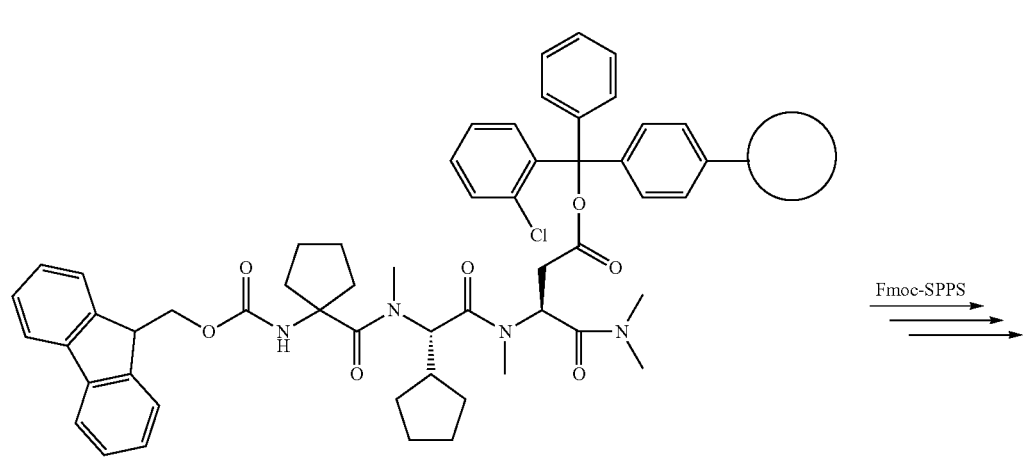
Compound 1217-c-resin -continued
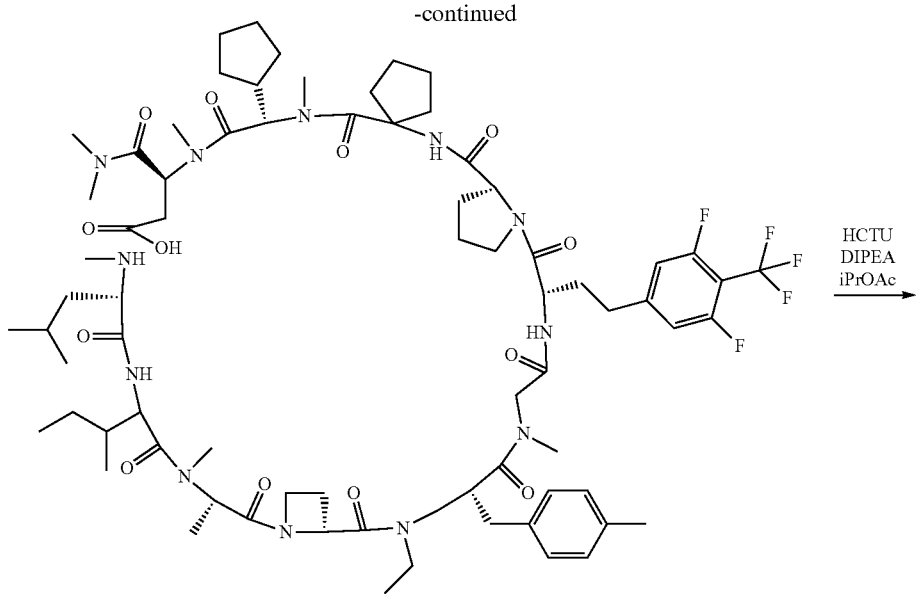
Compound 1217-d
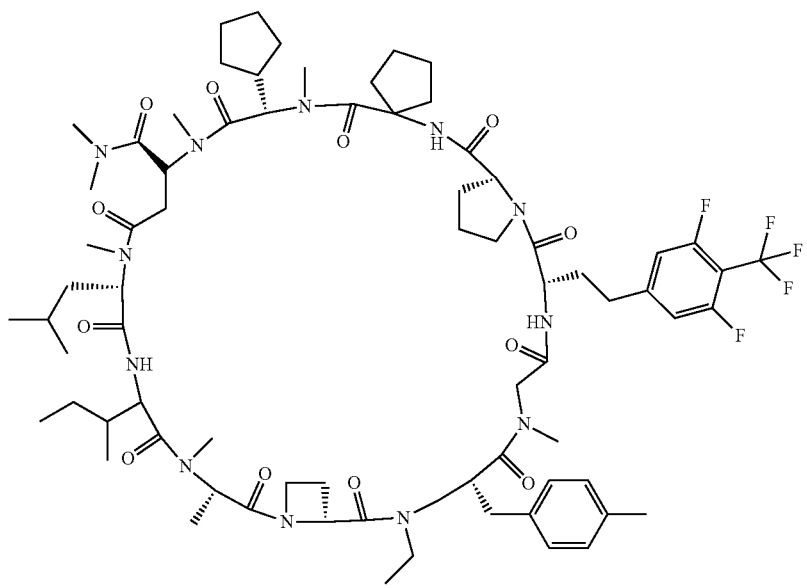
Compound 1

Synthesis of Compound aa033-b ((2S)-2-[9H-fluoren-9-ylmethoxycarbonyl-(methyl)amino]-4-oxo-4-prop-2-enoxybutanoic acid)

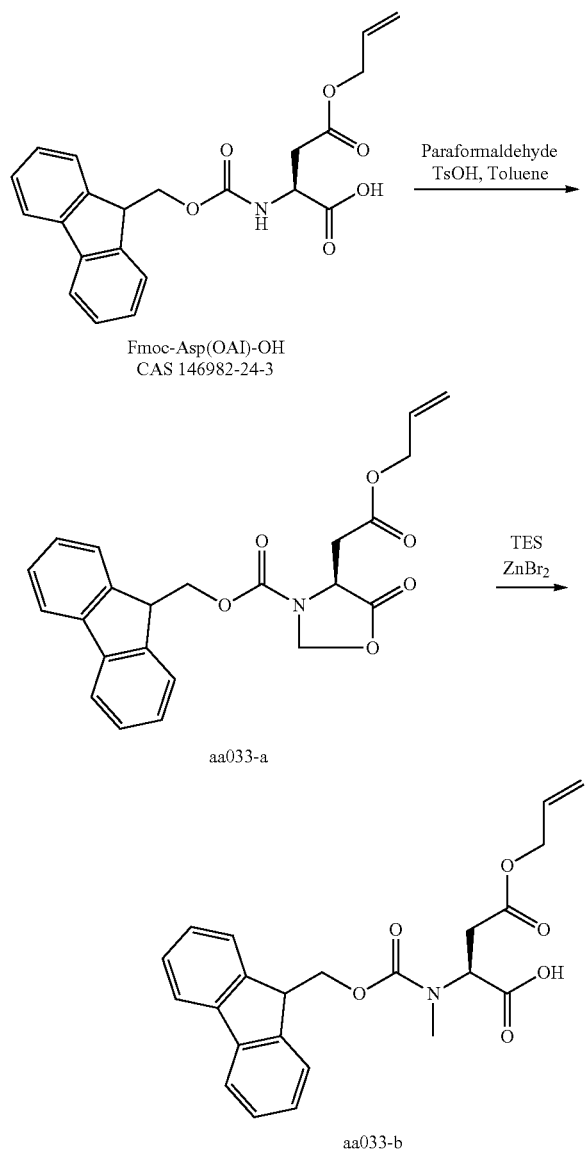 [SMILES: C=CCOC(=O)C[C@H](NC(=O)OCC1c2ccccc2-c2ccccc21)C(=O)O ; C=CCOC(=O)C[C@H]1C(=O)OCN1C(=O)OCC1c2ccccc2-c2ccccc21 ; C=CCOC(=O)C[C@@H](C(=O)O)N(C)C(=O)OCC1c2ccccc2-c2ccccc21]

Fmoc-Asp(OAI)-OH ((2S)-2-(9H-fluoren-9-ylmethoxycarbonylamino)-4-oxo-4-prop-2-enoxybutanoic acid, CAS No. 146982-24-3) (200 g, 506 mmol), p-toluene sulfonic acid (5.7 g, 0.05 equivalents), and paraformaldehyde (45.6 g, 3 equivalents) were mixed with toluene and the mixture was stirred at 110° C. for 16 hours. The solvent was distilled off under reduced pressure from the reaction mixture, the residue was dissolved in ethyl acetate, and the solution was washed twice with aqueous sodium hydrogen carbonate solution. The organic layer was dried over anhydrous sodium sulfate, and then the solvent was distilled off under reduced pressure. The residue was purified by silica gel column chromatography (ethyl acetate/petroleum ether, 0/100 to 30/70) to afford Compound aa033-a (9H-fluoren-9-ylmethyl (4S)-5-oxo-4-(2-oxo-2-prop-2-enoxyethyl)-1,3-oxazolidine-3-carboxylate) (175 g, 85%). Another batch synthesized similarly was combined, and this was used in the next reaction.

LCMS (ESI): m/z=408 (M+H)$^+$

Retention time: 1.407 minutes, (analysis conditions: SMDmethod_20)

A mixed solution of Compound aa033-a (100 g, 245 mmol), zinc bromide (ZnBr$_2$) (110 g, 496 mmol), and triethylsilane (TES) (56 g, 481.6 mmol) in dichloromethane (DCM) (1 L) was stirred under nitrogen atmosphere at room temperature for 48 hours. Four batches of the reaction solution of the same scale were mixed, and the solvent was distilled off under reduced pressure. The residue was dissolved in TBME, and this solution was extracted 10 times with a 0.5 M phosphate buffer (pH=approximately 7.5). The aqueous layers were combined, its pH was adjusted to 2 using a 5 M aqueous hydrochloric acid solution, and the mixture was extracted twice with isopropyl acetate (IPAC). The organic layers were combined and dried over anhydrous sodium sulfate, and then the solvent was distilled off under reduced pressure. To remove IPAC, addition of TBME to the resulting residue and distilling off the solvent under reduced pressure were repeated 6 times to afford Compound aa033-b ((2S)-2-[9H-fluoren-9-ylmethoxycarbonyl(methyl)amino]-4-oxo-4-prop-2-enoxybutanoic acid) (270 g, 54%).

LCMS (ESI): m/z=410 (M+H)$^+$

Retention time: 1.956 minutes, (analysis conditions: SMDmethod_05)

Synthesis of Compound aa011-a

Under nitrogen atmosphere, HOBt (17.72 g, 131 mmol) was added to a solution of WSCI·HCl (27.4 g, 143 mmol) in DMF (217 mL) while cooling with ice, a solution of compound aa033b (48.8 g, 119 mmol) in a mixed solvent of DCM (90 mL) and DMF (90 mL) was added, and the mixture was stirred at 0° C. for 30 minutes. To this mixture, a THF solution of dimethylamine (2 mol/L, 65.6 mL, 131 mmol) was added dropwise, and this was stirred at 0° C. for 30 minutes. The reaction mixture was diluted with ethyl acetate (488 mL) and the organic layer was washed twice with hydrochloric acid (1 mol/L, 390 mL), then twice with a mixed solution of saturated aqueous sodium hydrogen carbonate solution and water (1:1, 488 mL), and then once with a mixed solution of saturated saline solution and water (1:1, 488 mL). The resulting organic layer was dried over anhydrous sodium sulfate; and the solvent was distilled off under reduced pressure to afford Compound aa011-a (51.16 g, 98% yield).

LCMS (ESI) m/z=437.0 (M+H)$^+$

Retention time: 1.262 minutes, (analysis condition: SMDFA05)

Synthesis of Compound aa079 ((2S)-2-cyclopentyl-2-[9H-fluoren-9-ylmethoxycarbonyl(methyl)amino] acetic acid (Fmoc-MeGly(cPent)-OH))

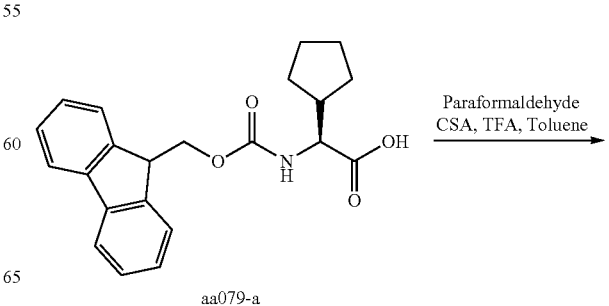

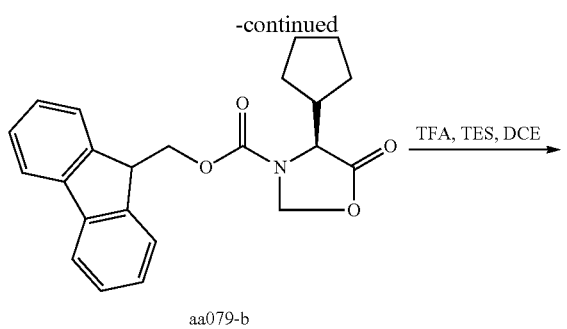

aa079-b

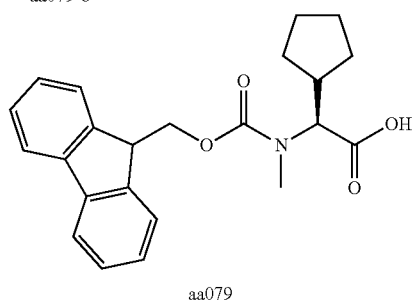

aa079

To a mixed solution of Compound aa079-a ((2S)-2-cyclopentyl-2-[9H-fluoren-9-ylmethoxycarbonylamino]acetic acid, Fmoc-Gly(cPent)-OH) (CAS No. 220497-61-0) ((30.0 g, 82 mmol), paraformaldehyde (7.39 g, 246 mmol), and CSA (0.954 g, 4.10 mmol) in toluene (160 mL), trifluoroacetic acid (TFA) (9.0 mL) was added, and then the mixture was stirred at 60° C. for 4 hours. After cooling the reaction mixture to room temperature, the solids were removed by filtration. The filtrate was concentrated under reduced pressure and then diluted with ethyl acetate (220 mL), and subsequently the mixture was washed sequentially with a saturated aqueous sodium hydrogen carbonate solution and saturated saline solution. The organic layer was dried over anhydrous sodium sulfate, filtered, and then concentrated under reduced pressure to afford Compound aa079-b as a crude product. The next reaction was carried out without further purification.

LCMS (ESI) m/z=378 (M+H)$^+$
Retention time: 1.01 minutes, (analysis condition: SQDFA05)

Using the entire amount of Compound aa079-b obtained above, trifluoroacetic acid (TFA) (76 mL, 984 mmol) was added to a mixed solution of triethylsilane (TES) (65.5 mL, 410 mmol) and aa079-b in dichloroethane (DCE) (90 mL), and the mixture was stirred at 60° C. for 16 hours. The reaction mixture was cooled to room temperature and then concentrated under reduced pressure, and the resulting solid was washed with n-hexane/ethyl acetate (95/5) and then dried under reduced pressure to afford Compound aa079 ((2S)-2-cyclopentyl-2-[9H-fluoren-9-ylmethoxycarbonyl (methyl)amino]acetic acid, Fmoc-MeGly(cPent)-OH) (29.1 g, 93% in two steps)

LCMS (ESI) m/z=380 (M+H)$^+$
Retention time: 0.92 minutes, (analysis condition: SQDFA05)

Synthesis of Compound 1217-a

To a solution of Compound aa079 (42.2 g, 111 mmol) and Oxyma (19.99 g, 141 mmol) in DMF (391 mL), WSCI·HCl (31.5 g, 164 mmol) was added at room temperature, and the mixture was stirred for 30 minutes to obtain Solution A.

Under nitrogen atmosphere, DBU (17.49 mL, 117 mmol) was added dropwise at room temperature to a solution of Compound aa011-a (51.16 g, 117 mmol) in DMF (391 mL), and the mixture was stirred for 5 minutes. Pyridine hydrochloride (14.9 g, 129 mmol) was added and the mixture stirred for 10 minutes. Solution A and DIPEA (22.46 mL, 129 mmol) were then added and the mixture was stirred under nitrogen atmosphere at room temperature for 7 hours. The reaction mixture was diluted with ethyl acetate (422 mL) and washed twice with hydrochloric acid (1 mol/L, 422 mL), and the obtained aqueous layer was extracted twice with ethyl acetate (422 mL). All of the organic layers were combined and washed sequentially with water (422 mL), a mixed solution of saturated aqueous sodium hydrogen carbonate solution and water (1:1, 422 mL), and a mixed solution of saturated saline solution and water (1:1, 422 mL), then the obtained organic layer was dried over sodium sulfate, and the solvent was distilled off under reduced pressure. DCM (422 mL) was added to the resulting residue, and the solution was stirred for 0.5 hours. Magnesium sulfate (30 g) was added to this, and after stirring this for 30 minutes, the solids were removed by filtration. The resulting solution was purified by silica gel column chromatography (hexane/ethyl acetate) to afford Compound 1217-a (55.55 g, 87% yield).

LCMS (ESI) m/z=598.2 (M+Na)$^+$
Retention time: 1.320 minutes, (analysis condition: SMDAM05)

Synthesis of Compound 1217-b

Under nitrogen atmosphere, tetrakis(triphenylphosphine)palladium (0) (1.115 g, 0.965 mmol) was added to a solution of Compound 1217-a (55.55 g, 96 mmol) in DCM (193 mL) at room temperature, then phenylsilane (8.31 mL, 67.5 mmol) was added dropwise, and then the mixture was stirred for 30 minutes. The reaction mixture was diluted with MTBE (556 mL), and this was extracted with a mixed solution of saturated aqueous sodium hydrogen carbonate solution and water (1:1, 556 mL). The resulting organic layer was extracted with water (278 mL). The aqueous layers were combined, and DCM (556 mL) was added. Phosphoric acid (56.7 g, 579 mmol) was added dropwise to this mixture to adjust the pH to 2 to 3, and after separating the organic layer, the aqueous layer was extracted with DCM (556 mL). The resulting organic layers were combined and washed with a mixed solution of saturated saline solution and water (1:1, 556 mL) and dried over sodium sulfate, and the solvent was distilled off under reduced pressure to afford Compound 1217-b (48.87 g, 95% yield)

LCMS (ESI) m/z=536 (M+H)$^+$
Retention time: 1.138 minutes, (analysis condition: SMDAM05)

Synthesis of Compound 1217-b-Resin

2-Chlorotrityl chloride resin (purchased from SUNRESIN, 1.36 mmol/g, 114 g, 155 mmol) was placed into a reaction vessel equipped with a filter, DCM (1140 mL) was added, and after stirring this at 25° C. for 45 minutes, the solvent was removed through the filter. A solution of Compound 1217-b (48.87 g, 91 mmol), methanol (29.6 mL, 730 mmol), and DIPEA (76 mL, 438 mmol) in DCM (798 mL) was added to the reaction vessel, the mixture was stirred at 25° C. for 60 minutes, and the solution was removed through the filter. Then, a solution of methanol (111 mL, 2737 mmol) and DIPEA (76 mL, 438 mmol) in DCM (684 mL) was added to the reaction vessel, the mixture was stirred at 25° C. for 90 minutes, and the solution was removed through the filter. After DCM (570 mL) was added to the reaction vessel, the mixture was stirred for 5 minutes, and the solution was removed through the filter. Washing operation on this resin was repeated 4 more times, and the resulting resin was dried under reduced pressure to afford Compound 1217-b-resin (140.5 g). By quantifying the Fmoc group of the compound loaded to the resin, the loaded amount was calculated to be 0.482 mmol/g.

Synthesis of Compound 1217-c-Resin

The resin obtained above (0.482 mmol/g, 60 g, 28.92 mmol) was placed into a plastic solid-phase reaction vessel. At room temperature, DCM (600 mL) was added to this solid-phase reaction vessel, and after shaking for 5 minutes, the solvent was removed through the frit. DMF (420 mL) was added to this solid-phase reaction vessel, and after shaking for 5 minutes, the solvent was removed through the frit. This step of washing the resin was repeated one more time. A DMF solution of diazabicycloundecene (DBU) (2 v/v %, 420 mL) was added to this solid-phase reaction vessel for Fmoc group deprotection. After shaking for 10 minutes, the solution was removed through the frit. DMF (420 mL) was added to this solid-phase reaction vessel, and after shaking for 5 minutes, the solution was removed through the frit. A solution of triethylamine hydrochloride (7.96 g, 57.8 mmol) in DCM (420 mL) was added to this solid-phase reaction vessel, and after shaking for 5 minutes, the solution was removed through the frit. DCM (420 mL) was added to this solid-phase reaction vessel, and after shaking for 5 minutes, the solution was removed through the frit. DMF (420 mL) was added to this solid-phase reaction vessel, and after shaking for 5 minutes, the solution was removed through the frit. This step of washing the resin with DMF was repeated one more time.

A solution of Fmoc-cLeu-OH (37.98 g, 108 mmol) (CAS No. 117322-30-2) and Oxyma (9.6 g, 67.6 mmol) in DMF (180 mL), and a DMF solution of N,N'-diisopropylcarbodiimide (DIC) (10%, 216 mL) were combined, and 2 minutes later, the mixture was added to the solid-phase reaction vessel obtained as described above. This solid-phase reaction vessel was shaken at 50° C. for 24 hours, and then the solution was removed through the frit. DMF (420 mL) was added to this solid-phase reaction vessel, and after shaking this at room temperature for 5 minutes, the solution was removed through the frit. This step of washing the resin with DMF was repeated 4 more times. DCM (420 mL) was added to this solid-phase reaction vessel, and after shaking this at room temperature for 5 minutes, the solution was removed through the frit. This step of washing the resin with DCM was repeated 5 more times. The obtained resin was dried under reduced pressure to afford Compound 1217-c-resin (62.5 g).

Synthesis of Compound aa134

Synthesis of Compound aa134 ((2S)-4-[3,5-difluoro-4-(trifluoromethyl)phenyl]-2-(9H-fluoren-9-ylmethoxycarbonylamino)butanoic acid, Fmoc-Hph (4-CF3-35-F2)-OH)

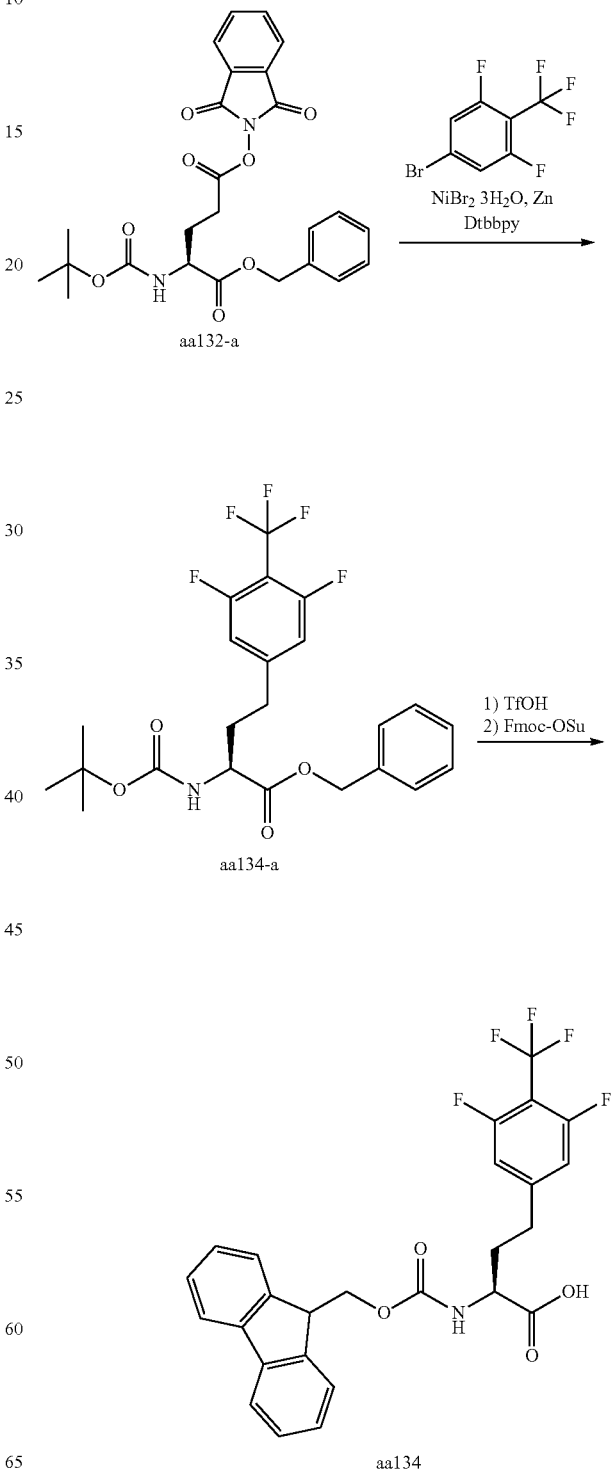

Synthesis of Compound aa132-a (1-O-benzyl 5-O-(1,3-dioxoisoindol-2-yl) (2S)-2-[(2-methylpropan-2-yl)oxycarbonylamino]pentanedioate)

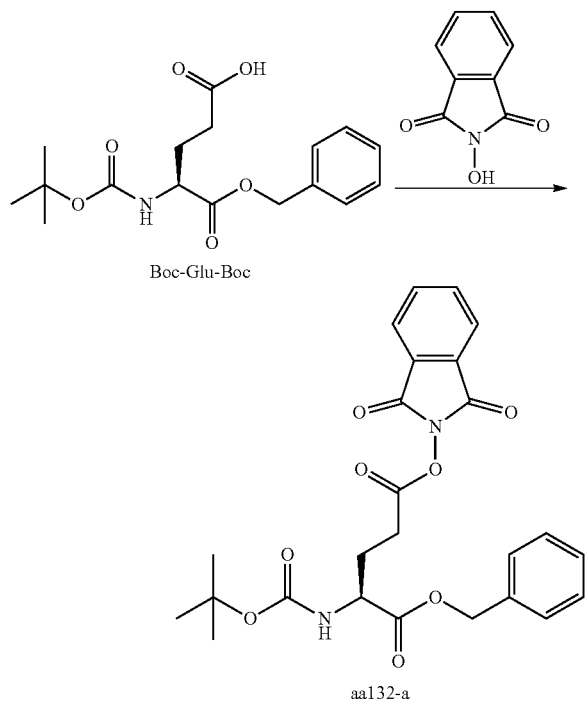

To a solution of (4S)-4-[(2-methylpropan-2-yl)oxycarbonylamino]-5-oxo-5-phenylmethoxypentanoic acid (Boc-Glu-OBn, CAS No. 30924-93-7) (200 g, 592.82 mmol), N-hydroxyphthalimide (106 g, 649.78 mmol, 1.10 equivalents), and DMAP (3.6 g, 29.47 mmol, 0.05 equivalents) in THF (2L), under nitrogen atmosphere, DIC (138 mL, 1.54 equivalents) was added dropwise at 0° C. The reaction mixture was stirred at 25° C. for 16 hours, the solids were removed by filtration, and the filtrate was concentrated under reduced pressure to distill off the solvent. The residue was diluted with toluene, the solids that formed were removed by filtration, and the filtrate was concentrated under reduced pressure to distill off the solvent. The residue was purified by recrystallization (acetone/heptane) to afford Compound aa132-a (1-O-benzyl 5-O-(1,3-dioxoisoindol-2-yl) (2S)-2-[(2-methylpropan-2-yl)oxycarbonylamino]pentanedioate) (230 g, 80%).

LCMS (ESI) m/z=505.2 (M+Na)$^+$

Retention time: 0.992 minutes, (analysis condition: SMD-method_16)

Nickel bromide trihydrate (NiBr$_2$·3H$_2$O) (13.5 g, 49.7 mmol, 0.3 equivalents) and 4,4'-di-tert-butyl-2,2'-bipyridyl (dtbbpy, CAS No. 72914-19-3) (13.3 g, 49.7 mmol, 0.3 equivalents) were added to DMA (400 mL), and the mixture was stirred under nitrogen atmosphere at 50° C. for 3 hours to prepare a Ni solution.

A mixed solution of Compound aa132-a (1-O-benzyl 5-O-(1,3-dioxoisoindol-2-yl) (2S)-2-[(2-methylpropan-2-yl)oxycarbonylamino]pentanedioate) (80 g, 166 mmol), zinc powder (54.2 g, 829 mmol, 5 equivalents), and 4-bromo-1,3-difluoro-2-(trifluoromethyl)benzene (CAS No. 156243-64-0, 86.6 g, 332 mmol, 2 equivalents) in DMA (400 mL) was stirred under nitrogen atmosphere at room temperature for 1 hour, the Ni solution prepared in advance was added to it, and the mixture was stirred at room temperature for 16 hours. An aqueous solution of EDTA-2Na (800 mL, 10%) was added to the reaction mixture, and the solids were removed by filtration. The filtrate was extracted with ethyl acetate, and the combined organic layers were washed with saturated saline solution, then dried over anhydrous sodium sulfate, and the solvent was distilled off under reduced pressure. The resulting residue was purified by silica gel column chromatography (ethyl acetate/petroleum ether) to afford Compound aa134-a (57.2 g, 69%).

LCMS (ESI) m/z=496 (M+Na)$^+$

Retention time: 1.544 minutes, (analysis condition: SMD-method_15)

A mixed solution of Compound aa134-a (57.2 g, 121 mmol) in toluene (690 mL) was cooled to 0° C., and trifluoromethanesulfonic acid (TfOH) (54.4 g, 362 mmol, 3 equivalents) was added dropwise. After stirring the mixture at room temperature for 1 hour, water (58 mL) was added. This mixed solution was extracted with water, and the combined aqueous layers were extracted with ethyl acetate. The combined organic layers were washed with water and dried over anhydrous sodium sulfate, and then the solvent was distilled off under reduced pressure to give 60 g of residue. Acetonitrile/water (400/400 mL) was added to this residue, and its pH was adjusted to 7 using an aqueous sodium hydroxide solution (48%). Fmoc-OSu (36.6 g, 108.6 mmol, 0.9 equivalents) was added to this solution, its pH was adjusted to 8.0 using an aqueous sodium hydroxide solution (48%), and then the mixture was stirred at room temperature for 16 hours. The reaction solution was filtered to remove the solid components by washing with acetonitrile/water (1/1), the filtrate was diluted with acetonitrile, and acidified with 6 mol/L aqueous hydrochloric acid solution to precipitate the solid, and the resulting solids were collected by filtration to afford Compound aa134 ((2S)-4-[3,5-difluoro-4-(trifluoromethyl)phenyl]-2-(9H-fluoren-9-ylmethoxycarbonylamino)butanoic acid, Fmoc-Hph(4-CF3-35-F2)-OH) (52 g, 83%).

LCMS (ESI) m/z=528.45 (M+Na)$^+$

Retention time: 3.538 minutes, (analysis condition: SMD-method_14)

$^1$H-NMR (300 MHz, DMSO-d$_6$) δ: 12.69 (s, 1H), 7.90 (d, J=7.5 Hz, 2H), 7.78-7.54 (m, 3H), 7.48-7.20 (m, 6H), 4.33 (d, J=6.3 Hz, 2H), 4.24 (t, J=6.9 Hz, 1H), 3.97-3.84 (m, 1H), 2.79-2.65 (m, 2H), 2.15-2.00 (m, 1H), 2.00-1.83 (m, 1H).

Synthesis of Compound aa113 ((2S)-2-[ethyl(9H-fluoren-9-ylmethoxy-carbonyl)amino]-3-(4-methylphenyl)propanoic acid (Fmoc-EtPhe(4-Me)-OH))

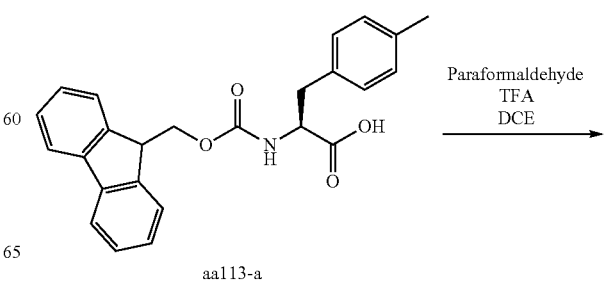

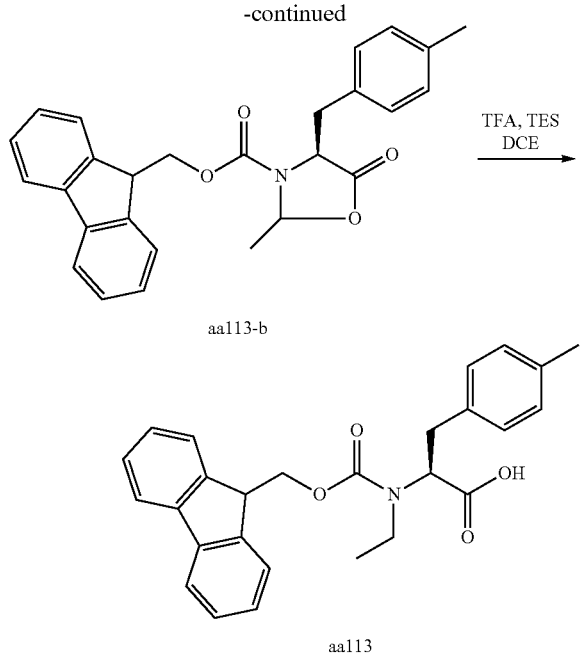

aa113-b aa113

Under nitrogen atmosphere, Compound aa113-a ((2S)-2-(9H-fluoren-9-ylmethoxycarbonylamino-3-(4-methylphenyl)propanoic acid, Fmoc-Phe(4-Me)-OH) (5.62 g, 14.0 mmol, CAS No. 199006-54-7) was suspended in dichloroethane (DCE) (17.5 mL), paraldehyde (5.61 mL, 42.0 mmol) and trifluoroacetic acid (TFA) (9.65 mL, 126 mmol) were added, and the mixture was stirred at 60° C. for 6 hours. The obtained reaction mixture containing Compound aa113-b was used in the next step without further treatment.

LCMS (ESI) m/z=428 (M+H)$^+$
Retention time: 1.03 minutes, (analysis condition: SQDFA05)

To the obtained reaction solution containing Compound aa113-b, dichloroethane (DCE) (17.5 mL), trifluoroacetic acid (TFA) (19.3 mL, 252 mmol), and triethylsilane (TES) (20.1 mL, 126 mmol) were added, and the mixture was stirred at 60° C. for 17 hours. The mixture was cooled to room temperature and concentrated under reduced pressure, then the resulting residue was dissolved in ethyl acetate (40 mL). The organic layer was washed with saturated aqueous sodium hydrogen carbonate solution (40 mL) and saturated saline solution (40 mL), and dried over anhydrous sodium sulfate, and then the solvent was distilled off under reduced pressure. The resulting residue was dissolved in acetonitrile (30 mL) and the solution was washed twice with hexane (15 mL), and the solvent was distilled off under reduced pressure. The resulting residue was purified by reverse-phase column chromatography (acetonitrile containing 0.1% formic acid/distilled water containing 0.1% formic acid) to afford Compound aa113 ((2S)-2-[ethyl(9H-fluoren-9-ylmethoxycarbonyl)amino]-3-(4-methylphenyl)propanoic acid (Fmoc-EtPhe(4-Me)-OH)) (4.4 g, 73% in two steps)

LCMS (ESI) m/z=430 (M+H)$^+$
Retention time: 0.95 minutes, (analysis condition: SQDFA05)

The following elongation of Fmoc-Pro-OH (CAS No. 71989-31-6), Fmoc-Hph (4-CF3-35-F2)-OH (Compound aa134), Fmoc-MeGly-OH (CAS No. 77128-70-2), Fmoc-EtPhe(4-Me)-OH (Compound aa113), Fmoc-Aze(2)-OH (CAS No. 136552-06-2), Fmoc-MeAla-OH (CAS No. 84000-07-7), and Fmoc-Ile-OH (CAS No. 71989-23-6) was performed by an Fmoc solid-phase synthesis method using a peptide synthesizer (Multipep RSi) manufactured by Intavis Inc. Specific procedures for the operation were performed according to the instructions attached to the synthesizer.

Compound 1217-c-resin obtained as described above was added to 30 solid-phase reaction vessels (200 mg per solid-phase reaction vessel), and these were placed into the peptide synthesizer. Dichloromethane (DCM) was added to all of the 30 solid-phase reaction vessels, and the resin was swollen by allowing this to stand for 1 hour. Then, the solvent was removed through the frit.

Elongation of Fmoc-Pro-OH

To all 30 solid-phase reaction vessels, a DMF solution of diazabicycloundecene (DBU) (2 v/v %, 1.4 mL per solid-phase reaction vessel) was added, this was warmed to 30° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, an NMP solution of Fmoc-Pro-OH (CAS No. 71989-31-6) (0.6 mol/L) and HOAt (0.375 mol/L) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and the mixture was added to all 30 of the solid-phase reaction vessels, and these were left to stand at 40° C. for 4 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-Hph (4-CF3-35-F2)-OH (Compound aa134)

To all 30 of the solid-phase reaction vessels containing the resin obtained above, a DMF solution of diazabicycloundecene (DBU) (2 v/v %, 1.4 mL per solid-phase reaction vessel) was added, the mixture was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, an NMP solution of Fmoc-Hph(4-CF3-35-F2)-OH (Compound aa134) (0.45 mol/L) and HOAt (0.375 mol/L) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 40° C. for 2.5 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-MeGly-OH

To all 30 of the solid-phase reaction vessels containing the resin obtained above, a DMF solution of diazabicycloundecene (DBU) (2 v/v %, 1.4 mL per solid-phase reaction vessel) was added, this was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, an NMP solution of Fmoc-MeGly-OH (0.6 mol/L) and HOAt (0.375 mol/L) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 40° C. for 2.5 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-EtPhe (4-Me)-OH (Compound aa113)

To all 30 of the solid-phase reaction vessels containing the resin obtained above, a DMF solution of diazabicycloundecene (DBU) (2 v/v %, 1.4 mL per solid-phase reaction vessel) was added, this was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, a solution of Fmoc-EtPhe(4-Me)-OH (0.6 mol/L) prepared as described above and HOAt (0.375 mol/L) in NMP (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 40° C. for 2.5 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-Aze(2)-OH

To all 30 of the solid-phase reaction vessels containing the resin obtained above, a DMF solution of diazabicycloundecene (DBU) (2 v/v %, 1.4 mL per solid-phase reaction vessel) was added, this was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, a mixed solution of Fmoc-Aze(2)-OH (0.6 mol/L) and HOOBt (0.375 mol/L) in NMP and DMSO (7:3) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 60° C. for 5 hours. Thereafter, a DMF solution of N,N'-diisopropylcarbodiimide (DIC) (10 v/v %, 0.72 mL per solid-phase reaction vessel) was added to all 30 of the solid-phase reaction vessels, and these were left to stand at 60° C. for 5 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-MeAla-OH

To all 30 of the solid-phase reaction vessels containing the resin obtained above, a DMF solution of diazabicycloundecene (DBU) (2 v/v %, 1.4 mL per solid-phase reaction vessel) was added, this was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, an NMP solution of Fmoc-MeAla-OH (0.6 mol/L) and HOAt (0.375 mol/L) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 40° C. for 2.5 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times.

Elongation of Fmoc-Ile-OH

To all 30 of the solid-phase reaction vessels containing the resin obtained above, a DMF solution of diazabicycloundecene (DBU) (2 v/v %, 1.4 mL per solid-phase reaction vessel) was added, this was warmed to 35° C., and 10 minutes later, the solution was removed through the frit. To all 30 of the solid-phase reaction vessels, DMF (1.4 mL per solid-phase reaction vessel) was added, and the solvent was removed through the frit. This step of washing the resin with DMF was repeated three more times. Subsequently, an NMP solution of Fmoc-Ile-OH (0.6 mol/L) and HOAt (0.375 mol/L) (0.6 mL per solid-phase reaction vessel) and a DMF solution of N,N'-diisopropylcarbodiimide (DIC) (10 v/v %, 0.72 mL per solid-phase reaction vessel) were mixed in the mixing vial of the synthesizer and then added to all 30 of the solid-phase reaction vessels, and these were left to stand at 40° C. for 10 hours. Thereafter, the solution was removed through the frit. To all 30 of the solid-phase reaction vessels, DMF (1.4 mL per solid-phase reaction vessel) was added, and the solvent was removed through the frit. This step of washing the resin was repeated two more times. Subsequently, to all 30 of the solid-phase reaction vessels, DCM (1.6 mL per solid-phase reaction vessel) was added, and the solvent was removed through the frit. This step of washing the resin was repeated 5 more times. The resins were recovered from all 30 of the solid-phase reaction vessels, and after combining them, the next operation was performed.

Elongation of Fmoc-MeLeu-OH (CAS No. 103478-62-2)

The resins obtained above were added to a 200-mL plastic solid-phase reaction vessel, DCM (60 mL) was added to this, and after shaking this at 30° C. for 5 minutes, the solvent was removed through the frit. Toluene (50 mL) was added to this solid-phase reaction vessel, and after shaking this at 30° C. for 5 minutes, the solvent was removed through the frit. This step of washing the resin with toluene was repeated one more time. A toluene solution of diazabicycloundecene (DBU) (2 v/v %, 45 mL) was added to this solid-phase reaction vessel, and after shaking this at 30° C. for 5 minutes, the solution was removed through the frit.

Toluene (50 mL) was added to this solid-phase reaction vessel, and after shaking this at 30° C. for 5 minutes, the solvent was removed through the frit. This step of washing the resin with toluene was repeated one more time. DCM (50 mL) was added to this solid-phase reaction vessel, and after shaking this at 30° C. for 5 minutes, the solvent was removed through the frit. This step of washing the resin with DCM was repeated one more time. A solution of Fmoc-MeLeu-OH (4.25 g, 11.57 mmol), [ethylcyano(hydroxyimino)acetato-02]tri-1-pyrrolidinylphosphonium hexafluorophosphate (PyOxim) (6.10 g, 11.57 mmol), and DIPEA (3.03 mL, 17.35 mmol) in DCM (45 mL) was added to this solid-phase reaction vessel, and this was shaken at 30° C. for 3 hours. Subsequently, the solution was removed through the frit. DMF (50 mL) was added to this solid-phase reaction vessel, and after shaking this at 30° C. for 5 minutes, the solvent was removed through the frit. This step of washing the resin with DMF was repeated 4 more times. DCM (50 mL) was added to this solid-phase reaction vessel, and after shaking this at 30° C. for 5 minutes, the solvent was removed through the frit. This step of washing the resin with DCM was repeated 3 more times. Subsequently, the resulting resin was dried under reduced pressure.

DCM (60 mL) was added to the above-mentioned solid-phase reaction vessel, and after shaking this at 30° C. for 5 minutes, the solvent was removed through the frit. DMF (50 mL) was added to this solid-phase reaction vessel, and after shaking this at 30° C. for 5 minutes, the solvent was removed through the frit. This step of washing the resin with DMF was repeated one more time. A DMF solution of diazabicycloundecene (DBU) (2 v/v %, 45 mL) was added to this solid-phase reaction vessel, and after shaking this at 30° C. for 15 minutes, the solution was removed through the frit. DMF (50 mL) was added to this solid-phase reaction vessel, and after shaking this at 30° C. for 5 minutes, the solvent was removed through the frit. This step of washing the resin with DMF was repeated 4 more times. DCM (50 mL) was added to this solid-phase reaction vessel, and after shaking this at 30° C. for 5 minutes, the solvent was removed through the frit. This step of washing the resin with DCM was repeated 4 more times to afford the Compound 1217-d-loaded resin.

Synthesis of Compound 1217-d (Cleavage of the Peptide from the Resin)

To a solid-phase reaction vessel containing the resin obtained above, a mixed solution of 2,2,2-trifluoroethanol (TFE) (60 mL), DCM (60 mL), and DIPEA (0.909 mL) was added, and this was shaken at room temperature for 2 hours. Subsequently, the solution was collected through the frit. A mixed solution of 2,2,2-trifluoroethanol (TFE) (30 mL) and DCM (30 mL) was added to this solid-phase reaction vessel, this was shaken at room temperature for 5 minutes, and the solution was recovered through the frit. A mixed solution of 2,2,2-trifluoroethanol (TFE) (30 mL) and DCM (30 mL) was further added to this solid-phase reaction vessel, this was shaken at room temperature for 5 minutes, and the solution was recovered through the frit. All of the recovered solutions were combined, and the solvent was distilled off under reduced pressure to afford Compound 1217-d as a crude product (3.85 g).

LCMS (ESI) m/z=1453.9 (M−H)−

Retention time: 0.67 minutes, (analysis condition: SQDAA50)

Synthesis of Compound 1 (Peptide Cyclization and Purification)

Compound 1217-d (3.85 g) obtained as described above was dissolved in a mixed solution of isopropyl acetate (529 mL) and DIPEA (0.915 mL, 5.24 mmol), HCTU (O-(1H-6-chlorobenzotriazol-1-yl)-1,1,3,3-tetramethyluronium hexafluorophosphate, CAS No. 330645-87-9) (1.805 g, 4.36 mmol) was added, and this was stirred at room temperature for 21 hours. Then, the solvent was distilled off under reduced pressure until the liquid volume became approximately one half. To the resulting solution, a mixed solution of saturated aqueous ammonium chloride solution (40 mL) and water (40 mL) was added, and this was extracted with isopropyl acetate (350 mL). The obtained organic layer was sequentially washed with a mixed solution of saturated aqueous sodium hydrogen carbonate solution (40 mL) and water (40 mL) and a mixed solution of saturated saline solution (40 mL) and water (40 mL), then dried over sodium sulfate, and the solvent was distilled off under reduced pressure to yield 3.36 g of residue. The obtained residue was purified by reverse-phase silica gel column chromatography (Daisogel SP-120-40/60-ODS-RPS, using acetonitrile (containing 0.1% formic acid)/water (containing 0.1% formic acid) as the eluent), and the eluate containing the target molecule was freeze-dried to afford the amorphous state of Compound 1 (1.36 g, 34% yield). The mass spectral value and the liquid chromatography retention time of the obtained Compound 1 were as follows.

LCMS (ESI) m/z=1437.7 (M+H)+

Retention time: 7.496 minutes, (analysis condition: SSC-A-AF-01)

The analysis conditions for LC/MS in Preparation Example 1 are shown in Table 9.

TABLE 9

| Analysis condition | Apparatus | Column (I.D. × length) (mm) | Mobile phase | Gradient (A/B) | Flow rate (mL/min) | Column Temp. (° C.) | Wavelength | Remarks |
|---|---|---|---|---|---|---|---|---|
| SMDAM05 | Nexera/2020 | Ascentis Express RP-amide (2.1 × 50) | A) 0.1% FA, water B) 0.1% FA, acetonitrile | 95/5 (initial) => 0/100 (1.5 min) => 0/100 (0.5 min) | 1.0 | 35 | 210-400 nm PDA total | |
| SMDFA05 | Nexera/2020 | Ascentis Express C18 (2.1 × 50) | A) 0.1% FA, water B) 0.1% FA, acetonitrile | 95/5 (initial) => 0/100 (1.5 min) => 0/100 (0.5 min) | 1.0 | 35 | 210-400 nm PDA total | |
| SQDAA50 | Acquity UPLC/SQD or Acquity UPLC/SQD2 | Ascentis Express C18 (2.1 × 50) | A) 10 mM AcONH$_4$, water B) methanol | 50/50 (initial) => 0/100 (0.7 min) => 0/100 (0.7 min) | 1.0 | 35 | 210-400 nm PDA total | |
| SSC-A-AF-01 | Nexera UC/2020 | Ascentis Express C18 (2.1 × 50) | A) 10 mM NH$_4$HCO$_2$ water B) methanol | 70/30 (initial) => 0/100 (8.75 min) => 0/100 (1.25 min) | 0.5 | 50 | 210-400 nm PDA total | Loop injection |
| SQDFA05 | Acquity UPLC/SQD or Acquity UPLC/SQD2 | Ascentis Express C18 (2.1 × 50) | A) 0.1% FA, water B) 0.1% FA, acetonitrile | 95/5 (initial) => 0/100 (1.0 min) => 0/100 (0.4 min) | 1.0 | 35 | 210-400 nn PDA total | |

TABLE 9-continued

| Analysis condition | Apparatus | Column (I.D. × length) (mm) | Mobile phase | Gradient (A/B) | Flow rate (mL/min) | Column Temp. (° C.) | Wavelength | Remarks |
|---|---|---|---|---|---|---|---|---|
| SMDmethod_05 | Shimadzu LCMS-2020 | Shim-Pack XR-ODS (3.0 × 50) | A) 0.05% TFA, water B) 0.05% TFA, acetonitrile | 95/5 (initial) => 5/95 (2.0 min) => 5/95 (0.7 min) | 1.2 | 40 | 190-400 nm PDA total | |
| SMDmethod_14 | Shimadzu LCMS-2020 | Shim-Pack XR-ODS (3.0 × 50) | A) 0.05% TFA, water B) 0.05% TFA, acetonitrile | 70/30 (initial) => 20/80 (3.8 min) => 0/100 (0.3 min) => 0/100 (0.5 min) | 1.2 | 40 | 190-400 nm PDA total | |
| SMDmethod_15 | Shimadzu LCMS-2020 | Shim-Pack XR-ODS (3.0 × 50) | A) 0.05% TFA, water B) 0.05% TFA, acetonitrile | 95/5 (initial) => 0/100 (1.1 min) => 0/100 (0.6 min) | 1.2 | 40 | 190-400 nm PDA total | |
| SMDmethod_16 | Shimadzu LCMS-2020 | Accucore C18 (2.1 × 50) | A) 0.1% FA, water B) 0.1% FA, acetonitrile | 90/10 (initial) => 0/100 (1.1 min) => 0/100 (0.5 min) | 1.0 | 40 | 190-400 nm PDA total | |
| SMDmethod_20 | Shimadzu LCMS-2020 | Ascentis Express C18 (3.0 × 50) | A) 0.05% TFA, water B) 0.05% TFA, acetonitrile | 95/5 (initial) => 5/95 (1.1 min) => 5/95 (0.5 min) | 1.0 | 40 | 190-400 nm PDA total | |

TABLE 12

| Step (Compound No.) | LCMS analysis condition | Retention time (min) | MS Found (m/z) | MS polarity |
|---|---|---|---|---|
| Step H'1 (Compound a03) | method 3 | 4.499 | 447 | [M+H]+ |
| Step H'2-1 (Compound a04) | method 3 | 2.419 | 313 | [M+H]+ |
| Step H'2-2 (Compound a06) | method 3 | 4.458 | 540 | [M+Na]+ |
| Step H'3-1 (Compound a07) | method 3 | 2.848 | 384 | [M+H]+ |
| Step H'3-2 (Compound a09) | method 3 | 4.055 | 611 | [M+Na]+ |
| Step H'4-1 (Compound a10) | method 3 | 2.521 | 455 | [M+H]+ |
| Step H'4-2 (Compound a12) | method 1 | 4.006 | 703 | [M+H]+ |
| Step H'5-1 (Compound a13) | method 1 | 2.776 | 569 | [M+H]+ |
| Step H'5-2 (Compound a15) | method 1 | 4.919 | 840 | [M+H]+ |
| Step H'6 (Compound a16) | method 1 | 2.909 | 696 | [M+H]+ |
| Step S'0 (Compound a19) | method 3 | 3.934 | 405 | [M+H]+ |
| Step S'1-1 (Compound a20) | method 3 | 2.058 | 271 | [M+H]+ |
| Step S'1-2 (Compound a22) | method 3 | 4.428 | 518 | [M+H]+ |
| Step S'2-1 (Compound a23) | method 3 | 2.393 | 384 | [M+H]+ |
| Step S'2-2 (Compound a25) | method 3 | 4.002 | 613 | [M+Na]+ |
| Step S'3-1 (Compound a26) | method 3 | 2.868 | 517 | [M+Na]+ |
| Step S'3-2 (Compound a28) | method 3 | 4.323 | 748 | [M+Na]+ |
| Step S'4-1 (Compound a29) | method 3 | 2.970 | 592 | [M+H]+ |
| Step S'4-2 (Compound a31) | method 3 | 4.794 | 910 | [M+Na]+ |
| Step 1 (Compound a32) | method 3 | 4.001 | 831 | [M+H]+ |
| Step 2' (Compound a33) | method 4 | 10.65 | 1531 | [M+Na]+ |
| Step 3' (Compound a34) | method 4 | 9.26 | 1474 | [M+Na]+ |
| Step 4' (Compound a35) | method 4 | 12.39 | 1319 | [M+H]+ |
| Step 5' (Compound a36) | method 5 | 18.69 | 1300 | [M+H]+ |

Example 27 Step H' 1

Compound a03: Synthesis of tert-butyl 2-[[(2S)-2-[benzyloxycarbonyl(methyl)amino]-3-cyclohexyl-propanoyl]-methyl-amino]acetate

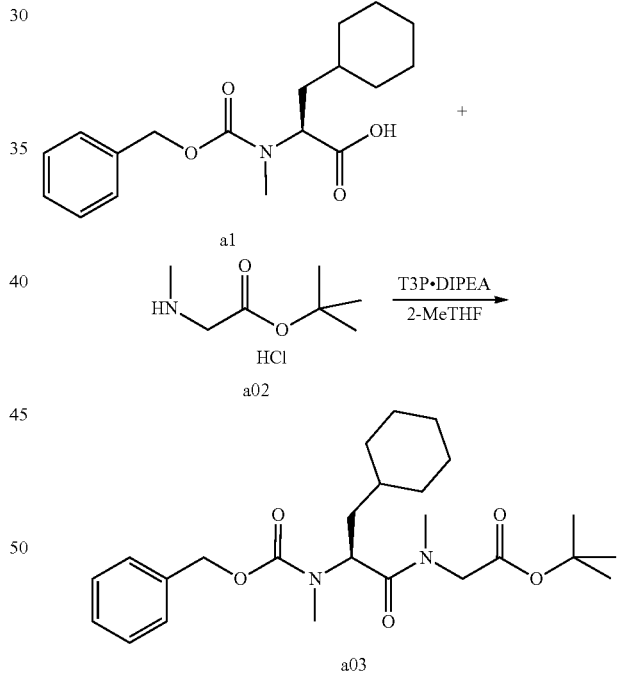

Compound a01 (2.00 g) and Compound a02 (1.37 g) were added to a reaction vessel, then 2-MeTHF (19.0 mL) was added, and this was stirred. After further adding DIPEA (5.5 mL), T3P (50 w/w % 2-MeTHF solution, 11.7 mL) was added dropwise while maintaining the internal temperature of the reaction mixture at 32° C. or lower, and then this was stirred at room temperature for 1 hour. While maintaining the internal temperature of the reaction mixture at 36° C. or lower, 5% aqueous sodium carbonate solution (12 mL) was added dropwise, this was stirred, and then the aqueous layer was removed. The obtained organic layer was washed with 5% aqueous sodium carbonate solution (12 mL×1), 5% aqueous sodium hydrogen sulfate monohydrate solution (12 mL×1), and 10% aqueous sodium chloride solution (50 mL×2). Concentrating the resulting organic layer under reduced pressure gave a residue (2.72 g) containing Compound a03.

Retention time by HPLC analysis: 4.499 minutes (HPLC analysis conditions: method 3)

Example 28 Step H'2-1

Compound a04: Synthesis of tert-butyl 2-[[(2S)-3-cyclohexyl-2-(methylamino)propanoyl]-methyl-amino]acetate

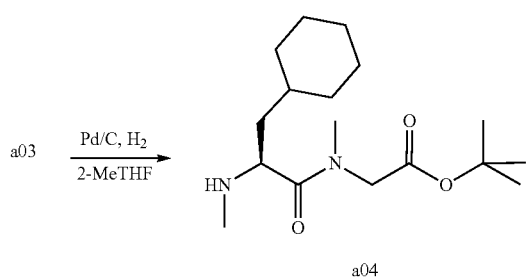 [SMILES: CN[C@@H](CC1CCCCC1)C(=O)N(C)CC(=O)OC(C)(C)C]

2-MeTHF (18 mL) was added to the residue (2.70 g) containing Compound a03 obtained in Step H'1, and then 5% Pd/C (1.27 g, 50% wetted with water) was added. Degassing and purging with hydrogen gas was performed 3 times, and then this was stirred for 2 hours. The reaction mixture was vacuum filtered through a filter paper, and the residue was washed with a 2-MeTHF solution (18 mL×3). The obtained filtrate and wash solution were combined and concentrated under reduced pressure to afford a residue (1.77 g) containing Compound a04.

Retention time by HPLC analysis: 2.419 minutes (HPLC analysis conditions: method 3)

Example 29 Step H'2-2

Compound a06: Synthesis of tert-butyl 2-[[(2S)-2-[[2-[benzyloxycarbonyl(methyl)-amino]acetyl]-methyl-amino]-3-cyclohexyl-propanoyl]-methyl-amino]acetate

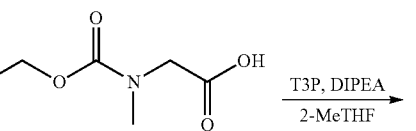

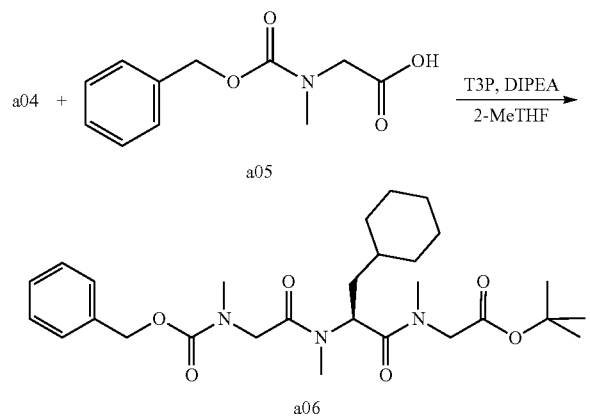

The residue (1.71 g) containing Compound a04 obtained in Step H'2-1 and Compound a05 (1.29 g) were dissolved in 2-MeTHF (11.6 mL) and then stirred. After further adding DIPEA (3.4 mL), T3P (50 w/w % 2-MeTHF solution, 7.2 mL) was added dropwise while maintaining the internal temperature of the reaction mixture at 27° C. or lower, and then this was stirred at room temperature for 2 hours. While maintaining the internal temperature of the reaction mixture at 29° C. or lower, 5% aqueous sodium carbonate solution (7.2 mL) was added dropwise, this was stirred, and then the aqueous layer was removed. The obtained organic layer was washed with 5% aqueous sodium carbonate solution (7.2 mL×1), 5% aqueous sodium hydrogen sulfate monohydrate solution (7.2 mL×1), and 10% aqueous sodium chloride solution (7.2 mL×2). Concentrating the resulting organic layer under reduced pressure afforded a residue (2.70 g) containing Compound a06.

Retention time by HPLC analysis: 4.458 minutes (HPLC analysis conditions: method 3)

Example 30 Step H'3-1

Compound a07: Synthesis of tert-butyl 2-[[(2S)-3-cyclohexyl-2-[methyl-[2-(methylamino)acetyl]amino]propanoyl]-methyl-amino]acetate

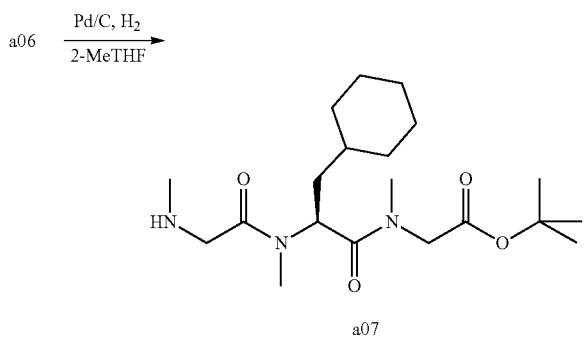

2-MeTHF (10 mL) was added to the residue (2.70 g) containing Compound a06 obtained in Step H'2-2, and then 5% Pd/C (0.71 g, 50% wetted with water) was added. Degassing and purging with hydrogen gas was performed 3 times, and then this was stirred for 2 hours. The reaction mixture was vacuum filtered through a filter paper, and the residue was washed with a 2-MeTHF solution (10 mL×3). The obtained filtrate and wash solution were combined and concentrated under reduced pressure to afford a residue (1.82 g) containing Compound a07.

Retention time by HPLC analysis: 2.848 minutes (HPLC analysis conditions: method 3)

161
Example 31 Step H'3-2

Compound a09: Synthesis of tert-butyl 2-[[(2S)-2-[[2-[[2-[benzyloxycarbonyl(methyl)-amino]acetyl]-methyl-amino]acetyl]-methyl-amino]-3-cyclohexyl-propanoyl]-methyl-amino]acetate

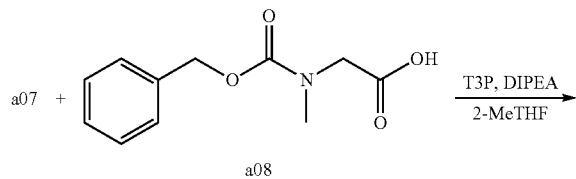

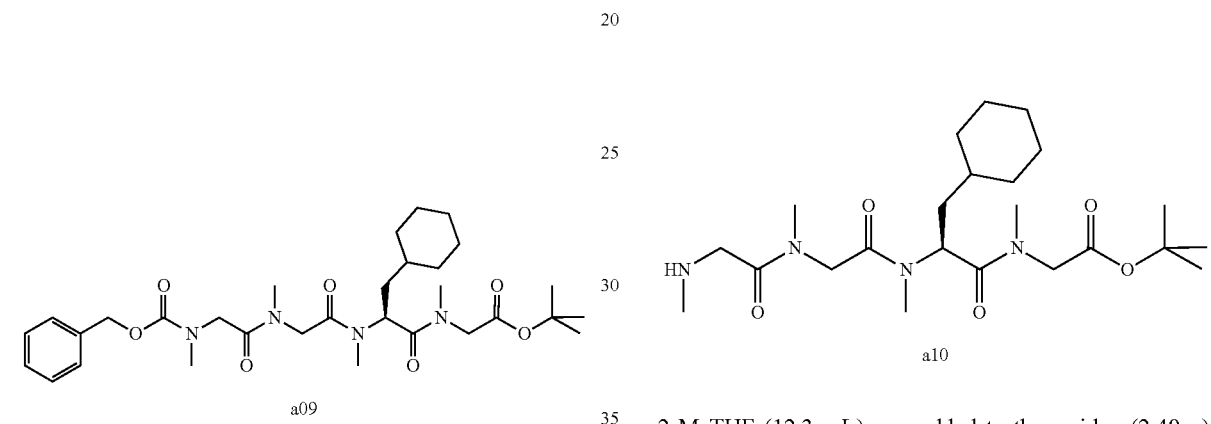

The residue (1.80 g) containing Compound a07 obtained in Step H'3-1 and Compound a08 (1.57 g) were dissolved in 2-MeTHF (14.2 mL) and then stirred. After further adding DIPEA (4.1 mL), T3P (50 w/w % 2-MeTHF solution, 8.8 mL) was added dropwise while maintaining the internal temperature of the reaction mixture at 30° C. or lower, and then this was stirred at room temperature for 2 hours. While maintaining the internal temperature of the reaction mixture at 33° C. or lower, 5% aqueous sodium carbonate solution (10.8 mL) was added dropwise, this was stirred, and then the aqueous layer was removed. The obtained organic layer was washed with 5% aqueous sodium carbonate solution (10.8 mL×1), 5% aqueous sodium hydrogen sulfate monohydrate solution (10.8 mL×1), and 5% aqueous sodium carbonate solution (10.8 mL×1). Concentrating the resulting organic layer under reduced pressure afforded a residue (2.61 g) containing Compound a09.

Retention time by HPLC analysis: 4.055 minutes (HPLC analysis conditions: method 3)

162
Example 32 Step H'4-1

Compound a10: Synthesis of tert-butyl 2-[[(2S)-3-cyclohexyl-2-[methyl-[2-[methyl-[2-(methylamino)acetyl]amino]acetyl]amino]propanoyl]-methyl-amino]acetate 2-MeTHF (12.3 mL) was added to the residue (2.40 g) containing Compound a09 obtained in Step H'3-2, and then 5% Pd/C (0.44 g, 50% wetted with water) was added. Degassing and purging with hydrogen gas was performed 3 times, and then this was stirred for 1 hour. The reaction mixture was vacuum filtered through a filter paper, and the residue was washed with a 2-MeTHF solution (12 mL×3). The obtained filtrate and wash solution were combined and concentrated under reduced pressure to afford a residue (1.97 g) containing Compound a10.

Retention time by HPLC analysis: 2.521 minutes (analysis conditions: method 3)

Example 33 Step H'4-2

Compound a12: Synthesis of tert-butyl 2-[[(2S)-2-[[2-[[2-[[(2S,3S)-2-(benzyloxycarbonylamino)-3-methyl-pentanoyl]-methyl-amino]acetyl]-methyl-amino]acetyl]-methyl-amino]-3-cyclohexyl-propanoyl]-methyl-amino]acetate

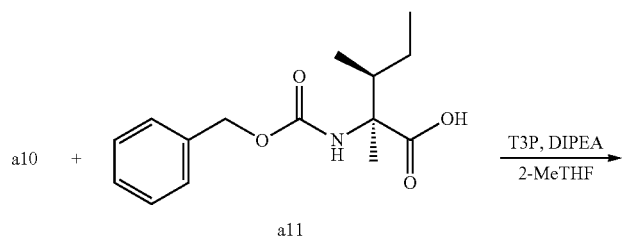

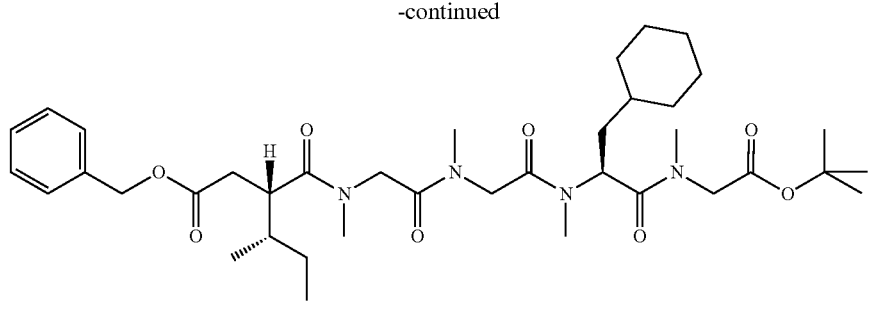

a12

The residue (1.92 g) containing Compound a10 obtained in Step H'4-1 and Compound a11 (1.69 g) were dissolved in 2-MeTHF (12.8 mL) and then stirred. After further adding DIPEA (3.7 mL), T3P (50 w/w % 2-MeTHF solution, 7.8 mL) was added dropwise while maintaining the internal temperature of the reaction mixture at 29° C. or lower, and then this was stirred at room temperature for 2 hours. While maintaining the internal temperature of the reaction mixture at 33° C. or lower, 5% aqueous sodium carbonate solution (14.4 mL) was added dropwise, this was stirred, and then the aqueous layer was removed. The obtained organic layer was washed with 5% aqueous sodium carbonate solution (14.4 mL×1), 5% aqueous sodium hydrogen sulfate monohydrate solution (14.4 mL×1), and 5% aqueous sodium carbonate solution (14.4 mL×1). The resulting organic layer was further subjected to two rounds of washing with 5% aqueous sodium hydrogen sulfate monohydrate solution (14.4 mL×1) and 5% aqueous sodium carbonate solution (14.4 mL×1). 2-MeTHF (14.4 mL) was added, and this was washed with 5% aqueous sodium hydrogen sulfate monohydrate solution (14.4 mL×1) and 5% aqueous sodium carbonate solution (14.4 mL×1). Furthermore, this was washed with 1% aqueous sodium carbonate solution (14.4 mL×3), 5% aqueous sodium carbonate solution (14.4 mL×5), 5% aqueous sodium hydrogen sulfate monohydrate solution (14.4 mL×1), 5% aqueous sodium carbonate solution (14.4 mL×1), 5% aqueous sodium hydrogen sulfate monohydrate solution (14.4 mL×1), and 5% aqueous sodium carbonate solution (14.4 mL×1, 7.2 mL×10). This was further washed with 2.5% aqueous ammonia (7.2 mL×3) and 10% aqueous sodium chloride solution (1 mL×1). Concentrating the resulting organic layer under reduced pressure afforded a residue (2.39 g) containing Compound a12.

Retention time by HPLC analysis: 4.006 minutes (HPLC analysis conditions: method 1)

Example 34 Step H'5-1

Compound a13: Synthesis of tert-butyl 2-[[(2S)-2-[[2-[[2-[[(2S,3S)-2-amino-3-methyl-pentanoyl]-methyl-amino]acetyl]-methyl-amino]acetyl]-methyl-amino]-3-cyclohexyl-propanoyl]-methyl-amino] acetate

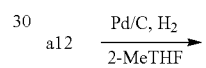

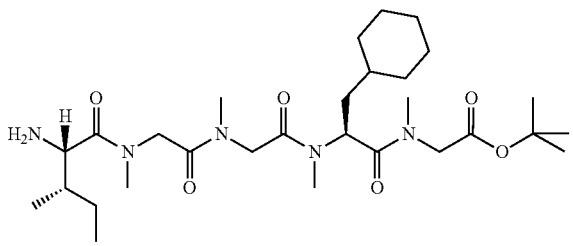

a13

2-MeTHF (9.3 mL) was added to the residue (2.15 g) containing Compound a12 obtained in Step H'4-2, and then 5% Pd/C (0.66 g, 50% wetted with water) was added. Degassing and purging with hydrogen gas was performed 3 times, and then this was stirred for 2 hours. The reaction mixture was vacuum filtered through a filter paper, and the residue was washed with a 2-MeTHF solution (10 mL×3). The obtained filtrate and wash solution were combined and concentrated under reduced pressure to afford a residue (1.95 g) containing Compound a13.

Retention time by HPLC analysis: 2.776 minutes (HPLC analysis conditions: method 1)

Example 35 Step H'5-2

Compound a15: Synthesis of tert-butyl 2-[[(2S)-3-cyclohexyl-2-[methyl-[2-[methyl-[2-[methyl-[(2S,3S)-3-methyl-2-[[(2S)-4-methyl-2-[methyl (2-trimethylsilylethoxycarbonyl)amino]pentanoyl]amino]pentanoyl]amino]acetyl]amino]acetyl]amino]propanoyl]-methyl-amino]acetate

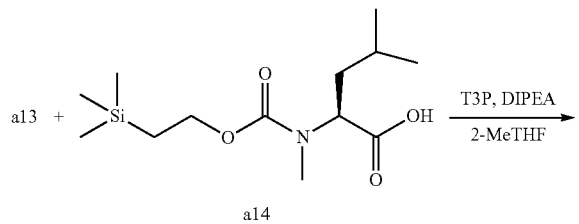

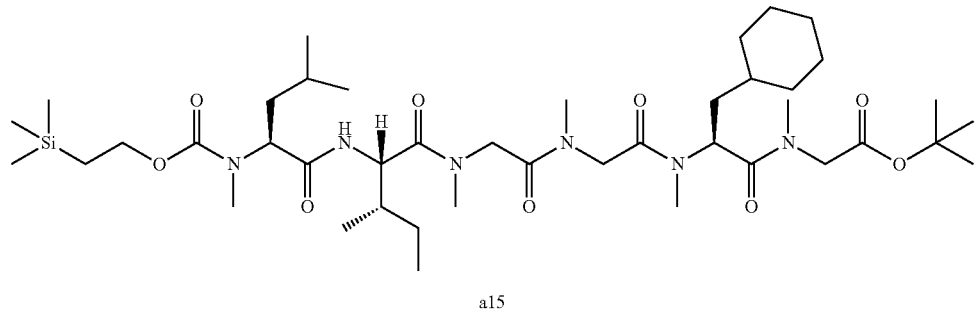

The residue (1.94 g) containing Compound a13 obtained in Step H'5-1 and Compound a14 (1.49 g) were dissolved in 2-MeTHF (10.3 mL) and then stirred. The reaction vessel was cooled in an ice bath, and after adding DIPEA (3.0 mL), T3P (50 w/w % 2-MeTHF solution, 6.3 mL) was added dropwise while maintaining the internal temperature of the reaction mixture at 9° C. or lower, then the ice bath was removed, and the mixture was stirred at room temperature for 1 hour. While maintaining the internal temperature of the reaction mixture at 22° C. or lower, 5% aqueous sodium carbonate solution (12 mL) was added dropwise, this was stirred, and then the aqueous layer was removed. The obtained organic layer was washed with 5% aqueous sodium carbonate solution (12 mL×1), 5% aqueous sodium hydrogen sulfate monohydrate solution (12 mL×1), and 5% aqueous sodium carbonate solution (12 mL×1), and the resulting organic layer was concentrated under reduced pressure. This was redissolved in 2-MeTHF (20 mL), and washed with 5% aqueous sodium hydrogen sulfate monohydrate solution (12 mL×2) and 5% aqueous sodium carbonate solution (12 mL×2). N-methylimidazole (0.3 mL) and 5% aqueous sodium carbonate solution (12 mL) were added to the organic layer, this was stirred for 6.5 hours, and then the aqueous layer was removed. Washing this with 5% aqueous sodium carbonate solution (12 mL×1), 5% aqueous sodium hydrogen sulfate monohydrate solution (12 mL×2), and 5% aqueous sodium carbonate solution (12 mL×2), was followed by concentration under reduced pressure. This was redissolved in 2-MeTHF (20 mL), Heptane:MTBE mixture (1.5:1) (20 mL) was further added, this was washed with 5% aqueous sodium carbonate solution (20 mL×2), and concentration under reduced pressure afforded a residue (2.38 g) containing Compound a15.

Retention time by HPLC analysis: 4.919 minutes (HPLC analysis conditions: method 1)

Example 36 Step H'6

Compound a16: Synthesis of tert-butyl 2-[[(2S)-3-cyclohexyl-2-[methyl-[2-[methyl-[2-[methyl-[(2S,3S)-3-methyl-2-[[(2S)-4-methyl-2-(methylamino)pentanoyl]amino]pentanoyl]amino]acetyl]amino]acetyl]amino]propanoyl]-methyl-amino]acetate

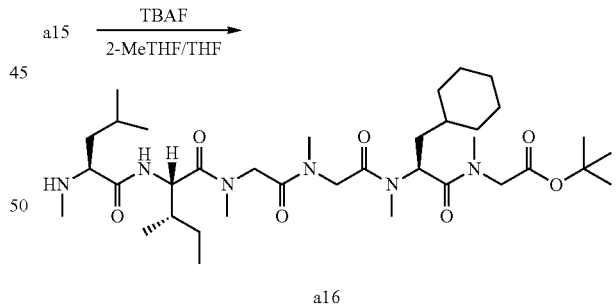

2-MeTHF (14 mL) was added to the residue (2.35 g) containing Compound a15 obtained in Step H'5-2, then the external temperature of the reaction vessel was set at 50° C., and tetrabutylammonium fluoride (1 M THF solution, 7.0 mL) was added. The reaction solution was stirred as it is for 2 hours. After cooling to room temperature, isopropyl acetate (7 mL) was added, this was washed with 5% aqueous potassium carbonate solution (7 mL×6), and then this was concentrated under reduced pressure to afford a residue (1.92 g) containing Compound a16.

Retention time by HPLC analysis: 2.909 minutes (HPLC analysis conditions: method 1)

167
Example 37 Step S'0

Compound a19: Synthesis of tert-butyl (3S)-3-[benzyloxycarbonyl(methyl)amino]-4-oxo-4-(1-piperidyl)butanoate

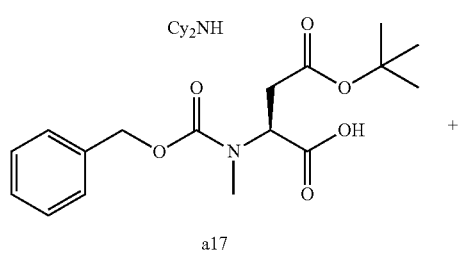

a17

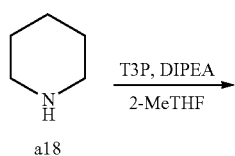

a18

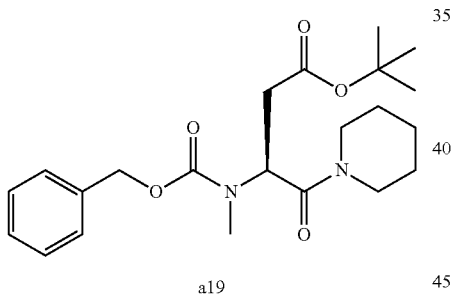

a19

Compound a17 (2.01 g) and 2-MeTHF (11.7 mL) were added to a reaction vessel, and this was stirred. After adding DIPEA (1.8 mL) and Compound a18 (0.53 mL), T3P (50 w/w % 2-MeTHF solution, 3.61 mL) was added at room temperature, and then this was stirred for 1 hour. After adding 10% aqueous citric acid solution (12 mL) while stirring, the aqueous layer was removed. The resulting organic layer was washed with 10% aqueous citric acid solution (12 mL×1) and 5% aqueous sodium carbonate solution (12 mL×2). Concentrating the obtained organic layer under reduced pressure afforded a residue (1.56 g) containing Compound a19.

Retention time by HPLC analysis: 3.934 minutes (HPLC analysis conditions: method 3)

168
Example 38 Step S'1-1

Compound a20: Synthesis of tert-butyl (3S)-3-(methylamino)-4-oxo-4-(1-piperidyl)butanoate

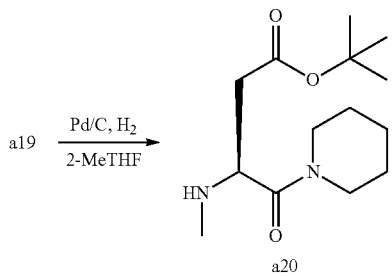 [SMILES: CN[C@@H](CC(=O)OC(C)(C)C)C(=O)N1CCCCC1]

a20

2-MeTHF (21.3 mL) was added to the residue (3.08 g) containing Compound a19 obtained in Step S'0, and then 5% Pd/C (4.09 g, 50% wetted with water) was added. Degassing and purging with hydrogen gas was performed 3 times, and then this was stirred for 2 hours. The reaction mixture was vacuum filtered through a filter paper, and the residue was washed with a 2-MeTHF solution (21.3 mL×3). The obtained filtrate and wash solution were combined and concentrated under reduced pressure to afford a residue (2.09 g) containing Compound a20.

Retention time by HPLC analysis: 2.058 minutes (HPLC analysis conditions: method 3)

Example 39 Step S'1-2

Compound a22: Synthesis of tert-butyl (3S)-3-[[(2S)-2-[benzyloxycarbonyl(methyl)amino]-3-methyl-butanoyl]-methyl-amino]-4-oxo-4-(1-piperidyl)butanoate

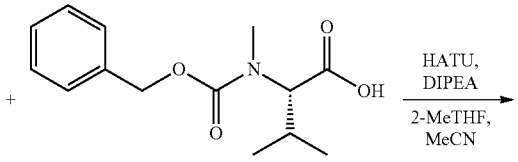

a21

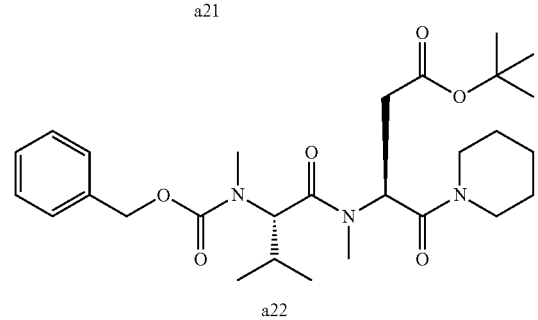

a22

The residue (2.04 g) containing Compound a20 obtained in Step S' 1-1 and Compound a21 (2.14 g) were dissolved in 2-MeTHF (6.3 mL) and then this was stirred. After further adding DIPEA (5.3 mL), HATU (3.95 g) dissolved in MeCN (4.1 mL) and 2-MeTHF (5.9 mL) was added at room temperature, and then this was stirred at 50° C. for 5 hours.

After adding CPME (5.3 mL) at room temperature, 5% aqueous potassium carbonate solution (4.1 mL) and NMI (0.55 mL) were added, and this was stirred for 1 hour 30 minutes. 2.5% aqueous ammonium solution (16.3 mL) was added while stirring, and then the aqueous layer was removed. The obtained organic layer was washed with 2.5% aqueous ammonium solution (16.3 mL×1), 10% aqueous sodium hydrogen sulfate monohydrate solution (20.4 mL×4), 5% aqueous potassium carbonate solution (20.4 mL×1), 10% aqueous sodium hydrogen sulfate monohydrate solution (20.4 mL×3), and 5% aqueous potassium carbonate solution (20.4 mL×1). Concentrating the resulting organic layer under reduced pressure afforded a residue (3.66 g) containing Compound a22.

Retention time by HPLC analysis: 4.428 minutes (HPLC analysis conditions: method 3)

Example 40 Step S'2-1

Compound a23: Synthesis of tert-butyl (3S)-3-[methyl-[(2S)-3-methyl-2-(methylamino)butanoyl]amino]-4-oxo-4-(1-piperidyl)butanoate

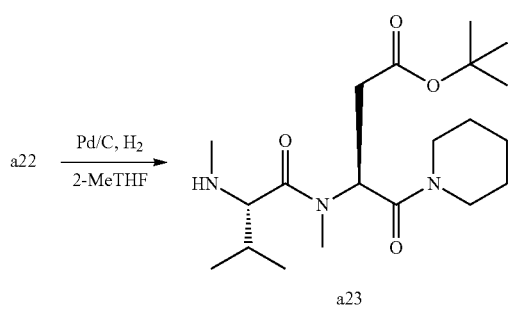 [SMILES: CN[C@H](C(=O)N(C)[C@@H](CC(=O)OC(C)(C)C)C(=O)N1CCCCC1)C(C)C]

2-MeTHF (18.3 mL) was added to the residue (3.56 g) containing Compound a22 obtained in Step S'1-2, and then 5% Pd/C (2.10 g, 50% wetted with water) was added. Degassing and purging with hydrogen gas was performed 3 times, and then this was stirred for 2 hours 30 minutes. The reaction mixture was vacuum filtered through a filter paper, and the residue was washed with 2-MeTHF (18.3 mL×3). The obtained filtrate and wash solution were combined and concentrated under reduced pressure to afford a residue (2.58 g) containing Compound a23.

Retention time by HPLC analysis: 2.393 minutes (HPLC analysis conditions: method 3)

Example 41 Step S'2-2

Compound a25: Synthesis of tert-butyl (3S)-3-[methyl-[(2S)-3-methyl-2-[methyl-[1-[(2,2,2-trifluoroacetyl)amino]cyclopentanecarbonyl]amino]butanoyl]amino]-4-oxo-4-(1-piperidyl)butanoate Compound a24 (2.90 g) was dissolved in 2-MeTHF (18.6 mL) and this was stirred. Further addition of DIPEA (5.4 mL) and the residue (2.50 g) containing Compound a23 obtained in Step S'2-1 was followed by addition of T3P (50 w/w % 2-MeTHF solution, 10.4 mL) and DMAP (1.59 g) at room temperature, and then this was stirred for 8 hours. Each of Compound a24 (1.47 g), DMAP (0.80 g), T3P (50 w/w % 2-MeTHF solution, 5.5 mL), and DIPEA (2.8 mL) were further added, and then this was stirred for 2 hours. 5% aqueous sodium carbonate solution (20.5 mL) was added while stirring, and then the aqueous layer was removed. The obtained organic layer was washed with 5% aqueous sodium hydrogen sulfate monohydrate solution (20.5 mL×4), 5% aqueous sodium carbonate solution (20.5 mL×2), 5% aqueous sodium hydrogen sulfate monohydrate solution (20.5 mL×2), and 5% aqueous sodium carbonate solution (20.5 mL×1). Concentrating the obtained organic layer under reduced pressure afforded a residue (3.45 g) containing Compound a25.

Retention time by HPLC analysis: 4.002 minutes (HPLC analysis conditions: method 3)

Example 42 Step S'3-1

Compound a26: Synthesis of tert-butyl (3S)-3-[[(2S)-2-[(1-aminocyclopentanecarbonyl)-methyl-amino]-3-methyl-butanoyl]-methyl-amino]-4-oxo-4-(1-piperidyl) butanoate The residue (3.41 g) containing Compound a25 obtained in Step S'2-2 was dissolved in 2-MeTHF (1362 mL) and MeOH (1.4 mL), and this was stirred. LiBH$_4$ (2 M THF solution, 4.5 mL) was added dropwise at −20° C., and then this was stirred for 2 hours. After dropwise addition of 2,2,2-trifluoroethanol (6.4 mL), the temperature was raised to 0° C., and then this was stirred for 20 minutes. 20% aqueous ammonium chloride solution (10.2 mL) was added dropwise, and then the aqueous layer was removed. Trifluoroacetic acid (0.69 mL) was added at room temperature to the obtained organic layer, and then this was stirred for 10 minutes. To a reaction vessel containing 2 M aqueous sodium hydroxide solution (44.3 mL), the reaction solution containing Compound a25 was added dropwise. After removing the aqueous layer, this was washed with 2 M aqueous sodium hydroxide solution (34.1 mL×2) and 10% aqueous dipotassium hydrogen phosphate solution (17.0 mL×1). Concentrating the resulting organic layer under reduced pressure afforded a residue (2.90 g) containing Compound a26.

Retention time by HPLC analysis: 2.868 minutes (HPLC analysis conditions: method 3)

Example 43 Step S'3-2

Compound a28: Synthesis of benzyl (2S)-2-[[1-[[(1S)-1-[[(1S)-3-tert-butoxy-3-oxo-1-(piperidine-1-carbonyl)propyl]-methyl-carbamoyl]-2-methyl-propyl]-methyl-carbamoyl]cyclopentyl]carbamoyl] pyrrolidine-1-carboxylate

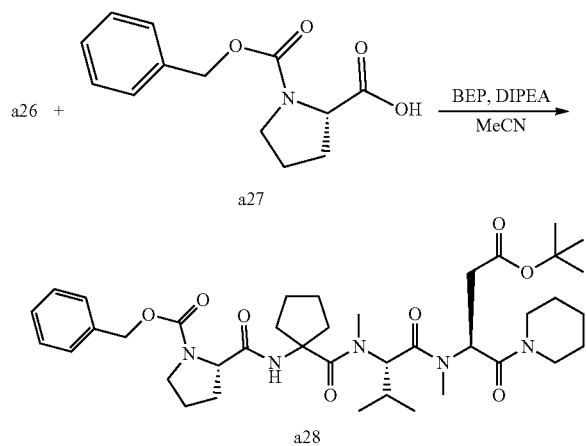

The residue (2.90 g) containing Compound a26 obtained in Step S'3-1 and Compound a27 (1.66 g) were dissolved in MeCN (14.5 mL) and then this was stirred. After further adding DIPEA (2.67 mL), BEP (2.11 g) was added at room temperature, and then this was stirred for 3 hours. After addition of CPME (29.3 mL), 5% aqueous potassium carbonate solution (17.4 mL) and N-methylimidazole (0.41 mL) were added, and this was stirred at room temperature for 30 minutes. After removing the aqueous layer, the obtained organic layer was washed with 5% aqueous sodium hydrogen sulfate monohydrate solution (17.4 mL×5), 5% aqueous sodium carbonate solution (17.4 mL×2), 5% aqueous sodium hydrogen sulfate monohydrate solution (17.4 mL×3), and 5% aqueous sodium carbonate solution (17.4 mL×2). Concentrating the resulting organic layer under reduced pressure afforded a residue (3.86 g) containing Compound a28.

Retention time by HPLC analysis: 4.323 minutes (HPLC analysis conditions: method 3)

Example 44 Step S'4-1

Compound a29: Synthesis of tert-butyl (3S)-3-[methyl-[(2S)-3-methyl-2-[methyl-[1-[[(2S)-pyrrolidine-2-carbonyl]amino]cyclopentanecarbonyl]amino]butanoyl]amino]-4-oxo-4-(1-piperidyl) butanoate

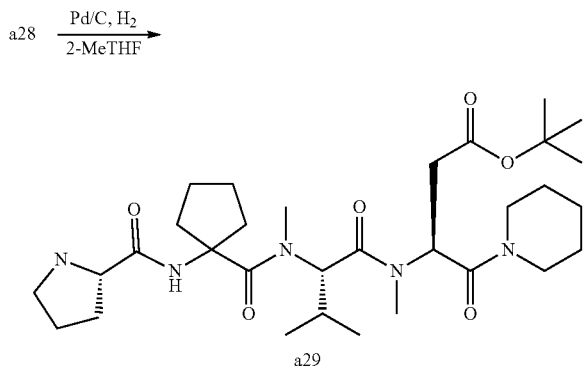

THF (16.8 mL) was added to the residue (3.81 g) containing Compound a28 obtained in Step S'3-2, and then 5% Pd/C (0.40 g, 50% wetted with water) was added. Degassing and purging with hydrogen gas was performed 3 times, and then this was stirred for 4 hours 30 minutes. Further addition of 5% Pd/C (0.20 g, 50% wetted with water) was then followed by stirring for 1 hour 30 minutes. The reaction mixture was vacuum filtered through a filter paper, and the residue was washed with a 2-MeTHF solution (6.6 mL×3). The obtained filtrate and wash solution were combined and concentrated under reduced pressure to afford a residue (3.12 g) containing Compound a29.

Retention time by HPLC analysis: 2.970 minutes (HPLC analysis conditions: method 3)

Example 45 Step S'4-2

Compound a31: Synthesis of tert-butyl (3S)-3-[[(2S)-2-[[1-[[(2S)-1-[(2S)-2-(benzyloxycarbonylamino)-4-phenyl-butanoyl]pyrrolidine-2-carbonyl]amino]cyclopentanecarbonyl]-methyl-amino]-3-methyl-butanoyl]-methyl-amino]-4-oxo-4-(1-piperidyl)butanoate

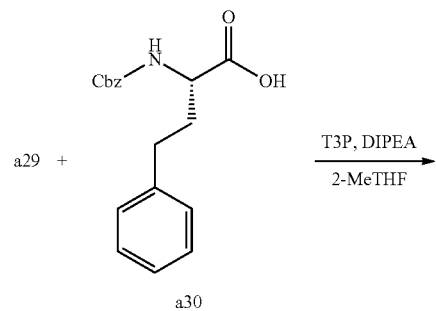

-continued

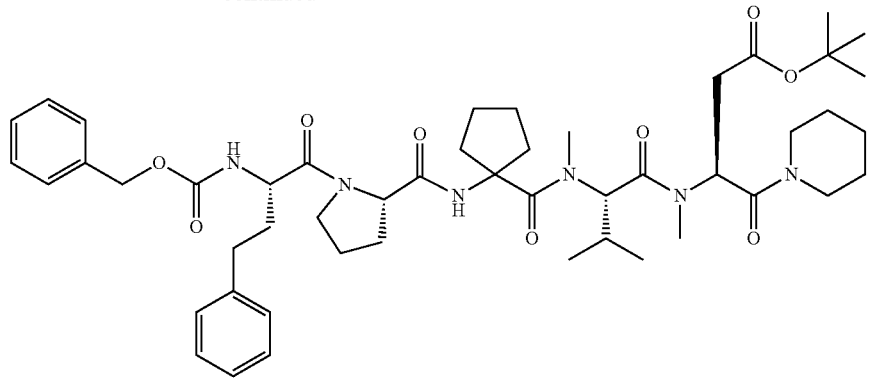

a31

The residue (2.06 g) containing Compound a29 obtained in Step S'4-1 and Compound a30 (1.10 g) were dissolved in 2-MeTHF (10.3 mL) and then this was stirred. After further adding DIPEA (2.8 mL), T3P (50 w/w % 2-MeTHF solution, 5.4 mL) was added at room temperature, and then this was stirred for 2 hours. Each of Compound a30 (0.55 g), DIPEA (1.1 mL), and T3P (50 w/w % 2-MeTHF solution, 2.2 mL) were additionally added, and then this was stirred for 5 hours. Furthermore, Compound a30 (0.57 g), DIPEA (1.1 mL), and T3P (50 w/w % 2-MeTHF solution, 2.2 mL) were additionally added, and this was left to stand overnight and then on the following day, stirred for 2 hours. 5% aqueous potassium carbonate solution (12.4 mL) and N-methylimidazole (0.29 mL) were added, and this was stirred at room temperature for 3 hours. N-methylimidazole (0.23 mL) was added, and after stirring this for 1 hour, the aqueous layer was removed. 2-MeTHF (12.4 mL), N-methylimidazole (0.23 mL), and 5% aqueous potassium carbonate solution (12.4 mL) were added, and after stirring this for 1 hour, the aqueous layer was removed. The obtained organic layer was washed with 10% aqueous sodium hydrogen sulfate monohydrate solution (12.4 mL×2) and 5% aqueous potassium carbonate solution (12.4 mL×1). To the organic layer, a mixed solution of heptane and MTBE (heptane/MTBE=1.5:1, 12.4 mL) and MeCN (4.7 mL) were added, and then the aqueous layer was removed. Addition of 2-MeTHF (2.1 mL) to the organic layer was followed by washing 7 times with MeCN (7.0 mL) and 5% aqueous potassium carbonate solution (17.7 mL). Isopropyl acetate (7.6 mL) was added to the organic layer, then this was concentrated under reduced pressure, and isopropyl acetate (7.6 mL) was added to the resulting residue to afford a solution (10.31 g) containing Compound a31.

Retention time by HPLC analysis: 4.794 minutes (HPLC analysis conditions: method 3)

Example 46 Step 1'

Compound a32: Synthesis of (3S)-3-[[(2S)-2-[[1-[[(2S)-1-[(2S)-2-(benzyloxycarbonyl-amino)-4-phenyl-butanoyl]pyrrolidine-2-carbonyl]amino]cyclopentanecarbonyl]-methyl-amino]-3-methyl-butanoyl]-methyl-amino]-4-oxo-4-(1-piperidyl)butanoic acid

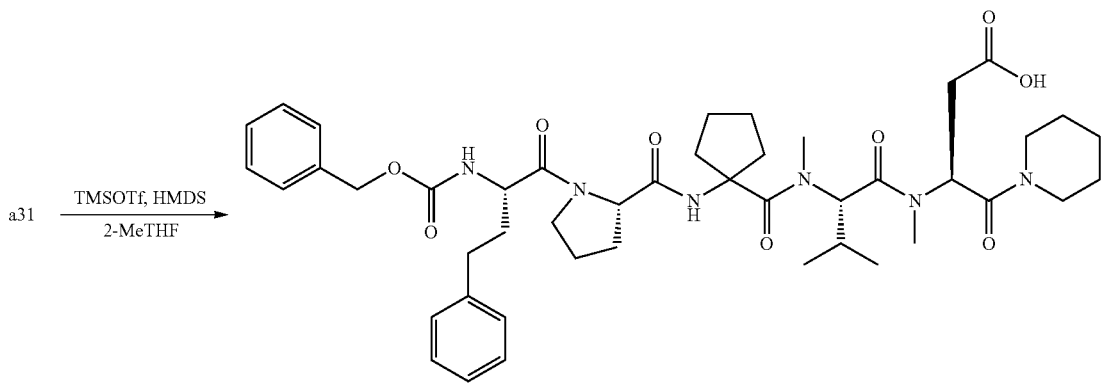

a32

The residue (10.27 g) containing Compound a31 obtained in Step S'4-2 was dissolved in isopropyl acetate (51.4 mL) and then stirred. After adding HMDS (2.1 mL), TMSOTf (1.4 mL) was added dropwise at 0° C., and then this was stirred at room temperature for 2 hours 30 minutes. 2-MeTHF (51.4 mL) and 5% aqueous dipotassium hydrogen phosphate solution (102.8 mL) were added at room temperature, and then the aqueous layer was removed. The organic layer was washed with 5% aqueous sodium dihydrogen phosphate solution (102.8 mL), then DIPEA (3.0 mL) was added to the resulting organic layer, this was concentrated under reduced pressure, and addition of isopropyl acetate (7.6 mL) to this afforded a solution (7.92 g) containing Compound a32.

Retention time by HPLC analysis: 4.001 minutes (HPLC analysis conditions: method 3)

Example 47 Step 2'

Compound a33: Synthesis of tert-butyl 2-[[(2S)-2-[[2-[[2-[[(2S,3S)-2-[[(2S)-2-[[(3S)-3-[[(2S)-2-[[1-[[(2S)-1-[(2S)-2-(benzyloxycarbonylamino)-4-phenyl-butanoyl]pyrrolidine-2-carbonyl]amino] cyclopentanecarbonyl]-methyl-amino]-3-methyl-butanoyl]-methyl-amino]-4-oxo-4-(1-piperidyl) butanoyl]-methyl-amino]-4-methyl-pentanoyl] amino]-3-methyl-pentanoyl]-methyl-amino]acetyl]-methyl-amino]acetyl]-methyl-amino]-3-cyclohexyl-propanoyl]-methyl-amino]acetate

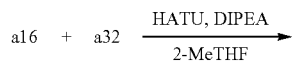

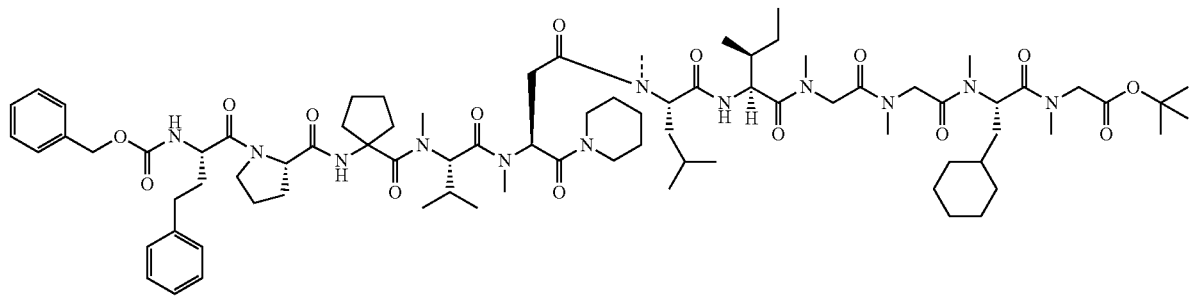

a33

The residue (7.92 g) containing Compound a32 obtained in Step 2' and the residue (1.33 g) containing Compound a16 obtained in Step H'6 were dissolved in 2-MeTHF (4.6 mL) and stirred. DIPEA (1.6 mL) and HATU (1.43 g) were added at room temperature, and then stirred for 2 hours. The residue (approximately 300 mg) containing Compound a16 was added, and this was further stirred for 2 hours. Subsequently, the residue (approximately 300 mg) containing Compound a16 was additionally added and this was stirred for 1 hour 30 minutes. HATU (0.79 g) was added and then stirred for 1 hour. CPME (3.5 mL), N-methylimidazole (0.13 mL), and 5% aqueous potassium carbonate solution (2.7 mL) were added, and this was stirred at room temperature for 3 hours. After removing the aqueous layer, this was washed with 2.5% aqueous ammonia solution (9.2 mL×1), 10% aqueous sodium hydrogen sulfate monohydrate solution (9.2 mL×1), 5% aqueous sodium carbonate solution (9.2 mL×1), 10% aqueous sodium hydrogen sulfate monohydrate solution (9.2 mL×3), and 5% aqueous sodium hydrogen carbonate solution (9.2 mL×2). Heptane/MTBE (1.5:1, 9.2 mL) was added to the organic layer, and then this was washed with 5% aqueous sodium carbonate solution. 2-MeTHF (9.2 mL) was added to the resulting organic layer, and concentrating this under reduced pressure afforded a residue (4.49 g) containing Compound a33.

Retention time by HPLC analysis: 10.65 minutes (HPLC analysis conditions: method 4)

Example 48 Step 3'

Compound a34: Synthesis of 2-[[(2S)-2-[[2-[[2-[[(2S,3S)-2-[[(2S)-2-[[(3S)-3-[[(2S)-2-[[1-[[(2S)-1-[(2S)-2-(benzyloxycarbonylamino)-4-phenyl-butanoyl]pyrrolidine-2-carbonyl]amino]cyclopentanecarbonyl]-methyl-amino]-3-methyl-butanoyl]-methyl-amino]-4-oxo-4-(1-piperidyl)butanoyl]-methyl-amino]-4-methyl-pentanoyl]amino]-3-methyl-pentanoyl]-methyl-amino]acetyl]-methyl-amino]acetyl]-methyl-amino]-3-cyclohexyl-propanoyl]-methyl-amino]acetic acid

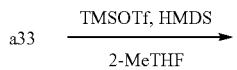

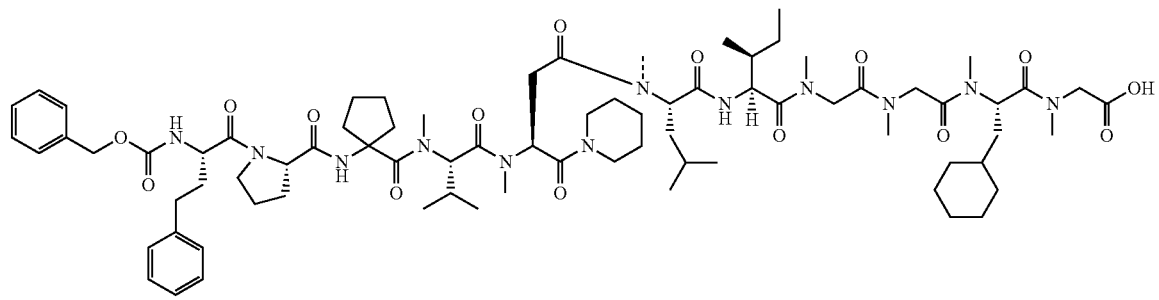

a34

The residue (4.49 g) containing Compound a33 obtained in Step 2' was dissolved in 2-MeTHF (49.5 mL) and stirred. HMDS (2.9 mL) and TMSOTf (2.1 mL) were added at room temperature, and then this was stirred for 2 hours. After adding 5% aqueous dipotassium hydrogen phosphate solution (14.2 mL), the aqueous layer was removed. The resulting organic layer was washed 3 times with a mixed solution of 10% aqueous citric acid solution (3.4 mL) and 5% aqueous dipotassium hydrogen phosphate solution (10.5 mL), and once with a 5% aqueous sodium carbonate solution. To the organic layer, THF (20.9 mL) was added and azeotropic dehydration was performed 3 times, and then addition of THF (5.9 mL) to the resulting residue afforded a solution (9.59 g) containing Compound a34.

Retention time by HPLC analysis: 9.26 minutes (Analysis conditions: method 4)

Example 49 Step 4'

Compound a35: Synthesis of 2-[[(2S)-2-[[2-[[2-[[(2S,3S)-2-[[(2S)-2-[[(3S)-3-[[(2S)-2-[[1-[[(2S)-1-[2S)-2-amino-4-phenyl-butanoyl]pyrrolidine-2-carbonyl]amino]cyclopentanecarbonyl]-methyl-amino]-3-methyl-butanoyl]-methyl-amino]-4-oxo-4-(1-piperidyl)butanoyl]-methyl-amino]-4-methyl-pentanoyl]amino]-3-methyl-pentanoyl]-methyl-amino]acetyl]-methyl-amino]acetyl]-methyl-amino]-3-cyclohexyl-propanoyl]-methyl-amino]acetic acid

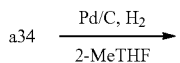

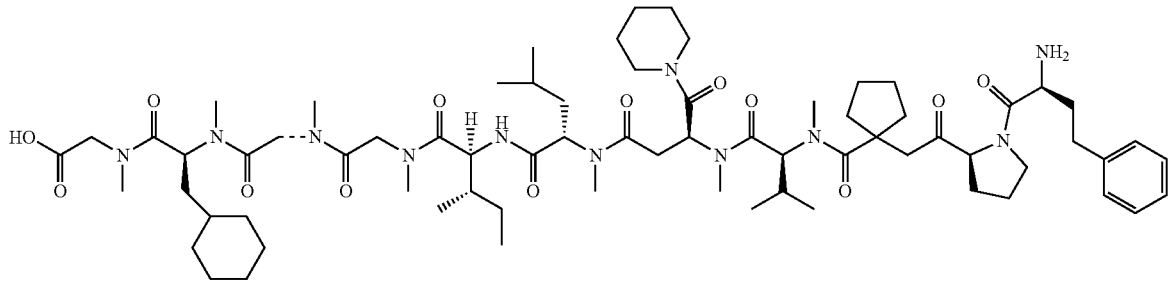

a35

5% Pd/C (0.49 g, 50% wetted with water) was added to a reaction vessel, and suspended in THF (8 mL), and this was stirred for 30 minutes under hydrogen atmosphere. Then, the vessel was purged with nitrogen, a solution of the residue (9.3 g) containing Compound a34 obtained in Step 3' dissolved in THF (8 mL) was added, and when this was stirred under hydrogen atmosphere for 6 hours, the reaction conversion rate was 76%. After purging with nitrogen, this was stored in a refrigerator overnight, and on the following day, when this was warmed to room temperature and stirred for 2 hours, the reaction conversion rate was 87%. After purging with nitrogen, a suspension of 5% Pd/C (0.24 g, 50% wetted with water) in THF (4 mL) was added to the reaction solution, and after purging with hydrogen, this was stirred for 4 hours (reaction conversion rate 99.0%). After purging with nitrogen, this was stored in a refrigerator overnight, and on the following day, when measured after warming this to room temperature, the reaction conversion rate was 99.4%. The reaction mixture was vacuum filtered through a filter paper, and the residue was washed with a 2-MeTHF solution (6.5 mL×10). The obtained filtrate and wash solution were combined and concentrated under reduced pressure. The resulting residue was dissolved in acetonitrile (16.3 mL) and 2-MeTHF (6.5 mL), and after washing this with heptane (37.1 mL), it was concentrated. The obtained residue was dissolved again in acetonitrile (16.3 mL) and 2-MeTHF (6.5 mL), and this was washed with heptane (37.1 mL) and then concentrated to afford a residue (2.96 g) containing Compound a35.

Retention time by HPLC analysis: 12.39 minutes (HPLC analysis conditions: method 4)

Example 50 Step 5'

Compound a36: Synthesis of (3S,9S,18S,21S,25S,28S,34S)-9-(cyclohexylmethyl)-21-isobutyl-28-isopropyl-7,10,13,16,22,26,29-heptamethyl-18-[(1S)-1-methylpropyl]-3-(2-phenylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecaone

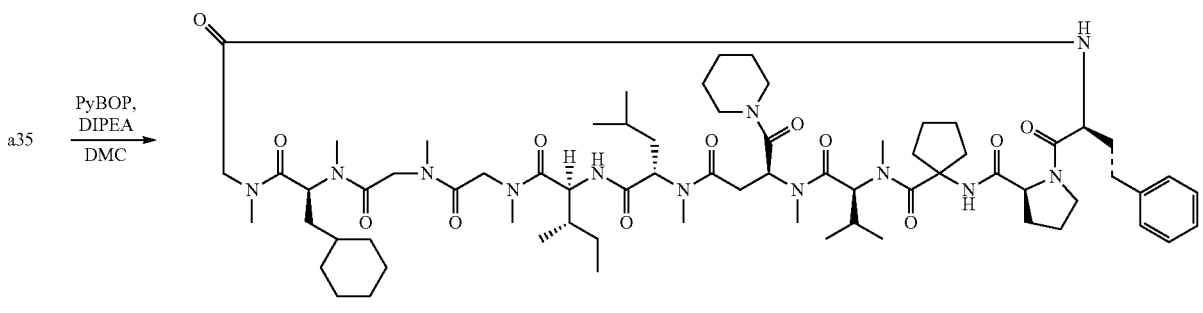

a36

A solution of the residue (2.90 g) containing Compound a35 obtained in the previous step and DIPEA (1.44 mL) in dimethyl carbonate (72.5 mL) was prepared, and this was added dropwise over 3 hours to a solution of PyBOP (4.34 g) in dimethylcarbonate (72.5 mL). The reaction was checked by sampling the mixture at 30 minutes after completion of the dropwise addition, insolubles were removed by vacuum filtration using a paper filter, and the residue was washed with dimethyl carbonate (15 mL). A solution obtained by combining the filtrate and the wash solution was washed with 2.5% aqueous ammonia solution (58 mL), 5% aqueous potassium hydrogen sulfate solution (58 mL), 5% aqueous disodium hydrogen phosphate solution (58 mL), 5% aqueous sodium chloride solution (58 mL), and 0.5% aqueous sodium chloride solution (58 mL). Concentration of the obtained organic layer under reduced pressure afforded a residue (2.72 g) containing Compound a36.

Retention time by HPLC analysis: 18.69 minutes (HPLC analysis conditions: method 5)

Example 50-1

Compound a36: Synthesis of (3S,9S,18S,21S,25S, 28S,34S)-9-(cyclohexylmethyl)-21-isobutyl-28-isopropyl-7,10,13,16,22,26,29-heptamethyl-18-[(1S)-1-methylpropyl]-3-(2-phenylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecaone (PyBOP was used as the condensing agent, and dimethyl carbonate was used as the solvent)

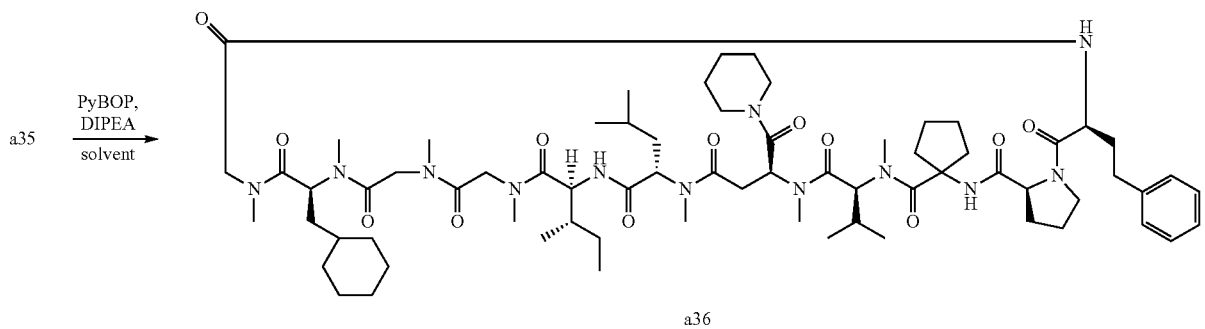 [SMILES: CC[C@H](C)[C@@H]1NC(=O)[C@H](CC(C)C)N(C)C(=O)C[C@@H](C(=O)N2CCCCC2)N(C)C(=O)[C@H](C(C)C)N(C)C(=O)C2(CCCC2)NC(=O)[C@@H]2CCCN2C(=O)[C@H](CCc2ccccc2)NC(=O)CN(C)C(=O)[C@H](CC2CCCCC2)N(C)C(=O)CN(C)C(=O)CN(C)C1=O]

a36

Compound a35 (9.7 mg was weighed into a reaction vessel an dissolved in dimethyl carbonate (2 mL). DIPEA (6.1 μL) was added while stirring at room temperature. PyBOP (14.9 mg) was added to this, and this mixture was stirred for 30 minutes. The reaction solution (50 μL) was diluted with a MeCN/propylamine (9:1) mixture (100 μL), and HPLC analysis was performed using this solution. The product of interest:cyclic dimer Area % ratio and the LC purity (%) of the product of interest are shown in Table 13.

Example 50-2

The results obtained when using anisole and 2-methyltetrahydrofuran as solvents are also shown in Table 13 (the experimental procedure was performed in a similar manner to Example 50-1). In either cases, the cyclic trimer was not observed.

Example 50-3

Compound a36: Synthesis of (3S,9S,18S,21S,25S, 28S,34S)-9-(cyclohexylmethyl)-21-isobutyl-28-isopropyl-7,10,13,16,22,26,29-heptamethyl-18-[(1S)-1-methylpropyl]-3-(2-phenylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecaone (PyBOP was used as the condensing agent, and dimethyl carbonate was used as the solvent; reverse dropwise addition)

PyBOP (59.9 mg) was weighed into a reaction vessel and suspended in dimethyl carbonate (1 mL). In another container, Compound a35 (39.9 mg) was dissolved in dimethyl carbonate (1 mL), and DIPEA (24.3 μL) was added thereto. The solution of this starting material was added to the PyBOP suspension using a syringe pump at room temperature over 3 hours. After completion of the addition, the starting material solution remaining in the container was washed in using dimethyl carbonate (0.2 mL), and then this was stirred for 30 minutes. The reaction solution (50 μL) was diluted with a MeCN/propylamine (9:1) mixture (100 μL), and HPLC analysis was performed using this solution. The results are shown in Table 13.

TABLE 13

| Condensing agent | Example No. | Solvent | Dropwise addition | Ratio of SM, TM, c-Dimer (%) | | | LC purity (%) |
|---|---|---|---|---|---|---|---|
| | | | | SM (a35) | TM (a36) | c-Dimer (a37) | |
| PyBOP | Example 50 | Dimethyl carbonate | Normal | 0.0 | 92.7 | 7.3 | 77.4 |
| | Example 50-1 | Anisole | Normal | 0.0 | 92.3 | 7.7 | 76.7 |
| | Example 50-2 | 2-methyl-tetrahydrofuran | Normal | 0.0 | 90.1 | 9.9 | 63.0 |
| | Example 50-3 | Dimethyl carbonate | Reverse | 0.0 | 95.4 | 4.6 | 78.7 |

TABLE 13-continued

| Condensing agent | Example No. | Solvent | Dropwise addition | Ratio of SM, TM, c-Dimer (%) | | | LC purity (%) |
|---|---|---|---|---|---|---|---|
| | | | | SM (a35) | TM (a36) | c-Dimer (a37) | |

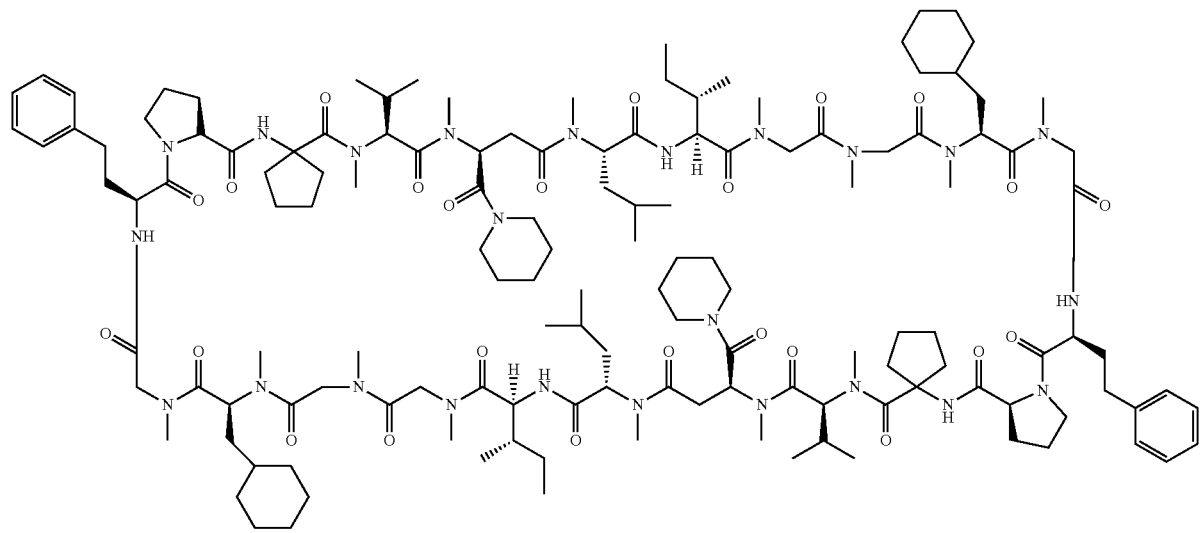

a37 a37: c-dimer in this derivative

Example 51

Synthesis of Compound b1: (3S)-3-[[(2S)-2-[[1-[[(2S)-1-benzyloxycarbonylpyrrolidine-2-carbonyl]amino]cyclopentanecarbonyl]-methyl-amino]-2-cyclopentyl-acetyl]-methyl-amino]-4-(dimethylamino)-4-oxo-butanoic acid

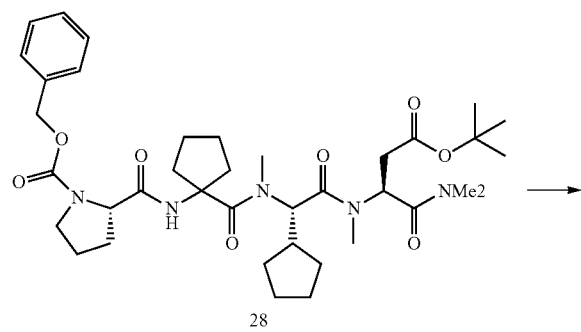

28

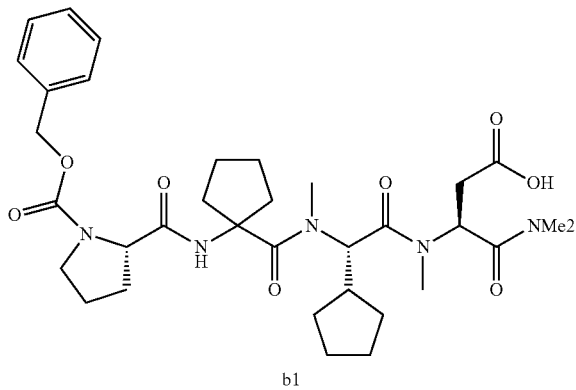

b1

A 2-MeTHF solution (17.45 g, 11.7 wt. %) containing Compound 28 was added to a reaction vessel and concentrated under reduced pressure, and to the resulting residue was added IPAc (10.2 mL). After adding HMDS (1.52 mL) with stirring at room temperature, the outside temperature was lowered to 0° C. and TMSOTf (1.04 mL) was slowly added dropwise. The temperature was raised to room temperature and the mixture was stirred for 30 minutes. The reaction mixture was sampled for sample preparation (Sample Preparation Method 1) and subjected to HPLC analysis to confirm that the reaction conversion rate was 99.9% or more (Calculation Formula 1 of the reaction conversion rate). The outside temperature was lowered to 0° C., and a 5% aqueous dipotassium hydrogenphosphate solution (14.3 mL) was added dropwise to the reaction mixture, and the mixture was stirred at room temperature for 10 minutes. The organic layer was removed, and a 0.5 M aqueous hydrochloric acid solution (11.2 mL) and IPAc (10.2 mL) were added to the aqueous layer, followed by stirring for 10 minutes. The aqueous layer was discharged, and after washing the organic layer with a 5% aqueous sodium chloride solution (14.3 mL), the aqueous layer was discharged. The resulting organic layer was concentrated under reduced pressure to dryness at an outside temperature of 30° C. to afford a residue (1.88 g, 94.1% yield) containing Compound b1.

LCMS (ESI): Retention time: 2.929 minutes, m/z=678.61 [M+Na]$^+$ (LCMS Analysis Condition: method 1).

Yield: 94.1% (the obtained residue and 3,5-bis(trifluoromethyl)benzoic acid were dissolved in DMSO-$d_6$ and subjected to qNMR analysis.).

Example 52

Synthesis of Compound b2: Benzyl (2S)-2-[[1-
[[(1S)-2-[[(1S)-3-[[(1S)-1-[[(1S,2S)-1-[[(1S)-2-
[(2S)-2-[[(1S)-2-[(2-tert-butoxy-2-oxo-ethyl)-
methyl-amino]-2-oxo-1-(p-tolylmethyl)ethyl]-ethyl-
carbamoyl]azetidine-1-yl]-1-methyl-2-oxo-ethyl]-
methyl-carbamoyl]-2-methyl-butyl]carbamoyl]-3-
methyl-butyl]-methyl-amino]-1-
(dimethylcarbamoyl)-3-oxo-propyl]-methyl-amino]-
1-cyclopentyl-2-oxo-ethyl]-methyl-carbamoyl]
cyclopentyl]carbamoyl]pyrrolidine-1-calboxylate

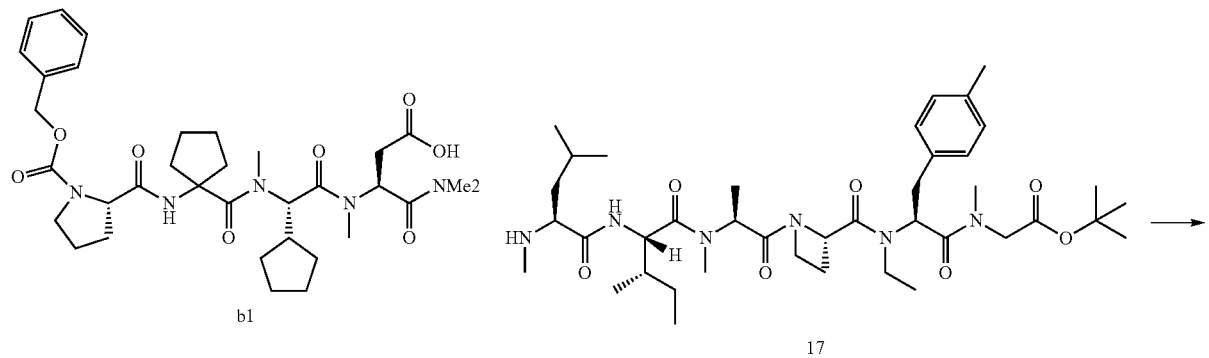

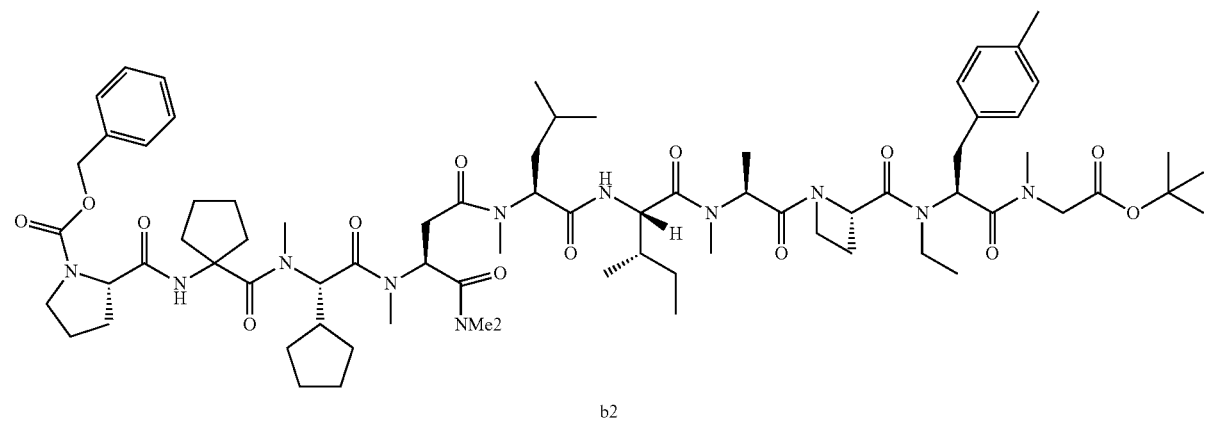

An IPAc solution (1.50 g, 55.0 wt. %) containing Compound 17 and Compound b1 (0.98 g, 78.3 wt. %) were weighed into a reaction vessel, and 2-MeTHF (5.44 mL) and MeCN (0.80 mL) were added. After adding DIPEA (1.05 mL) with stirring at room temperature, HATU (988.4 mg) was added. After stirring at room temperature for 4 hours, the reaction mixture was sampled for sample preparation (Sample Preparation Method 2) and subjected to HPLC analysis to confirm that the reaction conversion rate was 99.9% or more (Calculation Formula 2 of the reaction conversion rate). The outside temperature was lowered to 0° C., and N-methylimidazole (86 μL) and a 5% aqueous sodium carbonate solution (5.6 mL) were added to the reaction mixture, and the mixture was stirred at room temperature for 10 minutes. The aqueous layer was discharged, and the organic layer was washed with a 2.5% aqueous ammonia solution (5.6 mL), a 5% aqueous sodium hydrogensulfate solution (5.6 mL×2), and a 5% aqueous sodium carbonate solution (8.2 mL×3). The resulting organic layer was concentrated under reduced pressure to dryness at an outside temperature of 30° C. to afford a residue (1.88 g, 93.8% yield) containing Compound b2.

LCMS (ES1): Retention time: 21.17 minutes, m/z=1403.06 [M+Na]$^+$ (LCMS Analysis Condition: method 5).

Yield: 93.8% (the resulting residue and 3,5-bis(trifluoromethyl)benzoic acid were dissolved in DMSO-d$_6$, which was subjected to qNMR analysis.).

Example 53

Synthesis of Compound b3: 2-[[(2S)-2-[[(2S)-1-[(2S)-2-[[(2S,3S)-2-[[(2S)-2-[[(3S)-3-[[(2S)-2-[[1-[[(2S)-1-benzyloxycarbonylpyrrolidine-2-carbonyl]amino]cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino] acetic acid

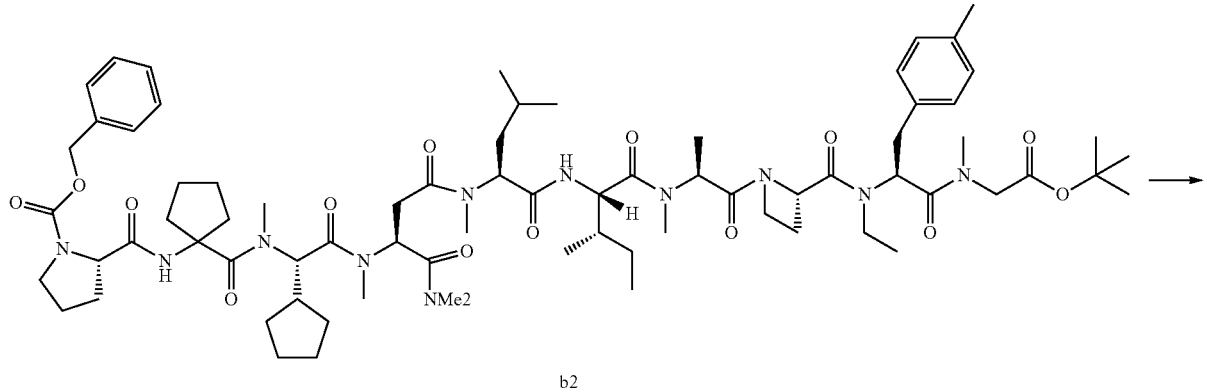

b2

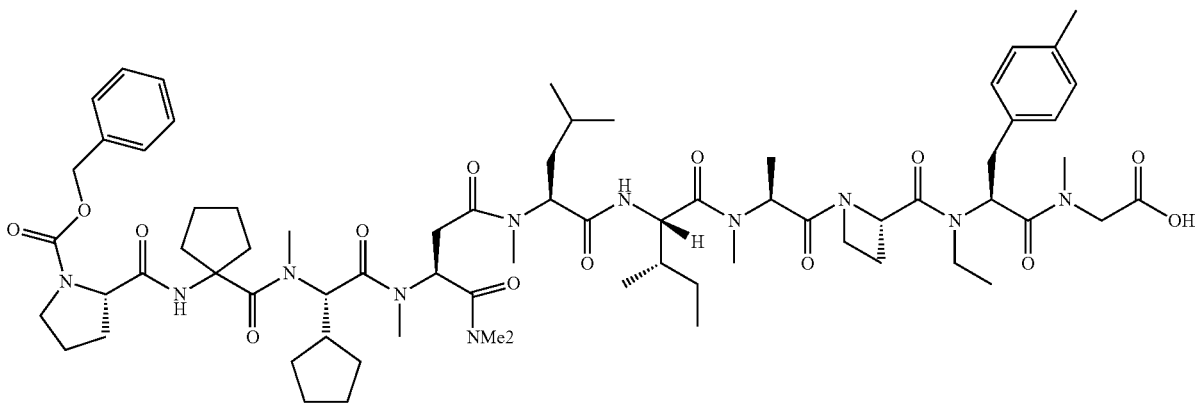

b3

The residue (1.44 g, 90.3 wt. %) containing Compound b2 obtained in Example 52 was added to a reaction vessel, and IPAc (6.50 mL) was added. After adding HMDS (0.50 mL) with stirring at room temperature, the outside temperature was lowered to 0° C. and TMSOTf (0.340 mL) was slowly added dropwise. The temperature was raised to room temperature and the mixture was stirred for 2 hours. The reaction mixture was sampled for sample preparation (Sample Preparation Method 1) and subjected to HPLC analysis to confirm that the reaction conversion rate was 99.9% or more (Calculation Formula 1 of the reaction conversion rate). A 5% aqueous dipotassium hydrogenphosphate solution (9.10 mL) was added dropwise to the reaction mixture, and the mixture was stirred at room temperature for 10 minutes. The organic layer was removed, and a 0.5 M aqueous hydrochloric acid solution (7.41 mL) and 2-MeTHF (9.0 mL) were added to the aqueous layer, followed by stirring for 10 minutes. The aqueous layer was discharged, and after washing the organic layer with a 5% aqueous sodium chloride solution (13.0 mL), the aqueous layer was discharged. The resulting organic layer was concentrated under reduced pressure to dryness at an outside temperature of 35° C. to afford a residue (3.36 g, 92.7% yield) containing Compound b3.

LCMS (ESI): Retention time: 18.19 minutes, m/z=1325.02 [M+H]$^+$ (LCMS Analysis Condition: method 5).

Yield: 92.7% (the resulting residue and 3,5-bis(trifluoromethyl)benzoic acid were dissolved in DMSO-$d_6$, which was subjected to qNMR analysis.).

Example 54

Synthesis of Compound b4: 2-[[(2S)-2-[[(2S)-1-[(2S)-2-[[(2S,3S)-2-[[(2S)-2-[[(3S)-3-[[(2S)-2-cyclopentyl-2-[methyl-[1-[[(2S)-pyrrolidine-2-carbonyl]amino]cyclopentane-carbonyl]amino]acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetic acid was 99.9% or more (Calculation Formula 1 of the reaction conversion rate). The reaction mixture was filtered through filter paper and membrane filters and the residue was washed with 2-MeTHF (5.0 mL×2). The resulting filtrate was concentrated under reduced pressure to afford a residue (1.43 g, 96.7% yield) containing Compound b4.

LCMS (ESI): Retention time: 2.921 minutes, m/z=1191.00 [M+H]$^+$ (LCMS Analysis Condition: method 1).

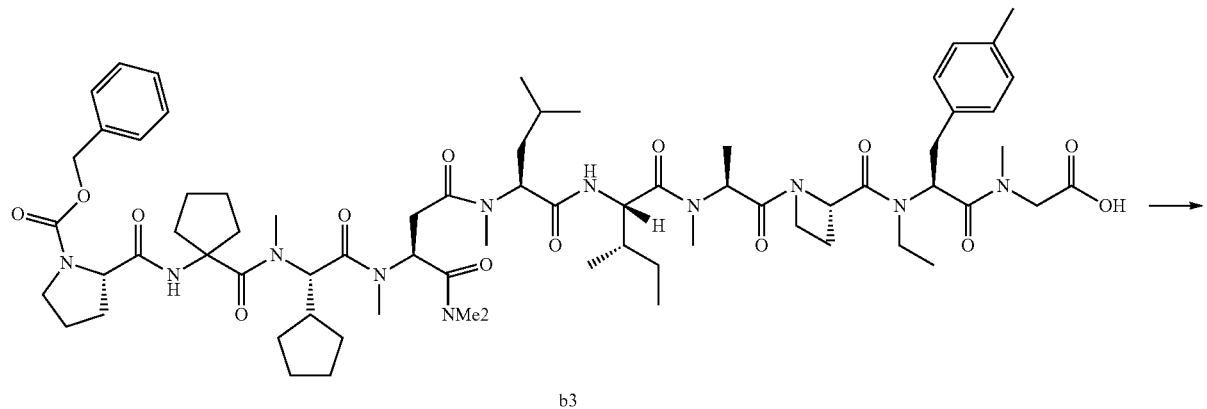

b3

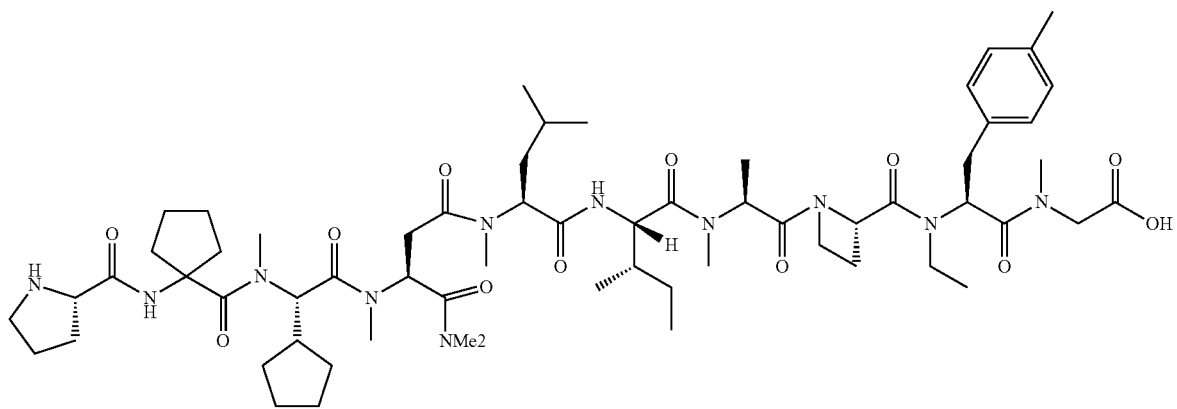

b4

Compound b3 (1.01 g, 0.762 mmol) obtained in Example 53, 2-MeTHF (2.02 mL), and THF (6.87 mL) were added successively to a reaction vessel at room temperature. After adding 5% Pd/C (0.162 g, 50% wet with water) to the reaction vessel, degassing and purging with a hydrogen gas were performed 3 times and the mixture was stirred for 2 hours. The reaction mixture was sampled for sample preparation (Sample Preparation Method 1) and subjected to HPLC analysis to confirm that the reaction conversion rate Yield: 96.7% (the resulting residue and 3,5-bis(trifluoromethyl)benzoic acid were dissolved in DMSO-d$_6$, which was subjected to qNMR analysis.).

Cyclization Reaction of Compound b4 (Study of Reaction Conditions of Example 55)

Using Compound b4 as a starting material, condensing agents and solvents in a cyclization reaction to Compound b5 were studied. The cyclization reaction was observed by HPLC analysis.

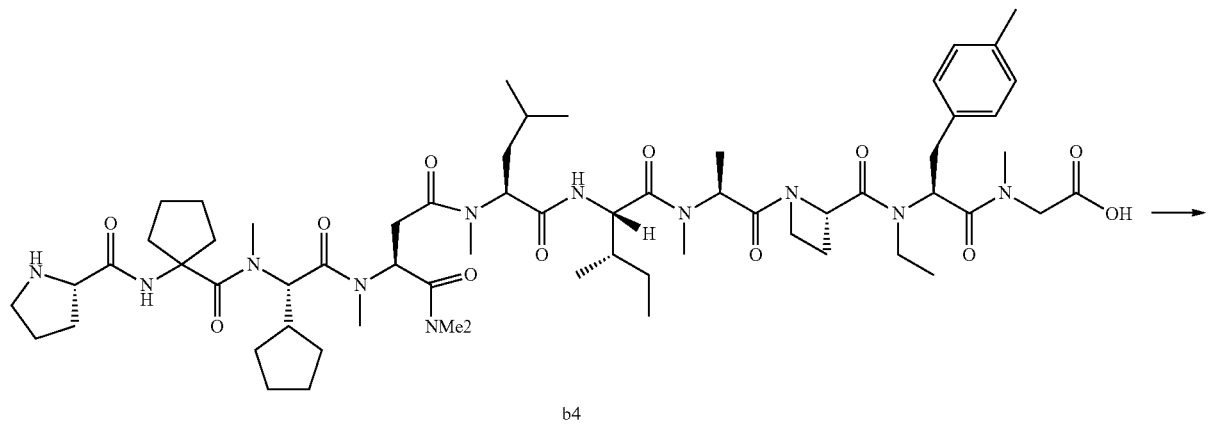

b4

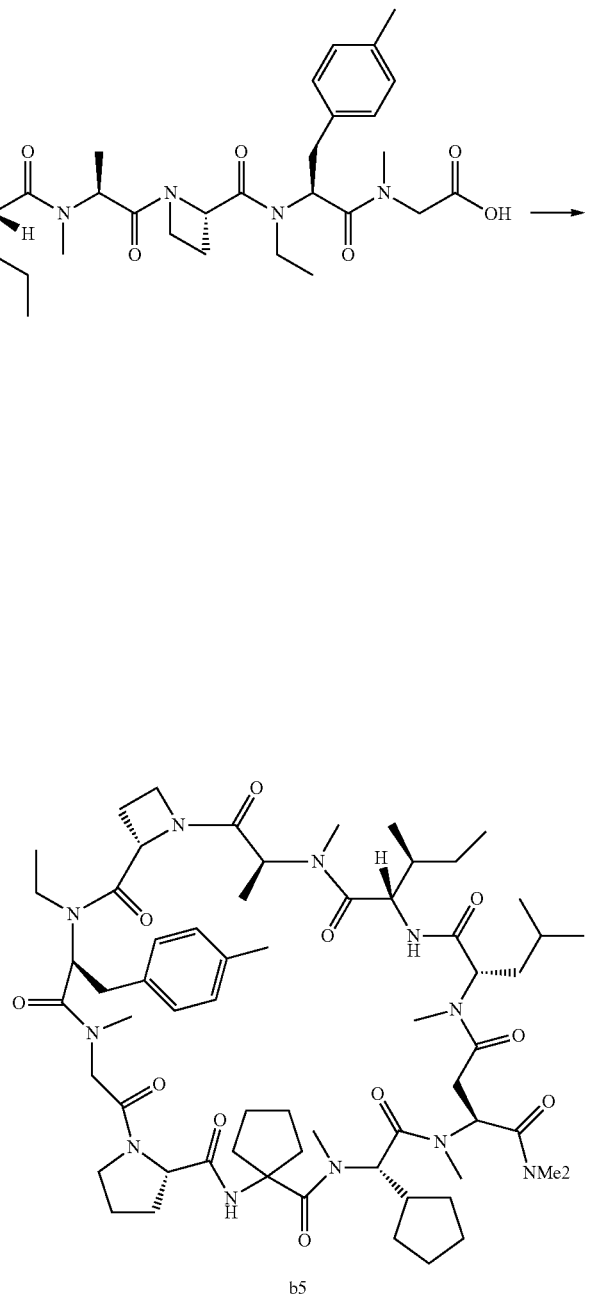

b5

Example 55-6

Synthesis of Compound b5: (6S,9S,14S,17S,20S, 24S,27S,33S)-27-cyclopentyl-7-ethyl-20-isobutyl-N, N,4,14,15,21,25,28-octamethyl-17-[(1S)-1-methylpropyl]-2,5,8,13,16,19,22,26,29,32-decaoxo-6-(p-tolylmethyl)spiro[1,4,7,12,15,18,21,25,28,31-decazatoricyclo[31.3.0.09,12]hexatriacontane-30,1'-cyclopentane]-24-carboxamide Compound b4 (9.99 mg (8.39 μmol)) was weighed into a reaction vessel, and a solvent (2-MeTHF, 2.0 mL (200 v/w)) was added. DIPEA (6.74 L (38.6 μmol)) was added with stirring at room temperature. The outside temperature of the reaction vessel was set to 25° C., to this was added a condensing agent (PyAOP, 17.2 mg (33.0 μmol)), and the resultant was stirred for 30 minutes. The reaction mixture (50 μL) was diluted with a MeCN/propylamine (9:1) mixture (100 μL), to prepare a solution for HPLC analysis.

LCMS (ESI) of Compound b5: Retention time: 16.81 minutes, m/z=1173.51 [M+H]$^+$ (LCMS Analysis Condition: method 5).

LCMS (ESI) of a cyclic dimer b6 (c-Dimer): Retention time: 22.36 minutes, m/z=2367.91 [M+Na]$^+$ (LCMS Analysis Condition: method 5).

LCMS (ESI) of a cyclic trimer b7 (c-Trimer): Retention time: 24.41 minutes, m/z=1759.26 [M+2H]$^{2+}$ (LCMS Analysis Condition: method 5).

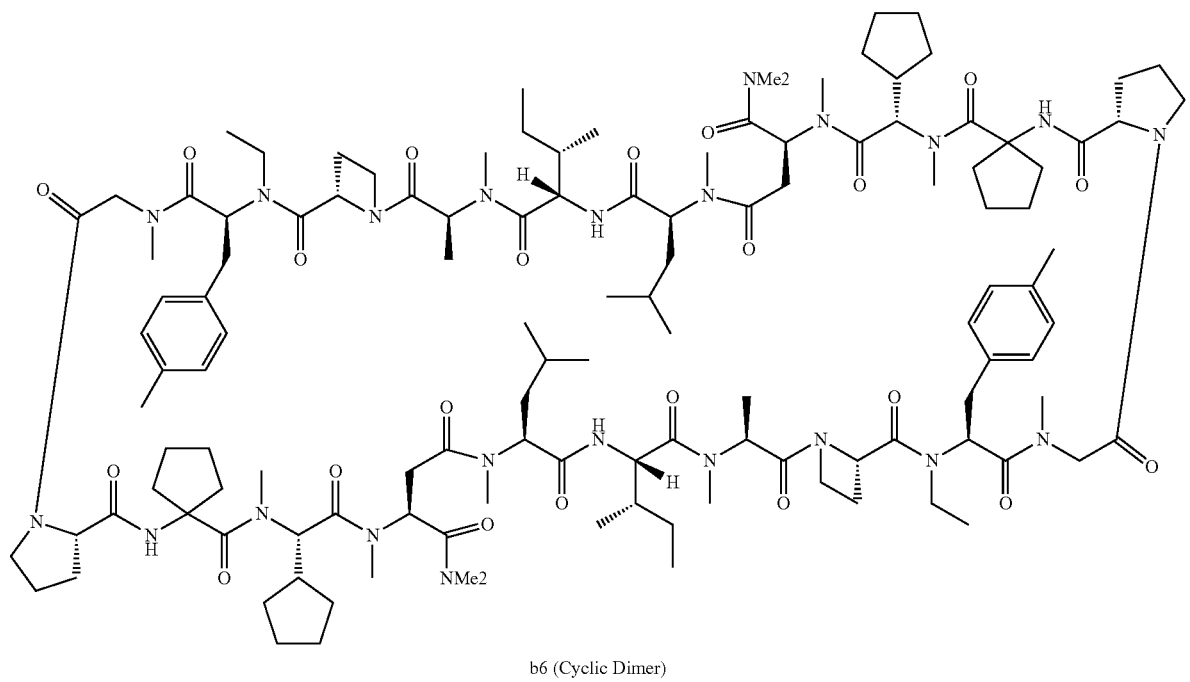
b6 (Cyclic Dimer)
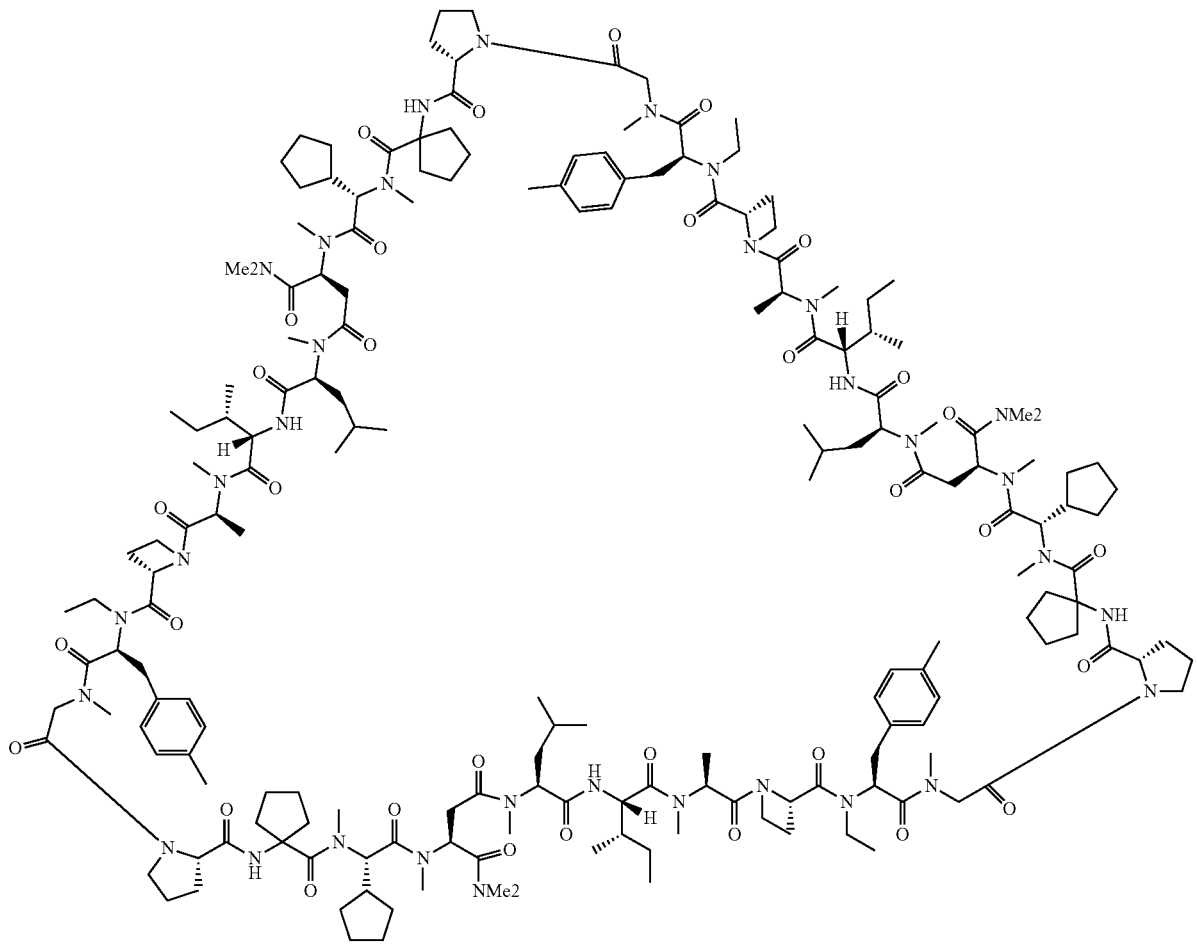
b7 (Cyclic Trimer)

By using the condensing agents and the solvents shown in the following Table, and performing the same operation as an experiment of Example 55-6 (using PyAOP as the condensing agent and 2-MeTHF as the solvent), consumption of the starting material (SM, Compound b5), generation of the target material (TM, Compound b5), and amounts of by-products (the cyclic dimer b6 (c-Dimer) and the cyclic trimer b7 (c-Trimer)) generated were measured to study preferable reaction conditions. Table summarizes area % ratio of the starting material: a propylamide form (Compound b8) in the starting material: the target material: the cyclic Dimer: the cyclic Trimer.

TABLE 14

| Condensing agent | Example No. | Solvent | Ratio of SM, TM, c-Dimer and c-Trimer (%) | | | | |
|---|---|---|---|---|---|---|---|
| | | | SM | SM-nPrNH | TM | c-Dimer | c-Trimer |
| HATU | Example 55-1 | MeCN | 0 | 0 | 46 | 39 | 15 |
| | Example 55-2 | 2-MeTHF | 44 | 26 | 12 | 15 | 3 |
| | Example 55-3 | Dimethyl carbonate | 0 | 0 | 35 | 45 | 20 |
| | Example 55-4 | Anisole | 51 | 5 | 14 | 24 | 6 |
| PyAOP | Example 55-5 | Dimethyl carbonate | 0 | 0 | 37 | 44 | 19 |
| | Example 55-6 | 2-MeTHF | 0 | 0 | 30 | 48 | 23 |
| | Example 55-7 | MeCN | 0 | 0 | 36 | 47 | 17 |
| PyOxim | Example 55-8 | Dimethyl carbonate | 0 | 0 | 34 | 46 | 20 |
| COMU | Example 55-9 | Dimethyl carbonate | 0 | 0 | 37 | 46 | 17 |
| DMT-MM | Example 55-10 | Dimethyl carbonate | 0 | 0 | 32 | 48 | 21 |

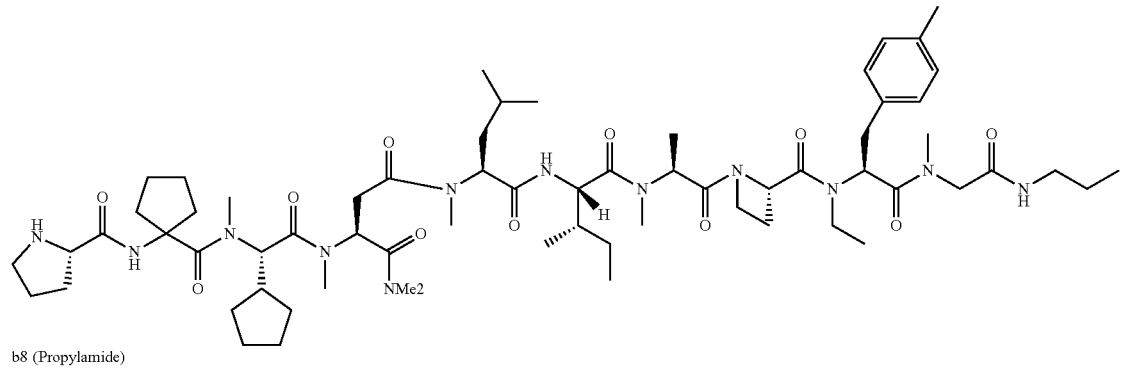

b8 (Propylamide)

Example 55-11 (Reverse Dropwise Addition of Example 55-6)

Compound b4 (9.89 mg (8.31 μmol)) and 2-MeTHF (0.99 mL (100 v/w)) were added to a vial and stirred at 50° C. for 10 minutes. After observation of dissolution of the starting material, DIPEA (6.67 μL (38.2 μmol)) was added and the reaction mixture was sucked up to a syringe. PyAOP (17.1 mg (32.8 μmol)) and 2-MeTHF (0.99 mL (100 v/w)) were added to another reaction vessel, and a solution in the above syringe was added dropwise over 3 hours while stirring at room temperature. After finishing dropwise addition, the reaction mixture (50 μL) was diluted with a MeCN/propylamine (9:1) mixture (100 μL) to prepare a solution for HPLC analysis.

TABLE 15

| Condensing agent | Example No. | Solvent | Ratio of SM, TM, c-Dimer and c-Trimer (%) | | | | |
|---|---|---|---|---|---|---|---|
| | | | SM | SM-nPrNH | TM | c-Dimer | c-Trimer |
| PyAOP | Example 55-11 | 2-MeTHF | 0 | 0 | 95 | 65 | 0 |

Example 56

Synthesis of Compound c1: tert-butyl (3S)-3-[[(2S)-2-[[1-(benzyloxycarbonylamino)-cyclopentanecarbonyl]-methyl-amino]-2-cyclopentyl-acetyl]-methyl-amino]-4-(dimethylamino)-4-oxo-butanoate

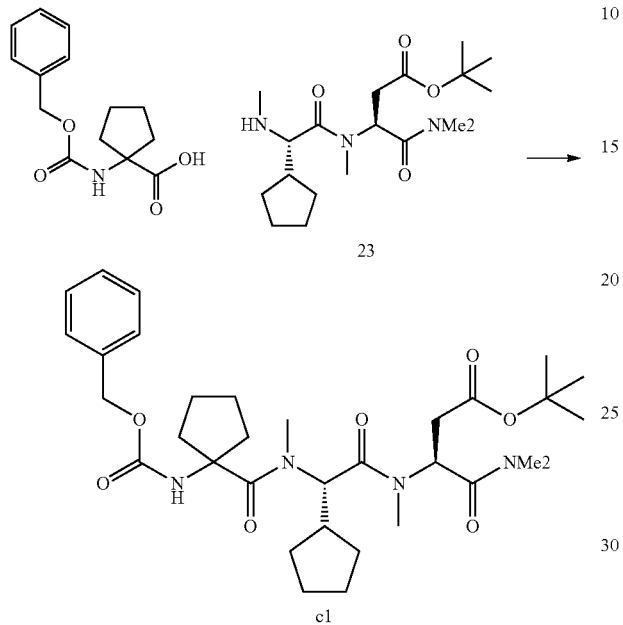

A 2-MeTHF solution (16.006 g, 32.5 wt. %) containing Compound 23 was added to a reaction vessel at room temperature and concentrated under reduced pressure. The residue was dissolved in MeCN (10.0 mL) and an operation of concentration under reduced pressure was repeated 3 times. MeCN (53.9 mL), 1-(((benzyloxy)carbonyl)-amino)cyclopentane-1-carbonic acid (9.604 g), and DIPEA (12.7 mL) were added to the reaction vessel at room temperature, and stirred. The outside temperature of the reaction vessel was set to 55° C., and HATU (15.257 g) was added in 2 portions to the reaction mixture with stirring, and further stirring for 6 hours. The reaction mixture was diluted with a MeCN/propylamine (9:1) mixture, which was subjected to HPLC analysis to confirm that the reaction conversion rate was 99.6% or more (Calculation Formula 2 of the reaction conversion rate). The N-methylimidazole (4.3 mL) was added to the reaction mixture and stirred for 5 minutes, and after adding tap water (27.0 mL) and stirring for 30 minutes, the outside temperature of the reaction vessel was lowered from 55° C. to 25° C., and the reaction mixture was stirred overnight. The reaction mixture was suction filtered through filter paper and the residue was washed with a mixture of MeCN (18.0 mL) and tap water (9.0 mL). The filtered crystals were vacuum dried at 40° C. for 3 hours to afford white powder (6.957 g) containing Compound c1. The crystals obtained were diluted with MeCN and subjected to LCMS measurement (Retention time of Compound c1: 6.914 minutes, m/z=637.30 [M+Na]$^+$) under the following analysis conditions.

LCMS Analysis Conditions
Apparatus: Waters ACQUITY UPLC H-Class+ACQUITY QDA
Column: CAPCELL CORE ADME (OSAKA SODA), 2.1 mm ID×50 mm, 2.7 m
Mobile Phase: 0.05% TFA/water (A), 0.05% TFA/MeCN (B)
Elution Method: B) 5% (0 min)→100% (10 min)→5% (10.1 min)→5% (12 min)
Flow Rate: 0.5 m/min
Column Temperature: 35° C.
Detection Wavelength: 210 nm (PDA)

The resulting residue and 3,5-bis(trifluoromethyl)benzoic acid were dissolved in DMSO-$d_6$, which was subjected to qNMR analysis (yield: 78.32%).

Example 57

Synthesis of Compound c2: (3S)-3-[[(2S)-2-[[1-(benzyloxycarbonylamino)cyclopentanecarbonyl]-methyl-amino]-2-cyclopentyl-acetyl]-methyl-amino]-4-(dimethylamino)-4-oxo-butanoic acid

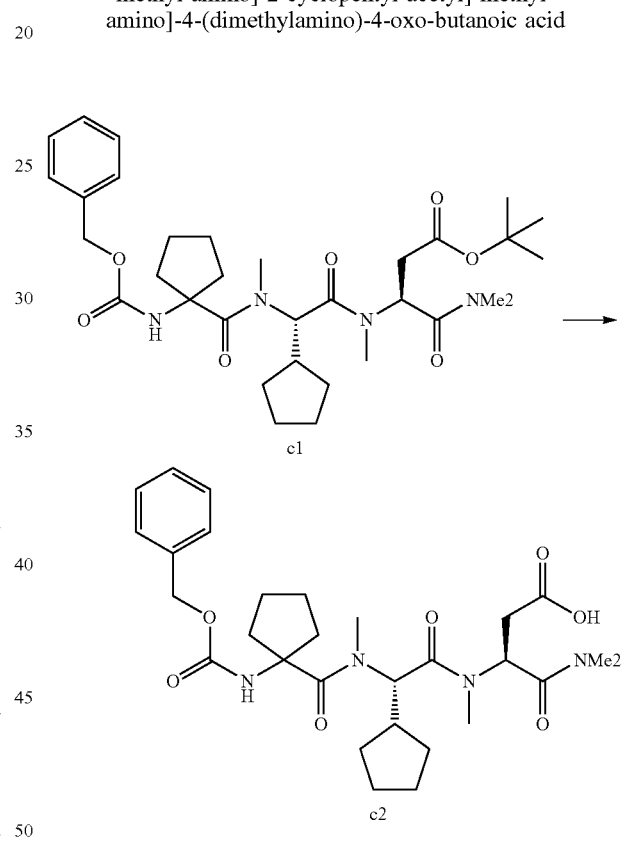

After adding the white powder (2.504 g, 95.9 wt. %) containing Compound c1 and dichloromethane (12.0 mL) to a reaction vessel at room temperature, HMDS (2.07 mL) was added. The reaction vessel was cooled in an ice bath and TMSOTf (1.41 mL) was added with stirring. The reaction vessel was removed from the ice bath and stirred at room temperature for 1 hour. The reaction mixture was diluted with MeCN, and subjected to HPLC analysis, to confirm that the reaction conversion rate was 99.9% or more (Calculation Formula 1 of the reaction conversion rate). The reaction vessel was cooled in an ice bath, to this were added dichloromethane (12.0 mL) and a 5% aqueous dipotassium hydrogenphosphate solution (24.0 mL) and the mixture was stirred for 10 minutes, and the organic layer was discharged. After adding 2-MeTHF (72.0 mL) to the aqueous layer, the organic layer was washed with a 0.5 M aqueous hydrochloric acid solution (12.0 mL), and a 5% aqueous sodium chloride solution (24.0 mL). The resulting organic layer was concentrated under reduced pressure to afford white powder (1.977 g) containing Compound c2. The white powder obtained was diluted with MeCN and subjected to the LCMS analysis (method 3: Retention time of Compound c2: 3.307 minutes, m/z=581.13 [M+Na]$^+$). The obtained white powder and 3,5-bis(trifluoromethyl)benzoic acid were dissolved in DMSO-d$_6$, which was subjected to qNMR analysis (Yield: 81.51%).

Example 58

Synthesis of Compound c3: tert-Butyl 2-[[(2S)-2-[[(2S)-1-[(2S)-2-[[(2S,3S)-2-[[(2S)-2-[[(3S)-3-[[(2S)-2-[[1-(benzyloxycarbonylamino)cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetate Compound c2 (618.1 mg, 90.0 wt. %) and a 2-MeTHF solution (1.22 g, 55.0 wt. %) containing Compound 17 were weighed into a reaction vessel, and 2-MeTHF (10.9 mL) and MeCN (1.22 mL) were added. After adding DIPEA (0.885 mL) with stirring at room temperature, HATU (792 mg) was added. After stirring at room temperature for 2 hours, the reaction mixture was sampled for sample preparation (Sample Preparation Method 2) and subjected to HPLC analysis to confirm that the reaction conversion rate was 99.9% or more (Calculation Formula 2 of the reaction conversion rate). The outside temperature was lowered to 0° C., and N-methylimidazole (72 μL) and a 5% aqueous sodium carbonate solution (10 mL) were added to the reaction mixture, and the mixture was stirred at room temperature for 10 minutes. The aqueous layer was discharged, and the organic layer was washed with a 2.5% aqueous ammonia solution (10 mL), a 5% aqueous sodium hydrogen-sulfate solution (10 mL×2), and a 5% aqueous sodium carbonate solution (10 mL×2). The resulting organic layer was concentrated under reduced pressure to dryness at an outside temperature of 30° C. to afford a residue (1.94 g, 91.2% yield) containing Compound c3.

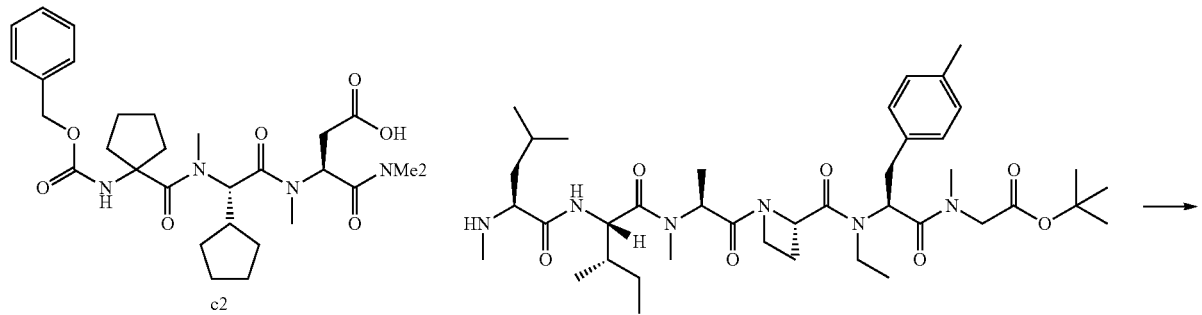

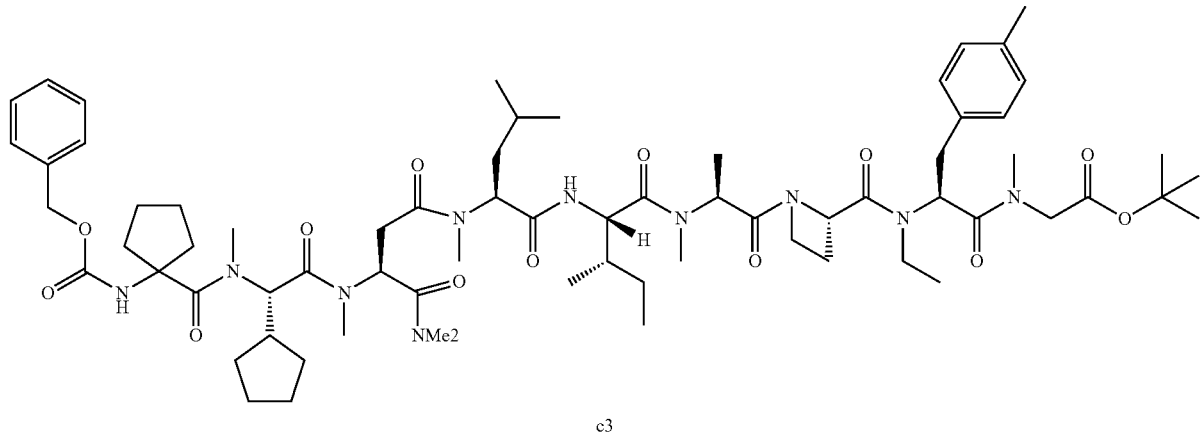

HPLC: Retention time: 4.606 minutes (HPLC Analysis Condition: method 1).

Yield: 91.2% (the resulting residue and 3,5-bis(trifluoromethyl)benzoic acid were dissolved in DMSO-$d_6$, which was subjected to qNMR analysis.).

Example 59

Synthesis of Compound c4: 2-[[(2S)-2-[[(2S)-1-[(2S)-2-[[(2S,3S)-2-[[(2S)-2-[[(3S)-3-[[(2S)-2-[[1-(benzyloxycarbonylamino)cyclopentanecarbonyl]-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetic acid preparation (Sample Preparation Method 1) and subjected to HPLC analysis to confirm that the reaction conversion rate was 99.9% or more (Calculation Formula 1 of the reaction conversion rate). The outside temperature was lowered to 0° C., and a 5% aqueous dipotassium hydrogenphosphate solution (5.25 mL) was added dropwise to the reaction mixture, and the mixture was stirred at room temperature for 10 minutes. The aqueous layer was discharged, and after washing an organic layer twice with a 5% aqueous dipotassium hydrogenphosphate solution (5.25 mL) and a 0.5 M aqueous hydrochloric acid solution (3.5 mL), the organic layer was further washed with a 5% aqueous sodium chloride solution (7.0 mL), and the aqueous layer was discharged. The resulting organic layer was concentrated under reduced pressure

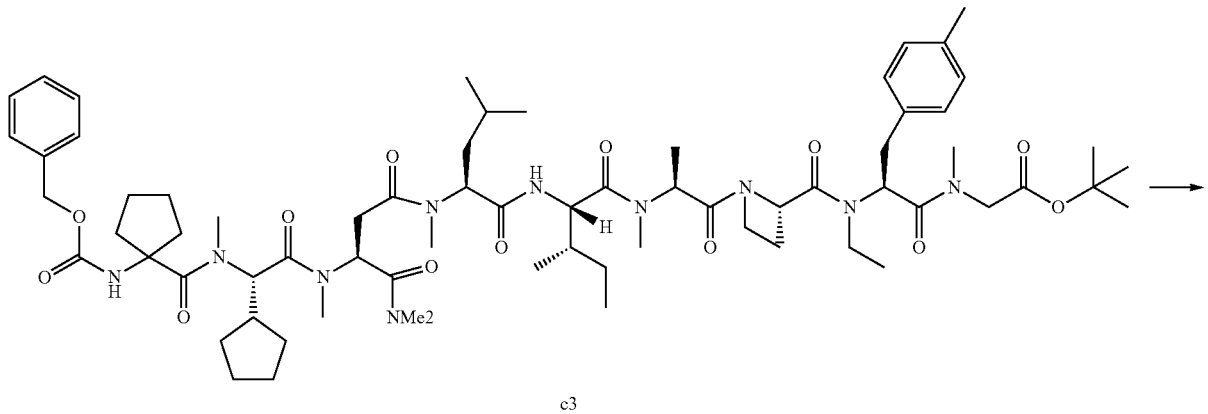

c3

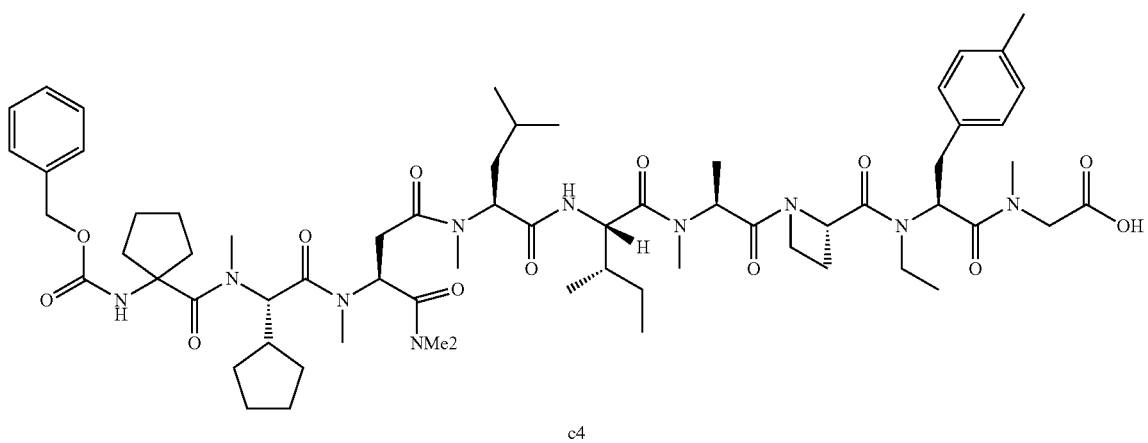

c4

The residue (1.41 g, 50.2 wt. %) containing Compound c3, which was obtained in Example 58, was added to a reaction vessel and 2-MeTHF (7.0 mL) was added. After adding HMDS (579 μL) with stirring at room temperature, the outside temperature was lowered to 0° C. and TMSOTf (394 μL) was slowly added dropwise. The temperature was raised to room temperature, and the mixture was stirred for 2 hours. The reaction mixture was sampled for sample to dryness at an outside temperature of 30° C. to afford a residue (0.85 g, 95.2% yield) containing Compound c4.

LCMS (ESI): Retention time: 3.974 minutes, m/z=1228.38 [M+H]$^+$ (LCMS Analysis Condition: method 1).

Yield: 95.2% (the resulting residue and 3,5-bis(trifluoromethyl)benzoic acid were dissolved in DMSO-$d_6$, which was subjected to qNMR analysis.).

Example 60

Synthesis of Compound c5: 2-[[(2S)-2-[[(2S)-1-[(2S)-2-[[(2S,3S)-2-[[(2S)-2-[[(3S)-3-[[(2S)-2-[1-aminocyclopentanecarbonyl)-methyl-amino]-2-cyclopentyl-acetyl]-methyl-amino]-4-(dimethylamino)-4-oxo-butanoyl]-methyl-amino]-4-methyl-pentanoyl]amino]-3-methyl-pentanoyl]-methyl-amino]propanoyl]azetidine-2-carbonyl]-ethyl-amino]-3-(p-tolyl)propanoyl]-methyl-amino]acetic acid

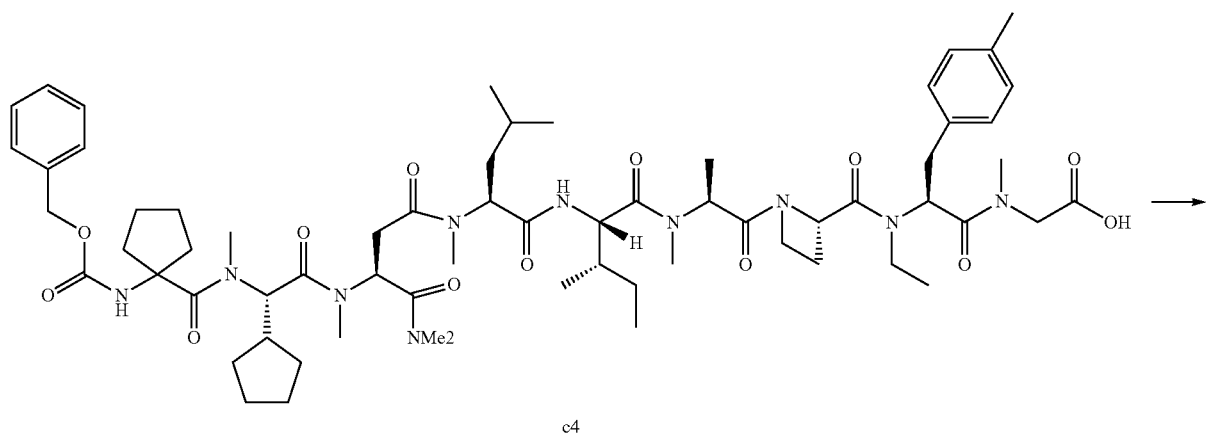

c4

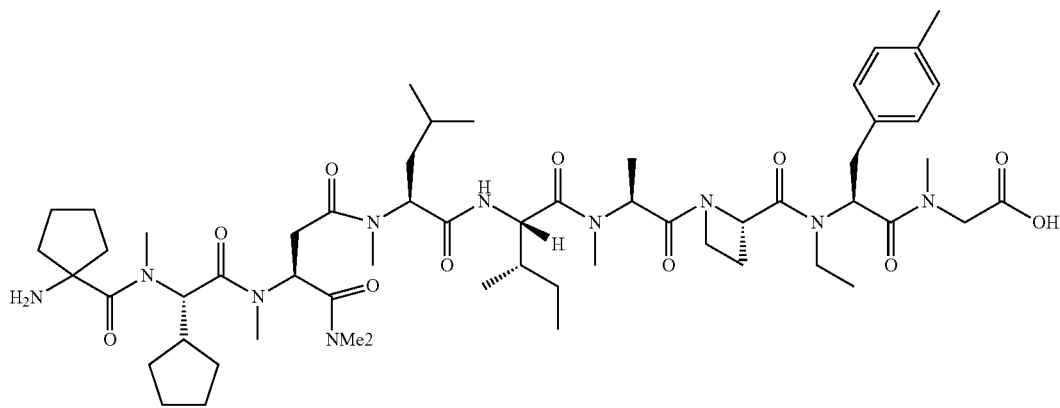

c5

Compound c4 (462 mg, 53.5 wt. %) obtained in Example 59 and 2-MeTHF (2.47 mL) were added successively to a reaction vessel at room temperature. After adding 5% Pd/C (74.7 mg, 50% wet with water) to the reaction vessel, degassing and purging with a hydrogen gas were performed 3 times and the mixture was stirred for 8 hours. The reaction mixture was sampled for sample preparation (Sample Preparation Method 1) and subjected to HPLC analysis to confirm that the reaction conversion rate was 99.7% (Calculation Formula 1 of the reaction conversion rate). After adding 2-MeTHF (10 mL) to the reaction mixture, the reaction mixture was filtered through filter paper and membrane filters and the residue was washed with 2-MeTHF (5.0 mL×2). The resulting filtrate was concentrated under reduced pressure to afford a solution (1.16 g, 91.0% yield) containing Compound c5.

LCMS (ESI): Retention time: 2.920 minutes, m/z=1093.88 [M+H]$^+$ (LCMS Analysis Condition: method 1).

Yield: 91.0% (the resulting residue and 3,5-bis(trifluoromethyl)benzoic acid were dissolved in DMSO-d$_6$, which was subjected to qNMR analysis.).

Cyclization Reaction of Compound c5 (Study of Reaction Conditions of Example 61)

Using Compound c5 as a starting material, condensing agents and solvents in a cyclization reaction to Compound c6 were studied. The cyclization reaction was observed by HPLC analysis.

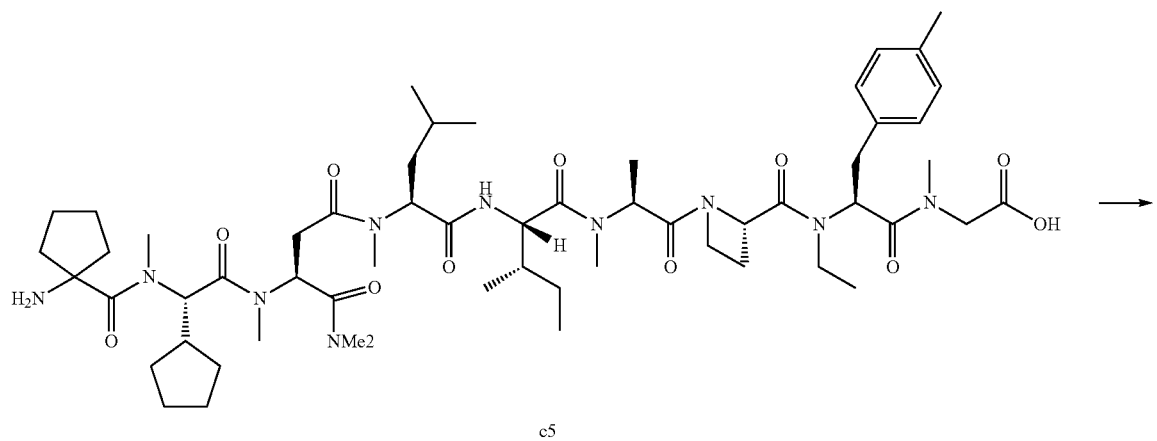

c5

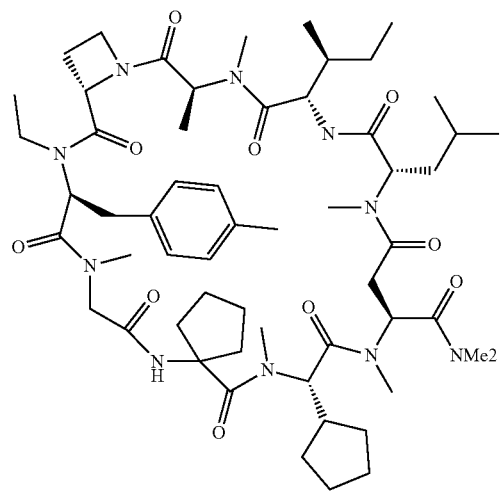

c6

Example 61-1

Synthesis of Compound c6: (3S,6S,9S,13S,16S,25S,28S)-16-cyclopentyl-26-ethyl-9-isobutyl-N,N,3,4,10,14,17,23-octamethyl-6-[(1S)-1-methylpropyl]-2,5,8,11,15,18,21,24,27-nonaoxo-25-(p-tolylmethyl)spiro[1,4,7,10,14,17,20,23,26-nonazabicyclo[26.2.0]triacontane-19,1'-cyclopentane]-13-carboxamide Compound c5 (44.19 mg, 21.8 wt. % (8.81 μmol)) was weighed into a reaction vessel, and after concentrating to dryness, a solvent (MeCN, 1.9 mL (200 v/w)) was added. DIPEA (7.19 μL (41.2 μmol)) was added with stirring at room temperature. A condensing agent (HATU, 12.84 mg, (33.8 μmol)) was added, and the resultant was stirred for 30 minutes. The reaction mixture (50 μL) was diluted with a MeCN/propylamine (9:1) mixture (100 μL), to prepare a solution for HPLC analysis.

LCMS (ESI) of Compound c6: Retention time: 17.22 minutes, m/z=1076.38 [M+H]$^+$ (LCMS Analysis Condition: method 5).

LCMS (ESI) of a cyclic dimer c7 (c-Dimer): Retention time: 21.85 minutes, m/z=2151.42 [M+H]$^+$ (LCMS Analysis Condition: method 5).

LCMS (ESI) of a cyclic trimer c8: Retention time: 24.50 minutes, m/z=1614.13 [M+2H]$^{2+}$ (LCMS Analysis Condition: method 5).

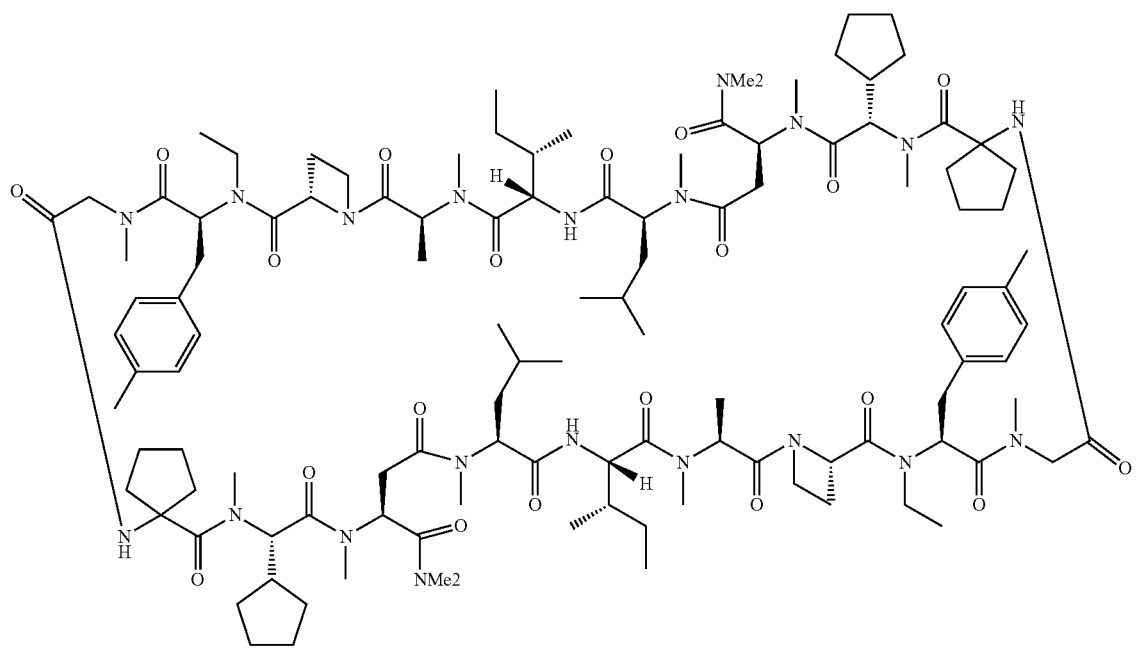

c7 (Cyclic Dimer)

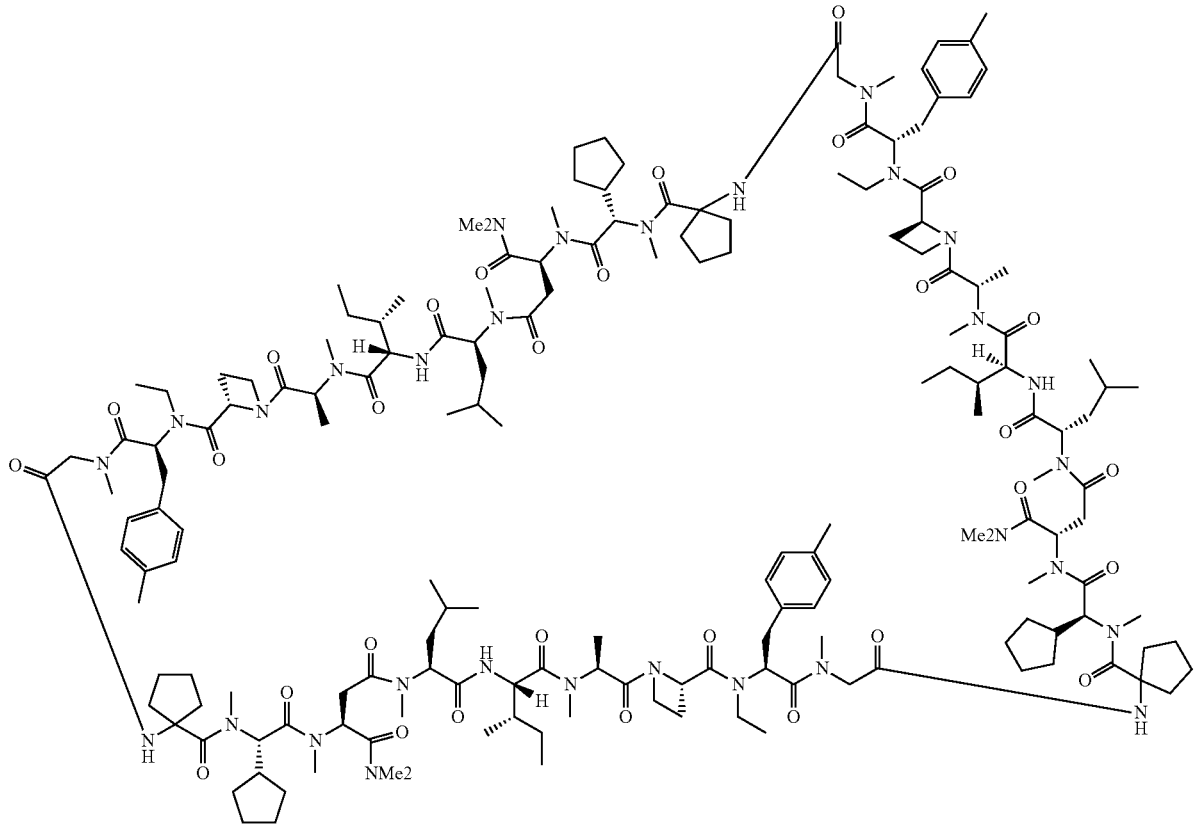

c8 (Cyclic Trimer)

By using condensing agents and solvents shown in the following Table, and performing the same operation as the experiment of Example 61-1 (using PyAOP as the condensing agent and 2-MeTHF as the solvent), consumption of the starting material (SM, Compound c5), generation of the target material (TM, Compound c6), and amounts of by-products (the cyclic dimer c7 (c-Dimer) and the cyclic trimer c8 (c-Trimer)) generated were measured to study preferable reaction conditions. Table summarizes area % ratio of the starting material: the propylamide form (Compound c9) in the starting material: the target material: the cyclic Dimer: the cyclic Trimer.

TABLE 16

| Condensing agent | Example No. | Solvent | Ratio of SM, TM, c-Dimer and c-Trimer (%) | | | | |
|---|---|---|---|---|---|---|---|
| | | | SM | SM-nPrNH | TM | c-Dimer | c-Trimer |
| HATU | Example 61-1 | MeCN | 0 | 0 | 38 | 49 | 14 |
| | Example 61-2 | 2-MeTHF | 34 | 35 | 17 | 13 | 2 |
| | Example 61-3 | Dimethyl carbonate | 0 | 0 | 38 | 47 | 15 |
| PyAOP | Example 61-4 | 2-MeTHF | 0 | 0 | 39 | 47 | 15 |

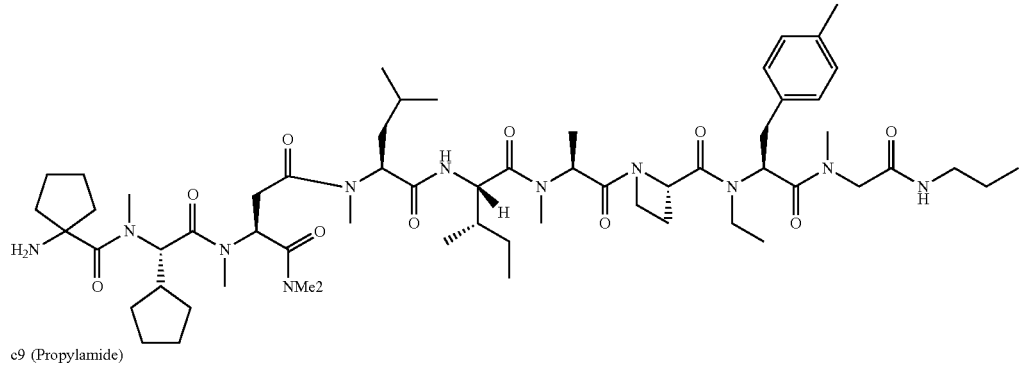

c9 (Propylamide)

Example 61-5 (Reverse Dropwise Addition of Example 61-4)

Compound c5 (45.0 mg, 21.8 wt. % (8.97 μmol)) was weighed into a vial, and after concentrating to dryness, 2-MeTHF (0.98 mL (100 v/w)) was added and the mixture was stirred at 50° C. for 10 minutes. After observation of dissolution of the starting material, DIPEA (7.21 μL) (41.2 μmol)) was added and the reaction mixture was sucked up to a syringe. PyAOP (17.8 mg (34.1 μmol)) and 2-MeTHF (0.98 mL (100 v/w)) were added to another reaction vessel, and a solution in the above syringe was added dropwise over 3 hours while stirring at room temperature. After finishing dropwise addition, the reaction mixture (50 μL) was diluted with a MeCN/propylamine (9:1) mixture (100 μL), to prepare a solution for HPLC analysis.

TABLE 17

| Condensing agent | Example No. | Solvent | Ratio of SM, TM, c-Dimer and c-Trimer (%) | | | | |
|---|---|---|---|---|---|---|---|
| | | | SM | SM-nPrNH | TM | c-Dimer | c-Trimer |
| PyAOP | Example 61-5 | 2-MeTHF | 0 | 0 | 89 | 11 | 0 |

INDUSTRIAL APPLICABILITY

The present invention provides methods for producing pharmaceutically useful cyclic peptide compounds, or salts or solvates of those compounds, and methods for producing peptide compounds that are used in the production of the cyclic peptide compounds or salts or solvates of those cyclic compounds.

The invention claimed is:

1. A method for producing a peptide compound by a liquid phase method, comprising:
    step 1: linking an N-protected amino acid or N-protected peptide to a C-protected amino acid or C-protected peptide;
    step 2: removing the N-protecting group after step 1; and optionally repeating steps 1 and 2 a plurality of times to produce the peptide compound;
    wherein the method does not comprise isolating the product of each of steps 1 and 2;
    wherein each of the steps comprised in the method for producing the peptide compound is carried out in Solvent B, which is one or more solvents selected independently from the group consisting of toluene, 2-methyltetrahydrofuran (2-MeTHF), methyl tert-butyl ether (MTBE), dimethyl carbonate, anisole, isopropyl acetate, heptane, ethyl acetate, and 4-methyltetrahydropyran;
    wherein workup in each of the steps comprised in the method for producing the peptide compound comprises one or more operations selected from the group consisting of a liquid separation operation, a filtration operation, and a concentration operation;
    wherein Solvent C is added for the liquid separation operation;
    wherein Solvent C is a water-immiscible solvent which comprises one or more solvents selected from the group consisting of 2-MeTHF, dimethyl carbonate, anisole, isopropyl acetate, ethyl acetate, MTBE, cyclopentyl methyl ether (CPME), 4-methyltetrahydropyran, and heptane;
    wherein the workup in the steps comprised in the method for producing the peptide compound comprises one or more of the liquid separation operation; and
    wherein the peptide compound comprises at least one N-alkyl amino acid residue.

2. The method of claim 1, wherein the method for producing a peptide compound further comprises step 3 of removing the C-protecting group.

3. The method of claim 1, wherein the liquid separation operation comprises a washing operation of the organic phase.

4. The method of claim 1, wherein step 1 comprises condensing the N-terminal amino group of a C-protected amino acid or C-protected peptide with the C-terminal carboxyl group of an N-protected amino acid or N-protected peptide.

5. The method of claim 4, wherein step 1 is carried out in the presence of a condensing reagent.

6. The method of claim 5, wherein the condensing reagent comprises a condensing agent selected from the group consisting of T3P, EDCI, HATU, COMU, BEP, PyBOP, DMT-MM, and PyOxim.

7. The method of claim 1, wherein the N-protecting group is selected from Cbz, p-nitrobenzyloxycarbonyl, 2-naphthylmethyloxycarbonyl, diphenylmethyloxycarbonyl, 9-anthrylmethyloxycarbonyl, Teoc, Boc, trifluoroacetyl, Fmoc, or Alloc.

8. The method of claim 1, wherein the C-protecting group is selected from t-Bu, trityl, cumyl, methyl, or ethyl.

9. The method of claim 1, wherein either or both of the C-protected peptide and the N-protected peptide comprise 2 to 20 amino acid residues, and wherein either or both of the C-protected peptide and the N-protected peptide comprise at least one unnatural-N-alkyl amino acid residue.

10. The method of claim 1, wherein either or both of the C-protected peptide and the N-protected peptide used in step 1 in the final round of the repetition consist of 5 or 6 amino acid residues and comprise 4 or 5 N-alkyl amino acid residues.

11. The method of claim 10, wherein the C-protected peptide used in step 1 in the final round of the repetition is C-protected MeLeu-Ile-MeAla-Aze(2)-EtPhe(4-Me)-MeGly, and the N-protected peptide used in step 1 in the final round of the repetition is N-protected Hph(4-CF3-35F2)-Pro-cLeu-MeGly(cPent)-MeAsp-NMe2.

12. The method of claim 1, wherein the C-protected amino acid or a salt thereof or the C-protected peptide or a salt thereof is:

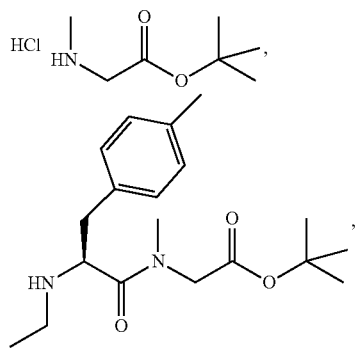

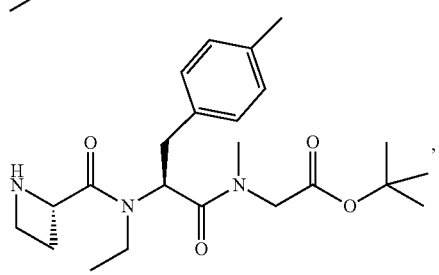

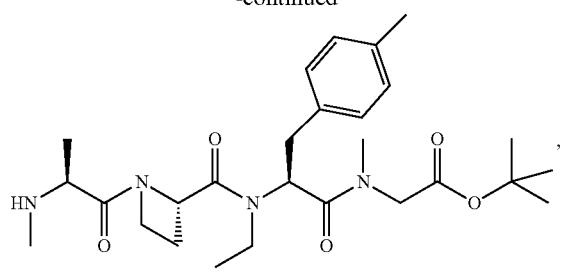

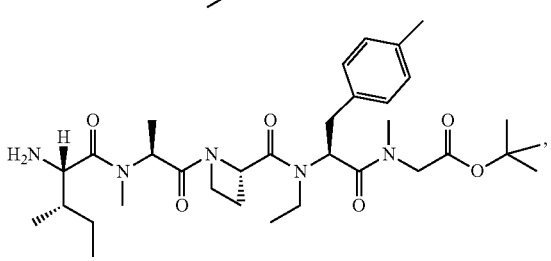

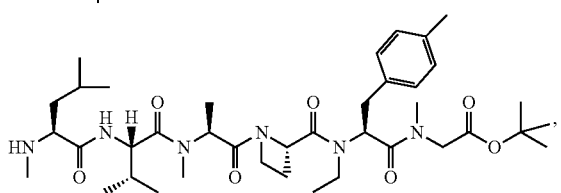

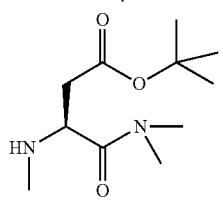

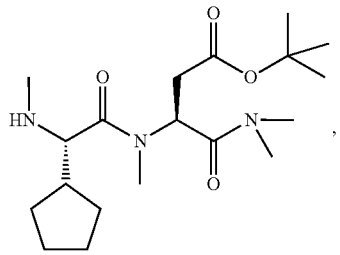

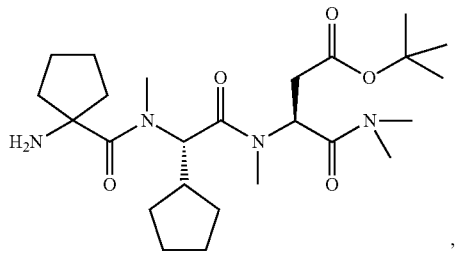

, or

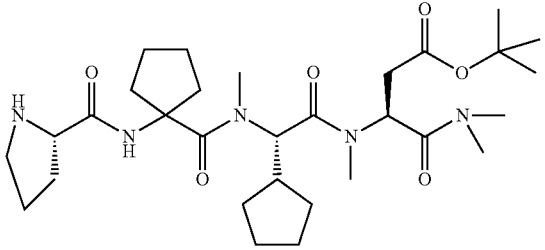

13. The method of claim 1, wherein the N-protected amino acid or a salt thereof or the N-protected peptide or a salt thereof is:
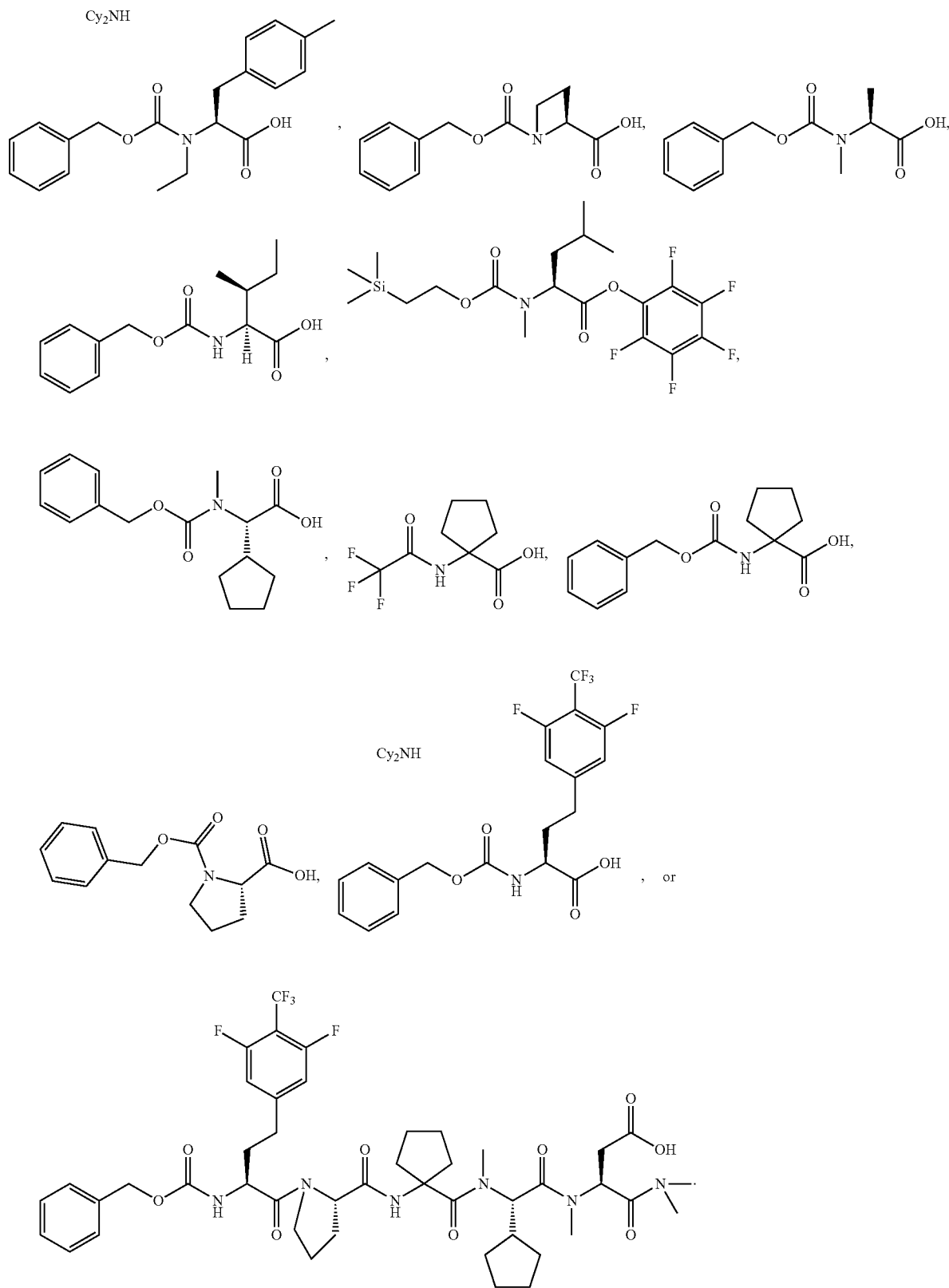

14. The method of claim 1, wherein the peptide compound is:
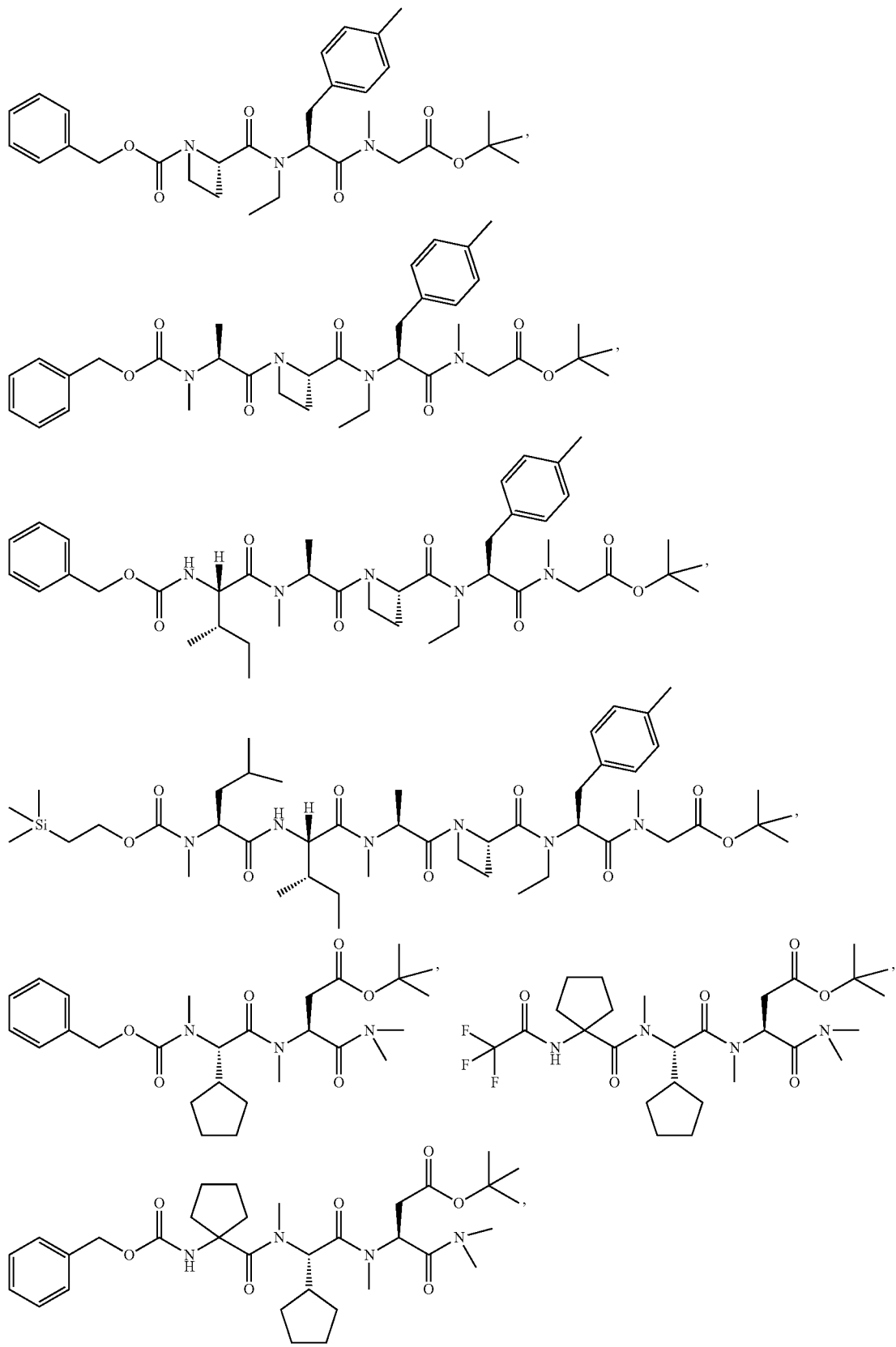

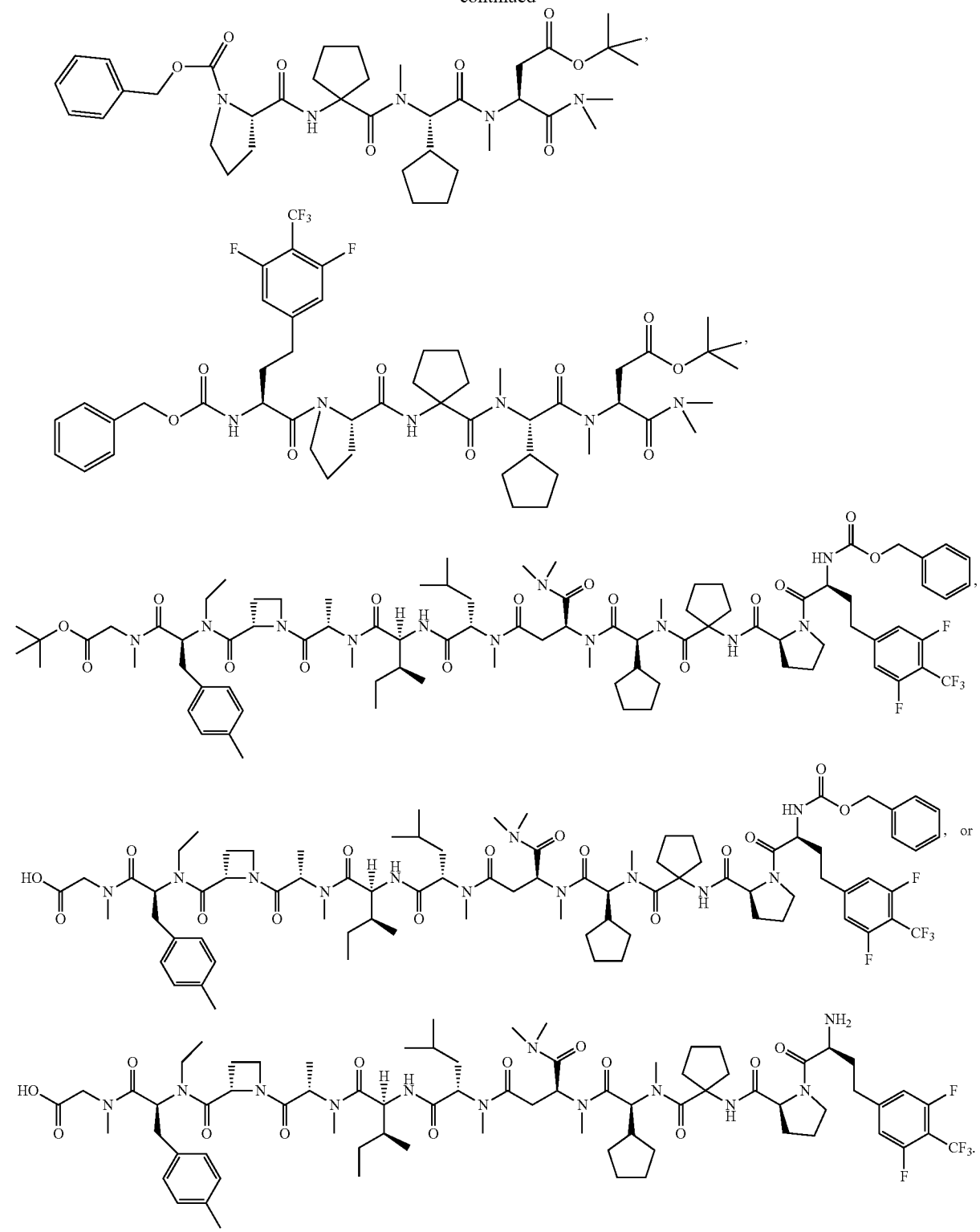

15. The method of claim 1, further comprising linking the N-terminal amino acid residue and the C-terminal amino acid residue of the peptide compound.

16. The method of claim 1, wherein Solvent B comprises one or more solvents selected from the group consisting of 2-MeTHF, MTBE, isopropyl acetate, and ethyl acetate.

17. The method of claim 1, wherein Solvent B comprises 2-MeTHF.

18. The method of claim 1, wherein Solvent C comprises 2-MeTHF.

19. The method of claim 1, wherein the peptide compound comprises 8 to 20 amino acid residues.

20. The method of claim 17, wherein step 1 is repeated a plurality of times, and Solvent B in step 1 contains 2-MeTHF in an amount of 50% or more by weight at least 50% of the total rounds of step 1.

21. The method of claim 17, wherein step 1 is repeated a plurality of times, and Solvent B in step 1 contains 2-MeTHF in an amount of 50% or more by weight at least 80% of the total rounds of step 1.

22. The method of claim 17, wherein step 1 is repeated a plurality of times, and Solvent B in step 1 contains 2-MeTHF in an amount of 80% or more by weight at least once.

23. The method of claim 17, wherein step 1 is repeated a plurality of times, and Solvent B in step 1 contains 2-MeTHF in an amount of 80% or more by weight at least twice.

24. The method of claim 1, wherein the linking step 1 is carried out in the presence of a condensing reagent selected from the group consisting of T3P, HATU, COMU, BEP, PyBOP, DMT-MM, and PyOxim.

25. The method of claim 1, wherein Solvent B is 2-MeTHF.

26. The method of claim 1, wherein Solvent C is 2-MeTHF.

27. A method for producing a peptide compound by a liquid phase method, comprising:
   step 1: linking an N-protected amino acid or N-protected peptide to a C-protected amino acid or C-protected peptide in the presence of a condensing reagent selected from the group consisting of T3P, HATU, COMU, BEP, PyBOP, DMT-MM, and PyOxim;
   step 2: removing the N-protecting group after step 1; and optionally repeating steps 1 and 2 a plurality of times to produce the peptide compound;
   wherein the method does not comprise isolating the product of each of steps 1 and 2;
   wherein each of the steps comprised in the method for producing the peptide compound is carried out in one or more solvents selected independently from the group consisting of toluene, 2-methyltetrahydrofuran (2-MeTHF), methyl tert-butyl ether (MTBE), dimethyl carbonate, anisole, isopropyl acetate, heptane, and 4-methyltetrahydropyran;
   wherein workup in each of the steps comprised in the method for producing the peptide compound comprises one or more operations selected from the group consisting of a liquid separation operation, a filtration operation, and a concentration operation;
   wherein a water-immiscible solvent is added for the liquid separation operation;
   wherein the water-immiscible solvent comprises one or more solvents selected from the group consisting of 2-MeTHF, dimethyl carbonate, anisole, isopropyl acetate, MTBE, cyclopentyl methyl ether (CPME), 4-methyltetrahydropyran, and heptane;
   wherein the workup in the steps comprised in the method for producing the peptide compound comprises one or more of the liquid separation operation; and
   wherein the peptide compound comprises at least one N-alkyl amino acid residue.

28. A method for producing a peptide compound by a liquid phase method, comprising:
   step 1: linking an N-protected amino acid or N-protected peptide to a C-protected amino acid or C-protected peptide in the presence of a condensing reagent selected from the group consisting of T3P, HATU, COMU, BEP, PyBOP, DMT-MM, and PyOxim;
   step 2: removing the N-protecting group after step 1; and optionally repeating steps 1 and 2 a plurality of times to produce the peptide compound;
   wherein the method does not comprise isolating the product of each of steps 1 and 2;
   wherein each of the steps comprised in the method for producing a peptide compound is carried out in one or more solvents, wherein the one or more solvents comprise 2-methyltetrahydrofuran (2-MeTHF);
   wherein workup in each of the steps comprised in the method for producing the peptide compound comprises one or more operations selected from the group consisting of a liquid separation operation, a filtration operation, and a concentration operation;
   wherein a water-immiscible solvent is added for the liquid separation operation;
   wherein the water-immiscible solvent comprises 2-MeTHF,
   wherein the workup in the steps comprised in the method for producing the peptide compound comprises one or more of the liquid separation operation; and
   wherein the peptide compound comprises at least one N-alkyl amino acid residue.

* * * * *